(12) United States Patent
Padmani et al.

(10) Patent No.: US 11,107,574 B2
(45) Date of Patent: Aug. 31, 2021

(54) MANAGEMENT OF MEDICATION PREPARATION WITH FORMULARY MANAGEMENT

(71) Applicant: Baxter Corporation Englewood, Englewood, CO (US)

(72) Inventors: Bhavesh S. Padmani, Port Orange, FL (US); Matthew A. Valentine, Ormond Beach, FL (US); Jayson Bender, Deland, FL (US); Matt Crooks, Daytona Beach, FL (US); Bapu Hirave, Daytona Beach, FL (US); Maher Yassine, Ormond Beach, FL (US); Ghalib Abbasi, Ormond Beach, FL (US); Kristina Yevseyeva, Daytona Beach, FL (US)

(73) Assignee: Baxter Corporation Englewood, Englewood, CO (US)

( * ) Notice: Subject to any disclaimer, the term of this patent is extended or adjusted under 35 U.S.C. 154(b) by 1138 days.

(21) Appl. No.: 14/868,625

(22) Filed: Sep. 29, 2015

(65) Prior Publication Data
US 2016/0092638 A1    Mar. 31, 2016

Related U.S. Application Data

(60) Provisional application No. 62/057,906, filed on Sep. 30, 2014.

(51) Int. Cl.
*G16H 40/20* (2018.01)
*G16H 10/00* (2018.01)
(Continued)

(52) U.S. Cl.
CPC ............ *G16H 40/20* (2018.01); *G16H 10/00* (2018.01); *G16H 40/67* (2018.01); *G16H 70/40* (2018.01)

(58) Field of Classification Search
None
See application file for complete search history.

(56) References Cited

U.S. PATENT DOCUMENTS 641,748 A    1/1900   Smith
819,339 A    5/1906   Cleland
(Continued)

FOREIGN PATENT DOCUMENTS

CN    1516257    5/1999
CN    2440518    8/2001
(Continued)

OTHER PUBLICATIONS

Texas Administrative Code, Title 22, Part 15, Ch 291, Rules 20, 36, and 71-74. Feb. 10, 2004.
(Continued)

*Primary Examiner* — Rachelle L Reichert
(74) *Attorney, Agent, or Firm* — K&L Gates LLP

(57) ABSTRACT

A pharmacy workflow management application with improved functionality related thereto. The improved functionality may include enhancements to a user interface for maintenance of a formulary at a local system executing the pharmacy workflow management application. The formulary management may include user interface elements provided at least partially based on a user profile. Additional enhancements to a user interface associated with a user profile may be provided for dose order record maintenance using the pharmacy workflow management application. Furthermore, enhancements to triggered scan events for updating a status of a dose order, situation board enhancements related to formatting of the situation board in relation to a user profile, encryption of communication by the pharmacy
(Continued)

workflow application, and improved methods of installing updates to terminals of the pharmacy workflow management application are discussed.

25 Claims, 50 Drawing Sheets

(51) Int. Cl.
*G16H 40/67* (2018.01)
*G16H 70/40* (2018.01)

(56) References Cited

U.S. PATENT DOCUMENTS

| | | | |
|---|---|---|---|
| 3,426,150 A | 2/1969 | Tygart |
| 3,739,943 A | 6/1973 | Williamsen et al. |
| 3,742,938 A | 7/1973 | Stern |
| 3,756,752 A | 9/1973 | Stenner |
| 3,774,762 A | 11/1973 | Lichtenstein |
| 3,786,190 A | 1/1974 | Pori |
| 3,809,871 A | 5/1974 | Howard et al. |
| 3,810,102 A | 5/1974 | Parks, III et al. |
| 3,848,112 A | 11/1974 | Weichselbaum et al. |
| 3,858,574 A | 1/1975 | Page |
| 3,878,967 A | 4/1975 | Joslin et al. |
| 3,910,257 A | 10/1975 | Fletcher et al. |
| 3,910,260 A | 11/1975 | Sarnoff et al. |
| 3,921,196 A | 11/1975 | Patterson |
| 3,971,000 A | 7/1976 | Cromwell |
| 3,995,630 A | 12/1976 | Verrdonk |
| 3,998,103 A | 12/1976 | Bjorklund et al. |
| 4,032,908 A | 6/1977 | Rice et al. |
| 4,078,562 A | 3/1978 | Friedman |
| 4,144,496 A | 3/1979 | Cunningham et al. |
| 4,151,407 A | 4/1979 | McBride et al. |
| 4,156,867 A | 5/1979 | Bench et al. |
| 4,164,320 A | 8/1979 | Irazoqui et al. |
| 4,173,971 A | 11/1979 | Karz |
| 4,199,307 A | 4/1980 | Jassawalla |
| 4,270,532 A | 6/1981 | Franetzki et al. |
| 4,273,121 A | 6/1981 | Jassawalla |
| 4,282,872 A | 8/1981 | Franetzki et al. |
| 4,308,866 A | 1/1982 | Jelliffe et al. |
| 4,319,338 A | 3/1982 | Grudowski et al. |
| 4,320,757 A | 3/1982 | Whitney et al. |
| 4,354,252 A | 10/1982 | Lamb et al. |
| 4,369,780 A | 1/1983 | Sakai |
| 4,370,983 A | 2/1983 | Lichtenstein |
| 4,373,527 A | 2/1983 | Fischell |
| 4,381,776 A | 5/1983 | Latham, Jr. |
| 4,385,630 A | 5/1983 | Gilcher et al. |
| 4,398,289 A | 8/1983 | Schoate |
| 4,398,908 A | 8/1983 | Siposs |
| 4,414,566 A | 11/1983 | Peyton et al. |
| 4,416,654 A | 11/1983 | Schoendorfer et al. |
| 4,425,114 A | 1/1984 | Schoendorfer et al. |
| 4,428,381 A | 1/1984 | Hepp |
| 4,443,216 A | 4/1984 | Chappell |
| 4,447,224 A | 5/1984 | DeCant, Jr. et al. |
| 4,449,538 A | 5/1984 | Corbitt et al. |
| 4,451,255 A | 5/1984 | Bujan et al. |
| 4,457,750 A | 7/1984 | Hill |
| 4,458,693 A | 7/1984 | Badzinski et al. |
| 4,460,358 A | 7/1984 | Somerville et al. |
| 4,464,172 A | 8/1984 | Lichtenstein |
| 4,469,481 A | 9/1984 | Kobayashi |
| 4,475,901 A | 10/1984 | Kraegen et al. |
| 4,476,381 A | 10/1984 | Rubin |
| 4,480,751 A | 11/1984 | Lueptow |
| 4,481,670 A | 11/1984 | Freeburg |
| 4,487,604 A | 12/1984 | Iwatschenko et al. |
| 4,490,798 A | 12/1984 | Franks et al. |
| 4,496,351 A | 1/1985 | Hillel et al. |
| 4,511,352 A | 4/1985 | Theeuwes et al. |
| 4,525,861 A | 6/1985 | Freeburg |
| 4,526,574 A | 7/1985 | Pekkarinen |
| 4,529,401 A | 7/1985 | Leslie et al. |
| 4,531,527 A | 7/1985 | Reinhold, Jr. et al. |
| 4,538,138 A | 8/1985 | Harvey et al. |
| 4,545,071 A | 10/1985 | Freeburg |
| 4,551,133 A | 11/1985 | Zegers de Beyl et al. |
| 4,559,038 A | 12/1985 | Berg et al. |
| 4,560,979 A | 12/1985 | Rosskopf |
| 4,561,443 A | 12/1985 | Hogrefe et al. |
| 4,562,751 A | 1/1986 | Nason |
| 4,564,054 A | 1/1986 | Gustavsson |
| 4,590,473 A | 5/1986 | Burke et al. |
| 4,602,249 A | 7/1986 | Abbott |
| 4,619,653 A | 10/1986 | Fischell |
| 4,622,979 A | 11/1986 | Katchis et al. |
| 4,624,661 A | 11/1986 | Arimond |
| 4,636,950 A | 1/1987 | Caswell et al. |
| 4,637,817 A | 1/1987 | Archibald et al. |
| 4,650,469 A | 3/1987 | Berg et al. |
| 4,652,262 A | 3/1987 | Veracchi |
| 4,653,010 A | 3/1987 | Figler et al. |
| 4,676,776 A | 6/1987 | Howson |
| 4,681,563 A | 7/1987 | Deckert et al. |
| 4,688,167 A | 8/1987 | Agarwal |
| 4,691,580 A | 9/1987 | Fosslien |
| 4,695,954 A | 9/1987 | Rose et al. |
| 4,696,671 A | 9/1987 | Epstein et al. |
| 4,697,928 A | 10/1987 | Csongor |
| 4,702,595 A | 10/1987 | Mutschler et al. |
| 4,705,506 A | 11/1987 | Archibald |
| D293,135 S | 12/1987 | Medema et al. |
| 4,714,462 A | 12/1987 | DiComenico |
| 4,717,042 A | 1/1988 | McLaughlin |
| 4,718,576 A | 1/1988 | Tamura et al. |
| 4,722,224 A | 2/1988 | Scheller et al. |
| 4,722,349 A | 2/1988 | Baumberg |
| 4,722,734 A | 2/1988 | Kolln |
| 4,730,849 A | 3/1988 | Siegel |
| 4,731,058 A | 3/1988 | Doan |
| 4,732,411 A | 3/1988 | Siegel |
| 4,741,732 A | 5/1988 | Crankshaw et al. |
| 4,741,736 A | 5/1988 | Brown |
| 4,756,706 A | 7/1988 | Kerns et al. |
| 4,759,756 A | 7/1988 | Forman |
| 4,770,184 A | 9/1988 | Greene et al. |
| 4,778,449 A | 10/1988 | Weber et al. |
| 4,779,626 A | 10/1988 | Peel et al. |
| 4,784,645 A | 11/1988 | Fischell |
| 4,785,799 A | 11/1988 | Schoon et al. |
| 4,785,969 A | 11/1988 | McLaughlin |
| 4,796,644 A | 1/1989 | Polaschegg |
| 4,797,840 A | 1/1989 | Fraden |
| 4,803,625 A | 2/1989 | Fu et al. |
| 4,810,090 A | 3/1989 | Boucher |
| 4,810,243 A | 3/1989 | Howson |
| 4,811,844 A | 3/1989 | Moulding, Jr. et al. |
| 4,816,208 A | 3/1989 | Woods et al. |
| 4,817,044 A | 3/1989 | Ogren |
| 4,828,545 A | 5/1989 | Epstein et al. |
| 4,829,524 A | 5/1989 | Yoshida |
| 4,830,018 A | 5/1989 | Treach |
| 4,831,562 A | 5/1989 | Mcintosh et al. |
| 4,832,033 A | 5/1989 | Maher et al. |
| 4,835,372 A | 5/1989 | Gombrich et al. |
| 4,835,521 A | 5/1989 | Andrejasich et al. |
| 4,838,275 A | 6/1989 | Lee |
| 4,839,806 A | 6/1989 | Goldfischer et al. |
| 4,845,644 A | 7/1989 | Anthias et al. |
| 4,847,764 A | 7/1989 | Halvorson |
| 4,850,009 A | 7/1989 | Zook et al. |
| 4,850,972 A | 7/1989 | Schulman et al. |
| 4,853,521 A | 8/1989 | Claeys et al. |
| 4,854,324 A | 8/1989 | Hirschman et al. |
| 4,857,713 A | 8/1989 | Brown |
| 4,857,716 A | 8/1989 | Gombrich et al. |
| 4,865,584 A | 9/1989 | Epstein et al. |
| 4,871,351 A | 10/1989 | Feingold |
| 4,878,175 A | 10/1989 | Norden-Paul et al. |
| 4,880,013 A | 11/1989 | Chio |

(56) References Cited

U.S. PATENT DOCUMENTS

| | | |
|---|---|---|
| 4,889,132 A | 12/1989 | Hutcheson et al. |
| 4,889,134 A | 12/1989 | Greenwold et al. |
| 4,893,270 A | 1/1990 | Beck et al. |
| 4,897,777 A | 1/1990 | Janke et al. |
| 4,898,209 A | 2/1990 | Zbed |
| 4,898,576 A | 2/1990 | Philip |
| 4,898,578 A | 2/1990 | Rubalcaba, Jr. |
| 4,901,728 A | 2/1990 | Hutchison |
| 4,905,163 A | 2/1990 | Garber et al. |
| 4,908,017 A | 3/1990 | Howson et al. |
| 4,912,623 A | 3/1990 | Rantala et al. |
| 4,916,441 A | 4/1990 | Gombrich et al. |
| 4,922,922 A | 5/1990 | Pollock et al. |
| 4,925,444 A | 5/1990 | Orkin et al. |
| 4,933,843 A | 6/1990 | Scheller et al. |
| 4,937,777 A | 6/1990 | Flood et al. |
| 4,941,808 A | 7/1990 | Qureshi et al. |
| 4,943,279 A | 7/1990 | Samiotes et al. |
| 4,943,987 A | 7/1990 | Asahina et al. |
| 4,946,445 A | 8/1990 | Lynn |
| 4,949,274 A | 8/1990 | Hollander et al. |
| 4,952,928 A | 8/1990 | Carroll et al. |
| 4,953,074 A | 8/1990 | Kametani et al. |
| 4,960,230 A | 10/1990 | Marelli |
| 4,964,847 A | 10/1990 | Prince |
| 4,966,579 A | 10/1990 | Polaschegg |
| 4,967,928 A | 11/1990 | Carter |
| 4,968,295 A | 11/1990 | Neumann |
| 4,975,647 A | 12/1990 | Downer et al. |
| 4,977,590 A | 12/1990 | Milovancevic |
| 4,978,335 A | 12/1990 | Arthur, III |
| 4,991,091 A | 2/1991 | Allen |
| 4,992,926 A | 2/1991 | Janke et al. |
| 4,993,068 A | 2/1991 | Piosenka et al. |
| 4,993,506 A | 2/1991 | Angel |
| 4,998,249 A | 3/1991 | Bennett et al. |
| 5,002,055 A | 3/1991 | Merki et al. |
| 5,003,296 A | 3/1991 | Lee |
| 5,006,699 A | 4/1991 | Felkner et al. |
| 5,007,429 A | 4/1991 | Treatch et al. |
| 5,012,402 A | 4/1991 | Akiyama |
| 5,012,411 A | 4/1991 | Policastro et al. |
| 5,014,875 A | 5/1991 | McLaughlin et al. |
| 5,016,172 A | 5/1991 | Dessertine |
| 5,023,770 A | 6/1991 | Siverling |
| 5,025,374 A | 6/1991 | Roizen et al. |
| 5,036,852 A | 8/1991 | Leishman |
| 5,038,800 A | 8/1991 | Oba |
| 5,041,086 A | 8/1991 | Koenig et al. |
| 5,045,048 A | 9/1991 | Kaleskas et al. |
| 5,047,959 A | 9/1991 | Phillips et al. |
| 5,053,031 A | 10/1991 | Borsanyi |
| 5,053,990 A | 10/1991 | Kreifels et al. |
| 5,055,001 A | 10/1991 | Natwick et al. |
| 5,057,076 A | 10/1991 | Polaschegg |
| 5,061,243 A | 10/1991 | Winchell et al. |
| 5,072,356 A | 12/1991 | Watt et al. |
| 5,072,383 A | 12/1991 | Brimm et al. |
| 5,072,412 A | 12/1991 | Henderson, Jr. et al. |
| 5,078,683 A | 1/1992 | Sancoff et al. |
| 5,084,828 A | 1/1992 | Kaufman et al. |
| 5,087,245 A | 2/1992 | Doan |
| 5,088,904 A | 2/1992 | Okada |
| 5,088,981 A | 2/1992 | Howson et al. |
| 5,088,990 A | 2/1992 | Hivale et al. |
| 5,096,385 A | 3/1992 | Georgi et al. |
| 5,098,377 A | 3/1992 | Borsanyi et al. |
| 5,100,380 A | 3/1992 | Epstein et al. |
| 5,100,394 A | 3/1992 | Dudar et al. |
| 5,103,211 A | 4/1992 | Daoud et al. |
| 5,104,374 A | 4/1992 | Bishko et al. |
| 5,108,131 A | 4/1992 | Nassim |
| 5,108,363 A | 4/1992 | Tuttle et al. |
| 5,108,367 A | 4/1992 | Epstein et al. |
| 5,108,372 A | 4/1992 | Swenson |
| 5,109,487 A | 4/1992 | Ohgomori et al. |
| 5,109,849 A | 5/1992 | Goodman et al. |
| 5,112,319 A | 5/1992 | Lai |
| 5,116,203 A | 5/1992 | Natwick et al. |
| 5,116,312 A | 5/1992 | Blankenship et al. |
| 5,131,092 A | 7/1992 | Sackmann et al. |
| 5,134,574 A | 7/1992 | Beaverstock et al. |
| 5,135,500 A | 8/1992 | Zdeb |
| 5,137,023 A | 8/1992 | Mendelson et al. |
| 5,151,978 A | 9/1992 | Bronikowski et al. |
| 5,152,296 A | 10/1992 | Simons |
| 5,153,416 A | 10/1992 | Neeley |
| 5,153,827 A | 10/1992 | Coutre et al. |
| 5,155,693 A | 10/1992 | Altmayer et al. |
| 5,157,595 A | 10/1992 | Lovrenich |
| 5,158,091 A | 10/1992 | Butterfield et al. |
| 5,159,673 A | 10/1992 | Sackmann et al. |
| 5,160,320 A | 11/1992 | Yum et al. |
| 5,161,211 A | 11/1992 | Taguchi et al. |
| 5,167,235 A | 12/1992 | Seacord et al. |
| 5,169,642 A | 12/1992 | Brinker et al. |
| 5,172,698 A | 12/1992 | Stanko |
| 5,176,004 A | 1/1993 | Gaudet |
| 5,179,569 A | 1/1993 | Sawyer |
| 5,179,700 A | 1/1993 | Aihara et al. |
| 5,181,910 A | 1/1993 | Scanlon |
| 5,190,185 A | 3/1993 | Blechl |
| 5,190,522 A | 3/1993 | Wojcicki et al. |
| 5,191,891 A | 3/1993 | Righter |
| 5,208,762 A | 5/1993 | Charhut et al. |
| 5,208,907 A | 5/1993 | Shelton et al. |
| 5,211,849 A | 5/1993 | Kitaevich et al. |
| 5,213,099 A | 5/1993 | Tripp, Jr. |
| 5,213,232 A | 5/1993 | Kraft et al. |
| 5,213,568 A | 5/1993 | Lattin et al. |
| 5,219,330 A | 6/1993 | Bollish et al. |
| 5,219,331 A | 6/1993 | Vanderveen |
| 5,225,974 A | 7/1993 | Mathews et al. |
| 5,226,425 A | 7/1993 | Righter |
| 5,228,450 A | 7/1993 | Sellers |
| 5,231,990 A | 8/1993 | Gauglitz |
| 5,234,404 A | 8/1993 | Tuttle et al. |
| 5,235,510 A | 8/1993 | Yamada et al. |
| 5,236,416 A | 8/1993 | McDaniel et al. |
| 5,238,001 A | 8/1993 | Gallant et al. |
| 5,240,007 A | 8/1993 | Pytel et al. |
| 5,244,463 A | 9/1993 | Cordner, Jr. et al. |
| 5,245,704 A | 9/1993 | Weber et al. |
| 5,254,096 A | 10/1993 | Rondelet et al. |
| 5,256,156 A | 10/1993 | Kern et al. |
| 5,256,157 A | 10/1993 | Samiotes et al. |
| 5,261,884 A | 11/1993 | Stern et al. |
| 5,262,943 A | 11/1993 | Thibado et al. |
| 5,265,010 A | 11/1993 | Evans-Paganelli et al. |
| 5,265,431 A | 11/1993 | Gaudet et al. |
| 5,267,174 A | 11/1993 | Kaufman et al. |
| 5,271,405 A | 12/1993 | Boyer et al. |
| 5,272,318 A | 12/1993 | Gorman |
| 5,272,321 A | 12/1993 | Otsuka et al. |
| 5,273,517 A | 12/1993 | Barone et al. |
| 5,277,188 A | 1/1994 | Selker |
| 5,283,861 A | 2/1994 | Dangler et al. |
| 5,284,150 A | 2/1994 | Butterfield et al. |
| 5,286,252 A | 2/1994 | Tuttle et al. |
| 5,292,029 A | 3/1994 | Pearson |
| 5,297,257 A | 3/1994 | Struger et al. |
| 5,298,021 A | 3/1994 | Sherer |
| 5,304,126 A | 4/1994 | Epstein et al. |
| 5,307,263 A | 4/1994 | Brown |
| 5,307,372 A | 4/1994 | Sawyer et al. |
| 5,307,463 A | 4/1994 | Hyatt et al. |
| 5,311,908 A | 5/1994 | Barone et al. |
| 5,314,243 A | 5/1994 | McDonald et al. |
| 5,315,505 A | 5/1994 | Pratt et al. |
| 5,317,506 A | 5/1994 | Coutre et al. |
| 5,319,363 A | 6/1994 | Welch et al. |
| 5,319,543 A | 6/1994 | Wilhelm |
| 5,321,618 A | 6/1994 | Gessman |
| 5,321,829 A | 6/1994 | Zifferer |

(56) References Cited

U.S. PATENT DOCUMENTS

| | | | |
|---|---|---|---|
| 5,324,422 | A | 6/1994 | Colleran et al. |
| 5,325,478 | A | 6/1994 | Shelton et al. |
| 5,327,341 | A | 7/1994 | Whalen et al. |
| 5,331,549 | A | 7/1994 | Crawford, Jr. |
| 5,336,245 | A | 8/1994 | Adams et al. |
| 5,337,230 | A | 8/1994 | Baumgartner et al. |
| 5,337,747 | A | 8/1994 | Neftel |
| 5,337,919 | A | 8/1994 | Spaulding et al. |
| 5,338,157 | A | 8/1994 | Blomquist |
| 5,339,421 | A | 8/1994 | Housel, III |
| 5,339,821 | A | 8/1994 | Fujimoto |
| 5,341,291 | A | 8/1994 | Roizen et al. |
| 5,341,412 | A | 8/1994 | Ramot et al. |
| 5,348,008 | A | 9/1994 | Bornn et al. |
| 5,348,539 | A | 9/1994 | Herskowitz |
| 5,349,675 | A | 9/1994 | Fitzgerald et al. |
| 5,356,378 | A | 10/1994 | Doan |
| 5,360,410 | A | 11/1994 | Wacks |
| 5,361,202 | A | 11/1994 | Doue |
| 5,361,758 | A | 11/1994 | Hall et al. |
| 5,366,896 | A | 11/1994 | Margrey et al. |
| 5,366,904 | A | 11/1994 | Qureshi et al. |
| 5,367,555 | A | 11/1994 | Isoyama |
| 5,368,562 | A | 11/1994 | Blomquist et al. |
| 5,370,612 | A | 12/1994 | Maeda et al. |
| 5,371,687 | A | 12/1994 | Holmes, II et al. |
| 5,374,251 | A | 12/1994 | Smith |
| 5,374,813 | A | 12/1994 | Shipp |
| 5,374,965 | A | 12/1994 | Kanno |
| 5,375,604 | A | 12/1994 | Kelly et al. |
| 5,376,070 | A | 12/1994 | Purvis et al. |
| 5,377,864 | A | 1/1995 | Blechl et al. |
| 5,378,231 | A | 1/1995 | Johnson et al. |
| 5,379,214 | A | 1/1995 | Arbuckle et al. |
| 5,389,078 | A | 2/1995 | Zalesky et al. |
| 5,390,238 | A | 2/1995 | Kirk et al. |
| 5,392,951 | A | 2/1995 | Gardner et al. |
| 5,395,320 | A | 3/1995 | Padda et al. |
| 5,395,321 | A | 3/1995 | Kawahara et al. |
| 5,398,336 | A | 3/1995 | Tantry et al. |
| 5,401,059 | A | 3/1995 | Ferrario |
| 5,404,292 | A | 4/1995 | Hendrickson |
| 5,404,384 | A | 4/1995 | Colburn et al. |
| 5,406,473 | A | 4/1995 | Yoshikura et al. |
| 5,412,715 | A | 5/1995 | Volpe |
| 5,415,167 | A | 5/1995 | Wilk |
| 5,416,695 | A | 5/1995 | Stutman et al. |
| 5,417,222 | A | 5/1995 | Dempsey et al. |
| 5,420,977 | A | 5/1995 | Sztipanovits et al. |
| 5,421,343 | A | 6/1995 | Feng |
| 5,423,746 | A | 6/1995 | Burkett et al. |
| 5,429,602 | A | 7/1995 | Hauser |
| 5,431,201 | A | 7/1995 | Torchia et al. |
| 5,431,299 | A | 7/1995 | Brewer et al. |
| 5,431,627 | A | 7/1995 | Pastrone et al. |
| 5,433,736 | A | 7/1995 | Nilsson |
| 5,438,607 | A | 8/1995 | Przygoda, Jr. et al. |
| 5,440,699 | A | 8/1995 | Farrand et al. |
| 5,441,047 | A | 8/1995 | David et al. |
| 5,445,294 | A | 8/1995 | Gardner et al. |
| 5,445,621 | A | 8/1995 | Poli et al. |
| 5,446,868 | A | 8/1995 | Gardea, II et al. |
| 5,453,098 | A | 9/1995 | Botts et al. |
| 5,455,851 | A | 10/1995 | Chaco et al. |
| 5,458,123 | A | 10/1995 | Unger |
| 5,460,294 | A | 10/1995 | Williams |
| 5,460,605 | A | 10/1995 | Tuttle et al. |
| 5,461,665 | A | 10/1995 | Shur et al. |
| 5,462,051 | A | 10/1995 | Oka et al. |
| 5,464,392 | A | 11/1995 | Epstein et al. |
| 5,465,286 | A | 11/1995 | Clare et al. |
| 5,467,773 | A | 11/1995 | Bergelson et al. |
| 5,468,110 | A | 11/1995 | McDonald et al. |
| 5,469,855 | A | 11/1995 | Pompei et al. |
| 5,471,382 | A | 11/1995 | Tallman et al. |
| 5,474,552 | A | 12/1995 | Palti |
| 5,482,043 | A | 1/1996 | Zulauf |
| 5,482,446 | A | 1/1996 | Williamson et al. |
| 5,485,408 | A | 1/1996 | Blomquist |
| 5,490,610 | A | 2/1996 | Pearson |
| 5,494,592 | A | 2/1996 | Latham, Jr. et al. |
| 5,496,265 | A | 3/1996 | Langley et al. |
| 5,496,273 | A | 3/1996 | Pastrone et al. |
| 5,502,944 | A | 4/1996 | Kraft et al. |
| 5,507,412 | A | 4/1996 | Ebert et al. |
| 5,508,912 | A | 4/1996 | Schneiderman |
| 5,509,318 | A | 4/1996 | Gomes |
| 5,509,422 | A | 4/1996 | Fukami |
| 5,513,957 | A | 5/1996 | O'Leary |
| 5,514,088 | A | 5/1996 | Zakko |
| 5,514,095 | A | 5/1996 | Brightbill et al. |
| 5,515,426 | A | 5/1996 | Yacenda et al. |
| 5,520,450 | A | 5/1996 | Colson, Jr. et al. |
| 5,520,637 | A | 5/1996 | Pager et al. |
| 5,522,396 | A | 6/1996 | Langer et al. |
| 5,522,798 | A | 6/1996 | Johnson et al. |
| 5,526,428 | A | 6/1996 | Arnold |
| 5,528,503 | A | 6/1996 | Moore et al. |
| 5,529,063 | A | 6/1996 | Hill |
| 5,531,680 | A | 7/1996 | Dumas et al. |
| 5,531,697 | A | 7/1996 | Olsen et al. |
| 5,531,698 | A | 7/1996 | Olsen |
| 5,533,079 | A | 7/1996 | Colburn et al. |
| 5,533,981 | A | 7/1996 | Mandro et al. |
| 5,534,691 | A | 7/1996 | Holdaway et al. |
| 5,536,084 | A | 7/1996 | Curtis et al. |
| 5,537,313 | A | 7/1996 | Pirelli |
| 5,537,853 | A | 7/1996 | Finburgh et al. |
| 5,542,420 | A | 8/1996 | Goldman et al. |
| 5,544,649 | A | 8/1996 | David et al. |
| 5,544,651 | A | 8/1996 | Wilk |
| 5,544,661 | A | 8/1996 | Davis et al. |
| 5,545,140 | A | 8/1996 | Conero et al. |
| 5,546,580 | A | 8/1996 | Seliger et al. |
| 5,547,470 | A | 8/1996 | Johnson et al. |
| 5,549,117 | A | 8/1996 | Tacklind et al. |
| 5,549,460 | A | 8/1996 | O'Leary |
| 5,553,609 | A | 9/1996 | Chen et al. |
| 5,558,638 | A | 9/1996 | Evers et al. |
| 5,558,640 | A | 9/1996 | Pfeiler et al. |
| 5,560,352 | A | 10/1996 | Heim et al. |
| 5,562,232 | A | 10/1996 | Pearson |
| 5,562,621 | A | 10/1996 | Claude et al. |
| 5,563,347 | A | 10/1996 | Martin et al. |
| 5,564,434 | A | 10/1996 | Halperin et al. |
| 5,564,803 | A | 10/1996 | McDonald et al. |
| 5,568,912 | A | 10/1996 | Minami et al. |
| 5,569,186 | A | 10/1996 | Lord et al. |
| 5,569,187 | A | 10/1996 | Kaiser |
| 5,571,258 | A | 11/1996 | Pearson |
| 5,573,502 | A | 11/1996 | LeCocq et al. |
| 5,573,506 | A | 11/1996 | Vasko |
| 5,575,632 | A | 11/1996 | Morris et al. |
| 5,576,952 | A | 11/1996 | Stutman et al. |
| 5,579,001 | A | 11/1996 | Dempsey et al. |
| 5,579,378 | A | 11/1996 | Arlinghaus, Jr. |
| 5,581,369 | A | 12/1996 | Righter et al. |
| 5,581,687 | A | 12/1996 | Lyle et al. |
| 5,582,593 | A | 12/1996 | Hultman |
| 5,583,758 | A | 12/1996 | Mcilroy et al. |
| 5,588,815 | A | 12/1996 | Zaleski, II |
| 5,589,932 | A | 12/1996 | Garcia-Rubio et al. |
| 5,590,648 | A | 1/1997 | Mitchell et al. |
| 5,591,344 | A | 1/1997 | Kenley et al. |
| 5,593,267 | A | 1/1997 | McDonald et al. |
| 5,594,637 | A | 1/1997 | Eisenberg et al. |
| 5,594,786 | A | 1/1997 | Chaco et al. |
| 5,597,995 | A | 1/1997 | Williams et al. |
| 5,598,536 | A | 1/1997 | Slaughter, III et al. |
| 5,601,445 | A | 2/1997 | Schipper et al. |
| 5,609,575 | A | 3/1997 | Larson et al. |
| 5,609,576 | A | 3/1997 | Voss et al. |
| 5,613,115 | A | 3/1997 | Gihl et al. |
| 5,619,428 | A | 4/1997 | Lee et al. |

(56) References Cited

U.S. PATENT DOCUMENTS

| | | |
|---|---|---|
| 5,619,991 A | 4/1997 | Sloane |
| 5,623,652 A | 4/1997 | Vora et al. |
| 5,623,925 A | 4/1997 | Swenson et al. |
| 5,626,144 A | 5/1997 | Tacklind et al. |
| 5,628,619 A | 5/1997 | Wilson |
| 5,630,710 A | 5/1997 | Tune et al. |
| 5,631,844 A | 5/1997 | Margrey et al. |
| 5,633,910 A | 5/1997 | Cohen |
| D380,260 S | 6/1997 | Hyman |
| 5,634,893 A | 6/1997 | Rishton |
| 5,637,082 A | 6/1997 | Pages et al. |
| 5,637,093 A | 6/1997 | Hyman et al. |
| 5,640,301 A | 6/1997 | Roecher et al. |
| 5,640,953 A | 6/1997 | Bishop et al. |
| 5,641,628 A | 6/1997 | Bianchi |
| 5,643,193 A | 7/1997 | Papillon et al. |
| 5,643,212 A | 7/1997 | Coutre et al. |
| 5,647,853 A | 7/1997 | Feldmann et al. |
| 5,647,854 A | 7/1997 | Olsen et al. |
| 5,651,775 A | 7/1997 | Walker et al. |
| 5,652,566 A | 7/1997 | Lambert |
| 5,658,240 A | 8/1997 | Urdahl et al. |
| 5,658,250 A | 8/1997 | Blomquist et al. |
| 5,661,978 A | 9/1997 | Holmes et al. |
| 5,664,270 A | 9/1997 | Bell et al. |
| 5,666,404 A | 9/1997 | Ciccotelli et al. |
| D385,646 S | 10/1997 | Chan |
| 5,678,562 A | 10/1997 | Sellers |
| 5,678,568 A | 10/1997 | Uchikubo et al. |
| 5,681,285 A | 10/1997 | Ford et al. |
| 5,682,526 A | 10/1997 | Smokoff et al. |
| 5,683,367 A | 11/1997 | Jordan et al. |
| 5,685,844 A | 11/1997 | Marttila |
| 5,687,717 A | 11/1997 | Halpern |
| 5,687,734 A | 11/1997 | Dempsey et al. |
| 5,695,473 A | 12/1997 | Olsen |
| 5,697,951 A | 12/1997 | Harpstead |
| 5,700,998 A | 12/1997 | Palti |
| 5,701,894 A | 12/1997 | Cherry et al. |
| 5,704,351 A | 1/1998 | Mortara et al. |
| 5,704,364 A | 1/1998 | Saltzstein et al. |
| 5,704,366 A | 1/1998 | Tacklind et al. |
| 5,712,798 A | 1/1998 | Langley et al. |
| 5,712,912 A | 1/1998 | Tomko et al. |
| 5,713,485 A | 2/1998 | Liff et al. |
| 5,713,856 A | 2/1998 | Eggers et al. |
| 5,715,823 A | 2/1998 | Wood et al. |
| 5,716,114 A | 2/1998 | Holmes et al. |
| 5,716,194 A | 2/1998 | Butterfield et al. |
| 5,718,562 A | 2/1998 | Lawless et al. |
| 5,719,761 A | 2/1998 | Gatti et al. |
| RE35,743 E | 3/1998 | Pearson |
| 5,724,025 A | 3/1998 | Tavori |
| 5,724,580 A | 3/1998 | Levin et al. |
| 5,732,709 A | 3/1998 | Tacklind et al. |
| 5,733,259 A | 3/1998 | Valcke et al. |
| 5,735,887 A | 4/1998 | Barreras, Sr. et al. |
| 5,737,539 A | 4/1998 | Edelson et al. |
| 5,740,185 A | 4/1998 | Bosse |
| 5,740,800 A | 4/1998 | Hendrickson et al. |
| 5,745,366 A | 4/1998 | Higham et al. |
| 5,745,378 A | 4/1998 | Barker et al. |
| 5,752,917 A | 5/1998 | Fuchs |
| 5,752,976 A | 5/1998 | Duffin et al. |
| 5,755,563 A | 5/1998 | Clegg et al. |
| 5,758,095 A | 5/1998 | Albaum et al. |
| 5,764,923 A | 6/1998 | Tallman et al. |
| 5,766,155 A | 6/1998 | Hyman et al. |
| 5,769,811 A | 6/1998 | Stacey et al. |
| 5,771,657 A | 6/1998 | Lasher et al. |
| 5,772,585 A | 6/1998 | Lavin et al. |
| 5,772,586 A | 6/1998 | Heinonen et al. |
| 5,772,635 A | 6/1998 | Dastur et al. |
| 5,772,637 A | 6/1998 | Heinzmann et al. |
| 5,776,057 A | 7/1998 | Swenson et al. |
| 5,778,345 A | 7/1998 | McCartney |
| 5,778,882 A | 7/1998 | Raymond et al. |
| 5,781,442 A | 7/1998 | Engleson et al. |
| 5,782,805 A | 7/1998 | Meinzer et al. |
| 5,782,878 A | 7/1998 | Morgan et al. |
| 5,785,650 A | 7/1998 | Akasaka et al. |
| 5,788,669 A | 8/1998 | Peterson |
| 5,788,851 A | 8/1998 | Kenley et al. |
| 5,790,409 A | 8/1998 | Fedor et al. |
| 5,791,342 A | 8/1998 | Woodard |
| 5,791,880 A | 8/1998 | Wilson |
| 5,793,861 A | 8/1998 | Haigh |
| 5,793,969 A | 8/1998 | Kamentsky et al. |
| 5,795,317 A | 8/1998 | Brierton et al. |
| 5,795,327 A | 8/1998 | Wilson et al. |
| 5,797,515 A | 8/1998 | Liff et al. |
| 5,800,387 A | 9/1998 | Duffy et al. |
| 5,801,755 A | 9/1998 | Echerer |
| 5,803,906 A | 9/1998 | Pratt et al. |
| 5,805,442 A | 9/1998 | Crater et al. |
| 5,805,454 A | 9/1998 | Valerino et al. |
| 5,805,456 A | 9/1998 | Higham et al. |
| 5,805,505 A | 9/1998 | Zheng et al. |
| 5,807,321 A | 9/1998 | Stoker et al. |
| 5,807,322 A | 9/1998 | Lindsey et al. |
| 5,807,336 A | 9/1998 | Russo et al. |
| 5,810,747 A | 9/1998 | Brudny et al. |
| 5,812,410 A | 9/1998 | Lion et al. |
| 5,814,015 A | 9/1998 | Gargano et al. |
| 5,815,566 A | 9/1998 | Ramot et al. |
| 5,818,528 A | 10/1998 | Roth et al. |
| 5,822,418 A | 10/1998 | Yacenda et al. |
| 5,822,544 A | 10/1998 | Chaco et al. |
| 5,823,949 A | 10/1998 | Goltra |
| 5,826,237 A | 10/1998 | Macrae et al. |
| 5,829,438 A | 11/1998 | Gibbs et al. |
| 5,832,447 A | 11/1998 | Rieker et al. |
| 5,832,448 A | 11/1998 | Brown |
| 5,832,450 A | 11/1998 | Myers et al. |
| 5,833,599 A | 11/1998 | Schrier et al. |
| 5,835,897 A | 11/1998 | Dang |
| 5,836,910 A | 11/1998 | Duffy et al. |
| 5,841,975 A | 11/1998 | Layne et al. |
| 5,842,841 A | 12/1998 | Danby et al. |
| 5,842,976 A | 12/1998 | Williamson |
| 5,845,253 A | 12/1998 | Rensimer et al. |
| 5,848,593 A | 12/1998 | McGrady et al. |
| 5,851,186 A | 12/1998 | Wood et al. |
| 5,852,590 A | 12/1998 | De La Huerga |
| 5,853,387 A | 12/1998 | Clegg et al. |
| 5,855,550 A | 1/1999 | Lai et al. |
| 5,857,967 A | 1/1999 | Frid et al. |
| 5,859,972 A | 1/1999 | Subramaniam et al. |
| 5,865,745 A | 2/1999 | Schmitt et al. |
| 5,865,786 A | 2/1999 | Sibalis et al. |
| 5,867,821 A | 2/1999 | Ballantyne et al. |
| 5,871,465 A | 2/1999 | Vasko |
| 5,876,926 A | 3/1999 | Beecham |
| 5,880,443 A | 3/1999 | McDonald et al. |
| 5,882,338 A | 3/1999 | Gray |
| 5,883,370 A | 3/1999 | Walker et al. |
| 5,883,576 A | 3/1999 | De La Huerga |
| 5,884,273 A | 3/1999 | Sattizahn et al. |
| 5,884,457 A | 3/1999 | Ortiz et al. |
| 5,885,245 A | 3/1999 | Lynch et al. |
| 5,891,035 A | 4/1999 | Wood et al. |
| 5,891,734 A | 4/1999 | Gill et al. |
| 5,893,697 A | 4/1999 | Zimi et al. |
| 5,894,273 A | 4/1999 | Meador et al. |
| 5,895,371 A | 4/1999 | Levitas et al. |
| 5,897,493 A | 4/1999 | Brown |
| 5,897,530 A | 4/1999 | Jackson |
| 5,897,989 A | 4/1999 | Beecham |
| 5,899,665 A | 5/1999 | Makino et al. |
| 5,899,855 A | 5/1999 | Brown |
| 5,901,150 A | 5/1999 | Jhuboo et al. |
| 5,904,668 A | 5/1999 | Hyman et al. |
| 5,905,653 A | 5/1999 | Higham et al. |
| 5,907,291 A | 5/1999 | Chen et al. |

(56) References Cited

U.S. PATENT DOCUMENTS

| | | |
|---|---|---|
| 5,907,493 A | 5/1999 | Boyer et al. |
| 5,908,027 A | 6/1999 | Butterfield et al. |
| 5,910,107 A | 6/1999 | Iliff |
| 5,910,252 A | 6/1999 | Truitt et al. |
| 5,911,132 A | 6/1999 | Sloane |
| 5,911,687 A | 6/1999 | Sato et al. |
| 5,912,818 A | 6/1999 | McGrady et al. |
| 5,913,197 A | 6/1999 | Kameda |
| 5,913,310 A | 6/1999 | Brown |
| 5,915,089 A | 6/1999 | Stevens et al. |
| 5,915,240 A | 6/1999 | Karpf |
| 5,919,154 A | 7/1999 | Toavs et al. |
| 5,921,938 A | 7/1999 | Aoyama et al. |
| 5,923,018 A | 7/1999 | Kameda et al. |
| 5,924,074 A | 7/1999 | Evans |
| 5,924,103 A | 7/1999 | Ahmed et al. |
| 5,927,540 A | 7/1999 | Godlewski |
| 5,931,791 A | 8/1999 | Saltzstein et al. |
| 5,935,060 A | 8/1999 | Iliff |
| 5,935,099 A | 8/1999 | Peterson et al. |
| 5,935,106 A | 8/1999 | Olsen |
| 5,938,413 A | 8/1999 | Makino et al. |
| 5,939,326 A | 8/1999 | Chupp et al. |
| 5,939,699 A | 8/1999 | Perttunen et al. |
| 5,940,306 A | 8/1999 | Gardner et al. |
| 5,940,802 A | 8/1999 | Hildebrand et al. |
| 5,941,829 A | 8/1999 | Saltzstein et al. |
| 5,941,846 A | 8/1999 | Duffy et al. |
| 5,942,986 A | 8/1999 | Shabot et al. |
| 5,943,423 A | 8/1999 | Muftic |
| 5,943,633 A | 8/1999 | Wilson et al. |
| 5,944,659 A | 8/1999 | Flach et al. |
| 5,945,651 A | 8/1999 | Chorosinski et al. |
| 5,946,083 A | 8/1999 | Melendez et al. |
| 5,946,659 A | 8/1999 | Lancelot et al. |
| D414,578 S | 9/1999 | Chen et al. |
| 5,950,006 A | 9/1999 | Crater et al. |
| 5,951,300 A | 9/1999 | Brown |
| 5,951,510 A | 9/1999 | Barak |
| 5,954,640 A | 9/1999 | Szabo |
| 5,954,885 A | 9/1999 | Bollish et al. |
| 5,954,971 A | 9/1999 | Pages et al. |
| 5,956,023 A | 9/1999 | Lyle et al. |
| 5,957,885 A | 9/1999 | Bollish et al. |
| 5,959,529 A | 9/1999 | Kail, IV |
| 5,960,085 A | 9/1999 | de la Huerga |
| 5,960,403 A | 9/1999 | Brown |
| 5,960,991 A | 10/1999 | Ophardt |
| 5,961,446 A | 10/1999 | Beller et al. |
| 5,961,448 A | 10/1999 | Swenson et al. |
| 5,961,487 A | 10/1999 | Davis |
| 5,961,923 A | 10/1999 | Nova et al. |
| 5,963,641 A | 10/1999 | Crandall et al. |
| 5,964,700 A | 10/1999 | Tallman et al. |
| 5,966,304 A | 10/1999 | Cook et al. |
| 5,967,975 A | 10/1999 | Ridgeway |
| 5,970,423 A | 10/1999 | Langley et al. |
| 5,971,593 A | 10/1999 | McGrady |
| 5,971,921 A | 10/1999 | Timbel |
| 5,971,948 A | 10/1999 | Pages et al. |
| 5,974,124 A | 10/1999 | Schlueter, Jr. et al. |
| 5,975,737 A | 11/1999 | Crater et al. |
| 5,980,490 A | 11/1999 | Tsoukalis |
| 5,983,193 A | 11/1999 | Heinonen et al. |
| 5,987,519 A | 11/1999 | Peifer et al. |
| 5,991,731 A | 11/1999 | Colon et al. |
| 5,993,046 A | 11/1999 | McGrady et al. |
| 5,993,420 A | 11/1999 | Hyman et al. |
| 5,995,077 A | 11/1999 | Wilcox et al. |
| 5,995,939 A | 11/1999 | Berman et al. |
| 5,995,965 A | 11/1999 | Experton |
| 5,997,167 A | 12/1999 | Crater et al. |
| 5,997,476 A | 12/1999 | Brown |
| 6,003,006 A | 12/1999 | Colella et al. |
| 6,004,020 A | 12/1999 | Bartur |
| 6,004,276 A | 12/1999 | Wright et al. |
| 6,006,191 A | 12/1999 | DiRienzo |
| 6,006,946 A | 12/1999 | Williams et al. |
| 6,009,333 A | 12/1999 | Chaco |
| 6,010,454 A | 1/2000 | Arieff et al. |
| 6,011,858 A | 1/2000 | Stock et al. |
| 6,011,999 A | 1/2000 | Holmes |
| 6,012,034 A | 1/2000 | Hamparian et al. |
| 6,013,057 A | 1/2000 | Danby et al. |
| 6,014,631 A | 1/2000 | Teagarden et al. |
| 6,016,444 A | 1/2000 | John |
| 6,017,318 A | 1/2000 | Gauthier et al. |
| 6,018,713 A | 1/2000 | Coli et al. |
| 6,019,745 A | 2/2000 | Gray |
| 6,021,392 A | 2/2000 | Lester et al. |
| 6,022,315 A | 2/2000 | Iliff |
| 6,023,522 A | 2/2000 | Draganoff et al. |
| 6,024,539 A | 2/2000 | Blomquist |
| 6,024,699 A | 2/2000 | Surwit et al. |
| 6,027,217 A | 2/2000 | McClure et al. |
| 6,029,138 A | 2/2000 | Khorasani et al. |
| 6,032,119 A | 2/2000 | Brown et al. |
| 6,032,155 A | 2/2000 | de la Huerga |
| 6,033,076 A | 3/2000 | Braeuning et al. |
| 6,039,251 A | 3/2000 | Holowko et al. |
| 6,039,467 A | 3/2000 | Holmes |
| 6,047,259 A | 4/2000 | Campbell et al. |
| 6,048,086 A | 4/2000 | Valerino |
| 6,050,940 A | 4/2000 | Braun et al. |
| 6,055,487 A | 4/2000 | Margery et al. |
| 6,057,758 A | 5/2000 | Dempsey et al. |
| 6,059,736 A | 5/2000 | Tapper |
| 6,061,603 A | 5/2000 | Papadopoulos et al. |
| 6,065,819 A | 5/2000 | Holmes et al. |
| 6,068,153 A | 5/2000 | Young et al. |
| 6,068,156 A | 5/2000 | Liff et al. |
| 6,073,046 A | 6/2000 | Patel et al. |
| 6,074,345 A | 6/2000 | van Oostrom et al. |
| 6,079,621 A | 6/2000 | Vardanyan et al. |
| 6,080,106 A | 6/2000 | Lloyd et al. |
| 6,081,048 A | 6/2000 | Bergmann et al. |
| 6,081,786 A | 6/2000 | Barry et al. |
| 6,082,776 A | 7/2000 | Feinberg |
| 6,083,206 A | 7/2000 | Molko |
| 6,093,146 A | 7/2000 | Filangeri |
| 6,095,985 A | 8/2000 | Raymond et al. |
| 6,096,561 A | 8/2000 | Tayi |
| 6,098,892 A | 8/2000 | Peoples, Jr. |
| 6,101,407 A | 8/2000 | Groezinger |
| 6,101,478 A | 8/2000 | Brown |
| 6,102,856 A | 8/2000 | Groff et al. |
| 6,108,399 A | 8/2000 | Hernandez-Guerra et al. |
| 6,108,588 A | 8/2000 | McGrady |
| 6,109,774 A | 8/2000 | Holmes et al. |
| 6,112,224 A | 8/2000 | Peifer et al. |
| RE36,871 E | 9/2000 | Epstein et al. |
| 6,113,554 A | 9/2000 | Gilcher et al. |
| 6,116,461 A | 9/2000 | Broadfield et al. |
| 6,117,940 A | 9/2000 | Mjalli |
| 6,123,524 A | 9/2000 | Danby et al. |
| 6,125,350 A | 9/2000 | Dirbas |
| 6,129,517 A | 10/2000 | Danby et al. |
| 6,132,371 A | 10/2000 | Dempsey et al. |
| 6,134,504 A | 10/2000 | Douglas et al. |
| 6,135,949 A | 10/2000 | Russo et al. |
| 6,139,177 A | 10/2000 | Venkatraman et al. |
| 6,139,495 A | 10/2000 | De La Huerga |
| 6,141,412 A | 10/2000 | Smith et al. |
| 6,144,922 A | 11/2000 | Douglas et al. |
| 6,145,695 A | 11/2000 | Garrigues |
| 6,146,523 A | 11/2000 | Kenley et al. |
| 6,148,297 A | 11/2000 | Swor et al. |
| 6,149,063 A | 11/2000 | Reynolds et al. |
| 6,151,536 A | 11/2000 | Arnold et al. |
| 6,152,364 A | 11/2000 | Schoonen et al. |
| 6,154,668 A | 11/2000 | Pedersen et al. |
| 6,154,726 A | 11/2000 | Rensimer et al. |
| 6,157,914 A | 12/2000 | Seto et al. |
| 6,158,965 A | 12/2000 | Butterfield et al. |

(56) References Cited

U.S. PATENT DOCUMENTS

| | | | |
|---|---|---|---|
| 6,160,478 A | 12/2000 | Jacobsen et al. |
| 6,161,095 A | 12/2000 | Brown |
| 6,161,141 A | 12/2000 | Dillon |
| 6,163,737 A | 12/2000 | Fedor et al. |
| 6,165,154 A | 12/2000 | Gray et al. |
| 6,168,563 B1 | 1/2001 | Brown |
| 6,170,007 B1 | 1/2001 | Venkatraman et al. |
| 6,170,746 B1 | 1/2001 | Brook et al. |
| 6,171,112 B1 | 1/2001 | Clark et al. |
| 6,171,237 B1 | 1/2001 | Avitall et al. |
| 6,171,264 B1 | 1/2001 | Bader |
| 6,173,198 B1 | 1/2001 | Schulze et al. |
| 6,175,779 B1 | 1/2001 | Barrett |
| 6,175,977 B1 | 1/2001 | Schumacher et al. |
| 6,176,392 B1 | 1/2001 | William et al. |
| 6,182,047 B1 | 1/2001 | Dirbas |
| 6,183,417 B1 | 2/2001 | Geheb et al. |
| 6,186,145 B1 | 2/2001 | Brown |
| 6,192,320 B1 | 2/2001 | Margrey et al. |
| 6,193,480 B1 | 2/2001 | Butterfield |
| 6,195,887 B1 | 3/2001 | Danby et al. |
| 6,198,394 B1 | 3/2001 | Jacobsen et al. |
| 6,200,264 B1 | 3/2001 | Satherley et al. |
| 6,200,289 B1 | 3/2001 | Hochman et al. |
| 6,202,923 B1 | 3/2001 | Boyer et al. |
| 6,203,495 B1 | 3/2001 | Bardy |
| 6,203,528 B1 | 3/2001 | Deckert et al. |
| 6,206,238 B1 | 3/2001 | Ophardt |
| 6,206,829 B1 | 3/2001 | Iliff |
| 6,210,361 B1 | 4/2001 | Kamen et al. |
| 6,213,391 B1 | 4/2001 | Lewis |
| 6,213,738 B1 | 4/2001 | Danby et al. |
| 6,213,972 B1 | 4/2001 | Butterfield et al. |
| 6,219,439 B1 | 4/2001 | Burger |
| 6,219,587 B1 | 4/2001 | Ahlin et al. |
| 6,221,009 B1 | 4/2001 | Doi et al. |
| 6,221,011 B1 | 4/2001 | Bardy |
| 6,221,012 B1 | 4/2001 | Maschke et al. |
| 6,222,619 B1 | 4/2001 | Herron et al. |
| 6,224,549 B1 | 5/2001 | Drongelen |
| 6,225,901 B1 | 5/2001 | Kail, IV |
| 6,226,564 B1 | 5/2001 | Stuart |
| 6,226,745 B1 | 5/2001 | Wiederhold |
| 6,230,142 B1 | 5/2001 | Benigno et al. |
| 6,230,927 B1 | 5/2001 | Schoonen et al. |
| 6,234,997 B1 | 5/2001 | Kamen et al. |
| 6,245,013 B1 | 6/2001 | Minoz et al. |
| 6,246,473 B1 | 6/2001 | Smith, Jr. et al. |
| 6,248,063 B1 | 6/2001 | Barnhill et al. |
| 6,248,065 B1 | 6/2001 | Brown |
| 6,255,951 B1 | 7/2001 | De La Huerga |
| 6,256,643 B1 | 7/2001 | Cork et al. |
| 6,256,967 B1 | 7/2001 | Hebron et al. |
| 6,259,355 B1 | 7/2001 | Chaco et al. |
| 6,259,654 B1 | 7/2001 | De La Huerga |
| 6,260,021 B1 | 7/2001 | Wong et al. |
| 6,266,645 B1 | 7/2001 | Simpson |
| 6,269,340 B1 | 7/2001 | Ford et al. |
| D446,854 S | 8/2001 | Cheney, II et al. |
| 6,270,455 B1 | 8/2001 | Brown |
| 6,270,457 B1 | 8/2001 | Bardy |
| 6,272,394 B1 | 8/2001 | Lipps |
| 6,272,505 B1 | 8/2001 | De La Huerga |
| 6,277,072 B1 | 8/2001 | Bardy |
| 6,278,999 B1 | 8/2001 | Knapp |
| 6,283,322 B1 | 9/2001 | Liff et al. |
| 6,283,944 B1 | 9/2001 | McMullen et al. |
| 6,290,646 B1 | 9/2001 | Cosentino et al. |
| 6,290,650 B1 | 9/2001 | Butterfield et al. |
| 6,294,999 B1 | 9/2001 | Yarin et al. |
| 6,295,506 B1 | 9/2001 | Heinonen |
| 6,304,788 B1 | 10/2001 | Eady et al. |
| 6,306,088 B1 | 10/2001 | Krausman et al. |
| 6,307,956 B1 | 10/2001 | Black |
| 6,308,171 B1 | 10/2001 | De La Huerga |
| 6,311,163 B1 | 10/2001 | Sheehan et al. |
| 6,312,227 B1 | 11/2001 | Davis |
| 6,312,378 B1 | 11/2001 | Bardy |
| 6,314,384 B1 | 11/2001 | Goetz |
| 6,317,719 B1 | 11/2001 | Schrier et al. |
| 6,319,200 B1 | 11/2001 | Lai et al. |
| 6,321,203 B1 | 11/2001 | Kameda |
| 6,322,502 B1 | 11/2001 | Schoenberg et al. |
| 6,322,504 B1 | 11/2001 | Kirshner |
| 6,322,515 B1 | 11/2001 | Goor et al. |
| 6,330,491 B1 | 12/2001 | Lion |
| 6,332,090 B1 | 12/2001 | DeFrank et al. |
| RE37,531 E | 1/2002 | Chaco et al. |
| 6,337,631 B1 | 1/2002 | Pai et al. |
| 6,338,007 B1 | 1/2002 | Broadfield et al. |
| 6,339,732 B1 | 1/2002 | Phoon et al. |
| 6,345,260 B1 | 2/2002 | Cummings, Jr. et al. |
| 6,346,886 B1 | 2/2002 | De La Huerga |
| 6,347,553 B1 | 2/2002 | Morris et al. |
| 6,352,200 B1 | 3/2002 | Schoonen et al. |
| 6,353,817 B1 | 3/2002 | Jacobs et al. |
| 6,358,225 B1 | 3/2002 | Butterfield |
| 6,358,237 B1 | 3/2002 | Paukovits et al. |
| 6,361,263 B1 | 3/2002 | Dewey et al. |
| 6,362,591 B1 | 3/2002 | Moberg |
| 6,363,282 B1 | 3/2002 | Nichols et al. |
| 6,363,290 B1 | 3/2002 | Lyle et al. |
| 6,364,834 B1 | 4/2002 | Reuss et al. |
| 6,368,273 B1 | 4/2002 | Brown |
| 6,370,841 B1 | 4/2002 | Chudy et al. |
| 6,381,577 B1 | 4/2002 | Brown |
| 6,385,505 B1 | 5/2002 | Lipps |
| 6,393,369 B1 | 5/2002 | Carr |
| 6,397,190 B1 | 5/2002 | Goetz |
| 6,401,072 B1 | 6/2002 | Haudenschild et al. |
| 6,402,702 B1 | 6/2002 | Gilcher et al. |
| 6,406,426 B1 | 6/2002 | Reuss et al. |
| 6,407,335 B1 | 6/2002 | Franklin-Lees et al. |
| 6,408,330 B1 | 6/2002 | DeLaHuerga |
| 6,416,471 B1 | 7/2002 | Kumar et al. |
| 6,421,650 B1 | 7/2002 | Goetz et al. |
| 6,424,996 B1 | 7/2002 | Killcommons et al. |
| 6,427,088 B1 | 7/2002 | Bowman, IV et al. |
| 6,434,531 B1 | 8/2002 | Lancelot et al. |
| 6,434,569 B1 | 8/2002 | Tomlinson et al. |
| 6,438,451 B1 | 8/2002 | Lion |
| RE37,829 E | 9/2002 | Charhut et al. |
| 6,449,927 B2 | 9/2002 | Hebron et al. |
| 6,450,956 B1 | 9/2002 | Rappaport et al. |
| 6,458,102 B1 | 10/2002 | Mann et al. |
| 6,461,037 B1 | 10/2002 | O'Leary |
| 6,463,310 B1 | 10/2002 | Swedlow et al. |
| 6,468,242 B1 | 10/2002 | Wilson et al. |
| 6,470,234 B1 | 10/2002 | McGrady |
| 6,471,089 B2 | 10/2002 | Liff et al. |
| 6,471,645 B1 | 10/2002 | Warkentin et al. |
| 6,471,646 B1 | 10/2002 | Thede |
| 6,475,146 B1 | 11/2002 | Frelburger et al. |
| 6,475,148 B1 | 11/2002 | Jackson et al. |
| 6,475,180 B2 | 11/2002 | Peterson et al. |
| 6,478,737 B2 | 11/2002 | Bardy |
| 6,485,465 B2 | 11/2002 | Moberg et al. |
| 6,494,831 B1 | 12/2002 | Koritzinsky |
| 6,511,138 B1 | 1/2003 | Gardner et al. |
| 6,519,569 B1 | 2/2003 | White et al. |
| 6,537,244 B2 | 3/2003 | Paukovits |
| 6,542,902 B2 | 4/2003 | Dulong et al. |
| 6,542,910 B2 | 4/2003 | Cork et al. |
| 6,544,174 B2 | 4/2003 | West et al. |
| 6,544,228 B1 | 4/2003 | Heitmeier |
| 6,551,243 B2 | 4/2003 | Bocionek et al. |
| 6,551,276 B1 | 4/2003 | Mann et al. |
| 6,554,791 B1 | 4/2003 | Cartledge et al. |
| 6,554,798 B1 | 4/2003 | Mann et al. |
| 6,555,986 B2 | 4/2003 | Moberg |
| 6,558,321 B1 | 5/2003 | Burd et al. |
| 6,561,975 B1 | 5/2003 | Pool et al. |
| 6,562,001 B2 | 5/2003 | Lebel et al. |
| 6,564,104 B2 | 5/2003 | Nelson et al. |

(56) References Cited

U.S. PATENT DOCUMENTS

| | | |
|---|---|---|
| 6,564,105 B2 | 5/2003 | Starkweather et al. |
| 6,564,121 B1 | 5/2003 | Wallace et al. |
| 6,571,128 B2 | 5/2003 | Lebel et al. |
| 6,575,900 B1 | 6/2003 | Zweig et al. |
| 6,577,899 B2 | 6/2003 | Lebel et al. |
| 6,579,232 B2 | 6/2003 | Sakamaki et al. |
| 6,581,069 B1 | 6/2003 | Robinson et al. |
| 6,581,798 B2 | 6/2003 | Liff et al. |
| 6,584,336 B1 | 6/2003 | Ali et al. |
| 6,585,157 B2 | 7/2003 | Brandt et al. |
| 6,585,644 B2 | 7/2003 | Lebel et al. |
| 6,585,675 B1 | 7/2003 | O'Mahony et al. |
| 6,592,551 B1 | 7/2003 | Cobb |
| 6,593,528 B2 | 7/2003 | Franklin-Lees et al. |
| 6,602,469 B1 | 8/2003 | Maus et al. |
| 6,607,485 B2 | 8/2003 | Bardy |
| 6,610,973 B1 | 8/2003 | Davis, III |
| 6,613,009 B1 | 9/2003 | Bainbridge et al. |
| 6,616,633 B1 | 9/2003 | Butterfield et al. |
| 6,635,014 B2 | 10/2003 | Starkweather et al. |
| 6,648,821 B2 | 11/2003 | Lebel et al. |
| 6,659,948 B2 | 12/2003 | Lebel et al. |
| 6,664,893 B1 | 12/2003 | Eveland et al. |
| 6,668,196 B1 | 12/2003 | Villegas et al. |
| 6,669,663 B1 | 12/2003 | Thompson |
| 6,673,314 B1 | 1/2004 | Burbank et al. |
| 6,687,546 B2 | 1/2004 | Lebel et al. |
| 6,689,091 B2 | 2/2004 | Bui et al. |
| 6,694,191 B2 | 2/2004 | Starkweather et al. |
| 6,694,334 B2 | 2/2004 | DuLong et al. |
| 6,711,460 B1 | 3/2004 | Reese |
| 6,731,324 B2 | 5/2004 | Levy |
| 6,733,447 B2 | 5/2004 | Lai et al. |
| 6,735,497 B2 | 5/2004 | Wallace et al. |
| 6,740,075 B2 | 5/2004 | Lebel et al. |
| 6,746,398 B2 | 6/2004 | Hervy et al. |
| 6,758,810 B2 | 7/2004 | Lebel et al. |
| 6,768,425 B2 | 7/2004 | Flaherty et al. |
| 6,771,369 B2 | 8/2004 | Rzasa et al. |
| 6,775,602 B2 | 8/2004 | Gordon, Jr. et al. |
| 6,776,304 B2 | 8/2004 | Liff et al. |
| 6,790,198 B1 | 9/2004 | White et al. |
| 6,804,656 B1 | 10/2004 | Rosenfeld et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,811,707 B2 | 11/2004 | Rovatti et al. |
| 6,813,473 B1 | 11/2004 | Bruker |
| 6,813,519 B2 | 11/2004 | Lebel et al. |
| 6,814,255 B2 | 11/2004 | Liff et al. |
| 6,820,093 B2 | 11/2004 | De La Huerga |
| 6,842,736 B1 | 1/2005 | Brzozowski |
| 6,847,861 B2 | 1/2005 | Lunak et al. |
| 6,854,088 B2 | 2/2005 | Massengale et al. |
| 6,871,211 B2 | 3/2005 | Labounty et al. |
| 6,873,268 B2 | 3/2005 | Lebel et al. |
| 6,877,530 B2 | 4/2005 | Osborne et al. |
| 6,880,034 B2 | 4/2005 | Manke et al. |
| 6,885,288 B2 | 4/2005 | Pincus |
| 6,887,201 B2 | 5/2005 | Bardy |
| 6,892,941 B2 | 5/2005 | Rosenblum |
| 6,912,549 B2 | 6/2005 | Rotter et al. |
| 6,913,590 B2 | 7/2005 | Sorenson et al. |
| 6,915,265 B1 | 7/2005 | Johnson |
| 6,915,823 B2 | 7/2005 | Osborne et al. |
| 6,928,452 B2 | 8/2005 | De La Huerga |
| 6,950,708 B2 | 9/2005 | Bowman, IV et al. |
| 6,958,705 B2 | 10/2005 | Lebel et al. |
| 6,974,437 B2 | 12/2005 | Lebel et al. |
| 6,975,924 B2 | 12/2005 | Kircher et al. |
| 6,976,628 B2 | 12/2005 | Krupa |
| 6,979,306 B2 | 12/2005 | Moll |
| 6,980,958 B1 | 12/2005 | Surwit et al. |
| 6,981,644 B2 | 1/2006 | Cheong et al. |
| 6,985,870 B2 | 1/2006 | Martucci et al. |
| 6,991,002 B2 | 1/2006 | Osborne et al. |
| 6,995,664 B1 | 2/2006 | Darling |
| 7,006,893 B2 | 2/2006 | Hart et al. |
| 7,015,806 B2 | 3/2006 | Naidoo et al. |
| 7,017,622 B2 | 3/2006 | Osborne et al. |
| 7,017,623 B2 | 3/2006 | Tribble et al. |
| 7,028,723 B1 | 4/2006 | Alouani et al. |
| 7,096,212 B2 | 8/2006 | Tribble et al. |
| 7,117,902 B2 | 10/2006 | Osborne |
| 7,151,982 B2 | 12/2006 | Liff et al. |
| 7,194,336 B2 | 3/2007 | DiGianfilippo et al. |
| 7,209,891 B1 | 4/2007 | Addy et al. |
| 7,240,699 B2 | 7/2007 | Osborne et al. |
| 7,255,680 B1 | 8/2007 | Gharib |
| 7,277,579 B2 | 10/2007 | Huang |
| 7,277,757 B2 | 10/2007 | Casavant et al. |
| 7,317,967 B2 | 1/2008 | DiGianfilippo et al. |
| 7,321,861 B1 | 1/2008 | Oon |
| 7,343,224 B2 | 3/2008 | DiGianfilippo et al. |
| 7,403,901 B1 | 7/2008 | Carley et al. |
| 7,427,002 B2 | 9/2008 | Liff et al. |
| 7,493,263 B2 | 2/2009 | Helmus et al. |
| 7,499,581 B2 | 3/2009 | Tribble et al. |
| 7,509,280 B1 | 3/2009 | Haudenschild |
| 7,555,557 B2 | 6/2009 | Bradley et al. |
| 7,561,312 B1 | 7/2009 | Proudfoot et al. |
| 7,581,953 B2 | 9/2009 | Lehmann et al. |
| 7,599,516 B2 | 10/2009 | Limer et al. |
| 7,610,115 B2 | 10/2009 | Rob et al. |
| 7,630,908 B1 | 12/2009 | Amrien et al. |
| 7,636,718 B1 | 12/2009 | Steen et al. |
| 7,672,859 B1 | 3/2010 | Louie et al. |
| 7,698,019 B2 | 4/2010 | Moncrief et al. |
| 7,698,154 B2 | 4/2010 | Marchosky |
| 7,734,478 B2 | 6/2010 | Goodall et al. |
| 7,753,085 B2 | 7/2010 | Tribble et al. |
| 7,769,601 B1 | 8/2010 | Bleser et al. |
| 7,783,383 B2 | 8/2010 | Eliuk et al. |
| D624,225 S | 9/2010 | Federico et al. |
| 7,801,642 B2 | 9/2010 | Ansari et al. |
| 7,847,970 B1 | 12/2010 | McGrady |
| 7,853,621 B2 | 12/2010 | Guo |
| 7,904,822 B2 | 3/2011 | Monteleone et al. |
| 7,931,859 B2 | 4/2011 | Mlodzinski et al. |
| 7,937,290 B2 | 5/2011 | Bahir |
| 7,986,369 B1 | 7/2011 | Burns |
| 7,991,507 B2 | 8/2011 | Liff et al. |
| 8,046,242 B1 * | 10/2011 | daCosta ............ G06F 19/3456 705/2 |
| 8,170,271 B2 | 5/2012 | Chen |
| 8,191,339 B2 | 6/2012 | Tribble et al. |
| 8,215,557 B1 | 7/2012 | Reno et al. |
| 8,220,503 B2 | 7/2012 | Tribble et al. |
| 8,225,824 B2 | 7/2012 | Eliuk et al. |
| D667,961 S | 9/2012 | Marmier |
| 8,267,129 B2 | 9/2012 | Doherty et al. |
| 8,271,138 B2 | 9/2012 | Eliuk et al. |
| 8,280,549 B2 | 10/2012 | Liff et al. |
| 8,284,305 B2 | 10/2012 | Newcomb et al. |
| 8,374,887 B1 | 2/2013 | Alexander |
| 8,386,070 B2 | 2/2013 | Eliuk et al. |
| 8,548,824 B1 | 10/2013 | daCosta |
| 8,554,579 B2 | 10/2013 | Tribble et al. |
| D693,480 S | 11/2013 | Spiess et al. |
| 8,595,206 B1 | 11/2013 | Ansari |
| 8,666,541 B1 | 3/2014 | Ansari et al. |
| 8,678,047 B2 | 3/2014 | Tribble et al. |
| D715,958 S | 10/2014 | Bossart et al. |
| 9,053,218 B2 | 6/2015 | Osborne et al. |
| D733,480 S | 7/2015 | Shao |
| D738,152 S | 9/2015 | Grasselli et al. |
| D753,428 S | 4/2016 | Shao |
| 9,362,969 B1 | 6/2016 | Burgess et al. |
| 9,382,021 B2 | 7/2016 | Tribble et al. |
| 9,662,273 B2 | 5/2017 | Ranalletta et al. |
| 9,930,297 B2 | 3/2018 | Alexander et al. |
| 9,956,145 B2 | 5/2018 | Thompson et al. |
| 2001/0001237 A1 | 5/2001 | Stroda et al. |
| 2001/0003177 A1 | 6/2001 | Schena et al. |

(56) References Cited

U.S. PATENT DOCUMENTS

| | | |
|---|---|---|
| 2001/0007053 A1 | 7/2001 | Bardy |
| 2001/0007932 A1 | 7/2001 | Kamen et al. |
| 2001/0011153 A1 | 8/2001 | Bardy |
| 2001/0016699 A1 | 8/2001 | Burbank et al. |
| 2001/0017817 A1 | 8/2001 | De La Huerga |
| 2001/0021801 A1 | 9/2001 | Bardy |
| 2001/0025138 A1 | 9/2001 | Bardy |
| 2001/0025156 A1 | 9/2001 | Bui et al. |
| 2001/0027634 A1 | 10/2001 | Hebron et al. |
| 2001/0028308 A1 | 10/2001 | De La Huerga |
| 2001/0030234 A1 | 10/2001 | Wiklof |
| 2001/0031944 A1 | 10/2001 | Peterson et al. |
| 2001/0032101 A1 | 10/2001 | Statius Muller |
| 2001/0034502 A1 | 10/2001 | Moberg et al. |
| 2001/0034614 A1 | 10/2001 | Fletcher-Haynes et al. |
| 2001/0034616 A1 | 10/2001 | Giannini |
| 2001/0037057 A1 | 11/2001 | Bardy |
| 2001/0037083 A1 | 11/2001 | Hartlaub et al. |
| 2001/0037217 A1 | 11/2001 | Abensour et al. |
| 2001/0037220 A1 | 11/2001 | Merry et al. |
| 2001/0041920 A1 | 11/2001 | Starkweather et al. |
| 2001/0044588 A1 | 11/2001 | Mault |
| 2001/0044731 A1 | 11/2001 | Coffman et al. |
| 2001/0047125 A1 | 11/2001 | Quy |
| 2001/0051764 A1 | 12/2001 | Bardy |
| 2001/0053885 A1 | 12/2001 | Gielen et al. |
| 2002/0002326 A1 | 1/2002 | Causey, III et al. |
| 2002/0002473 A1 | 1/2002 | Schrier et al. |
| 2002/0004645 A1 | 1/2002 | Carlisle et al. |
| 2002/0007285 A1 | 1/2002 | Rappaport |
| 2002/0010568 A1 | 1/2002 | Rubbert et al. |
| 2002/0010679 A1 | 1/2002 | Felsher |
| 2002/0013612 A1 | 1/2002 | Whitehurst |
| 2002/0016567 A1 | 2/2002 | Hochman et al. |
| 2002/0016568 A1 | 2/2002 | Lebel et al. |
| 2002/0016719 A1 | 2/2002 | Nemeth et al. |
| 2002/0016722 A1 | 2/2002 | Kameda |
| 2002/0019606 A1 | 2/2002 | Lebel et al. |
| 2002/0019748 A1 | 2/2002 | Brown |
| 2002/0022776 A1 | 2/2002 | Bardy |
| 2002/0025796 A1 | 2/2002 | Taylor et al. |
| 2002/0026104 A1 | 2/2002 | Bardy |
| 2002/0029157 A1 | 3/2002 | Marchosky |
| 2002/0029776 A1 | 3/2002 | Blomquist |
| 2002/0032582 A1 | 3/2002 | Feeney et al. |
| 2002/0032602 A1 | 3/2002 | Lanzillo, Jr. et al. |
| 2002/0038392 A1 | 3/2002 | De La Huerga |
| 2002/0040208 A1 | 4/2002 | Flaherty et al. |
| 2002/0044043 A1 | 4/2002 | Chaco et al. |
| 2002/0046062 A1 | 4/2002 | Kameda |
| 2002/0046185 A1 | 4/2002 | Villart et al. |
| 2002/0046346 A1 | 4/2002 | Evans |
| 2002/0052539 A1 | 5/2002 | Haller et al. |
| 2002/0052542 A1 | 5/2002 | Bardy |
| 2002/0052574 A1 | 5/2002 | Hochman et al. |
| 2002/0062227 A1 | 5/2002 | Yuyama |
| 2002/0062229 A1 | 5/2002 | Alban et al. |
| 2002/0065540 A1 | 5/2002 | Lebel et al. |
| 2002/0065686 A1 | 5/2002 | Monteleone et al. |
| 2002/0067273 A1 | 6/2002 | Jaques et al. |
| 2002/0072733 A1 | 6/2002 | Flaherty |
| 2002/0073250 A1 | 6/2002 | Ommering |
| 2002/0077852 A1 | 6/2002 | Ford et al. |
| 2002/0077865 A1 | 6/2002 | Sullivan |
| 2002/0082480 A1 | 6/2002 | Riff et al. |
| 2002/0082865 A1 | 6/2002 | Bianco et al. |
| 2002/0082868 A1 | 6/2002 | Pories et al. |
| 2002/0084904 A1 | 7/2002 | De La Huerga |
| 2002/0087120 A1 | 7/2002 | Rogers et al. |
| 2002/0091309 A1 | 7/2002 | Auer |
| 2002/0099283 A1 | 7/2002 | Christ et al. |
| 2002/0099301 A1 | 7/2002 | Bardy |
| 2002/0100762 A1 | 8/2002 | Liff et al. |
| 2002/0107476 A1 | 8/2002 | Mann et al. |
| 2002/0107707 A1 | 8/2002 | Naparstek et al. |
| 2002/0116226 A1 | 8/2002 | Auer et al. |
| 2002/0116509 A1 | 8/2002 | De La Huerga |
| 2002/0128606 A1 | 9/2002 | Cowan et al. |
| 2002/0128871 A1 | 9/2002 | Adamson et al. |
| 2002/0128880 A1 | 9/2002 | Kunikiyo |
| 2002/0133377 A1 | 9/2002 | Brown |
| 2002/0140675 A1 | 10/2002 | Ali et al. |
| 2002/0143254 A1 | 10/2002 | Maruyama |
| 2002/0156462 A1 | 10/2002 | Stultz |
| 2002/0158128 A1 | 10/2002 | Ashiuro |
| 2002/0165491 A1 | 11/2002 | Reilly |
| 2002/0169636 A1 | 11/2002 | Eggers et al. |
| 2002/0173875 A1 | 11/2002 | Wallace et al. |
| 2002/0188467 A1 | 12/2002 | Eke |
| 2002/0198473 A1 | 12/2002 | Kumar et al. |
| 2002/0198513 A1 | 12/2002 | Lebel et al. |
| 2002/0198624 A1 | 12/2002 | Greenwald |
| 2003/0006878 A1 | 1/2003 | Chung |
| 2003/0023177 A1 | 1/2003 | Bardy |
| 2003/0033532 A1 | 2/2003 | Marks |
| 2003/0036783 A1 | 2/2003 | Bauhahn et al. |
| 2003/0046114 A1 | 3/2003 | Davies et al. |
| 2003/0046280 A1 | 3/2003 | Rotter et al. |
| 2003/0046439 A1 | 3/2003 | Manke et al. |
| 2003/0050621 A1 | 3/2003 | Lebel et al. |
| 2003/0050731 A1 | 3/2003 | Rosenblum |
| 2003/0052787 A1 | 3/2003 | Zerhusen |
| 2003/0060753 A1 | 3/2003 | Starkweather et al. |
| 2003/0060754 A1 | 3/2003 | Reilly |
| 2003/0060765 A1 | 3/2003 | Campbell et al. |
| 2003/0060768 A1 | 3/2003 | Kiyatake |
| 2003/0065287 A1 | 4/2003 | Spohn et al. |
| 2003/0076736 A1 | 4/2003 | Buker et al. |
| 2003/0078534 A1 | 4/2003 | Hochman et al. |
| 2003/0079746 A1 | 5/2003 | Hickle |
| 2003/0083901 A1 | 5/2003 | Bosch et al. |
| 2003/0088238 A1 | 5/2003 | Poulsen et al. |
| 2003/0097092 A1 | 5/2003 | Flaherty |
| 2003/0114836 A1 | 6/2003 | Estes et al. |
| 2003/0117580 A1 | 6/2003 | Franz et al. |
| 2003/0125609 A1 | 7/2003 | Becker |
| 2003/0125611 A1 | 7/2003 | Bardy |
| 2003/0139701 A1 | 7/2003 | White et al. |
| 2003/0144878 A1 | 7/2003 | Wilkes et al. |
| 2003/0149599 A1 | 8/2003 | Goodall et al. |
| 2003/0154108 A1 | 8/2003 | Fletcher-Haynes et al. |
| 2003/0158508 A1 | 8/2003 | DiGianfilippo |
| 2003/0160683 A1 | 8/2003 | Blomquist |
| 2003/0163088 A1 | 8/2003 | Blomquist |
| 2003/0163223 A1 | 8/2003 | Blomquist |
| 2003/0163789 A1 | 8/2003 | Blomquist |
| 2003/0167035 A1 | 9/2003 | Flaherty et al. |
| 2003/0176933 A1 | 9/2003 | Lebel et al. |
| 2003/0179287 A1 | 9/2003 | Kozic et al. |
| 2003/0181851 A1 | 9/2003 | Mann et al. |
| 2003/0182164 A1 | 9/2003 | Blomquist |
| 2003/0195397 A1 | 10/2003 | Bardy |
| 2003/0200117 A1 | 10/2003 | Manetta et al. |
| 2003/0201697 A1 | 10/2003 | Richardson |
| 2003/0212379 A1 | 11/2003 | Bylund et al. |
| 2003/0225596 A1 | 12/2003 | Richardson et al. |
| 2003/0225728 A1 | 12/2003 | Moura |
| 2003/0231803 A1 | 12/2003 | Huang |
| 2004/0002874 A1 | 1/2004 | Shaffer et al. |
| 2004/0017475 A1 | 1/2004 | Akers et al. |
| 2004/0019607 A1 | 1/2004 | Moubayed et al. |
| 2004/0115132 A1 | 1/2004 | Brown |
| 2004/0039260 A1 | 2/2004 | Bardy |
| 2004/0039264 A1 | 2/2004 | Bardy |
| 2004/0051368 A1 | 3/2004 | Caputo et al. |
| 2004/0055611 A1 | 3/2004 | Penny et al. |
| 2004/0064343 A1 | 4/2004 | Korpman et al. |
| 2004/0073329 A1 | 4/2004 | Engleson |
| 2004/0088187 A1 | 5/2004 | Chudy et al. |
| 2004/0088374 A1 | 5/2004 | Webb et al. |
| 2004/0111293 A1 | 6/2004 | Firanek et al. |
| 2004/0116862 A1 | 6/2004 | Ray |
| 2004/0117215 A1 | 6/2004 | Marchosky |
| 2004/0128162 A1 | 7/2004 | Schlotterbeck et al. |

(56) References Cited

U.S. PATENT DOCUMENTS

| | | |
|---|---|---|
| 2004/0129616 A1 | 7/2004 | Mori et al. |
| 2004/0148195 A1 | 7/2004 | Kalies |
| 2004/0158193 A1 | 8/2004 | Bui et al. |
| 2004/0172283 A1 | 9/2004 | Vanderveen et al. |
| 2004/0172289 A1 | 9/2004 | Kozic et al. |
| 2004/0172300 A1 | 9/2004 | Mihai et al. |
| 2004/0193328 A1 | 9/2004 | Zaitsu et al. |
| 2004/0193453 A1 | 9/2004 | Butterfield et al. |
| 2004/0204673 A1 | 10/2004 | Flaherty |
| 2004/0204954 A1 | 10/2004 | Lacko |
| 2004/0215490 A1 | 10/2004 | Duchon et al. |
| 2004/0220829 A1 | 11/2004 | Baharav et al. |
| 2004/0225528 A1 | 11/2004 | Brock |
| 2004/0235446 A1 | 11/2004 | Flaherty et al. |
| 2004/0236630 A1 | 11/2004 | Kost et al. |
| 2004/0248295 A1 | 12/2004 | Katsuhiko et al. |
| 2004/0260233 A1 | 12/2004 | Garibotto et al. |
| 2004/0260577 A1 | 12/2004 | Dahlin et al. |
| 2005/0001033 A1 | 1/2005 | Cheong et al. |
| 2005/0017864 A1 | 1/2005 | Tsoukalis |
| 2005/0033124 A1 | 2/2005 | Kelly et al. |
| 2005/0033773 A1 | 2/2005 | Roberge et al. |
| 2005/0038680 A1 | 2/2005 | McMahon |
| 2005/0039742 A1 | 2/2005 | Hickle |
| 2005/0043665 A1 | 2/2005 | Vinci et al. |
| 2005/0045548 A1 | 3/2005 | Brugger et al. |
| 2005/0054923 A1 | 3/2005 | Pan |
| 2005/0060372 A1 | 3/2005 | DeBettencourt et al. |
| 2005/0080651 A1 | 4/2005 | Morrison et al. |
| 2005/0187794 A1 | 8/2005 | Kimak |
| 2005/0209737 A1 | 9/2005 | Kircher |
| 2005/0228238 A1 | 10/2005 | Monitzer |
| 2005/0279419 A1 | 12/2005 | Tribble et al. |
| 2006/0084042 A1 | 4/2006 | Weaver et al. |
| 2006/0124656 A1 | 6/2006 | Popovic, Jr. |
| 2006/0136095 A1 | 6/2006 | Rob et al. |
| 2006/0149416 A1 | 7/2006 | Mohapatra et al. |
| 2006/0161294 A1 | 7/2006 | DiMaggio |
| 2006/0173714 A1 | 8/2006 | Grotzinger, Jr. |
| 2006/0178578 A1 | 8/2006 | Tribble et al. |
| 2006/0181391 A1 | 8/2006 | McNeill et al. |
| 2006/0235881 A1 | 10/2006 | Masarie et al. |
| 2007/0043767 A1 | 2/2007 | Osborne et al. |
| 2007/0047980 A1 | 3/2007 | Limer et al. |
| 2007/0088568 A1 | 4/2007 | Goodall et al. |
| 2007/0110305 A1 | 5/2007 | Corcoran et al. |
| 2007/0125442 A1 | 6/2007 | Tribble et al. |
| 2007/0156456 A1* | 7/2007 | McGillin ............ A61B 5/0022 705/2 |
| 2007/0168228 A1 | 7/2007 | Lawless |
| 2007/0179806 A1 | 8/2007 | Knowlton et al. |
| 2007/0189597 A1 | 8/2007 | Limer et al. |
| 2007/0192139 A1 | 8/2007 | Cookson et al. |
| 2007/0216998 A1 | 9/2007 | Sander |
| 2007/0239482 A1 | 10/2007 | Finn et al. |
| 2007/0239997 A1 | 10/2007 | Qu et al. |
| 2008/0046292 A1 | 2/2008 | Myers et al. |
| 2008/0056556 A1 | 3/2008 | Eller et al. |
| 2008/0059228 A1 | 3/2008 | Bossi et al. |
| 2008/0091467 A1 | 4/2008 | Moncrief et al. |
| 2008/0119958 A1 | 5/2008 | Bear et al. |
| 2008/0125897 A1 | 5/2008 | DiGianfilippo et al. |
| 2008/0147554 A1 | 6/2008 | Stevens et al. |
| 2008/0195246 A1 | 8/2008 | Tribble et al. |
| 2008/0306926 A1 | 12/2008 | Friedlander et al. |
| 2009/0024414 A1 | 1/2009 | Mansour et al. |
| 2009/0080408 A1 | 3/2009 | Natoli et al. |
| 2009/0097368 A1 | 4/2009 | Vlutters et al. |
| 2009/0138340 A1 | 5/2009 | Borr et al. |
| 2009/0188937 A1 | 7/2009 | Kim |
| 2009/0205877 A1 | 8/2009 | Claypool |
| 2009/0210252 A1 | 8/2009 | Silver |
| 2009/0235194 A1 | 9/2009 | Arndt et al. |
| 2009/0258331 A1 | 10/2009 | Do et al. |
| 2009/0285762 A1 | 11/2009 | Flower |
| 2009/0313044 A1 | 12/2009 | Haque et al. |
| 2009/0323170 A1 | 12/2009 | Lin |
| 2009/0324032 A1 | 12/2009 | Chen |
| 2010/0017031 A1 | 1/2010 | Rob et al. |
| 2010/0030574 A1* | 2/2010 | Coe ............ G06F 19/325 705/2 |
| 2010/0091281 A1 | 4/2010 | Suzuki |
| 2010/0094653 A1* | 4/2010 | Tribble ............ G06F 19/326 705/3 |
| 2010/0128165 A1 | 5/2010 | Newcomb et al. |
| 2010/0131883 A1* | 5/2010 | Linthicum ............ G06F 19/00 715/771 |
| 2010/0157293 A9 | 6/2010 | Rzasa et al. |
| 2010/0185456 A1 | 7/2010 | Kansal |
| 2010/0241270 A1 | 9/2010 | Eliuk et al. |
| 2011/0119088 A1 | 5/2011 | Gunn |
| 2011/0191121 A1 | 8/2011 | Fioravanti |
| 2011/0202366 A1 | 8/2011 | Akers et al. |
| 2011/0208350 A1 | 8/2011 | Eliuk et al. |
| 2011/0267465 A1 | 11/2011 | Alexander et al. |
| 2012/0097290 A1 | 4/2012 | Mikhaeil |
| 2012/0179492 A1* | 7/2012 | Rhodes ............ G06Q 50/22 705/3 |
| 2012/0200596 A1 | 8/2012 | Gotou et al. |
| 2012/0211565 A1 | 8/2012 | Colavito et al. |
| 2012/0303388 A1 | 11/2012 | Vishnubhatla et al. |
| 2013/0079581 A1 | 3/2013 | Agamaite et al. |
| 2013/0090947 A1 | 4/2013 | Nockley |
| 2013/0197445 A1 | 8/2013 | Schabbach et al. |
| 2013/0262138 A1 | 10/2013 | Jaskela et al. |
| 2013/0279774 A1 | 10/2013 | Helgason et al. |
| 2013/0304510 A1 | 11/2013 | Chan et al. |
| 2013/0314535 A1 | 11/2013 | Yuyama et al. |
| 2013/0342676 A1 | 12/2013 | Amano |
| 2014/0022569 A1 | 1/2014 | Matsui et al. |
| 2014/0156064 A1 | 6/2014 | Crawford et al. |
| 2014/0156294 A1 | 6/2014 | Tribble et al. |
| 2014/0214436 A1 | 7/2014 | Utech et al. |
| 2014/0350950 A1 | 11/2014 | Jaskela et al. |
| 2015/0205932 A1 | 7/2015 | Tribble |
| 2015/0227719 A1 | 8/2015 | Ranalletta |
| 2015/0272320 A1 | 10/2015 | Ranalletta et al. |
| 2015/0278477 A1 | 10/2015 | Tribble |
| 2015/0286799 A1 | 10/2015 | Padmani |
| 2016/0072985 A1 | 3/2016 | Sandmann et al. |
| 2016/0092638 A1 | 3/2016 | Padmani |
| 2016/0092639 A1 | 3/2016 | Padmani |
| 2016/0140315 A1 | 5/2016 | Diaz et al. |
| 2016/0210437 A1 | 7/2016 | Padmani et al. |
| 2016/0371462 A1 | 12/2016 | Wallen |
| 2017/0372034 A1 | 12/2017 | Tribble |

FOREIGN PATENT DOCUMENTS

| | | |
|---|---|---|
| CN | 1131076 | 12/2003 |
| EP | 0237588 | 9/1987 |
| EP | 0462466 | 12/1991 |
| EP | 0505627 | 9/1992 |
| EP | 0522527 | 1/1993 |
| EP | 0439355 | 9/1994 |
| EP | 0844581 | 5/1998 |
| EP | 0960627 | 12/1999 |
| EP | 0970655 | 1/2000 |
| EP | 1072994 | 2/2001 |
| EP | 1107158 A1 | 6/2001 |
| EP | 1097671 | 2/2003 |
| GB | 994977 A | 6/1965 |
| GB | 2210713 | 2/1987 |
| GB | 2279784 | 1/1995 |
| GB | 2285135 | 6/1995 |
| GB | 2379037 | 2/2003 |
| JP | 53137644 | 12/1978 |
| JP | 61066950 | 4/1986 |
| JP | 63068133 | 3/1988 |
| JP | 2111375 | 4/1990 |
| JP | 3423055 B2 | 1/1994 |
| JP | 6086813 | 3/1994 |
| JP | 06327636 | 11/1994 |

(56) References Cited

FOREIGN PATENT DOCUMENTS

| | | |
|---|---|---|
| JP | 07204253 A | 8/1995 |
| JP | 104585 | 1/1998 |
| JP | 10014890 | 1/1998 |
| JP | 10079770 | 3/1998 |
| JP | 2000036032 A | 2/2000 |
| JP | 03055131 | 4/2000 |
| JP | 2002011095 | 1/2002 |
| JP | 2002092181 A | 3/2002 |
| JP | 2002520718 | 7/2002 |
| JP | 2003022322 | 1/2003 |
| JP | 2004078970 | 3/2004 |
| JP | 2004326436 | 11/2004 |
| JP | 2004340770 A | 12/2004 |
| JP | 2005252710 A | 9/2005 |
| JP | 2006033291 A | 2/2006 |
| JP | 2006334062 | 12/2006 |
| JP | 2007198934 A | 8/2007 |
| JP | 2008139201 A | 6/2008 |
| JP | 4276654 B2 | 6/2009 |
| JP | 2009265827 A | 11/2009 |
| JP | 2010056619 A | 3/2010 |
| JP | 2010170504 A | 8/2010 |
| JP | 2010533927 A | 10/2010 |
| JP | 2011151430 A | 8/2011 |
| JP | 2012078265 | 4/2012 |
| JP | 5342197 B2 | 11/2013 |
| JP | 5747150 B2 | 7/2015 |
| JP | 6086813 | 3/2017 |
| KR | 20000036642 | 7/2000 |
| KR | 1020000036642 | 7/2000 |
| KR | 20010094703 A | 11/2001 |
| KR | 1020010094703 | 11/2001 |
| KR | 20050054379 | 12/2003 |
| KR | 20110115927 A | 10/2011 |
| KR | 1020110115927 | 10/2011 |
| KR | 20130001500 | 1/2013 |
| WO | WO8400493 | 2/1984 |
| WO | WO9524010 A1 | 9/1995 |
| WO | WO9634291 A1 | 10/1996 |
| WO | WO9741525 | 11/1997 |
| WO | WO9814275 A1 | 4/1998 |
| WO | WO9815092 A1 | 4/1998 |
| WO | WO9824358 A1 | 6/1998 |
| WO | WO9833433 A1 | 8/1998 |
| WO | WO9859487 | 12/1998 |
| WO | WO9904043 | 1/1999 |
| WO | WO9910029 | 3/1999 |
| WO | WO9942933 | 8/1999 |
| WO | WO9944162 | 9/1999 |
| WO | WO9959472 | 11/1999 |
| WO | WO0013588 | 3/2000 |
| WO | WO0029983 | 5/2000 |
| WO | WO0043941 | 7/2000 |
| WO | WO0052437 | 9/2000 |
| WO | WO0052626 | 9/2000 |
| WO | WO0057339 | 9/2000 |
| WO | WO0060449 | 10/2000 |
| WO | WO0069331 | 11/2000 |
| WO | WO0072181 | 11/2000 |
| WO | WO0078374 | 12/2000 |
| WO | WO0101305 | 1/2001 |
| WO | WO0102979 | 1/2001 |
| WO | WO0106468 | 1/2001 |
| WO | WO0145774 | 6/2001 |
| WO | WO0217777 | 7/2002 |
| WO | WO02091276 A1 | 11/2002 |
| WO | WO03025826 A2 | 3/2003 |
| WO | WO03094073 | 11/2003 |
| WO | WO2004070557 | 8/2004 |
| WO | WO2004070994 | 8/2004 |
| WO | WO-2013148353 A1 * | 10/2013 ............ G01N 33/15 |

OTHER PUBLICATIONS

Peterson, Charles D. and Anderson, Jr., Howard C.; "The North Dakota Telepharmacy Project: Restoring and Retaining Pharmacy Services in Rural Communities" Feb. 1, 2004.

Phillips, Jon, Associate Director of Telemedicine; "Telepharmacy at Texas Tech," presented Apr. 30, 2003, published at http://www.ttuhsc.edu/telemedicine/publication.htm at least by Jun. 22, 2003 Jun. 22, 2003.

AHRQ Health Information Technology Program-Update 2005-06 Fact Sheet http://www.ahrq.gov/research/findings/factsheets/it/hitfact/index.html—3 pages.

Albert A. Cook, "An integrated nursing-pharmacy approach to a computerized medication dispensing/administration system," Hospital Pharmacy, May 1985, pp. 321-325, vol. 20, JB Lippincott Company, Philadelphia, PA.

Allan T. Pryor, "Current State of Computer-based Patient Record Systems," Aspects of the Computer-based Patient Record, 1992, pp. 67-82, Springer-Verlag, New York, NY.

Anderson, Howard "A Narrative on the History of the Development of Telepharmacy in North Dakota from the Board of Pharmacy's Perspective Recorded by Excerpts from Board Minutes", Feb. 2006.

Angaran, "Telemedicine and telepharmacy: Current status and future implications", Am J Health-Syst Pharm, vol. 56, Jul. 15, 1999, pp. 1404-1405.

Ann Slone Endo, "Using Computers in Newborn Intensive Care Settings," American Journal of Nursing, Jul. 1981, pp. 1336-1337.

Anonymous, "Chains covet customized pharmacy integration" Drug Store New, Aug. 18, 2003, vol. 25, No. 10—p. 73.

Automated Dispensing Technologies: Directory of Vendors, http://pharmacyautomation.com/vendors.html, Jun. 5, 2003—3 pages.

Auto Syringe® AS40A Infusion Pump Technical Manual, 1995, 89 pages, Baxter Healthcare Corporation, Deerfield, IL.

Auto Syringe® AS40A: Model AS40A Infusion Pump Operation Manual, undated, 78 pages, Baxter Healthcare Corporation, Deerfield, IL.

Baxa Corporation, DoseEdge the Leading Edge in Dose Management, Brochure, published copyright date 2010—5 pages.

Baxa Corporation, Product Catalog 2010-2011, published at least by Sep. 15, 2012, https://web.archive.org/web/20120915210739http://www.baxa.com/resources/docs/BaxaCatalog.pdf (52 pages).

Bell Atlantic Healthcare Systems, Inc., court exhibit, StatLan Functions and Features, Specification, release 3.5, dated Nov. 12, 1992, 49 pages.

Ben Schneiderman, "Designing the User Interface: Strategies for Effective Human- Computer Interaction," 2d Ed., 1992, Chapter 5: Direct Manipulation (56 pages), Addison-Wesley Publishing Company.

"Block Medical: Growing with Home Infusion Therapy," taken from INVIVO, The Business and Medicine Report, Apr. 1991, pp. 7-9.

Bynum et al., "The Effect of Telepharmacy Counseling on Metered-Dose Inhaler Technique among Adolescents with Asthma in Rural Arkansas", Telemedicine Journal and e-health, vol. 7, No. 3, 2001, Mary AnnLiebert, Inc., pp. 207-218.

Cabral, Jr. et al., "Multmedia Systems for Telemedicine Systems for Telemedicine and Their Communications Requirements," IEEE Communications Magazine Jul. 1996, pp. 20-27.

Cardinal Health Introduces Rxe-source(SM) to Address Pharmacist Labor Shortage and Medication Safety Challenges at Hospitals. PR Newswire, Feb. 25, 2003—5 pages.

Casey, Michelle M. et al., "Pharmacist Staffing and the Use of Technology in Small Rural Hospitals: Implications for Medication Safety" Upper Midwest Rural Health Research Center, Dec. 2005—51 pages.

Cato Reference Manual, Support for Trial Version (Abridged), Vienna, May 2004 Jun. 1, 2004.

Cato Reference Manual, Vienna, May 2005 May 1, 2005.

(56) References Cited

OTHER PUBLICATIONS

Charles Safran, M.D. et al., "Computer-Based Support for Clinical Decision Making," Clinical Computin, vol. 7, No. 5 (1990), pp. 319-322.

Clayton M. Curtis, "A Computer-based Patient Record Emerging from the Public Sector: The Decentralized Hospital Computer Program," First Annual Nicholas E. Davies Award Proceedings of the CPR Recognition Symposium, 1995, pp. 75-132, Computer-based Patient Record Institute, Inc., Bethesda, MD.

Clement J. McDonald, M.D. et al, "The Three-Legged Stool: Regenstrief Institute for Health Care," Third Annual Nicholas E. Davies Award Proceedings of the CPR Recognition Symposium, 1997, pp. 131-158, Computer-based Patient Record Institute, Inc., Bethesda, MD.

Clement J. McDonald, M.D. et al., The Regenstrief Medical Record System: 20 Years of Experience in Hospitals, Clinics, and Neighborhood Health Centers,: M.D. Computing, 1992 pp. 206-217, vol. 9, No. 4, Springer-Verlag, New York, NY.

Clifton, G. Dennis et al., "Provision of pharmacy services to underserved populations via remote dispensing and two-way videoconferencing" Am J Health-Syst Pharm, vol. 60, Dec. 15, 2003 oe pp. 2577-2582.

Dan Murphy, "Nuclear Pharmacy Primer", Radiation Protection Management, vol. 20, No. 5 (2003), pp. 1-10.

Dan Scheraga; "Tech firms answer chain pharmacy's call for productivity," Drug Store News; Dec. 15, 2003; 25, 17; ProQuest Research Library, p. 31-32.

Daniel Andresen et al., "Scalability Issues for High Performance Digital Libraries on the World Wide Web," Proceedings of ADL '96, 1996, pp. 139-148, IEEE.

Daniel J. Nigrin et al., "Glucoweb: A Case Study of Secure, Remote Biomonitoring and Communication," Proceedings of the 2000, 5 pages, American Medical Informatics Association, Bethesda, MD.

Darryl V. Wareham et al., "Combination Medication Cart and Computer Terminal in Decentralized Drug Distribution," American Journal of Hospital Pharmacy, Jun. 1983, pp. 976-978, vol. 40, American Society of Hospital Pharmacists.

Dart, Luann, "Digital Doses" Rural Electric, Jan. 2005—pp. 28-31.

Deborah J. Mayhew, "Principles and Guidelines in Software user Interface Designs," 1992, selected portions of Chapter 9, 17 pages, Prentice- Hall, Inc.

Defendants Initial Invalidity Contentions with Exhibits A and B dated Sep. 8, 2014; Civil Action No. 1:14-cv-00222.

Dennis D. Cote et al., "Robotic system for i.v. antineoplastic drug preparation: Description and preliminary evaluation under simulated conditions," American Journal of Hospital Pharmacy, Nov. 1989, pp. 2286-2293, vol. 46, American Society of Hospital Pharmacists.

Donna Young; "Loan repayments help pharmacists provide care in medically underserved areas," American Journal of Health—System Pharmacy; Nov. 1, 2003, pp. 2186-2188, vol. 60.

Environmental Scan of Pharmacy Technicians; M. MacInnis; Canadian Pharmacists Association; Sep. 2001.

Exhibit 1, Publications Manually Reviewed for the Search to U.S. Pat. No. 8,347,887 titled "System and Method for Remotely Supervising and Verifying Pharmacy Functions" As of Jun. 25, 2014.

Exhibit 1001 U.S. Pat. No. 8,374,887, Alexander issued Feb. 12, 2013.

Exhibit 1002 Patent File History U.S. Pat. No. 8,374,887.

Exhibit 1003, Declaration of Mr. Brian T. Hart from U.S. Pat. No. 8,374,887.

Exhibit 1004, Declaration of Wayne H. Grant from U.S. Pat. No. 8,374,887.

Exhibit 1005, 22 TAC §§291.20, 291.36, and 291.71-291.74 date issued Mar. 5, 2015 from U.S. Pat. No. 8,374,887.

Exhibit 1006 U.S. Pat. No. 6,711,460 Reese issued Mar. 23, 2004 from U.S. Pat. No. 8,374,887.

Exhibit 1009, Peterson et al., The North Dakota Telepharmacy Project: Restoring and Retaining Pharmacy Services in Rural Communities; the journal of Pharmacy Technology, vol. 20, No. 1, Jan./Feb. 2004—pp. 1-39 from U.S. Pat. No. 8,374,887.

Exhibit 1010, Declaration of Benjamin E. Weed from U.S. Pat. No. 8,374,887.

Exhibit 1011, Complaint—Alexander v. Baxter, (W.D.Texas 2014) filed Mar. 13, 2014 from U.S. Pat. No. 8,374,887.

Exhibit 1012, Charles F. Seifert et al., "The Training of a Telepharmacist: Addressing the Needs of Rural West Texas," American Journal of Pharmaceutical Education, 2004; 68 (3) Article 60—pp. 1-9 from U.S. Pat. No. 8,374,887.

Exhibit 1013, Assignment Emily H. Alexander to Becton, Dickinson and Company; U.S. Appl. No. 13/747,231; Reel 034110/Frame 0789 from U.S. Pat. No. 8,374,887.

Exhibit 1014, Exhibit A—Corrected Parties' Claims Construction Terms, Proposed Construction and cites Civil, 1:14cv-00222-LY—pp. 1-7 from U.S. Pat. No. 8,374,887.

Exhibit 1015, Information about Telepharmacy presentation 42503 and Presentation Telepharmacy at Texas Tech; Jon Phillips—1-27 from U.S. Pat. No. 8,374,887.

Exhibit 1017, Declaration of Dr. Roger W. Anderson in Support of Becton, Dickinson & Company's Response to Baxter's Motion for Summary Judgment of Invalidity Based Upon 35 U.S.C. § 101 filed Jan. 15, 2015 from U.S. Pat. No. 8,374,887.

Exhibit 1018, Plaintiff's Claim Construction Brief, 1:14-cv-222-LY filed Oct. 17, 2014 from U.S. Pat. No. 8,374,887.

Exhibit 1019, Plaintiff's Reply Claim Construction Brief, 1:14-cv-222-LY filed Nov. 7, 2014 from U.S. Pat. No. 8,374,887.

Exhibit 1020, The United States Pharmacopeia—the Official Compendia of Standards; 2004 from U.S. Pat. No. 8,374,887.

Exhibit 1021, Curriculum Vitae of Brian T Hart from U.S. Pat. No. 8,374,887.

Exhibit 1022, Curriculum Vitae of Wayne H Grant—Expert oversight—Expert Witness—Litigation Support from U.S. Pat. No. 8,374,887.

Exhibit 1023, Charles D Peterson et al., "The North Dakota Telepharmacy Project: Restoring and Retaining Pharmacy Services in Rural Communities," J Pharm Technol, 2004; vol. 20—pp. 028-039 from U.S. Pat. No. 8,374,887.

Exhibit 1025, Affidavit of Christopher Butler with attached Telemedicine Report Archive dated Mar. 4, 2015—6 pages from U.S. Pat. No. 8,374,887.

Exhibit 1026, Affidavit of Christopher Butler with attached presentation Telepharmacy at Text Tech—Jon Phillips dated Mar. 4, 2015—31 pages from U.S. Pat. No. 8,374,887.

Exhibit 1027, Order on Motion for Summary Judgment filed Aug. 3, 2015 from U.S. Pat. No. 8,374,887.

Exhibit 1028, Final Judgment filed Aug. 3, 2015 from U.S. Pat. No. 8,374,887.

Exhibit 1029 Charles Seifert from U.S. Pat. No. 8,374,887.

Exhibit 1030 Deposition of Charles Seifert Dec. 4, 2015 from U.S. Pat. No. 8,374,887.

Exhibit 1031 Deposition of Diane B. Ginsburg, PhD. Dec. 16, 2015 from U.S. Pat. No. 8,374,887.

Exhibit 1032 Texas Administrative Code, Title 22, Chapter 291, Subchapter A, Section 291.23 as in effect on Feb. 1, 2004 from U.S. Pat. No. 8,374,887.

Felkey, Bill G., "Integrating Technology at the Point of Care", Insight, Jan. 2004—pp. 8-10.

Formula for Patient Safety; ScriptPro; Aug. 17, 2003.

Fred Puckett, "Medication-management component of a point-of-care information system," Am. J. Health-Syst.Pharm., Jun. 15, 1995, pp. 1305-1309, vol. 52, American Society of Health-System Pharmacists, Inc.

"GE ImageQuant TL 7.0 Image Analysis Software" User Manual, May 2007, http://nba.uth.tmc.edu/Assets/pdf/other/typhoon-supporting-files/IQTL-UserManual.pdf, Uppsala, Sweden.

Gerald E. Meyer et al., "Use of bar codes in inpatient drug distribution," Am. J. Hosp. Pharm., May 1991, pp. 953-966, vol. 48, American Society of Hospital Pharmacists, Inc.

Ghent, Natale, "Pharmacists go digital to fight shortage", Pharmacy Practice 20.11 (Nov. 2004): 47—2 pages.

Gilad J. Kuperman, M.D. et al., "Innovations and research review: The impact of the Help computer system on the LDS Hospital paper

(56) References Cited

OTHER PUBLICATIONS medical record," Topics in Health Record Management, 1991, pp. 76-85, vol. 12, Issue 2, Aspen Publishers, Inc.
"Global Med Announces First Safetrace TX™ Sale," Apr. 1, 1999, 2 pages.
Global Med Technologies, Inc. Introduces PeopleMed™.com, inc., A Chronic Disease Management Application Service Provider (ASP) Subsidiary, Jan. 11, 2000, 2 pages, Global med Technologies, Inc., Denver, CO.
Gretchen A. Barry et al., "Bar-code technology for documenting administration of large- volume intravenous solutions," American Journal of Hospital Pharmacy, Feb. 1989, pp. 282-287, vol. 46, American Society of Hospital Pharmacists.
H. Paul Hammann et al., "A World Wide Web Accessible Multi-Species ECG Database," 1997, pp. 7-12, ISA.
Halverson, Daniel R. IsoRx: TelePharmacy Software presentation—23 pages.
Henry J. Lowe et al., "WebReport: A World Wide Web Based Clinical Multimedia Reporting System," 1996, pp. 314-318, AMIA, Inc.
"Hospitals battle errors with bar codes," Mar. 24, 2004, 3 pages, MSNBC.
Howard L. Bleich et al., "Clinical Computing in a Teaching Hospital," Use and Impact of Computers in Clinical Medicine, 1987, pp. 205-223 and selected pages, Springer- Verlag, New York, NY.
http://isorx.com/ Jan. 29, 2004.
http://www.scriptpro.com/products//sp-200/main.htm, Feb. 13, 2004, Product listing for SP 200® Robotic Prescription Dispensing System.
http://www.scriptpro.com/products/space/space200.htm, Feb. 10, 2004, Product listing for SP Automation Center 200TM (Space 200TM) Prescription Dispensing Automation Center.
Hughes, Shirley, "Bedside Terminals: Clinicom," Clinical Computing, Jan./Feb. 1988, pp. 22-28, vol. 5, No. 1.
IPR Decision Paper No. 8 Entered Aug. 13, 2015 from U.S. Pat. No. 8,374,887.
IPR Final Written Decision Paper No. 29 Entered Jul. 11, 2016 from U.S. Pat. No. 8,374,887.
James Kazmer et al., "The Creation of Virtual Electronic Medical Record," 1996, 17 pages.
Jennifer Langham; "Taking Automation to New Levels," Insight, the QS/1 Magazine, Oct. 2002; pp. 2-5.
John Frady; "What's New in RxCare Plus 17.2," Insight, the QS/1 Magazine, Apr. 2002; pp. 2-3, 14.
Jones, et al., "Use of a remote computerized system for study documentation in clinical trials" Drug Information Journal, Oct.-Dec. 1998, vol. 32, No. 4 oe pp. 1153-1163.
Karen E. Bradshaw et al., "Physician decision-making—Evaluation of data used in a computerized ICU," International Journal of Clinical Monitoring and Computing, 1984, pp. 81-91, vol. 1, Martinus Nijhoff Publishers, Netherlands.
Kastango, Eric S. and Bradshaw, Brian D., "USP chapter 797: Establishing a practice standard for compounding sterile preparations in pharmacy" Am J Health-Syst Pharm., Sep. 15, 2004, vol. 61—pp. 1928-1938.
Kenneth N. Barker et al., "Effect of an automated bedside dispensing machine on medication errors," American Journal of Hospital Pharmacy, Jul. 1984, pp. 1352-1358, vol. 41, No. 7, American Society of Hospital Pharmacists.
Keeys, Christopher A. et al., "Providing nighttime pharmaceutical services through telepharmacy" Am J Health-Syst Pharm, Apr. 15, 2002, vol. 59—pp. 716-721.
Khan, Shamima et al., "Is There a Successful Business Case for Telepharmacy?" Telemedicine and e-Health, vol. 14, No. 3, Apr. 2008, pp. 235-245.
Kimber, Michael B. et al., "Telepharmacy—Enabling Technology to Provide Quality Pharmacy Services in Rural and Remote Communities" Journal of Pharmacy Practice and Research, vol. 36, No. 2, 2006—128-133.

Kodak DirectView PACS—Rural Hospital Joins the Big Leagues PACS/Enterprise Information management (EIM) Solution—www.kodak.com/go/medical—4 pages.
Kosub, David, "Device allows pharmacy care in remote areas" Pharmacy Practice, vol. 20, No. 10, Oct. 2004—pp. 12-13.
Koutnik, Eileen, Assistnat Editor, Pharmacy Times, "The Pharmacy of Tomorrow" Pharmacy Times, Aug. 1, 2003—3 pages.
Larry B. Grandia, B.S.E. et al., "Building a computer-based Patient Record System in an Evolving Integrated Health System," First Annual Nicholas E. Davies Award Proceedings of the CPR Recognition Symposium, 1995, pp. 19-55, Computer-based Patient Record Institute, Inc., Bethesda, MD.
Lefkowitz, Sheldon et al., "A Trial of the Use of Bar Code Technology to Restructure a Drug Distribution and Administration System," 1991, pp. 239-242, Hospital Pharmacy, vol. 26.
LP, "ATM-STyle Drug Dispensers Taking Hold in Areas With Limited Pharmacist Services" Pharmacy Practice News, Jan. 2004, vol. 31, No. 1—4 pages.
"The Longitudinal Clinical Record: A View of the Patient," taken from Proceedings of the 1994 Annual HIMSS Conference, Feb. 14, 1994, pp. 239-250, Healthcare Information and Management Systems Society, Chicago, Illinois, USA.
Lustig, Ahuva, "Medication error prevention by pharmacists—An Israeli solution" Pharmacy World & Science, 2000, vol. 22, No. 1—pp. 21-25.
Medicaid Memo—Department of Medical Assistance Services (Converting NDCs from 10-digits to 11-digits) May 31, 2007.
Medcin® Technical Overview, undated, 111 pages, Medicomp Systems.
Michael H. Mackin, "Impact of Technology on Environmental Therapeutic Device Design," Medical Instrumentation, Feb. 1987, pp. 33-35, vol. 21, No. 1, Association for the Advancement of Medical Instrumentation.
Michelle M. Casey, M.S., Jill Klingner, R.N., M.S., and Ira Moscovice, Ph.D.; "Access to Rural Pharmacy Services in Minnesota, North Dakota, and South Dakota," Working Paper Series, Jul. 2001, #36.
Monane et al., "Improving Prescribing Patterson for the Elderly Through an Online Drug Utilization Review Intervention", JAMA, Oct. 14,1998, vol. 280, No. 14—pp. 1249-1252.
Morris, Aisha M., Schneider, Philip J., Pedersen, Craig A. and Mirtallo, Jay M. "National survey of quality assurance activities for pharmacy-compounded sterile preparations" Am J Health-Syst Pharm, Dec. 15, 2003, vol. 60—pp. 2567-2576.
Murray, Michael D. et al. "Effects of Computer-based Prescribing on Pharmacist Work Patterns" Journal of the American Medical Informatics Association, Nov./Dec. 1998, vol. 5, No. 6—pp. 546-553.
Napoli, M. et al., "Picture archiving and communication in radiology", Rays. Jan.-Mar. 2003—PubMed—NCBI http://www.ncbi.nlm.m=nih.gov/pubmed/14509181—Abstract.
Nissen et al., Can telepharmacy provide pharmacy services in the bush, School of Pharmacy, University of Queensland, Brisbane, Australia, Journal of Telemedicine and Telecare 2003, vol. 9 (Suppl. 2): S2:39-41.
North Dakota Century Code Statute Law—State Board of Pharmacy—219 pages.
Parks, Liz, "Annual report of retail pharmacy: Using central-fill to maximize dispensing" Drug Store News, Aug. 20, 2001 vol. 24, No. 11—pp. 51, 75.
Parsons, et al., "Digital Media—Can I Change a Graphic's File Size?", New Perspectives on Computer Concepts—Course Technology, 2011, Cengage Learning, Boston, MA.
Paul H. Perlstein et al., "Computer-Assisted Newborn Intensive Care," Pediatrics, Apr. 1976, pp. 494-501, vol. 57, No. 4, American Academy of Pediatrics, Inc., Evanston, Illinois.
Paul H. Perlstein et al., "Future Directions for Device Design and Infant Management," Medical Instrumentation, Feb. 1987, pp. 36-41, vol. 21, No. 1, Association for the Advancement of Medical Instrumentation.
PCA II Multi-Mode Cartridge Operator's Manual, Sep. 1995, approx. 40 pages, Baxter Healthcare Corporation, Deerfield, IL.
Pesce, James, "Bedside Terminals: Medtake," Clinical Computing, Jan. /Feb. 1988, pp. 16-21, vol. 5, No. 1.

(56) References Cited

OTHER PUBLICATIONS

Peter Lord et al., MiniMed Technologies Programmable Implantable Infusion System, Annals New York Academy of Science, pp. 66-71, describing clinical trials from Nov. 1986.
Peterson et al., The North Dakota Telepharmacy Project Restoring and Retaining Pharmacy Services in Rural Communities—Presentation North Dakota State University, Fargo, North Dakota.
Petition for Inter Partes Review *Baxter International Inc.* v. *Becton, Dickinson and Company* for U.S. Pat. No. 8,374,887, pp. 1-69.
Pharmacy Automation Online Vendors Page; Internet Archive Wayback Machine; http://pharmacyautomation.com/vendors.html—3 pages.
Pharmacy Data Management (PDM) Technical Manual/Security Guide Version 1.0, Sep. 1997—55 pages.
Pharmacy education and practice out of sync? (Roundtable) Chain Drug Review, vol. 25, No. 6, Mar. 17, 2003, RX2 (6).
Prem S. Chopra, Virgil A. Thomason, and Dell M. Stinett; "Voice-Activated Networked Workstation for a Physically Disabled Physician," 10-7803-2050-6/94 1994 IEEE, pp. 478-479.
Product literature, Baxter Healthcare Corporation, "Flo-Gard® 6201 Volumetric Infusion Pump," 1992, 2 pages.
Product literature, Baxter Healthcare Corporation, "MultiPlex™ Series 100 Fluid Management System," 1988, 2 pages.
Product literature, Baxter Healthcare Corporation, "MultiPlex™ Series 100 Fluid Management System," undated, 2 pages.
Remote Dispensing Regulations, NABPLAW Sep. 2003.
Woodall, Sandra C., Remote Order Entry and Video Verification; Reducing After-Hours Medication Errors in a Rural Hospital; S. Woodall; Joint Commission on Accreditation of Healthcare Organizations; vol. 30; No. 8; Aug. 2004.
Rich Muller; "NRx QS/1's Premium Pharmacy Software," Insight, the QS/1 Magazine, Jul. 2003; pp. 2-3, 12-15.
Rouse, et al., Academy of Managed Care Pharmacy et al., "White paper on pharmacy technicians 2002: Needed changes can no longer wait" Am J Health-Syst Pharm, Jan. 1, 2003, vol. 60—pp. 37-51.
Rule Section 291.36—Class A Pharmacies Compounding Sterile Pharmaceuticals—1 page.
Schrenker, Richard and Cooper, Todd, "Building the Foundation for Medical Device Plug-and-Play Interoperability".
Seifert et al.; "The Training of a Telepharmacist: Addressing the Needs of Rural West Texas," American Journal of Pharmaceutical Education 2004; 68 (3) Article 60. Jul. 16, 2004.
Standard Specification for Transferring Clinical Laboratory Data Messages Between Independent computer Systems, Annual Book of ASTM Standards, Mar. 25, 1988, pp. 1-16, E 1238-88, Global Engineering Documents, Philadelphia, PA.
Standard Specification for Transferring Clinical Observations Between Independent Computer Systems, Annual Book of ASTM Standards, Jun. Mar. 1994, pp. 132-210, E 1238-94, Philadelphia, PA.
Standard Specification for Transferring Clinical Observations Between Independent Computer Systems, Aug. 10, 1997, 79 pages, ASTM E 1238-97, West Conshohocken, PA, United States.
Standard Specification for Transferring Information Between Clinical Instruments and Computer Systems, Annual Book of Astm Standards, Jun. 1991, 15 pages, E 1394-91, Philadelphia, PA.
Suzanne Carter, RN, Ed.D. et al., "The Computer-based Patient Record: The Jacobi Medical Center Experience," Second Annual Nicholas E. Davies Award Proceedings of the CPR Recognition Symposium, 1996, pp. 71-95, Computer-based Patient Record Institute, Inc., Bethesda, MD.
T. Allan Pryor et al., "help—A Total Hospital Information System," Proceedings of the Fourth Annual Symposium on Computer Applications in Medical Care, Nov. 2-5 1980, pp. 3-7, vol. 1, Institute for Electrical and Electronics Engineers, New York, NY.
T.E. Bozeman et al., "The Development and Implementation of a Computer-Based Patient Record in a Rural Integrated Health System," Third Annual Nicholas E. David Award Proceedings of the CPR Recognition Symposium, 1997, pp. 101-130, Computer-based Patient Record Institute, Inc., Bethesda, MD.
"Telepharmacy project expands students' practice experience" Telemedicine Report, vol. 6, No. 1, Jan. 2004 oe 4 pages.
The World's First Fully Integrated Workflow Manager for I.V. Rooms, IntelliFlowRx Brochure, for Health Technologies Inc,. United States, May 2008.
Title 22. Examining Boards, 22 TAC Section 1.161; texinfo.library.unt.edu/Texasregister/html/2001/sep-14/PROPOSED/22.EXAMING BOARDS.html—Sep. 20, 2014, pp. 1-70.
Ukens, Carol, "Pharmacist shortage boosts telepharmacy" Drug Topoics, Jun. 3, 2002; 146, 11—p. 53.
Valeriy Nenov et al., "Remote Analysis of Physiological Data from Neurosurgical ICU Patients," Journal of the American Medical Informatics Association, Sep./Oct. 1996, pp. 318-327, vol. 3, No. 5.
"Victor J. Perini et al.," "Comparison of automated medication-management systems,: Am. J. Hosp. Pharm., Aug. 1, 1994, pp. 1883-1891, vol. 51, American Society of Hospital Pharmacists, Inc.".
Vincenzo Della Mae et al., "HTML generation and semantic markup for telepathology," Computer Networks and ISDN Systems, 1996, pp. 1085-1094, vol. 28, Elsevier Science B.V.
Website information for Cartharsis Medical Technology Products, Dec. 9, 2001, 15 pages.
Website information for MedPoint™, Mar. 13, 2003, 20 pages, Bridge Medical, Solana Beach, CA.
William R. Dito et al., "Bar codes and the clinical laboratory: adaptation perspectives," Clinical Laboratory Management Review, Jan./Feb. 1992, pp. 72-85, Clinical Laboratory Management Association, Inc.
Wills, Robert D., "Drug Images and Drug Imprints" Insight, Apr. 2001—p. 7.
Yvonne Mari Abdoo, "Designing a Patient Care Medication and Recording System that Uses Bar Code Technology," Computers in Nursing, May/Jun. 1992, pp. 116-120, vol. 10, No. 3.
Jon Phillips, Telepharmacy at Texas Tech, PowerPoint, Jan. 26, 1997, https://web.archive.org/web/20040509162423/http:/www.ttuhsc.edu/telemedicine/Powerpoint/Telepharmacy%20presentation%2042503.ppt.
A.H. McMorris et al. "Are Process Control Rooms Obsolete?", Control Engineering, pp. 42-47, Jul. 1971.
Standard Specification for Transferring Clinical Observations between Indepdendent Computer Systems, Annual Book of ASTM Standards, Nov. 14, 1991, pp. 1-64, ASTM E 1238-91,Philadelphia, PA.
Standard Specification for Transferring Information Between Clinical Instruments and Computer Systems, Dec. 10, 1997; 15 pages, ASTM E 1394-97, West Conshohocken, PA, United States.
Web site information, Information Data Management, Inc.'s PCMS: Plasma Center Management System, Dec. 14, 2001, 11 pages.
Web site Information, Wyndgate Technologies' SafeTrace Tx™, undated, 15 pages.
Specification for Low-Level Protocol to Transfer Messages Between Clinical Laboratory Instruments and Computer Systems, Mar. 11, 1991; 7 pages, ASTM E 1381-91, Philadelphia, PA, United States.
Atherton, H.D., Dollberg, S., Donnelly, M.M., Perlstein, P. H. Roath, S.B., "Computerized Temperature Control of the Low-Birth-Weight Infant: A 20-Year Retrospective and Future Prospects," Biomedical Instrumentation and Technology, Jul./Aug. 1994, pp. 302-309, vol. 28 No. 4.
Friesdorf, W., Grob-Alltag, F., Konichezky, S., Schwilk, B., Fattroth, A., Fett, P., "Lessons learned while building an integrated ICU workstation," International Journal of Clinical Monitoring and Computing, 1994, pp. 89-97, vol. 11.
Gammon, K., Robinson, K., "Bedside Data System Aids Pharmacy," Computers in Healthcare, Dec. 1988, pp. 3537, vol. 9 No. 12.
Graseby 3100 Syringe Pump, Graseby Medical Ltd., A Cambridge Electronic Industries Company, England, 2 pages.
Kampmann, J., Lau, G., Kropp, ST., Schwarzer, E., Hernandez Sande, C., "Connection of electronic medical devices in ICU according to the standard 'MIB'," International Journal of Clinical Monitoring and Computing, 1991, pp. 163-166, vol. 8.
Angaran, "Telemedicine and telepharmacy: Current status and future implications", Am J Health-Syst Pharm, vol. 56, Jul. 15, 1999 (32 pages).
Carson, Ewart et al., "A Systems Methodology for the Development and Evaluation of a Telematic Home Haemodialysis Service,"

(56) References Cited

OTHER PUBLICATIONS

Proceedings—19th International Conference—IEEE/EMBS Oct. 30-Nov. 2, 1997, Chicago, Illinois, pp. 907-910.

* cited by examiner

| | | | | | | | |
|---|---|---|---|---|---|---|---|
| Dose ID | Description | Admin Due | Admin Due (from now) | Patient Name | Patient Id | Location | Priority |
| Ranch, Dill | | | | | | | |
| 100 | Dillution, Gentamicin 1mg/mL dilution in Dextros... | | | Ranch, Dill | | | Dilution |
| 101 | Dillution, Gentamicin 1mg/mL dilution in Dextros... | | | Ranch, Dill | | | Dilution |
| Lake, Adult | | | | | | | |
| 92 | Gentamicin 140 mg,0.9% sodium chloride 50 m... | 02/25/2014 15:50 | 20 days ago | Lake, Adult | 193396247 | 5S-562A | Batch |
| 136 | DC Gentamicin 140 mg, 0.9% sodium chloride... | 02/25/2014 18:25 | 20 days ago | Lake, Adult | 615098634 | 4E-460B | DC |
| 90 | Gentamicin 140 mg,0.9% sodium chloride 50 m... | 02/25/2014 19:57 | 20 days ago | Lake, Adult | 193396247 | 5S-562A | Batch |
| Evans, Dante | | | | | | | |
| 21 | ceFAZolin 200 mg in 2 mL | 02/25/2014 15:53 | 20 days ago | Evans, Dante | 492218426 | 8E-836B | Batch |
| Field, Khema | | | | | | | |
| 125 | Cisplatin 70 mg,0.9% sodium chloride 250 mL... | 02/25/2014 16:16 | 20 days ago | Field, Khema | 926296655 | 2E-250A | Batch |
| 124 | Cisplatin 70 mg,0.9% sodium chloride 250 mL... | 02/25/2014 16:54 | 20 days ago | Field, Khema | 926296655 | 2E-250A | Batch |
| Round, Tot | | | | | | | |
| 35 | ceFAZolin 200 mg in 2 mL | 02/25/2014 16:18 | 20 days ago | Round, Tot | 907186481 | 7W-793B | Batch |
| Day, Baby | | | | | | | |
| 18 | ceFAZolin 200 mg in 2 mL | 02/25/2014 16:22 | 20 days ago | Day, Baby | 562624367 | 3S-359A | Batch |
| Tona, Babino | | | | | | | |
| 23 | ceFAZolin 200 mg in 2 mL | 02/25/2014 16:23 | 20 days ago | Tona, Babino | 893966396 | 2E-269A | Batch |
| 24 | ceFAZolin 200 mg in 2 mL | 02/25/2014 19:30 | 20 days ago | Tona, Babino | 893966396 | 2E-269A | Batch |
| Greg, Nancy | | | | | | | |
| 68 | ceFAZolin 200 mg in 2 mL | 02/25/2014 16:29 | 20 days ago | Greg, Nancy | 709612392 | 8W-868A | Batch |
| Wood CC | | | | | | | |

Total Items: 27

Suspected duplicate doses

| | Dose ID | Description | Admin Due (from now) | Patient ID | Patient Name | Location | Status | Priority |
|---|---|---|---|---|---|---|---|---|
| ▲ Rock, Kid - ceFAZolin 200 mg in 2 mL (51) | | | | | | | | |
| Original | 51 | ceFAZolin 200 mg in 2 mL | 20 days ago | 086418945 | Rock, Kid | 6N-661B | At-Checking | Batch |
| | 52 | ceFAZolin 200 mg in 2 mL | 20 days ago | 086418945 | Rock, Kid | 6N-661B | At-Checking | Batch |
| ▲ Wood, CC - ceFAZolin 200 mg in 2 mL (65) | | | | | | | | |
| Original | 65 | ceFAZolin 200 mg in 2 mL | 20 days ago | 947497495 | Wood, CC | 3N-382B | At-Checking | Batch |
| | 66 | ceFAZolin 200 mg in 2 mL | 20 days ago | 947497495 | Wood, CC | 3N-382B | At-Checking | Batch |
| ▲ High, Lad - Gentamicin 110 mg, 0.9% sodium Choride 2.75 mL in 5 mL (95) | | | | | | | | |
| Original | 95 | Gentamicin 110 mg, 0.9% Sodium Chloride 2.75 ml... | 20 days ago | 793376910 | High, Lad | 7E-728A | At-Checking | Batch |
| | 96 | Gentamicin 110 mg, 0.9% Sodium Chloride 2.75 ml... | 20 days ago | 793376910 | High, Lad | 7E-728A | At-Checking | Batch |
| ▲ Deer, Chemo - Doxorubicin 50 mg in 25 mL (112) | | | | | | | | |
| Original | 112 | Doxorubicin 50 mg in 25 mL | 20 days ago | 506440894 | Deer, Chemo | 2W-277B | At-Checking | Batch |
| | 113 | Doxorubicin 50 mg in 25 mL | 20 days ago | 506440894 | Deer, Chemo | 2W-277B | At-Checking | Batch |
| ▲ Field, Khema - Cisplatin 70 mg, 0.9% sodium chloride 250 mL in 320 mL (124) | | | | | | | | |
| Original | 124 | Cisplatin 70 mg, 0.9% sodium chloride 250 mL in... | 20 days ago | 926296655 | Field, Khema | 2E-250A | At-Checking | Batch |
| | 125 | Cisplatin 70 mg, 0.9% sodium chloride 250 mL in 32... | 20 days ago | 926296655 | Field, Khema | 2E-250A | At-Checking | Batch |
| ▲ Wait, Ima - Ampicillin 1 g in 10 mL (126) | | | | | | | | |
| Original | 126 | Ampicillin 1 g in 10 mL | in 7 years | 048278670 | Wait, Ima | 1E-161B | Pending | Batch |
| | 127 | Ampicillin 1 g in 10 mL | in 7 years | 048278670 | Wait, Ima | 1E-161B | Pending | Batch |
| ▲ Engle, Hirisk - Insulin Regular (Recombinant) 100 units, 0.9% sodium chloride 100 mL in 100 mL (134) | | | | | | | | |
| Original | 134 | Insulin Regular (Recombinant) 100 units, 0.9% s... | 20 days ago | 035750319 | Engle, Hirisk | 8N-856A | At-Checking | Batch |
| | 135 | Insulin Regular (Recombinant) 100 units, 0.9% sodiu... | 20 days ago | 035750319 | Engle, Hirisk | 8N-856A | At-Checking | Batch |

Total Items: 14    Selected Items: 1

| DOSEDGE | Batch | Stock: Vancomycin 1gm in D5W 250 ml STOCK | | Demo Help Support |
|---|---|---|---|---|
| | | Stock Dose | | |

Summary

Dose Summary Dose ID 320

< Patient Summary | Patient Stock Order | ID N/A | | Pending

Special Notes 1

> Items

Attached Documents 0

| Verified Drug Name | Amount | | Product Group | + |
| Vancomycin | 1000 mg | | N/A | |
| Dextrose 5% in Water | 250 ml | | N/A | + |

Products And Procedures

> Ingredients

Additional Information

| Name | Amount | | Concentration | Volume | + |
| No Ingredients | | | | | |

Data Current As Of 09/25/2014 14:11:16
Next Update In 57 Seconds

> Dose History | Last Scan Event Dose Queued

Disposition / Requeue

| Event Name | Entry Date | Entry Time | User | Workstation | Event Description | + |
| Dose Queued | 09/04/2014 | 11:38:41 | N/A | N/A | Dose queued, awaiting preparation | |

Dose Pictures

No images of this dose available.

| DOSE■DGE | Batch | Stock: Vancomycin 1gm in D5W 250 ml STOCK | | Help Demo Support |
|---|---|---|---|---|
| Summary 3564 | Patient | N/A | Administer | 3500 |
| | Stock Order | Vancomycin 1 gm in D5W 250 ml STOCK | 09/05/2014 01:00:00 | Ordered by: System Administrator (Administrator) |
| Special Notes 1 | Aux1 | | Aux2 | N/A |
| Attached Documents 0 | Aux3 | Quantity ordered: 20 | Aux4 | N/A |
| | Aux5 | N/A | Aux6 | N/A |
| Products And Procedures | Aux7 | N/A | Aux8 | N/A |
| Additional Information | Aux9 | N/A | Aux10 | N/A |
| | Barcode | 320-Z634340207 | Dose Format | N/A |
| | Facility | N/A | Frequency | N/A |
| | Infuse Over | N/A | | |
| | 3520 | | | |
| | Items | | | + |
| Data Current As Of 09/25/2014 14:13:16 Next Update In 41 Seconds | Verified Drug | Amount | Product Group | Label Drug | Item Type | Original Item |
| | Vancomycin | 1000 mg | N/A | Vancomycin | Drug Request | Yes |
| Disposition / Requeue | | | | | | − |
| | Aux1 | N/A | N/A | Aux2 | N/A | |
| | Aux3 | N/A | N/A | Aux4 | N/A | |
| | Aux5 | N/A | N/A | Alternate Drug Name | N/A | |
| | Dextrose 5% in Water | 250 ml | N/A | Dextrose 5% in Water | Drug Request | Yes |
| | | | | | | − |

3510

| Clinical Data | | |
|---|---|---|
| Clinical Order Items | | |
| Clinical Item Name | Clinical Item Value | |
| Aminosyn II 15% | 75.0 gm/day | |
| Dextrose 70% | 350.0 gm/day | |
| Liposyn II 10% | 20.0 gm/day | |
| Sodium | 120.0 mEq/day | |
| Potassium | 93.5 mEq/day | |
| Chloride | 120.0 mEq/day | |
| Phosphate | 15.0 mM/day | |
| Acetate | 93.95 mEq/day | |
| M.V.I.-12 | 5.0 mL/day | |
| M.T.E.-4 | 5.0 mL/day | |

3574

| Items | | | | |
|---|---|---|---|---|
| Verified Drug | Amount | Label Drug | Item Type | Original Item |
| Potassium Chloride | 35.75mL | KCl | Drug Request | Yes |
| Sodium Chloride | 12.13mL | NaCl | Drug Request | Yes |
| Sodium Acetate | 20.08mL | Na Acetate | Drug Request | Yes |
| Multiple Vitamin Injection - 12 | 5mL | M.V.I.-12 | Drug Request | Yes |
| Multiple Trace Elements - 4 | 5mL | M.T.E.-4 | Drug Request | Yes |
| N/A | 500mL | Dextrose 70% | Drug Request | Yes |
| N/A | 1917.05mL | Sterile Water for Inj | Drug Request | Yes |
| Aminosyn II | 500mL | Aminosyn II 15% | Drug Request | Yes |
| N/A | 5mL | K Phosphate 3mMol/ml PO4 | Drug Request | Yes |

Doses Verified (last 30 min) (84)
*Default Sorting*

Cefazolin 500 mg in 5 mL — 2 minute(s)
Gonzalez, Helen (3W-700) Patient ID: 99203-25 Order ID:5493968
Admin: 2013-09-27 18:24:20

Cefazolin 500 mg in 5 mL — 2 minute(s)

4800

---

Doses Verified (last 30 min) (84)
*Elapsed Time Descending*

Cefazolin 500 mg in 5 mL — 2 minute(s)
Hildago, Jayson (0w-973) Patient ID: 99608-63 Order ID: 2838836
Admin: 2013-09-27 18:29:46

Cefazolin 500 mg in 5 mL — 2 minute(s)

4802

---

Doses Verified (last 30 min) (84)
*Elapsed Time Ascending*

Cefazolin 500 mg in 5 mL — 2 minute(s)
Hildago, Jayson (0w-973) Patient ID: 99608-63 Order ID: 2838836
Admin: 2013-09-27 18:29:46

Cefazolin 500 mg in 5 mL — 2 minute(s)

| Event Name | Entry Date | Entry Time | User | Workstation | EventDescription | |
|---|---|---|---|---|---|---|
| Dose Queued | 09/15/2013 | 11:07:36 | N/A | N/A | Dose queued, awaiting preparation | + |
| Dose Added to Wait/Hold | 09/15/2013 | 11:08:05 | Demo | IV Hood1 | Dose added to Wait/Hold queue | + |
| Dose Removed to Wait/Hold | 09/15/2013 | 11:08:24 | Administrator | IV Hood1 | Dose left 'Wait' wait Status or 'Hold' Status | + |
| Dose Added to Wait/Hold | 09/15/2013 | 11:08:38 | Administrator | IV Hood1 | Dose ladded Wait/Hold queue | + |
| Dose Removed from Wait/Hold | 09/15/2013 | 11:08:56 | Demo | IV Hood1 | Dose left 'Wait' wait Status or 'Hold' Status | + |
| Dose Prep Started | 09/15/2013 | 11:09:16 | Demo | IV Hood1 | Dose preparation started | + |
| Printed | 09/15/2013 | 11:09:16 | Demo | IV Hood1 | N/A | + |
| Preparation Cancelled | 09/15/2013 | 11:09:32 | Demo | IV Hood1 | Dose preparation cancelled | + |
| Dose Kitted | 09/15/2013 | 11:10:40 | Demo | IV Hood1 | Dose added to a preparation kit | + |
| Dose Removed from Kit | 09/15/2013 | 11:11:05 | Administrator | IV Hood1 | Dose removed from kit | + |
| ManualScanEventTest1 | 09/15/2013 | 11:12:44 | Administrator | IV Hood1 | Manual Scan Event from PrepStation Tracking Tab | + |
| Printed | 09/15/2013 | 11:28:12 | Administrator | IV Hood1 | N/A | + |
| Dose prep Started | 09/15/2013 | 11:28:12 | Administrator | IV Hood1 | Dose preparation started | + |
| Preparation Cancelled | 09/15/2013 | 11:28:32 | Administrator | IV Hood1 | Dose preparation cancelled | + |
| Printed | 09/15/2013 | 11:28:57 | Administrator | IV Hood1 | N/A | + |
| Dose Bypassed | 09/15/2013 | 11:28:57 | Administrator | IV Hood1 | Dose printed for bypass | + |

FIG. 49

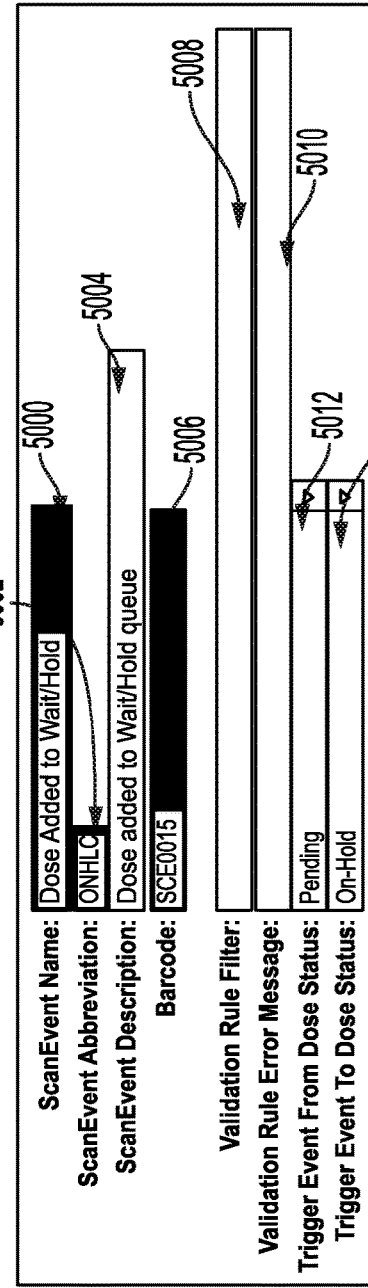

FIG. 50

MANAGEMENT OF MEDICATION PREPARATION WITH FORMULARY MANAGEMENT

CROSS-REFERENCE TO RELATED APPLICATION

This application claims priority from U.S. Provisional Application No. 62/057,906 filed on Sep. 30, 2014, entitled "MANAGEMENT OF MEDICATION PREPARATION WITH FORMULARY MANAGEMENT," the contents of which are incorporated by reference herein as if set forth in full.

BACKGROUND

In many medical facilities, medication orders are provided to a pharmacy for preparation of doses corresponding to the medication orders for administration to a patient. In this regard, orders must be entered, received by the pharmacy, validated, and prepared according to manufacturer's specifications or established institutional guidelines. The preparation process involves the selection and, where required, preparation of drug products for administration to patients in compliance with the validated order. Once filled, the resulting drug products (i.e., doses) must be delivered to the patient that requires them. One environment, by way of example, in which such processes occur is a hospital.

There are points in the foregoing process that may be susceptible to the loss or corruption of information due to miscommunication or other errors. This can be problematic in terms of logging and auditing of medication doses, which may be required by insurance and regulatory requirements. In turn, systems for management of pharmacy work flow have been proposed. For example, U.S. Provisional Patent Application No. 61/975,519 entitled "MANAGEMENT OF MEDICATION DOSE ORDERS" filed on Apr. 4, 2014, which is co-owned with the present application and incorporated by reference herein in the entirety, discloses certain embodiments of a pharmacy workflow management application. Accordingly, at least partially automated pharmacy workflow management applications have been devised to assist in management of the receipt, processing, organization, preparation, verification, and tracking of medication dose orders in the pharmacy or the like. However, further developments would be beneficial to assist in improvements to the pharmacy workflow management application to promote efficiency, reliability, and accuracy related to the preparation and management of medication dose orders.

SUMMARY

In view of the foregoing, the present disclosure is generally related to various embodiments of pharmacy workflow management applications. In certain embodiments of the pharmacy workflow management application described herein, improvements in the management of a formulary are presented. Additionally, the present disclosure includes embodiments that relate to improvements in user interface elements of a pharmacy workspace management tool. Further still, enhancements to the tracking of dose orders using the pharmacy workflow management application are also discussed. Further still, enhancements to a situation board for high-level overview displays in relation to current pharmacy work load and other pharmacy activities are discussed. Additionally, improvements with respect to secure communications at a facility and improvements in relation to workstation application updates are also discussed. Further still, improvements to the local installation of an updated software free from administrator-level credentials are also discussed.

The present disclosure generally includes discussion related to the configuration of a user interface in relation to a user profile in order to provide for a customized display of one or more records to a user with which the user profile is associated. In this regard, the user may provide user authentication information. This user authentication information may be particular to a given user. In turn, upon receipt of the user authentication information, the application may associate a user profile with a given user accessing the application. Various user interface elements presented to the user may be customized based upon the associated user profile. In particular, the user profile may allow for default configurations of user interface elements and/or configuration of user interface elements according to the last accessed configuration which is stored with user profile.

In this regard, a customized user interface associated with the user profile may be used to display records to a user. As may be appreciated, the records displayed to the user using the user interface may be retrieved from a database at the system executing the pharmacy workflow management application. In turn, the database records may relate to a number of various types of records maintained at the local system. In one specific example, the records may be formulary records related to a formulary database maintained at the local system at which the pharmacy workflow management application executes. In yet another specific example, the records may correspond to dose order records stored at the local system at which the pharmacy workflow management application executes. In either regard, upon display of the records to the user, the display may at least partially be based on the user profile of the user accessing the records.

In connection with the foregoing, the formulary may comprise a plurality of records stored in a database. In this regard, the formulary records may be related to (e.g., categorized according to) administration routes, drug categories, drugs, materials, product groups, and/or products that may be utilized by the pharmacy in the preparation of doses. The formulary records may be used during the preparation process by a pharmacy technician and/or the pharmacy workflow management application to assist in the preparation of a dose, the management of dose order records, or other activities related to the pharmacy workflow management application.

In additional embodiments described herein, improvements in relation to a pharmacy workspace queue for use in a pharmacy workflow management application are also discussed. The present disclosure also includes various aspects to facilitate administration of the pharmacy workflow, including tracking dose order status through triggered scan events, monitoring pending dose orders on a customizable situation board, encrypting web traffic associated with the workflow, and facilitating the local installation of updated software versions free from administrator-level credentials.

In this regard, a first aspect of the present disclosure includes a method for formulary management in a pharmacy workflow management application. The method includes receiving, at a processor that executes the pharmacy workflow management application, user authentication information corresponding to a given user of the system. The method further includes associating, by the processor, the user authentication information with a user profile for the given user. The method further includes accessing a plurality of formulary data records stored in a database accessible by the processor in response to a request for the plurality of formulary data records by the given user. The method further includes displaying, using the processor, the plurality of formulary data records to the given user at a user interface, wherein the user interface is configured at least partially based on the user profile for the given user.

A number of feature refinements and additional features are applicable to the first aspect. These feature refinements and additional features may be used individually or in any combination. As such, each of the following features that will be discussed may be, but are not required to be, used with any other feature combination of features of the first aspect.

For example, in an embodiment, the user interface may include a plurality of pages. Each of the plurality of pages may be associated with a formulary management function. A search area may be provided that is operable to receive a user input. The user interface may also include a data table corresponding to the plurality of formulary data records. The method may further include identifying, by the processor, associations between the user input of the search area and the plurality of formulary data records of the data table. The method may further include displaying, at the user interface, a filtered table result at least partially based on the associations.

Moreover, the formulary data records may belong to at least one of a class of formulary data records, such that the class of formulary data records is selected from the group consisting of: administration routes, drug categories, drugs, materials, product groups, and products. As such, the foregoing formulary management function may be selected from the group consisting of: management of administration routes, management of drug categories, management of drugs, management of materials, management of product groups, and management of products. In this regard different categories of formulary records may be managed. For instance, the management functions provided may depend upon the category of formulary record displayed.

In an embodiment, the user interface may also include a plurality of maintenance operations buttons displayable within each of the plurality of pages such that the plurality of maintenance operations buttons remains visible while each of the plurality of pages is scrolled. The management buttons presented may depend upon the type of formulary record displayed. In this regard, the user interface presented to the user may facilitate efficient management of different types of formulary records belonging to different corresponding categories.

In an embodiment, the plurality of pages may also include a plurality of collapsible areas configured to hide information when collapsed. Notably, the configuration of the plurality of collapsible areas may be associated with the user profile. The collapsible area may include data attributes of the formulary data records (e.g., the data attributes of a selected one of the formulary records) such that the data attributes of the formulary data records are modifiable in the collapsible area. Upon associating the user authentication information with a user profile the given user, the plurality of collapsible areas may be arranged in accordance with the user profile during the displaying. Moreover, each of the plurality of collapsible areas may include a help icon, accessible by the user and operable to display context-specific help information associated with the data attributes of the formulary record of each of the plurality of collapsible areas.

In an embodiment, the plurality of formulary data records may be associable with a data table of the user interface. Consequently, the method may include modifying the data table of the user interface. The method may also include associating the modified data table with the user profile. The method may also include presenting the modified data table to the user during a subsequent user interface session. During the foregoing modification of the data table the quantity of data attributes display in the data table may be changed or otherwise altered. Furthermore, the plurality of data attributes may be displayable in distinct columns of the data table. As such, during the data table modification the width of the distinct columns of the data table may be resized.

The at least one of the plurality of formulary data records may also include at least one data attribute defined by one or more selected values from a list comprising a plurality of values. Each of the plurality of values may be alterable within the list without deleting the value or adding a new value. The list may also include a query box operable to receive a user input. From this user input, the processor may identify, from the plurality of values, associations between the user input of the query box and the plurality of values of the list and display a filtered list result at least partially based on the identified associations.

In an embodiment, the displaying may include displaying the numerical values of the plurality of formulary data records according to Institute for Safe Medical Practice (ISMP) standard format. As such, the method may include modifying a given user input to conform to the ISMP standard format. In this regard, uniformity may be achieved such that errors based on misread, misunderstood, or incorrectly transcribed values.

Furthermore, in an embodiment of the formulary management in a pharmacy workflow management application, each of the plurality of formulary data records may comprise a plurality of characteristics of existing formulary data. In this regard, the method may include modifying at least one of the characteristics of at least one of the plurality of formulary data records, at the user interface, without deleting the at least one of the plurality of formulary data records or adding a new formulary data record to the plurality of formulary data records. The method may also include presenting the modified at least one of the plurality of formulary data records to the user during a subsequent session.

A second aspect includes a method for managing a pharmacy workspace queue in a pharmacy workflow management application. The method includes receiving, at a processor that executes the pharmacy workflow management application, user authentication information corresponding to a given user of the system. The method further includes associating, by the processor, the user authentication information with a user profile for the given user. The method further includes accessing a plurality of dose order records corresponding to dose orders received by the pharmacy workflow management application in response to a request for the plurality of dose order records by the given user. The method further includes displaying the plurality of dose order records to the given user at a user interface of the pharmacy workflow management application. Accordingly, the user interface is configured at least partially based on the user profile for the given user.

A number of feature refinements and additional features are applicable to the second aspect. These feature refinements and additional features may be used individually or in any combination. As such, each of the following features that will be discussed may be, but are not required to be, used with any other feature combination of features of the second aspect.

For example, in an embodiment, the plurality of dose order records may include at least a first dose order record corresponding to a first dose order that has not been prepared and at least a second dose order record corresponding to a second dose order that has been prepared and has not yet been verified by a pharmacist. Furthermore, the user interface may include a plurality of pages such that each of the plurality of pages is associated with a pharmacist workspace queue management function. The pharmacist workspace queue management function may be selected from the group of management functions, which consist of: managing dose order on wait/hold status, managing dose order on inline dose, managing dose order on STAT dose, managing dose order on final/STAT dose, and managing dose order being verified.

In an embodiment, the user interface may include a plurality of collapsible areas such that the collapsible areas include a plurality of data attributes of at least one of the plurality of dose order records and are associated with at least one of plurality of informational groups. The data attributes may be arranged with at least one of the plurality of collapsible areas at least partially based on an association between the data attributes and at least one of the plurality of informational groups. Furthermore, the plurality of informational groups may be selected from the group consisting of: dose information, patient information, clinical information, formulary information, and documentation information. Notably, the collapsible areas may be configured to hide information when collapsed, and the configuration of the plurality of collapsible areas may be associated with the user profile. Accordingly, the plurality of collapsible areas may be arranged in accordance with the user profile, such that the arranged configuration is displayed in the method.

In an embodiment, the pharmacy workflow management application includes various features pertaining the standard presentation of data, such as the plurality of dose order records. In this regard, the plurality of dose order records may be configured according to ISMP standard format. Furthermore, the method may include displaying a print view of at least one of the plurality of dose order records. In this regard, the print view may include detailed dose information and product information.

In an embodiment, the method may further comprise modifying at least one of the plurality of dose order records at the user interface. Specifically, an external document may be dragged to the user interface (e.g., to a document input page of the user interface) such that the external document is associated with at least one of the plurality of dose order records. The plurality of dose order records may include a plurality of external document attachments such that the displaying includes displaying the external document attachments for at least one of the plurality of dose order records. The attached document may comprise a number of file types such as word processing documents, spreadsheet documents, image files, portable document format (PDF) files, or the like.

In another embodiment, the plurality of dose order records may be associable with a data table of the user interface such that the plurality of dose order records includes a plurality of characteristics. In this regard, the method may also include modifying at least one of the plurality of characteristics of at least one of the dose order records. Furthermore, the data table may be configurable to display, for each of the plurality of dose order records, at least one of dose history, product history, or scan event data. Accordingly, each of the plurality of dose order records may be stored in corresponding relation to one or more dose order record data fields populated with dose order metadata regarding each dose order record. The at least one dose order record data field may correspond to a dose order status indication of the at least one dose order record in relation to a dose preparation step of the at least one dose order record such that the scan event data is at least partially based on the dose order status metadata.

A third aspect includes a method for management of dose order records. The method may include storing a plurality of dose order records in a database of a dose order management server such that each dose order record is stored in corresponding relation to one or more dose order record data fields populated with dose order metadata regarding each dose order record. Furthermore, the at least one dose order record data field for a given dose order record may correspond to a dose order status indicative of a status of the given dose order record relative to a particular dose preparation step in a dose preparation protocol for the at least one dose order record. The method further includes identifying a first dose order record. The method further includes modifying the dose order status for the given dose order from a first value to a second value at least partially in response to an input received from a user in connection with the dose preparation step. Notably, the dose preparation step is associated with an independent pharmacy workflow of the dose preparation protocol to prepare a dose corresponding to the at least one dose order record.

A number of feature refinements and additional features are applicable to the third aspect. These feature refinements and additional features may be used individually or in any combination. As such, each of the following features that will be discussed may be, but are not required to be, used with any other feature combination of features of the third aspect.

For example, in an embodiment, the independent pharmacy workflow operation may relate to preparation of a dose corresponding to the given dose order record free from modifying the dose order status value. The second dose order status may include a plurality of values associated with various indications of dose order status.

By way of illustration, numerous examples of the plurality of value of the second dose order status are described. For instance, the second dose order status value may include a preparation cancelled status such that the preparation cancelled status indicates the one or more dose orders of the first dose order record is, after being selected for preparation, returned to a queue of dose order records to be prepared. The second dose order status value may include a dose removed from wait/hold status such that the dose removed from wait/hold status indicates the one or more dose orders of the first dose order record is moved from a wait/hold queue. The second dose order status value may include a dose at inline verification status such that the dose at inline verification status indicates the one or more dose orders of the first dose order record is transmitted for remote inline verification in manner where the user input relates to scanning an intermediate product used in the preparation of the dose. The second dose order status value may include a dose reused status such that the dose reused status indicates the dose of the given dose order record is reused in another of the one or more dose orders in a manner where the user input includes an association of the dose to the another of one or more dose orders.

By way of continued illustration, the second dose order status value may include a dose kitted status such that the dose kitted status indicates the one or more dose orders of the first dose order record is added to a kit in a manner where the user input includes a scan to associate the dose corresponding to the given kit. The second dose order status value may include a dose at compounder status such that the dose at compounder status indicates the one or more dose orders of the first dose order record is printed for compounding. The second dose order status value may include a dose bypassed status such that the dose bypassed status indicates the one or more dose orders of the first dose order record is printed for preparation outside of the system. The second dose order status value may include a dose prep started status such that the dose prep started status indicates one or more dose orders of the first dose order record has begun a dose preparation process. In this regard, the status change may be accomplished in manner in which the user input includes a scan of a label corresponding to the given dose order to retrieve a dose preparation protocol for the given dose order record.

By way of additional illustration, the second dose order status value may include a dose sent for rework status such that the dose sent for rework status indicates one or more dose orders of the first dose order record is returned to a dose order queue for rework. The second dose order status value may include a dose lost status such that the dose lost status indicates the one or more dose orders of the dose order record is lost. The second dose order status value may include a dose rejected status such that the dose rejected status indicates the one or more dose orders of the dose order record is rejected. The second dose order status value may include a dose added to wait/hold status such that the dose added to wait/hold status indicates one or more dose orders of the dose order record is added to a wait/hold queue. The second dose order status value may include a dose removed from kit status such that the dose removed from kit status indicates one or more dose orders of the dose order record is removed from a kit. This may be accomplished in a manner where the user input includes a scan confirming receipt of the kit. The second dose order status value may include a dose discontinued status such that the dose discontinued status indicates one or more dose orders of the dose order is discontinued.

Furthermore, in an embodiment, the plurality of dose order records may be associable with a data table of the user interface such that the data table is configurable to display the scan event of the given dose order record. Further still, the first and/or second status associated with a scan event may be established using the user interface. In this regard, the nature of the scan even (e.g., the trigger of a change in status, the status from which the order is changed, and the status to which the order is changed) may be configured by a user.

A fourth aspect includes a method for use in communicating information pertaining to a pharmacy workspace queue in a pharmacy workflow management application. The method includes receiving, at a processor executing the pharmacy workflow management application, user authentication information corresponding to a given user of the system. The method further includes associating, by the processor, the user authentication information with a user profile for the given user. The method further includes accessing a plurality of dose order records corresponding to dose orders received at the pharmacy workflow management application in response to a request for the plurality of dose order records by the given user. The method also includes displaying the plurality of dose order records to the given user at a user interface of the server such that the first dose order record and the second dose order record each appear in at least one distinct module of a common dashboard. The dashboard may include a plurality of the modules and be configurable to communicate the status of at least one of the plurality of dose orders in the pharmacy workspace queue to a user such that the configuration is at least partially based on the user profile for the given user.

A number of feature refinements and additional features are applicable to the fourth aspect. These feature refinements and additional features may be used individually or in any combination. As such, each of the following features that will be discussed may be, but are not required to be, used with any other feature combination of features of the fourth aspect.

For example, in an embodiment, the plurality of dose order records may include at least a first dose order record corresponding to a first dose order that has not been prepared and at least a second dose order record corresponding to second dose order that has been prepared and has not yet be verified by a pharmacist. Moreover, the configuration of the foregoing dashboard may be at least partially based on a cascading style sheet declaration contained within a single file.

Furthermore, in an embodiment, the configuration of the modules may be associated with a module profile, such that the user profile may be associated with a module profile. In this regard, the plurality of modules may be displayed in accordance with the module profile. Additionally, the module profile may include alphanumerical customization preferences such that the alphanumerical customization preferences include at least a color preference, a font preference, a size preference, or a text effects preference.

In an embodiment, the method may further include sorting the plurality of dose orders of the at least one module at least partially based on a sorting criterion. The sorting criterion may include, for example, at least one of a dose priority, a patient name, an expiration data, or an expiration time. The sorting of the method may also include sorting the plurality of dose orders of the at least one module at least partially based on sorting criteria in ascending or descending order.

In a further embodiment, each of the plurality of dose order records may be associated with a durational indicator that indicates the length of time elapsed since a milestone event. In this regard, a milestone event may represent a change of status of at least one of the plurality of dose order records. Accordingly, the change of status corresponds to identifying modified dose order metadata regarding at least one of the plurality of dose order records such that the modified dose order metadata is modified with respect to corresponding portions of dose order metadata at least partially obtained in response to an input received from the user.

A fifth aspect includes a method for secure local network access of a pharmacy workflow management application. The method includes establishing an operative communication link between a terminal and the pharmacy workflow management application that stores a plurality of dose order records corresponding to dose orders received at the pharmacy workflow management application. The terminal may be disposed within at least one network of a local area network. The method further includes cryptographically manipulating data routed through the operative communication link such that the operative communication link provides a secure data connection between the terminal and the server. The method further includes accessing the server using the terminal to retrieve a plurality of dose order records from the pharmacy workflow management application. The method further includes displaying the plurality of dose order records to a user at the terminal.

A number of feature refinements and additional features are applicable to the fifth aspect. These feature refinements and additional features may be used individually or in any combination. As such, each of the following features that will be discussed may be, but are not required to be, used with any other feature combination of features of the fifth aspect.

For example, in an embodiment, the plurality of dose order records include at least a first dose order record corresponding to a first dose order that has not been prepared and at least a second dose order record corresponding to a second dose order that has been prepared and has not been verified by a pharmacist. The cryptographic manipulation of the method may further include translating the data routed through the operative communication link into an illegible format between the terminal and the pharmacy workflow management application. In this regard, the secure connection is operable to prevent third party interference of the data routed through the operative communication link. Notably, for example, the interference may include eavesdropping and tampering, which may at least in part be reduced using the cryptographic manipulation of the data communicated.

In other embodiments, the secure connection is provided via a secure socket layer cryptographic protocol. In this regard, the secure socket layer cryptographic protocol may translate the data into a legible format at each of the terminal and the server at least partially based on a signed digital certificate associated with an authenticated user.

A sixth aspect includes a method for use in upgrading a terminal of a local network system for management of medication dose orders. The method includes storing a workstation version in a database of a pharmacy workflow management application that stores a plurality of dose order records corresponding to dose orders received at the pharmacy workflow management application. The method further includes, identifying a workstation version of a terminal disposed within at least one network of a common enterprise network. The method further includes, establishing an operative communication link between the terminal and the pharmacy workflow management application. The method further includes, comparing the workstation version of the terminal with the workstation version stored in the database. The method further includes, determining whether the workstation version stored in the database supersedes the workstation version of the terminal. The method further includes, presenting to a user an option to download the workstation version stored in the database on to the terminal.

A number of feature refinements and additional features are applicable to the sixth aspect. These feature refinements and additional features may be used individually or in any combination. As such, each of the following features that will be discussed may be, but are not required to be, used with any other feature combination of features of the sixth aspect.

For example, in an embodiment, the method may further include downloading, in response to the user selected option, the workstation version stored in the database on to the terminal. In this regard, the workstation version stored in the database may be downloaded on to the terminal by the user. Notably, the user need not be an administrative user with credentials to upgrade the pharmacy workflow management application. Additionally, the method may further include downloading the workstation version stored in the database on to the terminal without hardware drivers or crystal reports.

A seventh aspect includes a system for formulary management in a pharmacy workflow management application. The system includes an access terminal remote from and in operative communication with the pharmacy workflow management application. The pharmacy workflow management application may therefore be operable to access a plurality of formulary data records stored in a database of the pharmacy workflow management application in response to a request for the plurality of formulary data records by a given user. The system further includes a user interface provided at the access terminal for displaying the plurality of formulary data records stored in the database. Furthermore, the pharmacy workflow management application may be operable to receive, at a processor of the pharmacy workflow management application, user authentication information corresponding to the given user of the system. Consequently, the pharmacy workflow management application is operable to associate, at the processor, the user authentication information with a profile for the given user such that the user interface is configured at least partially based on the user profile for the given user.

A number of feature refinements and additional features are applicable to the seventh aspect. These feature refinements and additional features may be used individually or in any combination. As such, each of the following features that will be discussed may be, but are not required to be, used with any other feature combination of features of the seventh aspect. For instance, any of the features discussed with any of the foregoing aspects, and in particular the first aspect, may be used in conjunction with the seventh aspect without limitation.

An eight aspect includes a system for pharmacy workspace queue management in a pharmacy workflow management application. The system includes an access terminal remote from and in operative communication with a pharmacy workflow management such that the pharmacy workflow management may be operable to access a plurality of dose order records corresponding to dose orders received at the server in response to a request for the plurality of dose order records by a given user. The system further includes a user interface provided at the access terminal for displaying the plurality of dose order records to the given user at a user interface of the server. Furthermore, the server is operable to receive, at a processor of the pharmacy workflow management, user authentication information corresponding to the given user of the system. Consequently, the pharmacy workflow management is operable to associate, at the processor, the user authentication information with a profile for the given user such that the user interface is configured at least partially based on the user profile of the given user.

A number of feature refinements and additional features are applicable to the eighth aspect. These feature refinements and additional features may be used individually or in any combination. As such, each of the following features that will be discussed may be, but are not required to be, used with any other feature combination of features of the eighth aspect. For instance, any of the features discussed with any of the foregoing aspects, and in particular the second aspect, may be used in conjunction with the seventh aspect without limitation.

A ninth aspect includes a system for the management of dose order records. The system includes an access terminal remote from and in operative communication with a dose management server. The dose management server may be operable to store a plurality of dose order records in a database of the dose order management server. Specifically, each dose order record is stored in corresponding relation to one or more dose order record data fields populated with dose order metadata regarding each dose order record such that at least one dose order record data field for a given dose order record corresponds to a dose order status indicative of a status of the given dose order record relative to a particular dose preparation step in a dose preparation protocol for the at least one dose order record. The system further includes a user interface provided at the remote access terminal. Furthermore, the dose management server may be operable to identify a first dose order record. Additionally, the dose management server may also be operable to modify the dose order status for the given order from a first value to a second value at least partially in response to an input received from a user in connection with the dose preparation step such that the dose preparation step is associated with an independent pharmacy workflow of the dose preparation protocol to prepare a dose corresponding to the at least one dose order record.

A number of feature refinements and additional features are applicable to the ninth aspect. These feature refinements and additional features may be used individually or in any combination. As such, each of the following features that will be discussed may be, but are not required to be, used with any other feature combination of features of the ninth aspect. For instance, any of the features discussed with any of the foregoing aspects, and in particular the third aspect, may be used in conjunction with the seventh aspect without limitation.

A tenth aspect includes, a system for use in communicating information pertaining to a pharmacy workspace queue in a pharmacy workflow management application. The system includes an access terminal remote from an in operative communication with a pharmacy workflow management application. The pharmacy workflow management application may be operable to access a plurality of dose order records corresponding to dose orders received at the server in response to a request for the plurality of dose order records by a given user. The system further includes a user interface provided at the remote access terminal for displaying the plurality of dose order records to the given user at the user interface such that the first dose order record and the second dose order record each appear in at least one distinct module of a common dashboard. Furthermore, the dashboard may include a plurality of the modules, which are configurable to communicate the status of at least one of the plurality of dose orders in the pharmacy workspace queue to the user such that the configuration is at least partially based on the user profile for the given user. Additionally, the server may be operable to receive, at a processor of the pharmacy workflow management application, user authentication information corresponding to the given user of the system such that the pharmacy workflow management application may be operable to associate, at the processor, the user authentication information with a profile for the given user. Accordingly, the user interface is configured at least partially based on the user profile for the given user.

A number of feature refinements and additional features are applicable to the tenth aspect. These feature refinements and additional features may be used individually or in any combination. As such, each of the following features that will be discussed may be, but are not required to be, used with any other feature combination of features of the tenth aspect. For instance, any of the features discussed with any of the foregoing aspects, and in particular the fourth aspect, may be used in conjunction with the seventh aspect without limitation.

An eleventh aspect includes a system for securing local network access of a pharmacy workflow management application. The system includes an access terminal remote from and in operative communication with a pharmacy workflow management application, over an operative communication link. In particular, the pharmacy workflow management application may be operable to store a plurality of dose order records corresponding to dose orders received at the pharmacy workflow management application. The terminal may be disposed within at least one network of a local areas network. The server may be operable to cryptographically manipulate data routed through the operative communication link such that the operative communication link provides a secure data connection between the terminal and the server. The system further includes a user interface provided at the remote access terminal for displaying the plurality of dose order records at the remote access terminal.

A number of feature refinements and additional features are applicable to the eleventh aspect. These feature refinements and additional features may be used individually or in any combination. As such, each of the following features that will be discussed may be, but are not required to be, used with any other feature combination of features of the eleventh aspect. For instance, any of the features discussed with any of the foregoing aspects, and in particular the fifth aspect, may be used in conjunction with the seventh aspect without limitation.

A twelfth aspect includes a system for use in upgrading a terminal of a local network system for management of medication dose orders. The system includes an access terminal remote from and in operative communication with a pharmacy workflow management application, over an operative communication link. The pharmacy workflow management application may be operable to store a workstation version in a database of the pharmacy workflow management application that stores a plurality of dose order records corresponding to dose orders received at the pharmacy workflow management application. Moreover, the pharmacy workflow management application may also be operable to identify a workstation version of the remote access terminal, which may be disposed within at least one network of a common enterprise network. Notably, the pharmacy workflow management application may be operable to compare the workstation version of the remote access terminal with the workstation version stored in the database, such that the pharmacy workflow management application is operable to determine whether the workstation version stored in the database supersedes the workstation version of the remote access terminal. The system further includes a user interface provided at the remote access terminal for presenting to a user an option to download the workstation version stored in the database to the terminal.

A number of feature refinements and additional features are applicable to the twelfth aspect. These feature refinements and additional features may be used individually or in any combination. As such, each of the following features that will be discussed may be, but are not required to be, used with any other feature combination of features of the twelfth aspect. For instance, any of the features discussed with any of the foregoing aspects, and in particular the sixth aspect, may be used in conjunction with the seventh aspect without limitation.

BRIEF DESCRIPTION OF THE DRAWINGS

Figure 8:
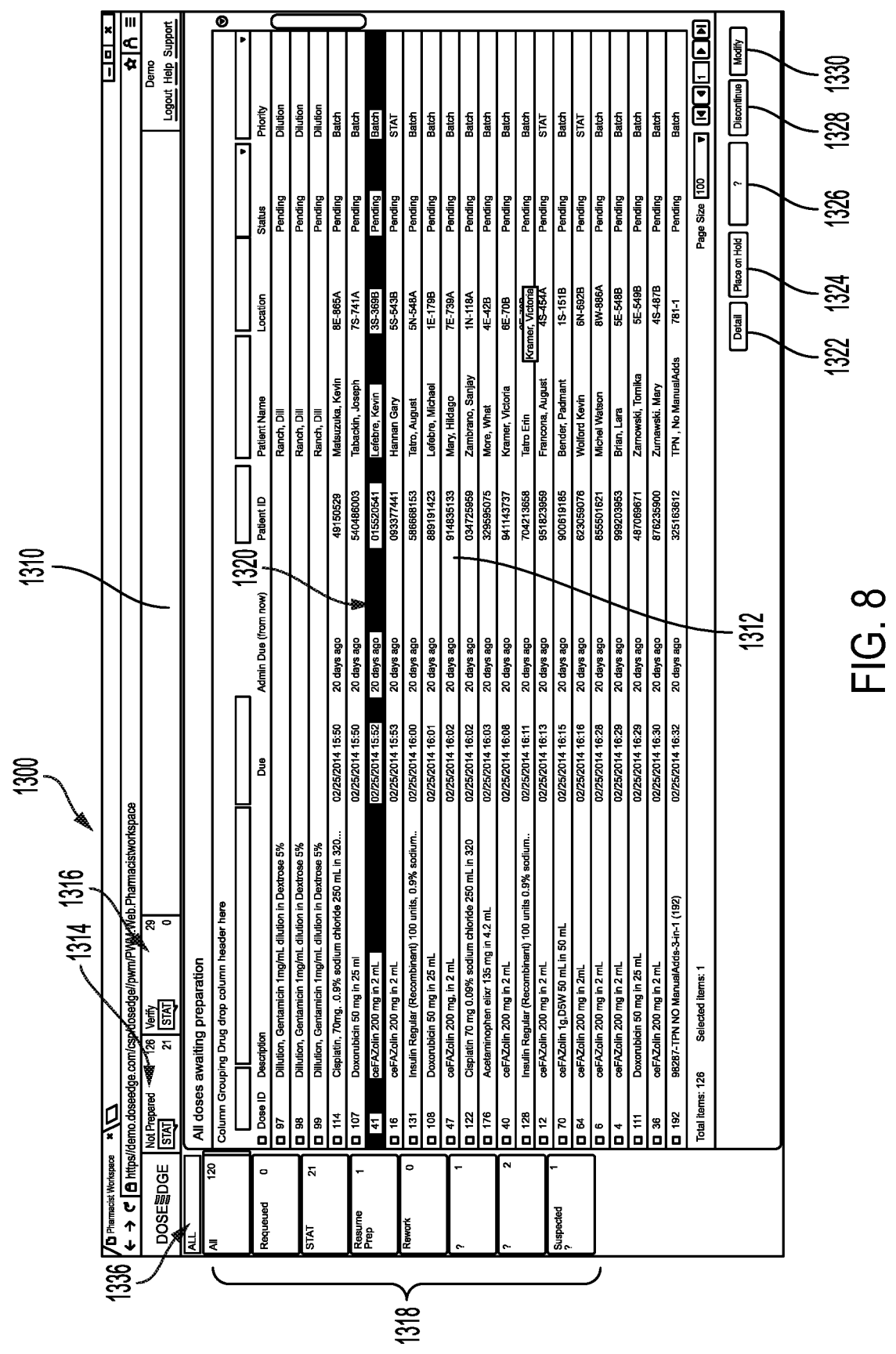

FIGS. 6-12 are views of an embodiment of a user interface of a pharmacy workflow management application that provides management of dose order records stored by the pharmacy workflow management application.

FIGS. 16-17 depict an embodiment of a user interface of the pharmacy workflow management application that may be presented to a pharmacist when reviewing a dose.

FIGS. 18, 19A, 19B, and 20 depict an embodiment of a user interface of a pharmacy workflow management application utilized by a pharmacist when reviewing a dose.

FIGS. 22-34 depict an embodiment of a user interface for use in formulary management.

FIGS. 35-46 depict an embodiment of a user interface for display of dose order record detail information for a dose order record.

FIG. 48 depicts an embodiment of a situation board display with customizable sorting options.

FIG. 49 depicts an embodiment of a plurality of scan events that are customizable with respect to modification of the dose status in relation to an independent pharmacy workflow operation in relation to preparation of a dose order record.

FIG. 50 depicts an embodiment of a user interface used to customize scan events in relation to the operation of a scan event relative to a dose order.

DETAILED DESCRIPTION

Figure 1:
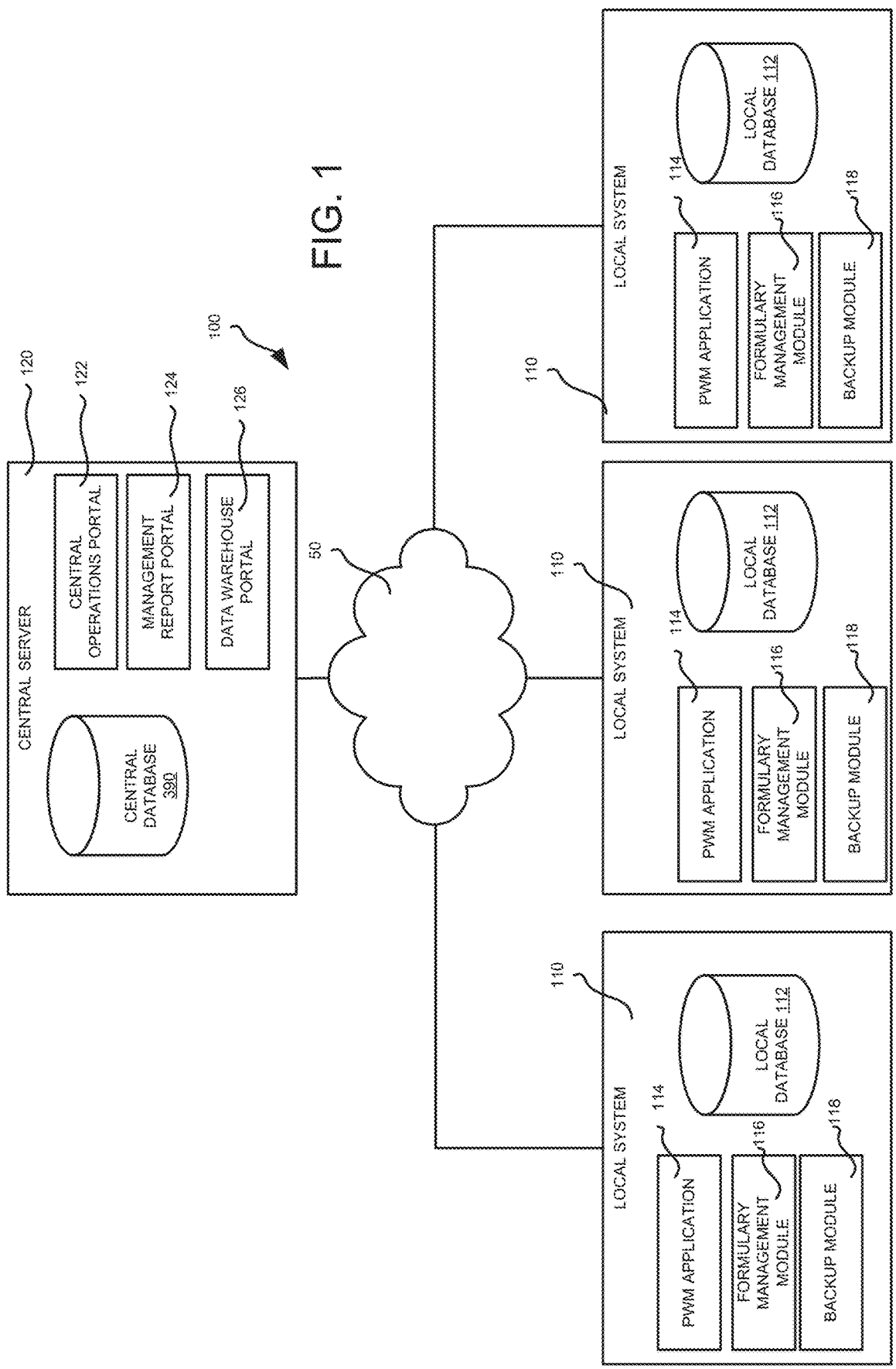
FIG. 1 is a schematic view of an embodiment of a system including a pharmacy workflow management application executed at a local system.

The following description is not intended to limit the invention to the forms disclosed herein. Consequently, variations and modifications commensurate with the following teachings, skill and knowledge of the relevant art, are within the scope of the present invention. The embodiments described herein are further intended to explain modes known of practicing the invention and to enable others skilled in the art to utilize the invention in such, or other embodiments and with various modifications required by the particular applications(s) or use(s) of the present invention.

The present disclosure contemplates a pharmacy workflow management application that may facilitate pharmacy workflow management in relation to preparation of one or more doses at a pharmacy, hospital, or other facility at which doses are prepared for administration to a patient. The pharmacy workflow management application may be executed at a local system (also referred to herein as a local node). The local node may correspond to a facility such as a hospital, pharmacy, or other facility capable of preparing a dose for administration to a patient. Pharmacy workflow management provided by the pharmacy workflow management application may include one or more activities within a pharmacy that may include management of a locally stored formulary, processing received medication dose orders at a pharmacy, creating corresponding dose order records for each received dose order, managing (e.g., viewing, sorting, prioritizing, etc.) dose order records, guiding a pharmacy technician in preparing the dose order medication, gathering information regarding the preparation of a dose to fulfill a dose order, reviewing the medication dose order, and/or tracking of medication dose order records in the pharmacy.

The local node may comprise one or more devices that may include hardware and/or software that may execute machine readable instructions stored as machine readable non-transitory data in a memory. The machine readable instructions, when executed by a processor may provide functionality related to the pharmacy workflow management application discussed herein. In this regard, the pharmacy workflow management application may include one or more processors operative to access machine-readable data stored in a storage medium (i.e., a memory) that provide instructions to the one or more processors for execution to provide the functionality described herein.

The local node executing the pharmacy workflow management application may be in operative communication with a central server. The central server may provide support services to the local node to support the pharmacy workflow management application and/or may provide additional services such as data backup, report generation, or access to data sets stored at the central server.

The present disclosure includes a description of an embodiment of dose order processing that may be performed by the pharmacy workflow management application. This dose order processing may include receiving dose orders and generating dose order records that are in turn stored by the application. Also described herein are embodiments that provide functionality related to the management of the dose order records within the pharmacy. The management functionality of the pharmacy workflow management application may include, but is not limited to, viewing, sorting, modifying, prioritizing, organizing, or otherwise managing dose order records. The pharmacy workflow management application may also distribute, provide, or assign dose order records to workstations for preparation of a dose (i.e., a physical dose form capable of being administered to a patient) that corresponds to a dose order record. The pharmacy workflow management application may provide a protocol in relation to a dose order record to assist a user in preparing a dose associated with a dose order record. During the preparation, dose order metadata regarding the dose prepared in connection with the dose order record may be recorded or acquired. In connection with the preparation of the dose, embodiments of functionality related to remote pharmacy verification are also described. Furthermore, features related to the ability to utilize the application to track dose orders in the pharmacy (e.g., with respect to physical location and/or processing status in or other relevant status indications) are described.

With initial reference to FIG. 1, a system 100 is depicted that includes a plurality of local systems 110. The local systems 110 may each comprise a local node in the system 100. The local systems 110 may each execute a pharmacy workflow management application 114. For instance, each local system 110 may include at least one local device executing a client application for providing functions related to the pharmacy workflow management application. As shown in FIG. 1, a plurality of local systems 110 may be provided that are each in operative communication with a central server 120. For example, the local systems 110 may be in operative communication the central server 120 by way of a wide area network 50 (e.g., the Internet).

Each local system 110 may be a healthcare facility such as a hospital, pharmacy, outpatient clinic, or the like, that prepares doses for administration to a patient. The respective pharmacy workflow management application 114 at each local system 110 may be operative to generate and/or capture medical information that may be provided to the central server 120 by way of the wide area network 50. As will come to be appreciated from the discussion below in relation to the pharmacy workflow management application 114, the medical information may include medication dose order data that may include metadata regarding the dose order record and/or dose. The pharmacy workflow management application 114 each local system 110 may allow for the pharmacy workflow management functions described in greater detail below. In any regard, any or all data generated by the pharmacy workflow management application may be provided to the central server 120. In this regard, central server 120 may provide for data collection and/or data backup services in relation to the local systems 110 as well as other functions described in greater detail below.

Accordingly, in at least one embodiment the local systems 110 may comprise unaffiliated and discrete healthcare facilities capable of preparing medication doses for administration to patients. The central server 120 may be hosted by another discrete and unaffiliated third-party that may be separate from any of entities of the local systems 110. For instance, the central server 120 may be hosted and/or executed by an application provider that provides one or more client applications for execution by the local systems 110 to facilitate the pharmacy workflow management application 114. Specifically, the central server 120 may be executed or hosted by an application provider that provides the pharmacy workflow management application each local system 110.

The central server 120 may provide, among other resources, a central operations portal 122, a management report portal 124, and/or a data warehouse portal 126. Generally, the central operations portal 122 may provide, among other resources, data backup services to the pharmacy workflow management application 114 of each local system 110. The management report portal 124 may allow a user accessing this resource to generate management reports that may relate to collectives of local systems 110 or individual local systems 110. For example, one or more local systems 110 may belong to an organization such that the data corresponding to the collective local systems 110 comprising the organization may be aggregated (e.g., at the central server 120). In this regard, organizational users may be defined that are members of local systems 110 belonging to an organization such that the organizational users may be able to access data related to any of the local systems 110 belonging to the organization. The management reports may include data in relation to the medical information received from one or more local systems 110.

Furthermore, a data warehouse portal 126 may be provided that may provide an aggregated source of medical information from local systems 110 and/or other data sources. The data warehouse portal 126 may provide functionality related to data aggregation and/or data formatting that allows multiple sources of medical information to be aggregated for purposes of data analytics the like. In this regard, the data warehouse portal 126 may provide functionality resources as described in U.S. Provisional Patent Application No. 62/019,227 entitled "MANAGED MEDICAL INFORMATION EXCHANGE" filed on Jun. 30, 2014, which is co-owned with the present application and is incorporated by reference herein in its entirety.

A local system 110 may include a local database 112 for storage of information. As may be appreciated, the local database 112 may in fact include a collection of one or more databases collectively referred to as the local database 112. In an implementation of the present invention, the local system 110 may include a server that facilitates access to the database 112. The database may store data related to the current in process work and/or store archival data related to prior work completed at the pharmacy. The local database 112 may be a high-performance, highly scalable and SQL-compliant object database. In this regard, the database may scale easily to handle thousands of simultaneous users and potentially terabytes of data.

In addition to storing information related to pharmacy work (i.e., dose order records), the database 112 may include information in a variety of contexts including information related to formulary information, administrative information, or other information related to the pharmacy workflow management application 114 at the local system 110. In any regard, the local system 110 may execute a number of services (e.g., provided by modules executed by a processor). For instance, a data backup module may be provided that provides a rule-base approach to data backup from the local system 110 to the central server 120. The data backup module may define the interval at which the local system 110 provides backup data to the central server 120 and/or may dictate what information is provided to the central server. The backup module may also provide an administrator (e.g., at the central server or the local system 110) with information relating to the success or failure of data backup operations, system slowdowns, and the like. For instance, the backup module may facilitate selective backup of the local database 112 as described in U.S. Patent Application No. 62/019,227 incorporated by reference above.

Each local system 110 may also include a formulary management module 116 that allows a pharmacy formulary to be maintained. As such, each local system 110 may have a formulary comprising a plurality formulary records stored at the local database 112. As may be appreciated, from time to time, formulary records within the formulary may need to be added, removed, or modified. In this regard, formulary management module 116 may provide a formulary management tool for use in maintaining the formulary (i.e., the formulary records comprising the formulary). The formulary records comprising the formulary may include records belonging to a number of categories of formulary records. For instance, corresponding records may be stored in relation to administration routes, drug categories, drugs, materials, product groups, and/or products. Collectively, these records may provide data to the pharmacy workflow management application 114 for use in the preparation or management of a dose order record. As discussed herein, the formulary management module 116 may provide functionality related to the management of the formulary records comprising the formulary.

Figure 6:
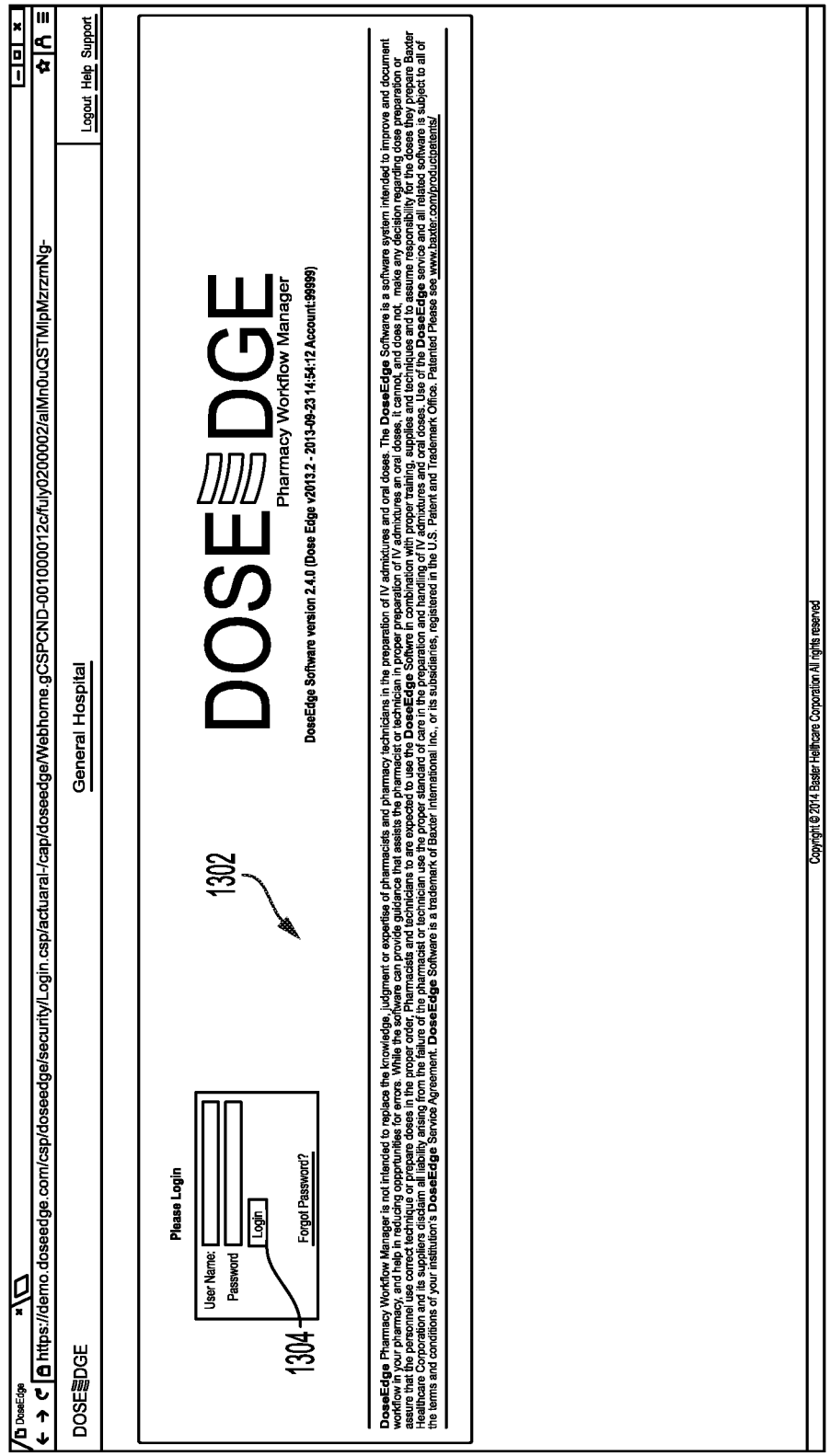

With brief reference to FIG. 6, an embodiment of a user interface screen for an embodiment of a pharmacy workflow management application 1300 is depicted. The application 1300 may be a web-based management tool that may be presented to a user in a web browser or the like. For instance, a user may navigate to a particular web address and be presented with a login screen 1302 as shown in FIG. 6. The login screen 1302 may include an authentication field 1304 that may require, for example, a user name and password be entered by the user to facilitate confirmation of a user's authorization to utilize the application 1300 and/or access various functionality of the application 1300. As may be appreciated, different user authorization levels may exist such that when a user logs in utilizing the authentication field 1304, various rights associated with the application 1300 may be allowed or blocked based upon the user credentials provided and the associated authorization level associated therewith.

Additionally, the provision of user authentication information at the login screen 1302 may allow for a user profile for a given user associated with the user authentication information to be identified. In this regard, the user profile may be associated with modifiable characteristics of the user interface of the application 1300. In this regard, customizable or configurable elements of user interfaces described herein may be associated with a user profile such that the default configuration may be defined for a user profile. Additionally or alternatively, user profile may be based upon the last status of customizable or configurable characteristics of user interface. For example, as will be discussed in more detail below, a user profile may indicate the configuration of one or more collapsible areas, which may be configured to hide information (i.e., the user profile may indicate which of the collapsible areas are operable to hide information upon a given user's initial system login). Further still, other user interface elements may be dictated based on a user profile. In any regard and as will be described in greater detail below, various aspects or characteristics of the user interface of the application 1300 may be at least partially based upon a user profile associated with user authentication information provided to access the application 1300.

Figure 7:
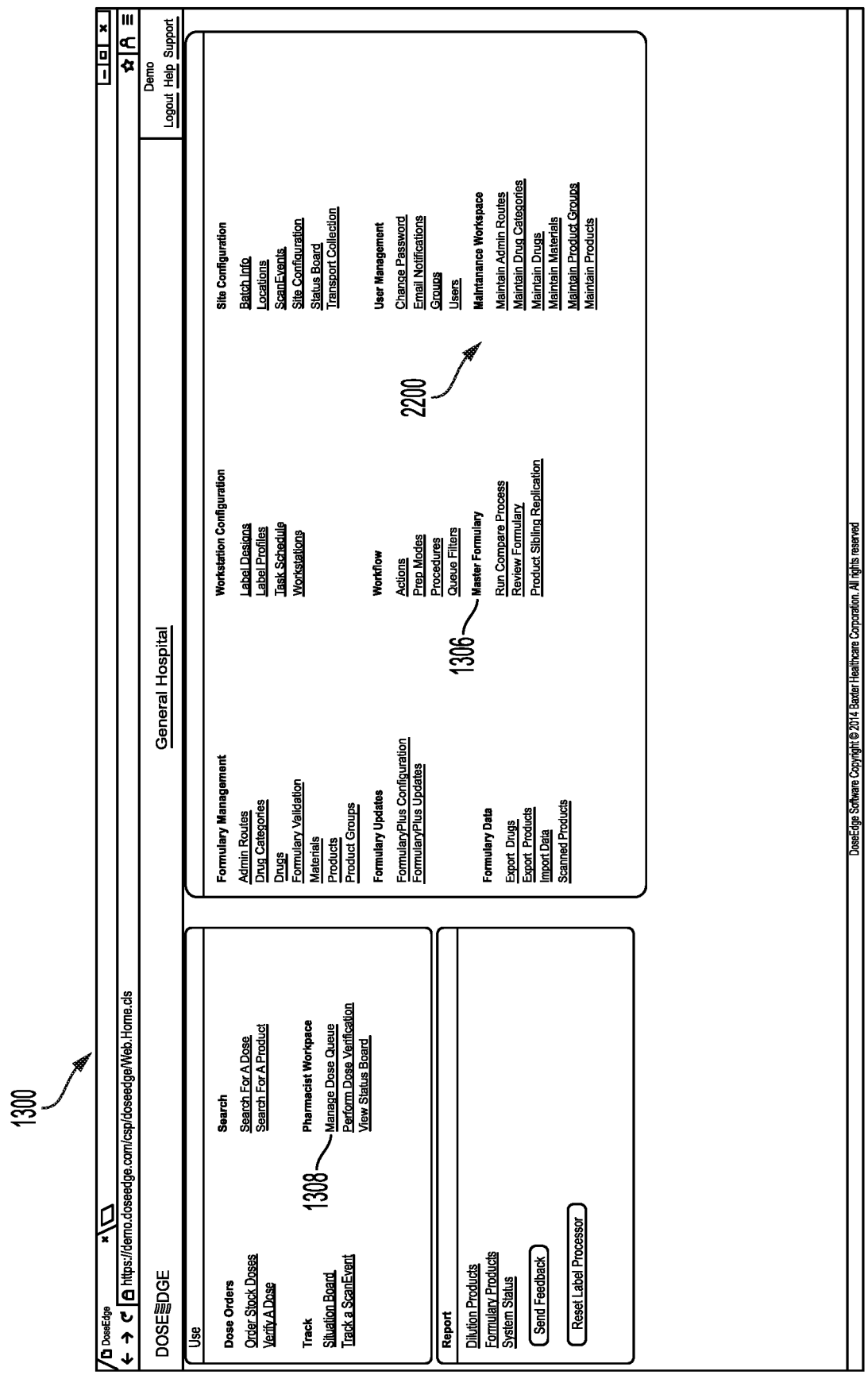

With further reference to FIG. 7, upon successfully authenticating the user, a navigation screen 1306 may be provided to the user. The navigation screen 1306 may include a plurality of links associated with various functions of the application 1300. For example, the navigation screen 1306 may facilitate access to a dose order record listing for review or management of dose orders as described in greater detail below. Also, the navigation screen 1306 may facilitate access to verification screens typically used by a pharmacist to review and verify doses that have been prepared in the pharmacy by a pharmacy technician, as are also described in greater detail below. The navigation screen 1306 may also have a number of formulary management links 2200. Selection of any one of the formulary management likes 2200 may direct a user to a formulary management workspace 2210 as shown in FIG. 22.

The formulary management workspace 2210 may include a number of navigational tabs 2212. The navigation tabs 2212 may generally correspond to different categories of formulary records and/or formulary management functions associated with the formulary records. In this regard, selection of one of the navigation tabs 2212 may result in the workspace 2210 displaying a record listing 2214 that contains formulary records associated with the corresponding categories of formulary records associated with the selected navigation tab 2212. Additionally, the workspace 2210 may include a record detail portion 2216.

Figure 22:
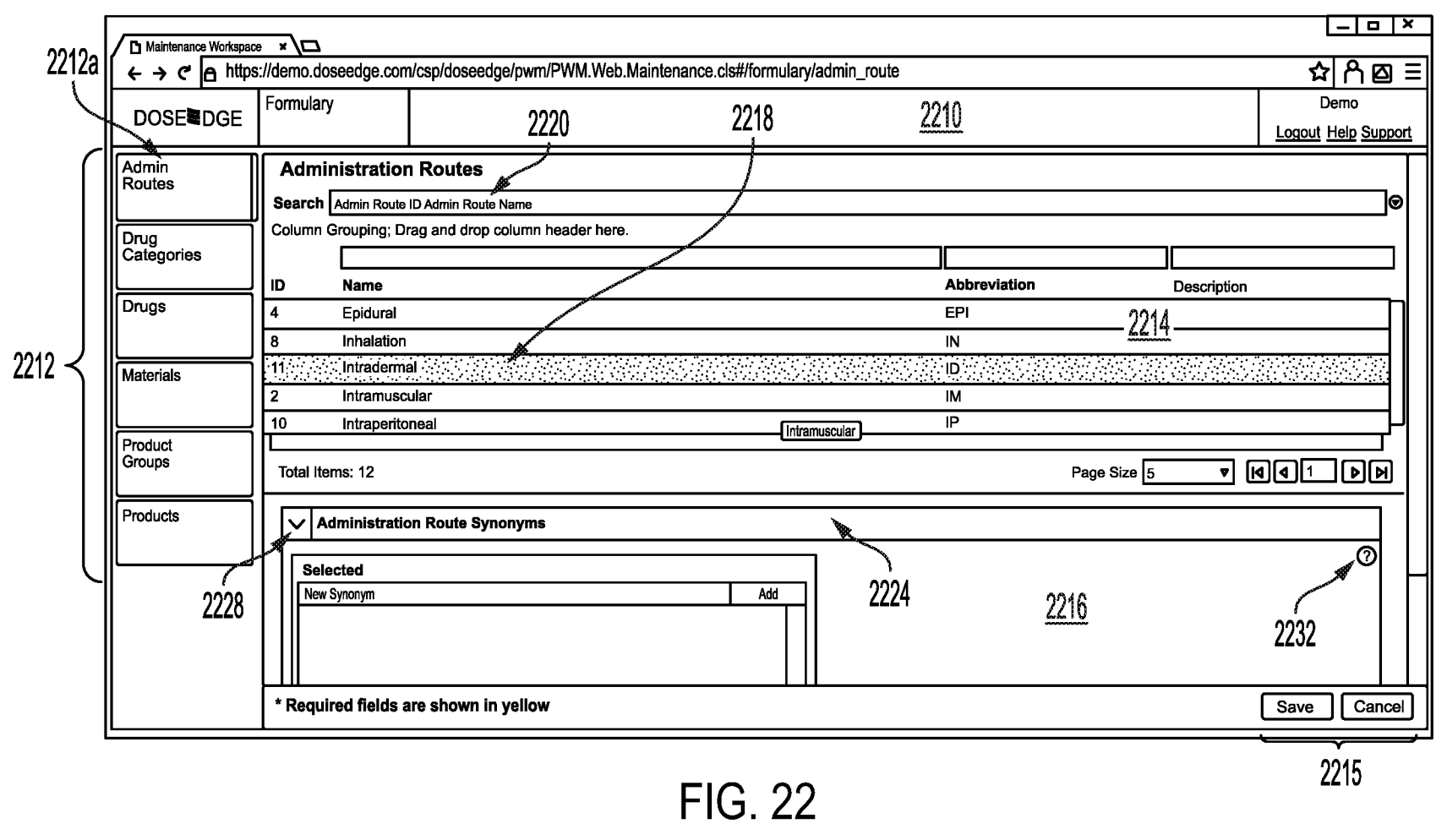

Accordingly, as depicted in FIG. 22, the navigation tab 2212 corresponding with "Administration Routes" 2212*a* has been selected. In turn, formulary records associated with the category of administration routes are displayed in the record listing 2214. Selection of a given record 2218 from the record listing 2214 may display details regarding the record 2218 in a record detail portion 2216 of the workspace 2210. As will be appreciated from the discussion that follows, the record detail portion 2216 may include specific record detail fields. Notably, each of the specific records details may be altered without deleting the specific record detail or adding a new record detail. That is, the record details may be modified "in-line."

As depicted in FIG. 22, the record detail fields for the administration routes 2212*a* category may include an administration routes synonyms field 2224. Each specific record detail field may comprise a collapsible area that is selectively collapsible or expandable by the user to hide or display the data contained within the given record data field. For example, the information associated with administration route synonyms data field 2224, discussed in greater detail below, may be selectively collapsed or expanded by activating collapsible area button 2228. Each specific record detail field may also include a help icon, such as help icon 2232 of administration route synonyms 2224. The help icon may be operable to display context-specific information associated with information of each record detail portion 2216, respectively. It will be appreciated that each records detail portion 2216 of the various disclosed categories of navigation tab 2212 may include a collapsible area and help icon in an analogous manner.

Additionally, the record listing 2214 may be manipulated such that the column headings, record groupings, or other configurable table elements are modified in accordance with the discussion presented below in relation to FIGS. 8-12 such as resizing, sorting, or filtering the columns of record listing 2214.

In this regard, various elements of the user interface comprising the workspace 2210 may be modifiable, configurable, or customizable by the user. In turn, default configuration in relation to these user interface components may be associated with the user profile. In turn, upon accessing the workspace 2210, a given user associated with the user profile may be presented a user interface having the user interface elements defined based on the user profile. Again, the user profile may have default configurations selectable by the user, or the user profile may correspond to the configuration last displayed to the user. In any regard, the user profile may span user access sessions such that a subsequent session is at least partially based on a previous session or a default configuration profile associated with the user profile.

The workspace 2210 may further include a search area 2220. Upon entry of a query into the search area 2220, the record listing 2214 may be filtered such that a filtered table result may be displayed to the user. In this regard, upon entry of a query into the search area 2220, associations between the query provided in the search area 2220 and the plurality of formulary records displayed in the record listing 2214 may be identified. In turn, the filtered table presented to the user may be at least partially based upon the associations between the query provided in the search area 2220 and the records listing 2214 such that the filtered results correspond with record listings 2214 having data matching the query. The workspace 2210 may also include a plurality of maintenance operations buttons 2215 that are displayable with each respective navigation tab 2212 such that the maintenance operations buttons remain visible while the information of each category is scrolled. The maintenance operation button 2215 may include a button to create a new record for a given category of records, a button to delete a record, a button to modify a record, a button to save a modified record, a button to cancel modifications made to a record, a button to create a new record based on a selected record, or other appropriate button to take a specific action with respect to a record.

Returning to the discussion of FIG. 22, upon selection of a record 2218 corresponding to the administration route category 2212a, the record detail portion 2216 may include an administration route synonyms field 2224. A user may provide synonyms related to the selected administration route record 2218 by providing this information in the administration routes synonyms field 2224.

Figure 23:
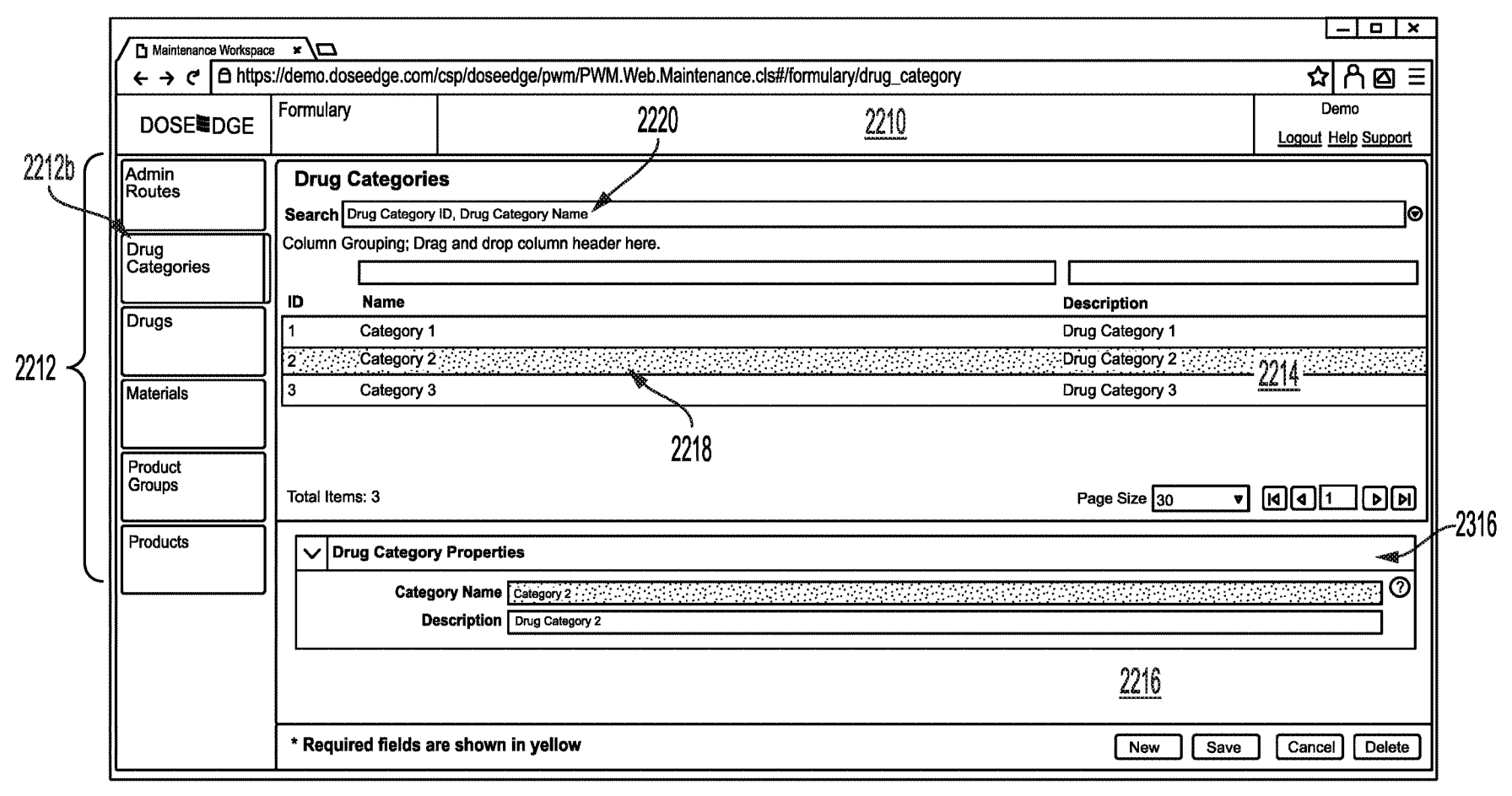

With further reference to FIG. 23, the "Drug Categories" tab 2212b is selected. In turn, formulary records associated with the drug categories category of formulary records are displayed in the record listing 2214. Upon selection of a given one of the records 2218, details regarding the record are displayed in the record detail portion 2216. The record detail portion 2216 shown in FIG. 23 that corresponds to the formulary records associated with the category of drug categories 2212b may include a field related to drug category properties 2316. In turn, user may provide details regarding a category name and category description related to the selected one of the drug categories selected from the record listing 2214.

Figure 24:
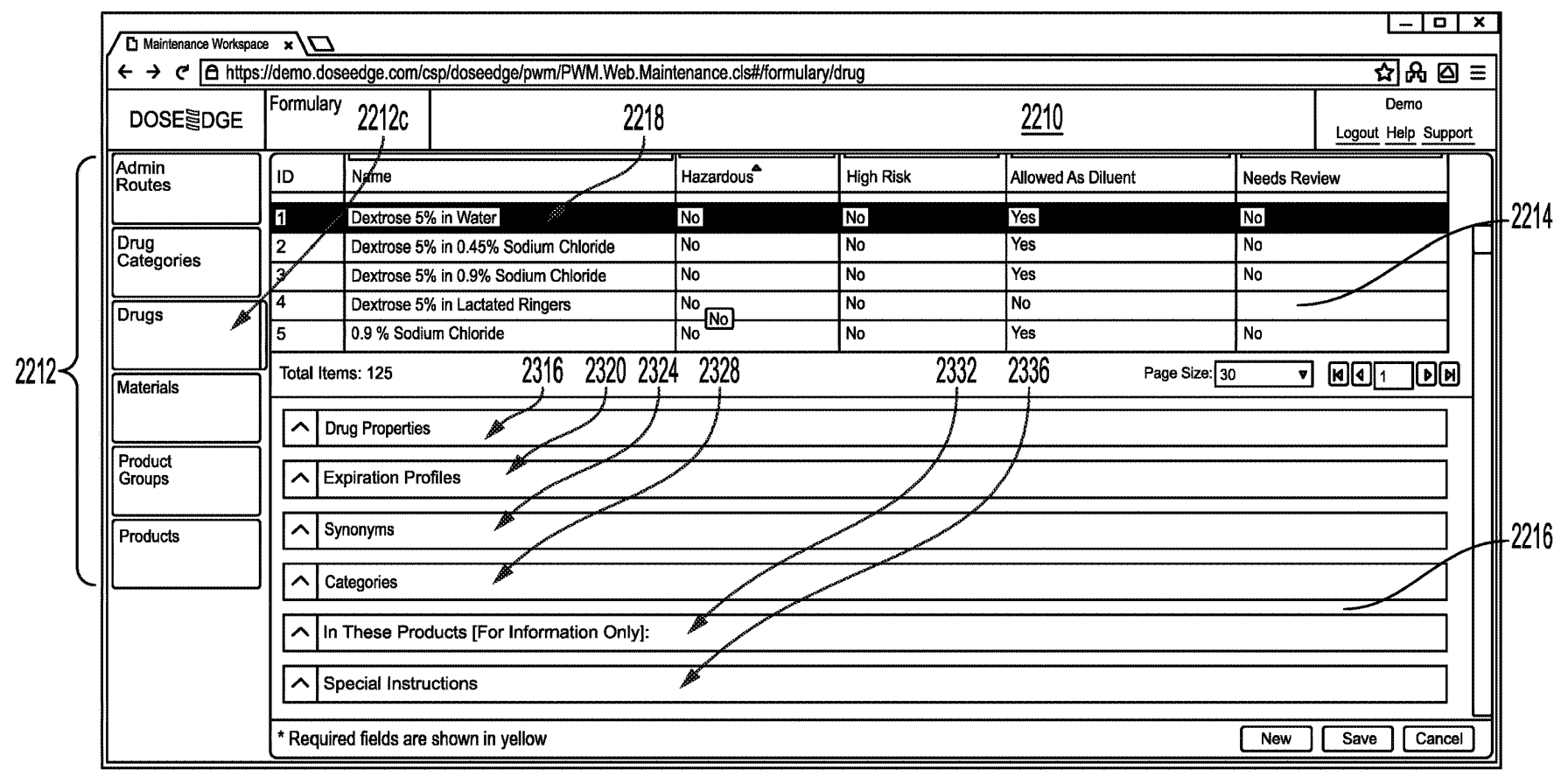

With further reference to FIG. 24, a "Drugs" tab 2212c is selected. In turn, formulary records associated with the category of drugs are displayed in the record listing 2214. Upon selection of a given one of the records 2218, details regarding the record are displayed in the record detail portion 2216. The record detail portion 2216 shown in FIG. 24 that corresponds to the drug formulary record category may include fields related to drug properties 2316, expiration profiles 2320, synonyms 2324, categories 2328, contained product information 2332, and special instructions for the selected record 2336. As may be appreciated in FIG. 24, each of these fields are collapsed. With further reference to FIGS. 25-28, respective ones of these fields are shown in an expanded configuration.

Figure 25:
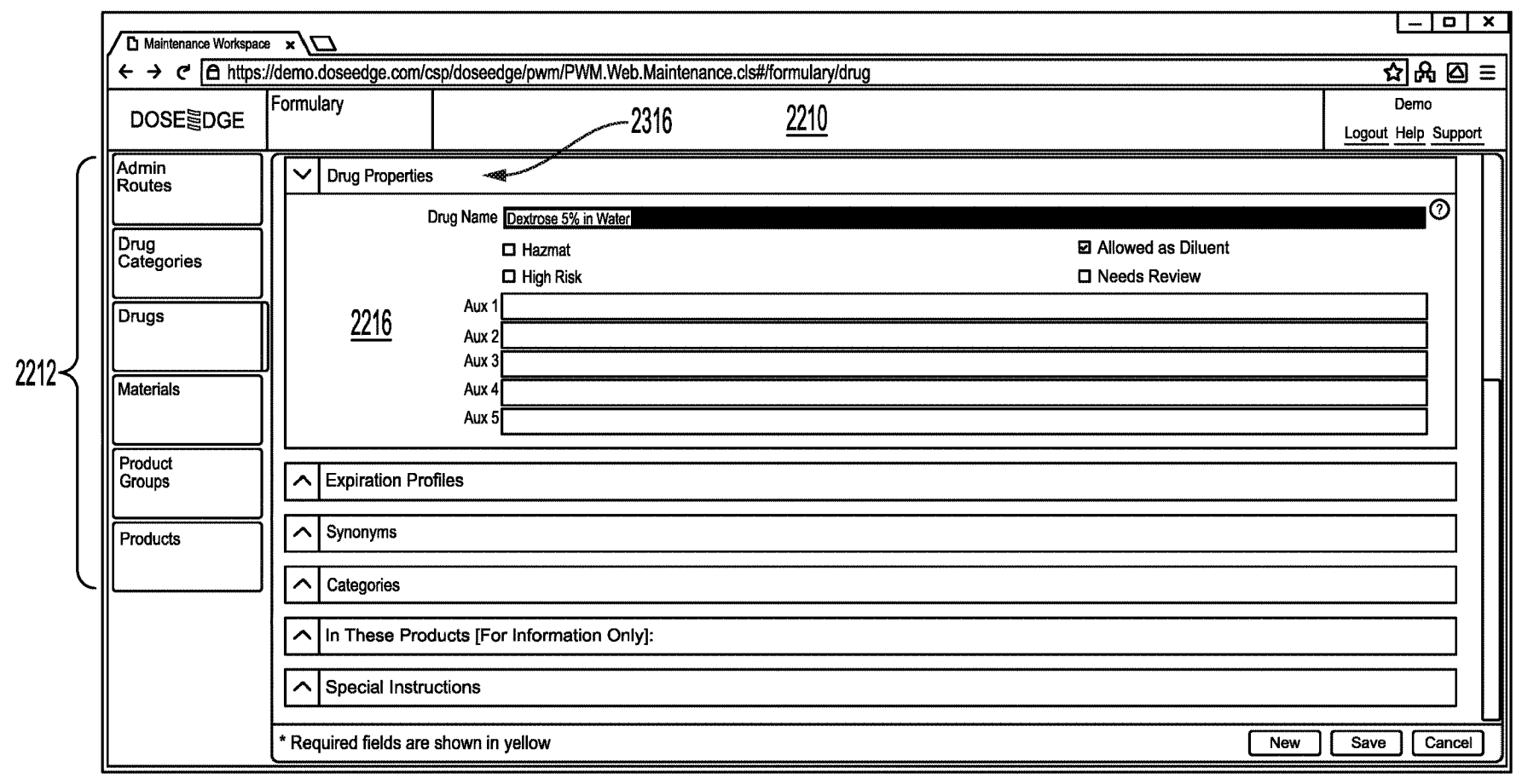

For instance, in FIG. 25, the drug properties field 2316 has been expanded. In turn, a user may provide a drug name for the selected record 2218 in the record listing 2214 (e.g., shown in FIG. 24). Additionally, user may indicate whether the selected drug corresponds with a hazmat drug, a high risk drug, whether the drug is allowed as a diluent, or whether the drug requires review. Furthermore, auxiliary data fields are provided for additional information regarding the selected record 2218 to be provided.

Figure 26:
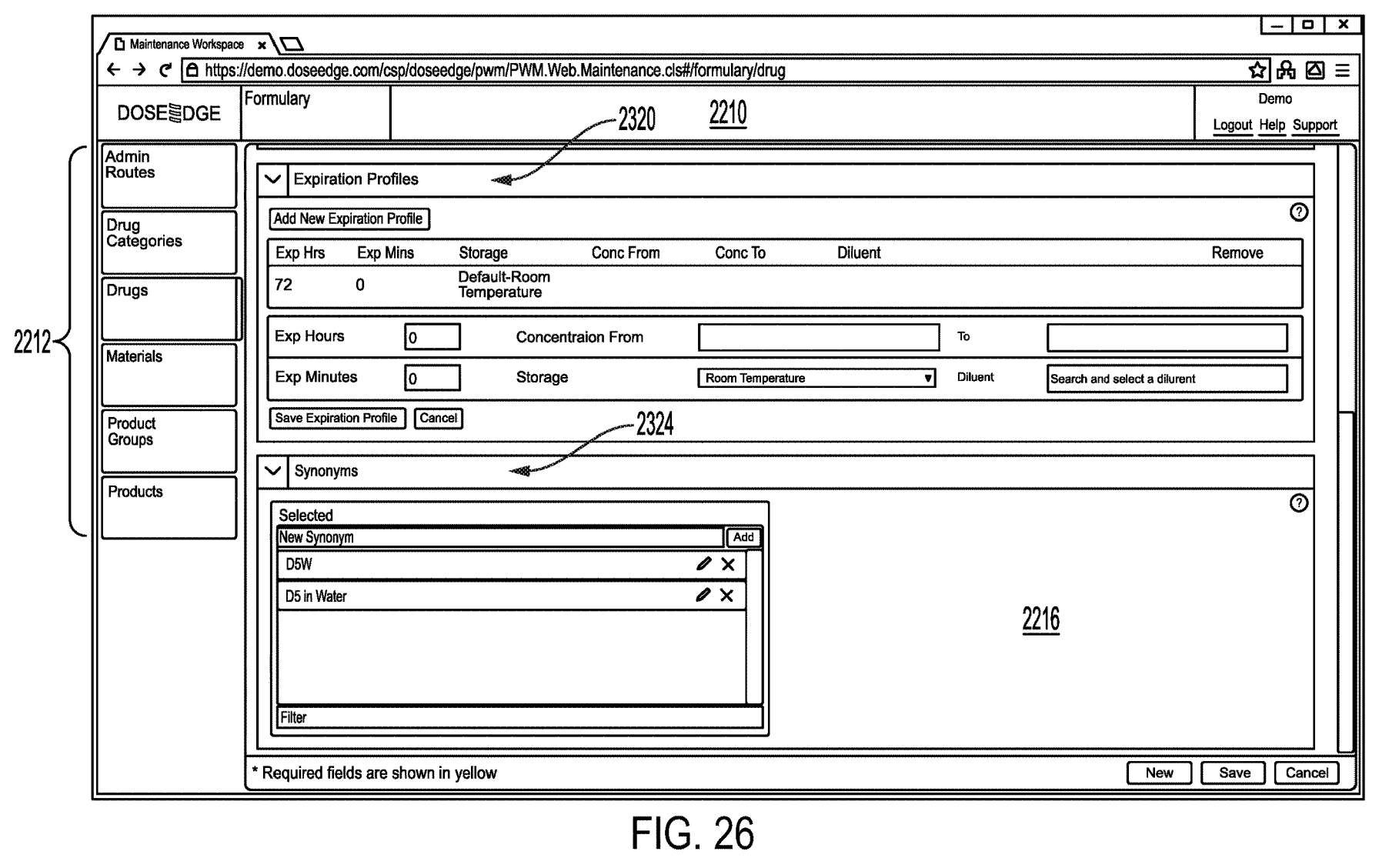

FIG. 26 depicts the expanded expiration profiles field 2320 and synonyms field 2324. In the expiration profiles field 2320, expiration profiles regarding the selected drug formulary record 2218 may be provided. The expiration profile may define a time after which a drug expires for different circumstances. For example, as shown in FIG. 26, the selected drug record may have expiration profile of 72 hours if the drug is maintained at room temperature. Further expiration profiles may be defined relative to variables such as the nature of the storage of the drug, the diluent used, the concentration of the drug, or other relevant characteristics that affect expiration profile of a drug. FIG. 26 also depicts a synonyms field 2324 in expanded form. In the synonyms field 2324, user may define synonyms for the selected drug record.

Figure 27:
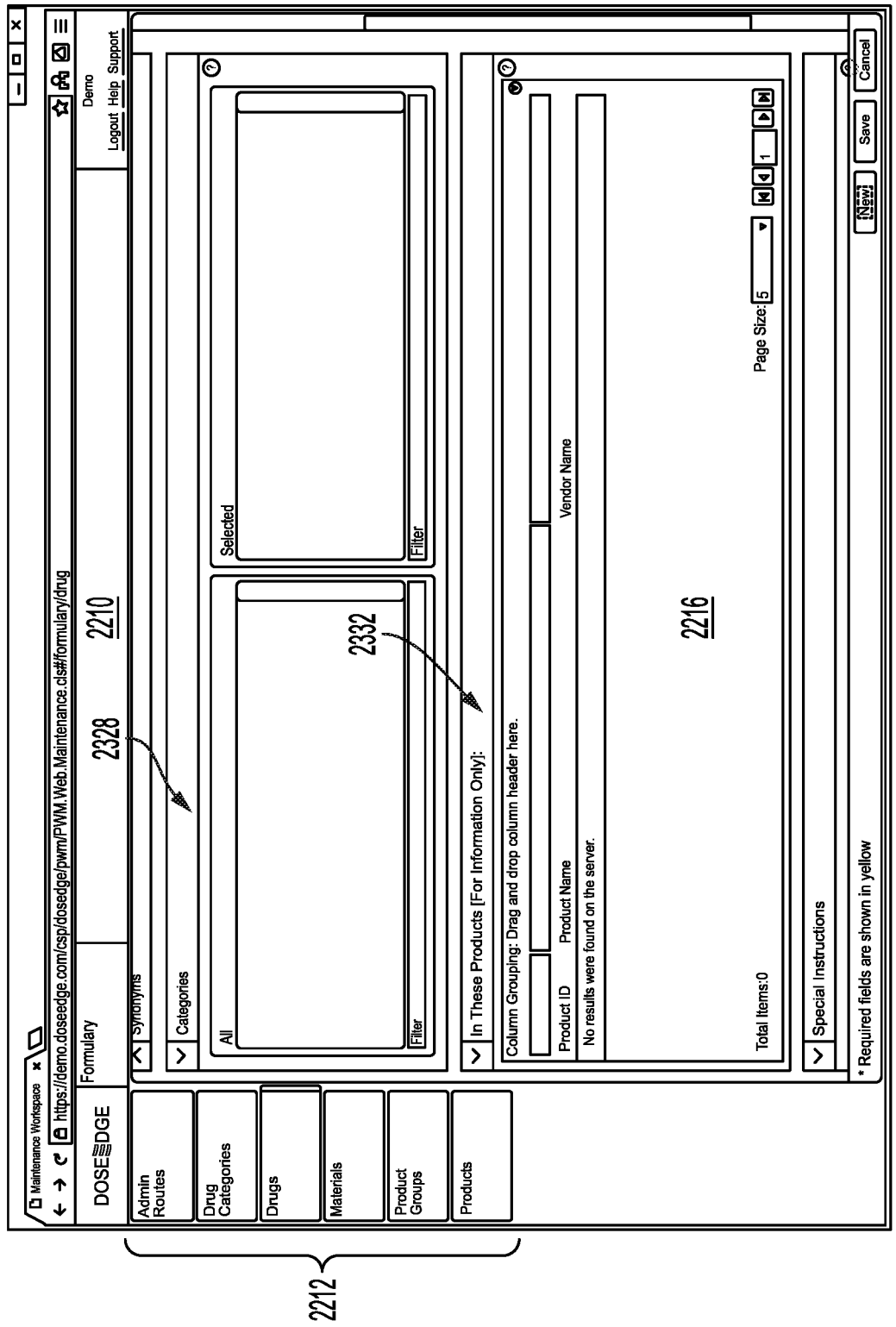
Figure 28:
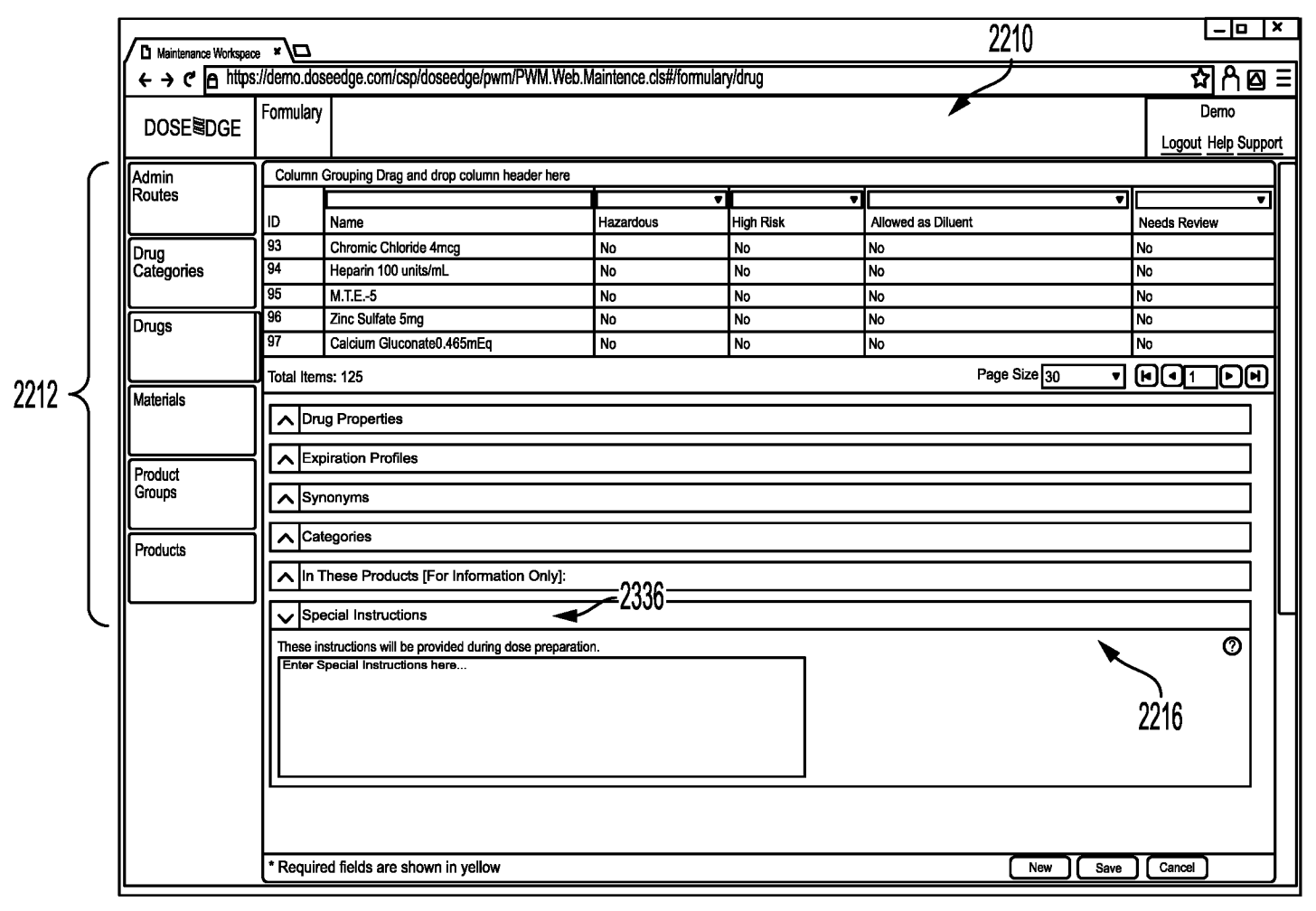

FIG. 27 depicts the expanded categories field 2328. In this regard, a user may provide a selection of drug categories (e.g., from the listing of drug categories displayed in FIG. 23) to which the selected drug record 2218 is associated. Additionally, the contained product information field 2332 is expanded in FIG. 27. The contained product field 2332 may allow for a user to define products (e.g., from a listing of product records contained in the formulary as described in greater detail below) that contain the drug corresponding to the selected drug record 2218. With further reference to FIG. 28, the special instructions field 2336 is also expanded. In this regard, user may provide special instructions with respect to the selected drug record 2218.

Figure 29:
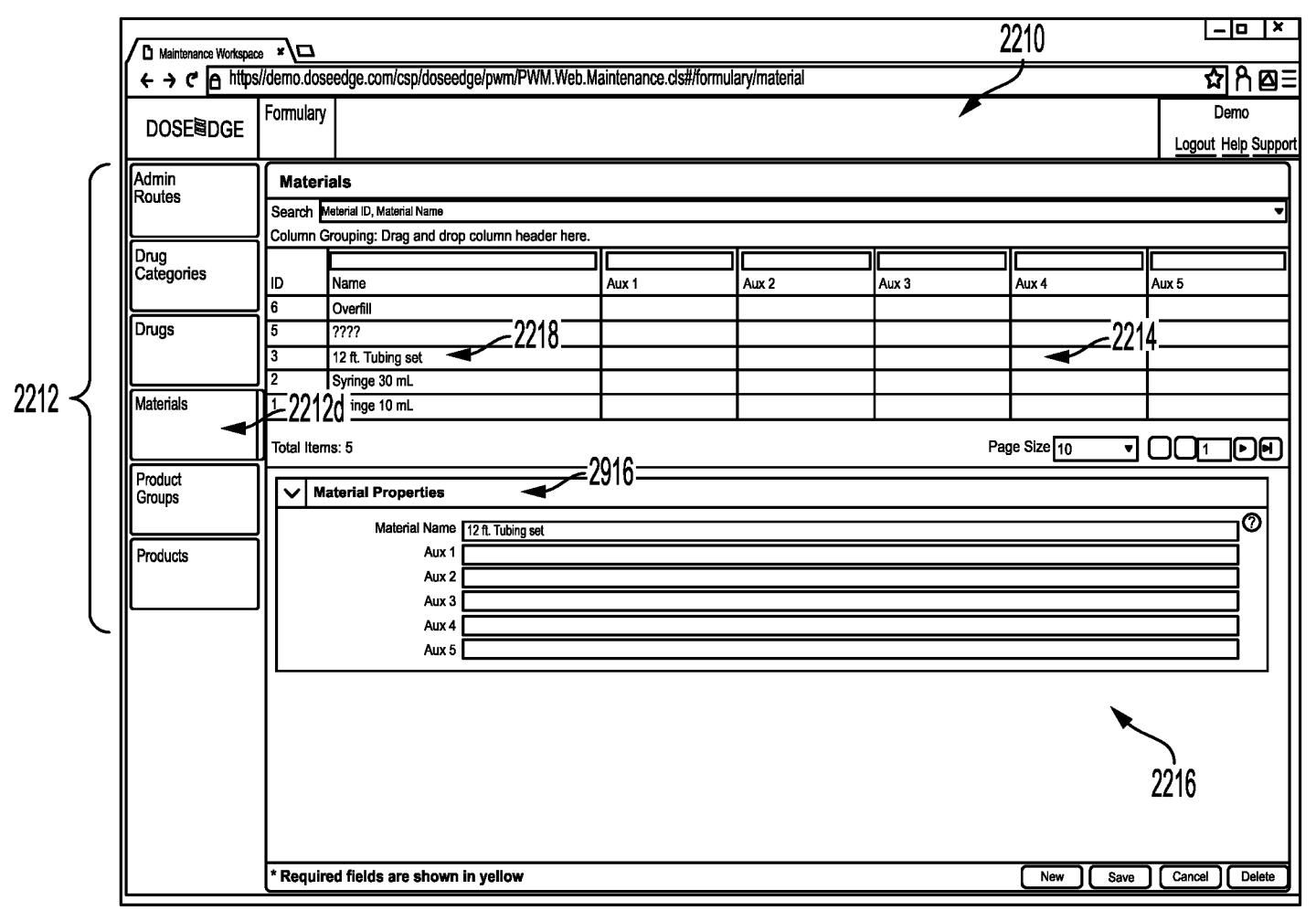

FIG. 29 depicts the workspace 2210 when the "Materials" tab 2212d is selected. In turn, formulary records in the materials category are displayed in the record listing 2214. Upon selection of a selected record 2218, the record detail portion 2216 may include an expandable and collapsible material properties field 2916. The materials properties field 2916 may allow for a user to define a material name and may include various auxiliary property information regarding the selected material record 2218.

Figure 30:
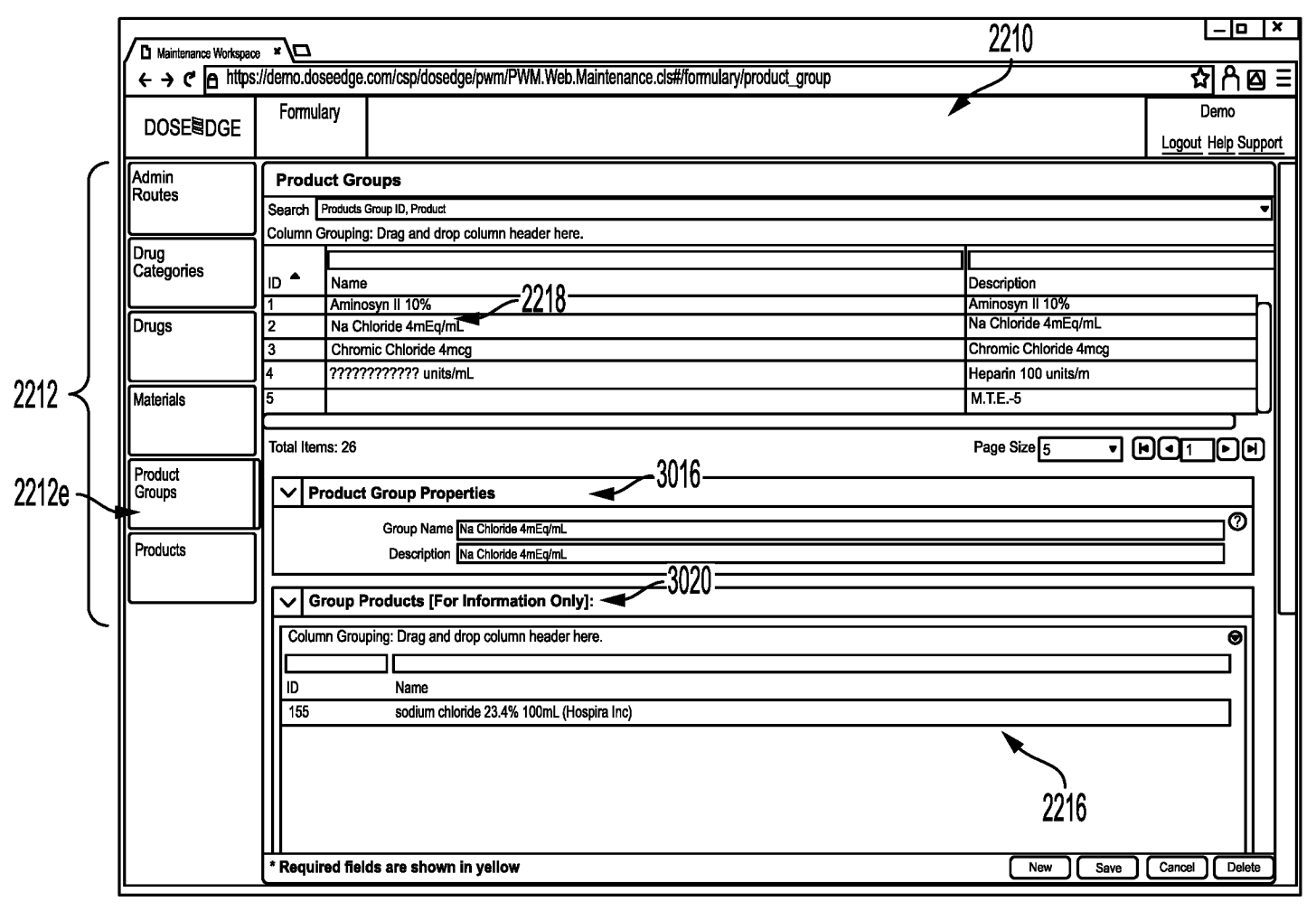

FIG. 30 depicts the workspace 2210 when the "Product Groups" tab 2212e is selected. Upon selection of the product groups 2212e navigation tab 2212, formulary records associated with the product groups category are displayed in the record listing 2214. Upon selection of a given record 2218, the record detail portion 2216 may allow for modification of details regarding the record in a product group properties field 3016 and a group products field 3020. The product group properties field 3016 may allow for a group name and description to be provided to the selected group record 2218. The group products field 3020 may allow for product records (e.g., as described below) to be associated with the selected product group 2218.

Figure 31:
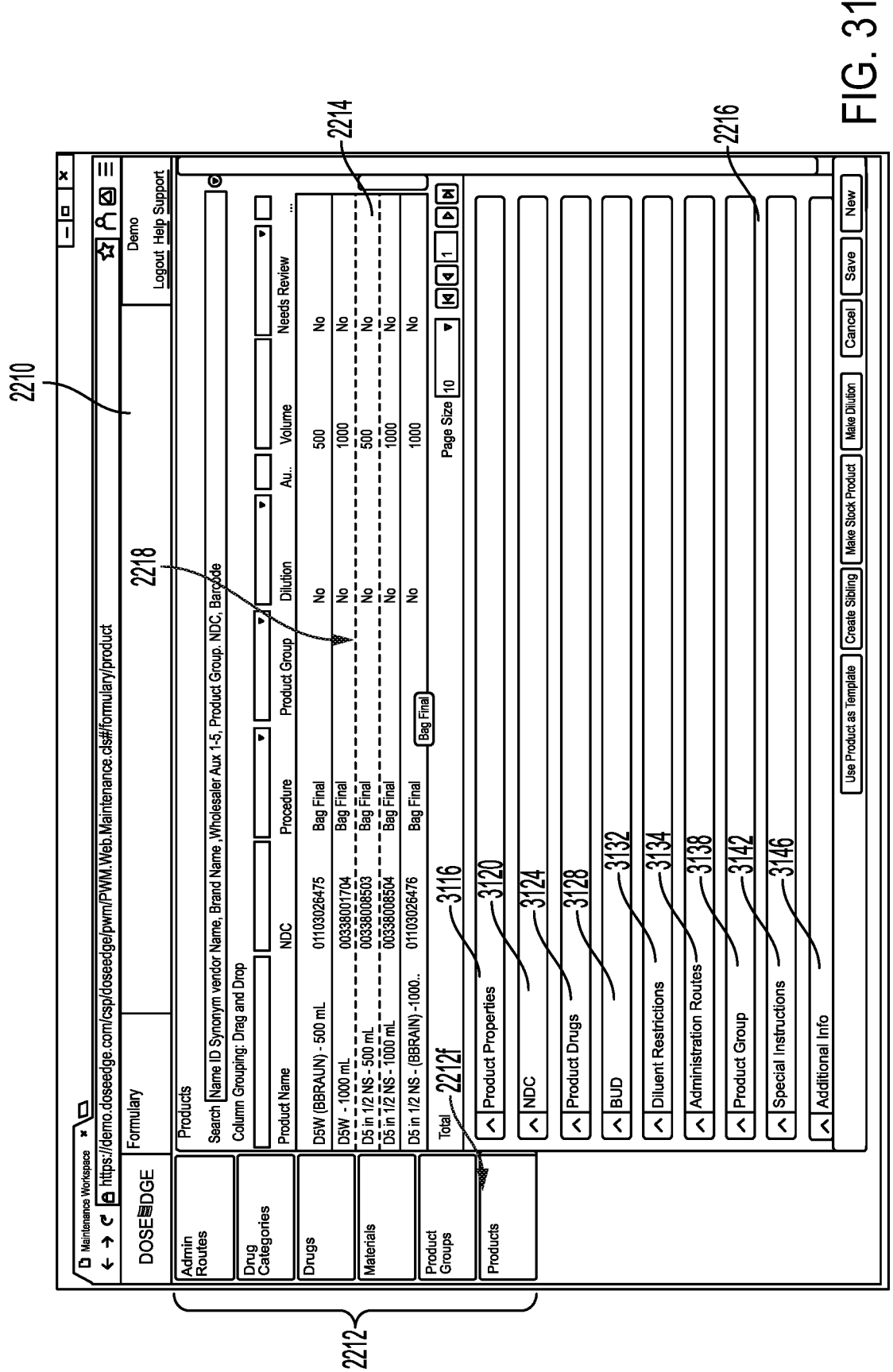
Figure 32:
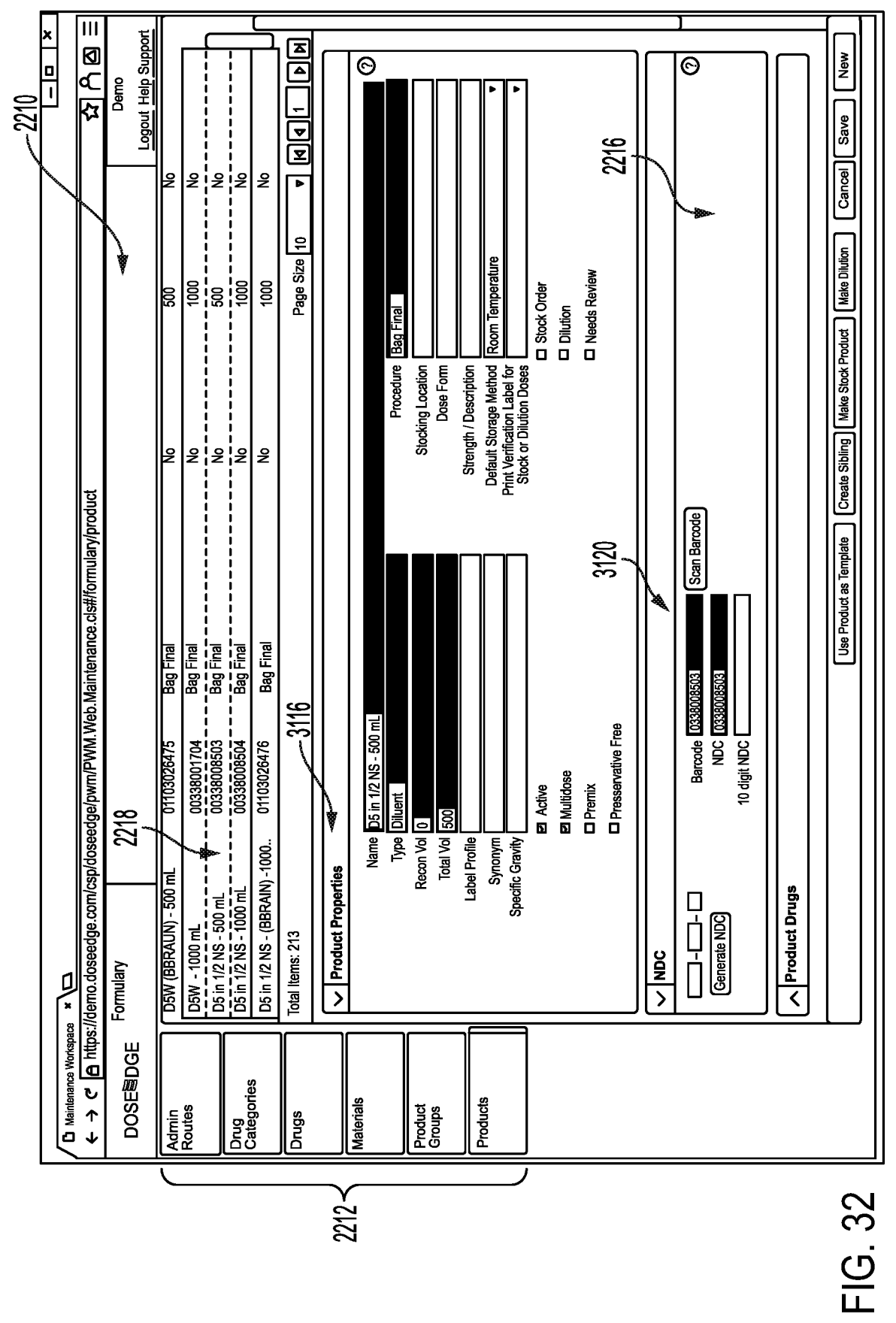
Figure 33:
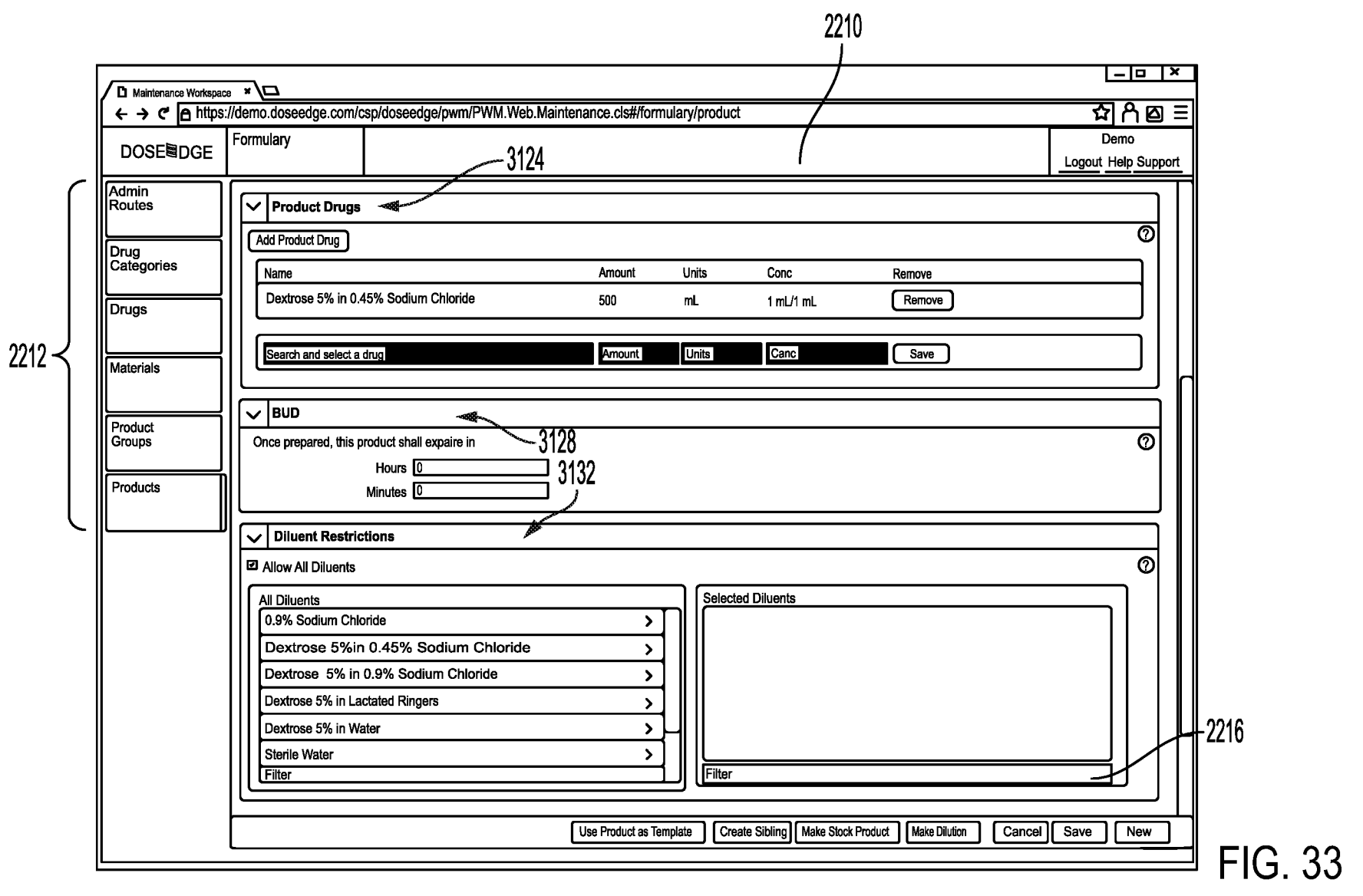
Figure 34:
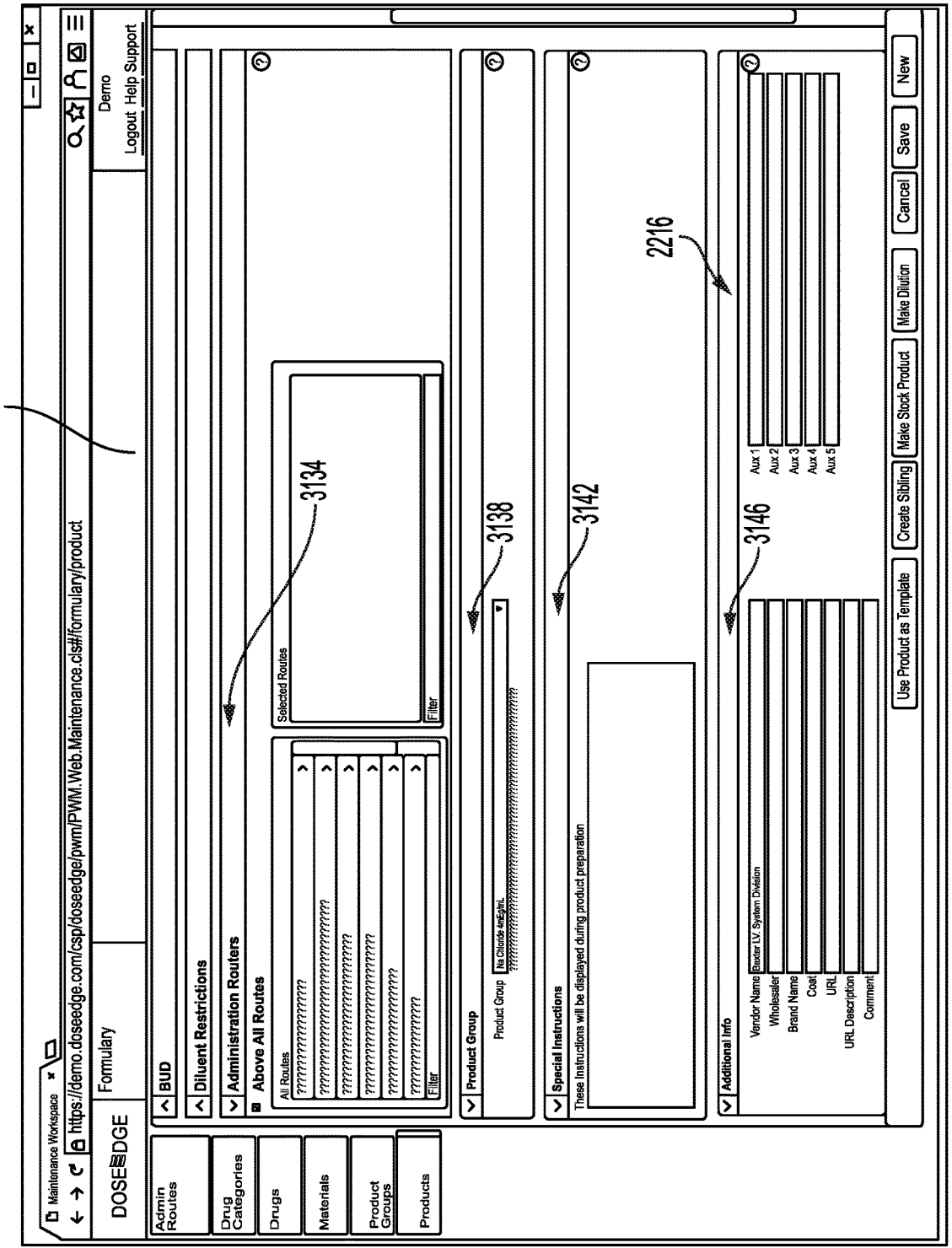

FIG. 31 depicts the workspace 2210 when the "Products" category tab 2212f is selected. Upon selection of the "Products" category tab 2212f of navigation tab 2212, formulary records corresponding with formulary records in the products category are displayed in the record listing 2214. Selection of a given product record 2218 allows for the modification the product record in the record detail portion 2216. A number of expandable collapsible fields are provided in relation to the products records. For example, expandable fields may include a product properties field 3116, a national drug code (NDC) field 3120, a product drugs field 3124, beyond use date field 3128, a diluent restrictions field 3132, an administration routes field 3134, a product group field 3138, a special instructions field 3142, and an additional information field 3146. With further reference to FIGS. 32-34, the various ones of these fields are shown in an expanded configuration.

For instance, with reference to FIG. 32, the product properties field 3116 is shown in an expanded configuration. In turn, user may provide details for the selected product record 2218 including the product name, the product type, a procedure with which the product is associated (e.g., for presentation of a protocol related to the product to a user for use with making the product), the reconstituted volume of the product, the stocking location of the product, the total volume of the product, the dose form associated with the product, a label profile associated with the product, a strength/description of the product, synonyms for the product, default storage methods for the product, specific gravity of the product, and a selection of whether to print a verification label for stock or dilution doses. Furthermore, the user may select whether the product is active, a multidose product, a premix product, a preservative free product, relates to a stock order, whether the product relates to a dilution, or whether the product needs review.

FIG. 32 also shows the NDC field 3120 in an expanded configuration. The NDC field 3120 allows the user to provide barcode or NDC data (e.g., 10 digit or 11 digit NDC data) related to the product. Also, the NDC field may allow for a user to input a given NDC for a product and allow for generation of a NDC code based on a 10 digit to 11 digit NDC conversion as discussed in U.S. provisional Patent Application No. 61/975,519, incorporated by reference above.

FIG. 33 depicts the product drugs field 3124 in an expanded configuration. The product drugs field 3124 allows for a drug (e.g., a drug record as shown in the record listing 2214 when the drugs navigation tab 2212c selected) to be identified as being contained within the selected product record. The beyond use date ("BUD") field 3128 is also expanded in FIG. 33. The BUD field 3128 may allow a user to identify a time period (e.g., in hours and minutes) beyond which a product, once prepared, expires. FIG. 33 also depicts a diluent restrictions field 3132. The diluents restriction field 3132 allows a user to identify acceptable diluents used to prepare the product corresponding to the selected product record 2218. The diluents restrictions field 3132 also provides an "Allow All Diluents" selection whereby all available diluents may be selected. Alternatively, selected ones of the diluents in the all diluents field may be selected for inclusion the selected diluents field. In this instance, only the selected diluents appearing in the selected diluents field may be identified as an appropriate diluent for the product corresponding to the selected product record 2218.

In FIG. 34, the administration routes field 3134, the product group field 3138, the special instructions field 3142, and additional info field 3146 are shown in expanded format. In the administration routes field 3134, appropriate administration routes (e.g., selected from the list of administration routes shown in FIG. 22) for the selected product record may be selected. Again, an "Allow All Routes" selection may be provided that allows a user to select all available administration routes. Alternatively, selected ones of the administration routes (e.g., the administration routes appearing in the record listing 2214 upon selection of the administration routes navigation tab 2212a as shown in FIG. 22) may be selected by including the appropriate administration route from the All Routes field into the Selected Routes field is displayed in FIG. 34. The product group field 3138 may allow for a product group (e.g., a product group is appearing in the record listing 2214 upon selection of the product group navigation tab 2212e) may be selected to identify the product group to which the selected product record 2218 belongs. The special instructions field 3142 allows for the user to provide special instructions with respect to the selected product record 2218. Furthermore, the additional information field 3146 may allow for the user provide additional information regarding the selected product record 2218. Examples of additional information that may be provided by the user may include a vendor name of the product, a wholesaler of the product, a brand name of the product, a cost of the product, a URL associated with the product, a URL description associated with the product, a comment associated with the products, or a number of auxiliary fields used to describe the characteristics or other information related to the product.

Accordingly, it may be appreciated that the formulary for a given local system 110 may be managed by way of the formulary management workspace 2210. In this regard, various formulary records corresponding to different formulary record categories may be selectively displayed, modified, added, or deleted, using the workspace 2210. In turn, upon the addition of records belonging to one or more categories such as administration routes, drug categories, drugs, materials, product groups, products, a user may access the formulary management workspace 2210 and perform the necessary modifications to the formulary records stored at the local database 112 to reflect the update to the formulary.

Figure 2:
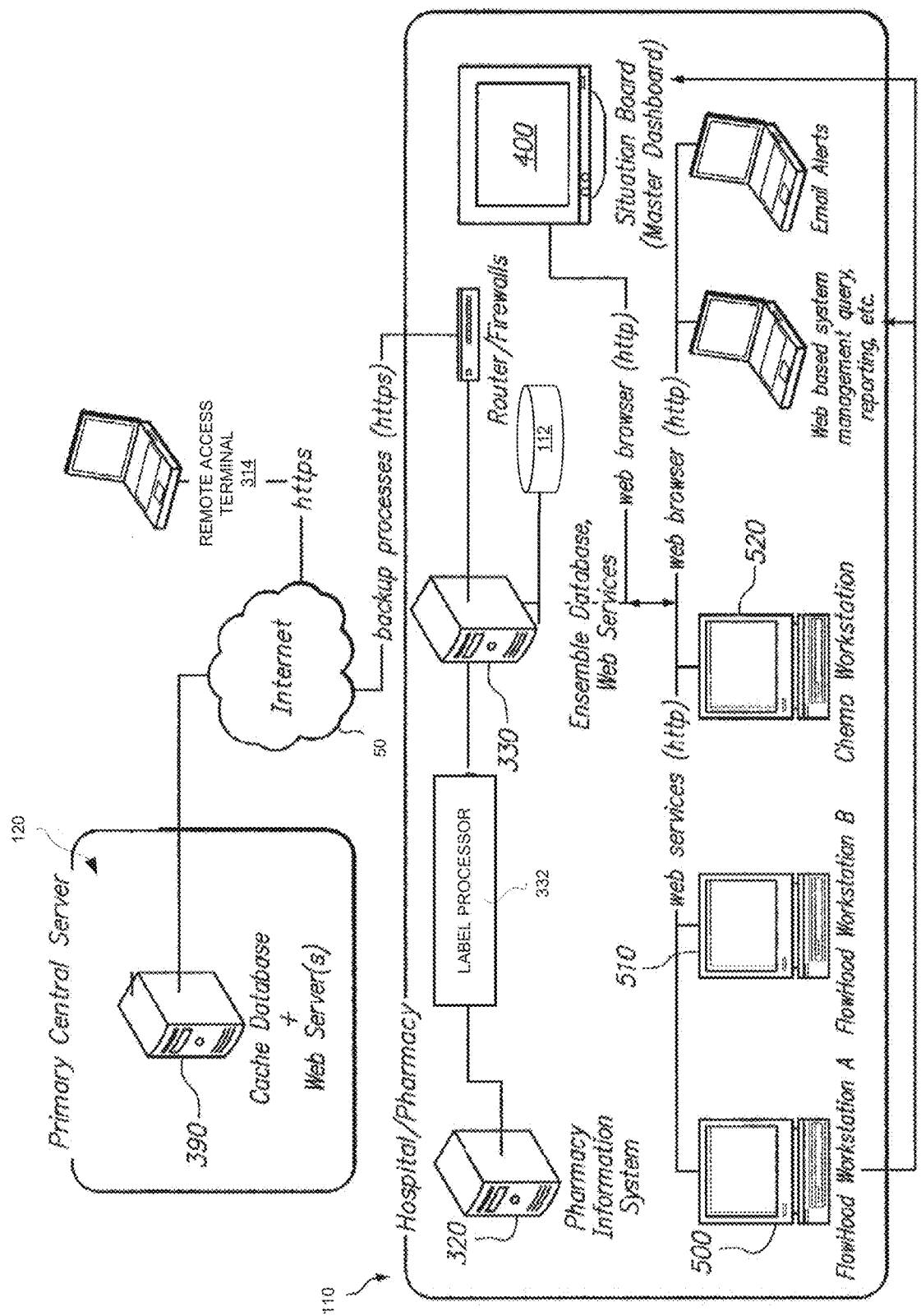
FIG. 2 is a schematic view of an embodiment of a local system comprising a pharmacy workflow management application.

With further reference to FIG. 2, a schematic view of an embodiment of a local system 110 in operative communication with a central server 120 is depicted. Again, the local system 110 may execute a pharmacy workflow management application 114 for processing dose orders to prepare corresponding doses for administration to a patient (e.g., at least partially based on the formulary records of the local system). As may be appreciated, the local system 110 may, in at least one embodiment, include a pharmacy information system 320. The pharmacy information system 320 may communicate to a local server 330. The local server 330 may store and/or provide access to the local database 112. A label processing module 332 may be provided in operative communication with the pharmacy information system 320 and the local server 330. The label processing module 332 may intercept a message or data stream from the pharmacy information system 320. In turn, the label processing module 332 may provide data to the local server 330 for creation of a dose order record at the local server 330 in response to the label processor 332 receiving dose order information from the pharmacy information system 320.

As such, the local system 110 (i.e., a pharmacy, hospital, or other facility capable of preparing doses for administration to a patient) may receive or generate dose orders. Dose orders may be received at the local system 110 in one or more different ways. By way of example, in an embodiment a doctor or other appropriate medical personnel may enter one or more dose orders directly using the pharmacy information system 320. In this regard, the pharmacy information system 320 may provide an appropriate terminal that is accessible by the appropriate medical personnel for entry of the dose order (e.g., a physician order entry "POE" system or terminal, etc.). Additionally or alternatively, appropriate medical personnel may enter dose orders at a remote access terminal 314 that may provide order data to the label processor 332 in the local system 110 by way of the wide area network 50. As may be appreciated, the remotely entered dose orders may be communicated to the label processor 332 by way of a local server 330. In this regard, the local server 330 may include web services that facilitate the communication of dose orders from the remote access terminal 314 to the label processor 332. As the remote access terminal 314 may be remote from the local system 110, one or more routers and/or firewalls be provided to assist in providing and securing the communication between the remote access terminal 314 and the local server 330. Further still, the pharmacy information system 320 may receive dose orders from and/or be a component of a larger hospital information system that may be capable of receiving and/or generating dose orders. In this regard, the hospital information system may provide information to the pharmacy information system 320 and/or directly to the label processor 332 as described in greater detail below. Any communication into or out of the local system 110 and/or any communication within the local system 110 may be secure. For example, various security protocols such as https, SSH, VPN, DES encryption, RSA encryption, or any other known security protocol to secure communication between nodes in the network.

In any regard, the pharmacy information system 320 may receive data from which information related to one or more dose orders may be extracted. That is, dose orders corresponding to requested doses for administration to a patient may received at the local system 110 and routed to the label processor 332. While present disclosure generally includes a description of label processing, label processing module may also be of any type described in commonly assigned U.S. Pat. No. 7,069,212, which is hereby incorporated by reference in its entirety.

In traditional approaches to pharmacy management, when dose orders are received at a facility, a corresponding physical label for the dose order is printed within the pharmacy. In turn, traditional workflow management in the pharmacy is relegated to management of physical labels, which may be disadvantageous in that the physical labels may be lost, the physical labels may be difficult to organize, the use of physical labels introduces additional potential for human error, and the production of physical labels may not provide reliable logging for later auditing.

In contrast, when the dose orders are processed by the label processor 332, rather than only a label for medication order being printed, data related to the order (e.g. data that have traditionally been printed on the label corresponding to the order) may be captured, processed, and parsed in the computer implemented system to create individual medical dose order records, each of which corresponds to a corresponding dose order, that are in turn stored in the local server 330. That is, rather than only printing a label for a medication order, the order may be utilized to generate a digital dose order record that is stored at the local server 330 (i.e., in the local database 112). Data used to generate the digital dose order record may be taken from the medication order data received at the local system 110. As such, a dose order record may be generated and stored at the local server 330 that corresponds to each medication order received at the local system 110. Thus, rather than having to manage physical printed labels at the local system 110, the received medication orders may be managed digitally utilizing the local server 330 that stores the dose order records corresponding to each medication order received.

Figure 3:
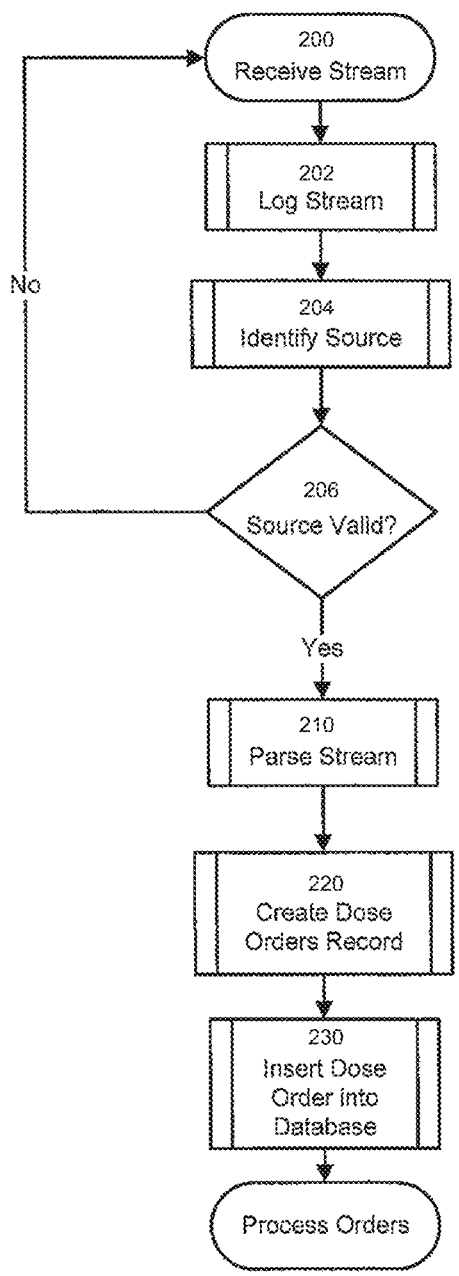
FIG. 3 is a flow chart depicting an embodiment of a method for receipt and processing of dose orders.

With reference now to FIG. 3, an embodiment of process is illustrated in which dose orders are received and processed to generate and store dose order records at the local system 110. At step 200, one or more medication order streams are received at the local system 110 (e.g., from a local data stream or a remote data stream as described above) and are processed by a label processing module 332. The label processing module 332 may comprise a processor that accesses a memory comprising code that is executed by the processor (e.g., at the local server 330) to perform the processes in FIG. 3. That is, the label processing module 332 may be separate from or comprise a part of the local server 330. In one specific embodiment, the medication order data can be captured by a monitoring module comprising computer code executing on a processor in the pharmacy for monitoring a port normally connected to a pharmacy printer, network monitoring for medication order information, or software application monitoring for events related to the input of medication orders. As described above, traditionally these order streams may represent data intended to be printed on labels on a printer, and oftentimes comprise serial data streams.

The medication order streams may contain a list of medication doses to prepare. Each dose order and dose may be associated with additional related data such as, for example, the patient for whom the medication is intended, by when the dose should be delivered, to where the dose should be delivered, the ordering doctor, the time and date the dose order was entered, the reason for medication, and other relevant information associated with the dose order or any other appropriate metadata described in further detail below that may be present in the mediation order stream for each dose order contained in the stream. Such information may be used when generating a dose order record to populate appropriate dose order record data fields for a dose order record that correspond to respective ones of the medication dose orders contained in the medication order streams. As will be discussed in greater detail below, additional dose order metadata may be added to the dose order record during the preparation, approval, and/or distribution of the dose order that corresponds to the dose order record. The dose order record and all related dose order metadata may be stored in the local database 112.

Data streams containing medication dose order data that are received at the local system 110 are preferably logged at step 202 by a monitoring computer. Preferably, streams are logged in the local database 112 or other computer accessible medium (e.g., at the local server 330). Logging data streams enables extensive auditing and monitoring of the pharmacy, hospital, or other facility that prepares and/or the dose. Because all data is logged, preferably in its raw form when it is first received by the pharmacy, no information is lost, corrupted, or disassociated during the processing or distribution of the medication. If necessary, an audit can be performed manually, off-line, or by a separate software program to reconstruct the data stream and all processing that should have or did occur after the pharmacy received the data stream.

Preferably, a data stream containing dose orders that is received at the local system 110 has an identifiable source. The source can be explicitly identified within the stream of data, or it can be determinable by the system. Source determination can include, for example, examining TCP/IP packet or header/footer information, examining cryptographic signatures of the stream, or data retrieved through additional network communication requesting the source. In any regard, the source may be identified at step 204.

At step 206, the system may be configured to determine whether the data stream originated from one of a set of valid sources. This can include identifying the source of the data stream and testing that it is one of the sources among those in the set. Validating the source ensures each medication dose prepared by the pharmacy workflow management application 114 is legitimate and originating from an authorized prescribing or ordering entity. Alternatively, the validation can ensure that the prescribing entity is presently entitled to have its prescriptions filled by the pharmacy. If the source is not valid, the system returns to step 200 to receive additional streams. Optionally, notifications can be sent to the source to inform it that there were validation issues or that the window for continued validation has one or more constraints (e.g., will expire in so-many days due to an overdue invoice).

After determining that the source is valid, the stream may be parsed to extract relevant information at step 210. The system can parse various message and data formats. Moreover, the parser can be extensible, such that as new formats are implemented or included within the networked environment, a parser extension can be included in the system to parse the new format. For example, if the data stream is a serial printer data stream, the system can determine the format of the data and pass the stream to the appropriate serial printer data parser. The printer data parser is configured to extract the dose order information contained within the stream and may populate dose order record data fields of a dose order record with the parsed data from the data stream corresponding to any one or more portions of dose order metadata described in more detail below. Preferably, the parser extracts all relevant data contained within the stream and maintains a record of the extracted data. The parsing methodology is preferably encapsulated in a library or set of modules that are called upon, as necessary, to parse a stream of any determined format. Each library entry or module operates as a "parser," as that term is used herein.

As described above, the data stream may contain one or more dose orders. For example, the stream may contain a single dose request by a doctor for a single patient. Alternatively, the stream can include multiple dose orders that may be delineated by the parser into separate dose order records corresponding to each distinct dose order. That is, the parser is preferably configured to recognize and discriminate between individual dose orders within a stream. In turn, dose order records may be created and populated for each corresponding one of the individual dose orders within a stream. The discrimination of individual dose orders can be accomplished by recognizing an order delimiter, or alternatively can be defined by the format of the data stream.

In any regard, once the stream is parsed at step 210, a dose order record may be created at step 220. In turn, the dose order record may be stored at the local database 330 at step 222. In this regard, the data stream may be received 200, logged 202, and parsed 210 to create a corresponding dose order record for each dose order contained within the stream. In turn, the medication stream received at the local system 110 may be used to generate dose order records stored in a local server 330 for each medication dose order to be prepared at the local system 110.

As briefly described above, having dose order records stored digitally in the local database 330 may facilitate improved management of the dose order records in the pharmacy. In turn, the following describes some embodiments of dose order record management performed at the local server 330 to facilitate pharmacy workflow management by the pharmacy workflow management application 114. Specifically, dose order records may be easily viewed, sorted, searched, prioritized, or otherwise organized by pharmacy technicians or other personnel who have appropriate access to the local database 330. Furthermore, as data is generated in the pharmacy regarding the dose order (e.g., during the preparation, approval, or distribution of a dose), such data may be stored in relation to the medication dose order record to provide a more robust data set associated with each medication dose prepared at the pharmacy. As may be appreciated, the amount of data related to each digital dose order record may be extensive. The data related to the dose order record may be referred to as dose order metadata. In turn, dose order metadata may be stored in corresponding dose order record data fields and may describe various characteristics of the dose order, a dose corresponding to the dose order, the preparation of a dose, or other relevant characteristics related to the dose or dose order. In some embodiments, the dose order metadata may facilitate dose ordering tracking via triggered scan events, as discussed in more detail below.

For instance, examples of dose order record data fields may include, but are not limited to:
dose order status information indicative of at least one of:
a preparation status of the dose order (e.g., pending, at preparation station, ready for verification, undergoing verification, approved, rework, requeue, awaiting sort, discontinued, etc.),
a priority status of the dose order (e.g., STAT, first dose, etc.),
a wait status (e.g., including a time at which the dose order become available to be made),
a hold status,
dose order administration data indicative of at least one of:
a patient to whom the dose order is to be administered,
a time of administration (e.g., including date and time of administration),
a beyond use date (BUD) indicative of an expiration (e.g., time and/or date) of the dose order,
an administration route of the dose order,
a preparation mode of the dose order,
dose order identification information indicative of at least one of:
a dose order identifier (e.g., a dose order record number),
medication source data indicative of at least one of:
a manufacturer of a component of a product corresponding to the dose order,
a lot number of a component of a product corresponding to the dose order,
an expiration date of a component of a product corresponding to the dose order,
a serial number of a component of a product corresponding to the dose order, or
a drug code indicative of the identity of a component of a product corresponding to the dose order;
chain of custody data indicative of at least one of:
a listing of entities in possession of a component of a product corresponding to the dose order or a product corresponding to the dose order,
a listing of users that have taken an action with respect to a product corresponding to the dose order, wherein the listing of users is correlated to specific actions taken by each user, or
tracking information corresponding to physical movement of a component of a product corresponding to the dose order or a product corresponding to the dose order;
fulfillment data indicative of at least one of:
image data corresponding with a component of a product corresponding to the dose order or a product corresponding to the dose order,
scanned data obtained from a component of a product corresponding to the dose order,
analytic data regarding a component of a product corresponding to the dose order or a product corresponding to the dose order,
pharmacist review data corresponding with at least one pharmacist review of a component of a product corresponding to the dose order or a product corresponding to the dose order,
compliance data corresponding with best practices associated with a component of a product corresponding to the dose order or a product corresponding to the dose order, sterility assessment data corresponding to a component of a product corresponding to the dose order or a product corresponding to the dose order, a listing of actions corresponding to a component of a product corresponding to the dose order or a product corresponding to the dose order, timestamp data corresponding to actions corresponding to a component of a product corresponding to the dose order or a product corresponding to the dose order, or a listing of life cycle events taken with respect a component of a product corresponding to the dose order or a product corresponding to the dose order; or environmental data indicative of at least one of:

a temperature to which a component of a product corresponding to the dose order or a product corresponding to the dose order has been exposed, a temperature to which and corresponding time period for which a component of a product corresponding to the dose order or a product corresponding to the dose order has been exposed, whether a component of a product corresponding to the dose order or a product corresponding to the dose order is refrigerated, whether a component of a product corresponding to the dose order or a product corresponding to the dose order is frozen, a temperature profile experienced by a component of a product corresponding to the dose order or a product corresponding to the dose order, or accelerometer data corresponding to forces experienced by a component of a product corresponding to the dose order or a product corresponding to the dose order.

Furthermore, because the dose order records are stored digitally at the local server 330, remote access be provided to those outside of the pharmacy to view, modify, and/or otherwise manage the digital dose order records stored at the local server 330. In turn, access to the data associated with the medication dose order records may be provided to remote users to assist in the management of pharmacy resources or the like. Accordingly, as will be discussed herein, a number of approaches to pharmacy workflow management may be facilitated that utilize the medication dose order records stored in the local server 330.

With returned reference to FIG. 2, the local server 330 may be in operative communication with one or more local clients at the local system 110. For instance, the local client may comprise thick or thin clients executing at a terminal or workstation. In this regard, the pharmacy workflow management application 114 may comprise a web services application provided by the local server 330 accessed at a thin client by way of a web server.

Additionally or alternatively, the pharmacy workflow management application may include thick client applications executing at a client that may communicate with the local server 330. The client applications may be provided at one more terminals locally at the local system 110 and/or remote from the local system 110. For instance, a client application may be provided on workstations that are equipped to prepare doses or terminals that provide access to information stored on the client server 330. The terminals executing the client application may include management terminals that may access and/or modify dose order records, review terminals that may allow a pharmacist to review doses, a situation board that displays relevant pharmacy information, or other appropriate terminals that facilitate functionality related to the pharmacy workflow management.

In the specific context of a thick client, the pharmacy workflow management application executing at the terminal may, from time to time, require updating. In traditional approaches to updating the thick client at a given terminal at the local system 110, a support user or the like with access privileges to update equipment at the local system 110 may be required to login to each terminal for upgrading of the thick client at each terminal. However, as contemplated herein, a terminal executing a thick client may allow for installations without the need for administrator privileges. Specifically, the version of the thick client at the terminal (e.g., workstation) may be compared with a current version of the thick client software stored locally at the client server 330. In this regard, the version of the thick client may be compared to the current version of the thick client software available at the client server 330. If the thick client software is out of date, a user of the thick client (e.g., without administrator rights to update the client server 330) may be presented an option to download the updated thick client version to the terminal. The updated thick client version may be downloaded to the terminal and installed thereon in response to a request by the user to do so. In turn, the updating of thick clients within the local system 110 may be streamlined in that a user with administrative privileges may simply be required to load a single updated version of the thick client software to the client server 330. In turn, upon access of the terminals executing a thick client by ordinary users (e.g., users without administrative privileges relative to the client server), the user of the client may be presented the option to update the thick client version at the terminal.

In the case of locally resident terminals, the communication between the local server 330 and the locally resident terminals may include communication over a local area network or the like. In this regard, operative communication may be established between a terminal and the local server 330 over a local area network. In an embodiment, the communication between the locally resident terminal and the local server 330 over the local area network may be cryptographically manipulated (e.g., encrypted). In this regard, communication over the local area network may provide a secure data connection between the locally resident terminal and the local server 330. Specifically, data communicated between the locally resident terminal and the local server 330 may be translated into an illegible format when communicated. This may help to prevent third-party interference with the data communicated between the locally resident terminals and the local server 330. In one example, the encryption of the data transmitted between the locally resident terminal and the local server 330 may be a secure socket layer (SSL) protocol.

In an embodiment, at least one of the terminals may be provided as a remote access terminal 314 to facilitate access to the local server 330 from outside the local system 110. Such remote access by a client may be facilitated by way of secure communications (e.g., use of secure socket layer (SSL) communication, encryption, or other means of secure communication over a network such as those described above). Accordingly, once appropriate security measures of been taken, the remote access terminal 314 may execute a client application operable to communicate with the local server 330 in a manner similar to the local instances of a client within the local system 110. That is, the remote access terminal 314 may be provided with any or all the functionality associated with any of the local client device is described herein.

Given the foregoing architecture at the local system 110 where clients may access the local server 330 to manage various features of the pharmacy workflow management application, it may be appreciated that the local system 110 may be scalable with the addition of additional terminals, each executing a thick or thin client in operative communication with local server 330. Also, the architecture allows for remote access as described above. Further still, access by a terminal may be subject to the role-based security described above. That is, because dose order records stored locally at the local database 112 and are accessed by way of the client application, the management of the dose order records may be substantially simplified. For instance, while a client application may modify dose order record, the modification to the dose order record will be reflected at the local database 112. In turn, another terminal in operative communication with a local database 112 may be configured to receive updated data from the local database 112 (e.g., in substantially real-time) such that the modification of the dose order record from the client application may be reflected throughout the terminal with access to the local server 112. This distributed model of dose order record management may provide robust capabilities, especially in the context of collaborative management dose order records.

A workstation (i.e., a terminal where doses are prepared) may include a touchscreen, one or more barcode scanners, a label printer, a camera, etc. Additional hardware that may be present at the workstation may include a scale, a reconstitution module (mixing station) and/or a security ID badge reader. The hardware at the workstation may be operative to collect information regarding the preparation of a dose that may be stored in corresponding relation to the dose order record. Furthermore, the workstation may include traditional preparation apparatus used to prepare doses such as, laminar flow hoods, biological safety cabinets, or other pharmacy equipment used in the preparation of a dose.

In any regard, the local server 330 may be in bidirectional communication with any number of workstations to allow the workstations (e.g., 500, 510, 520, etc. as shown in FIG. 2) to receive information from the local server 330. For instance, each workstation may receive data regarding the dose order records stored at the local database 112 by way of the local server 330. This data may include all dose order records, collectively referred to as the dose order queue, stored at the local server 330 or may comprise a filtered dose order listing that only displays a selected number of dose order records from the dose order queue at a given workstation, referred to herein as a dose order record listing.

Figure 4:
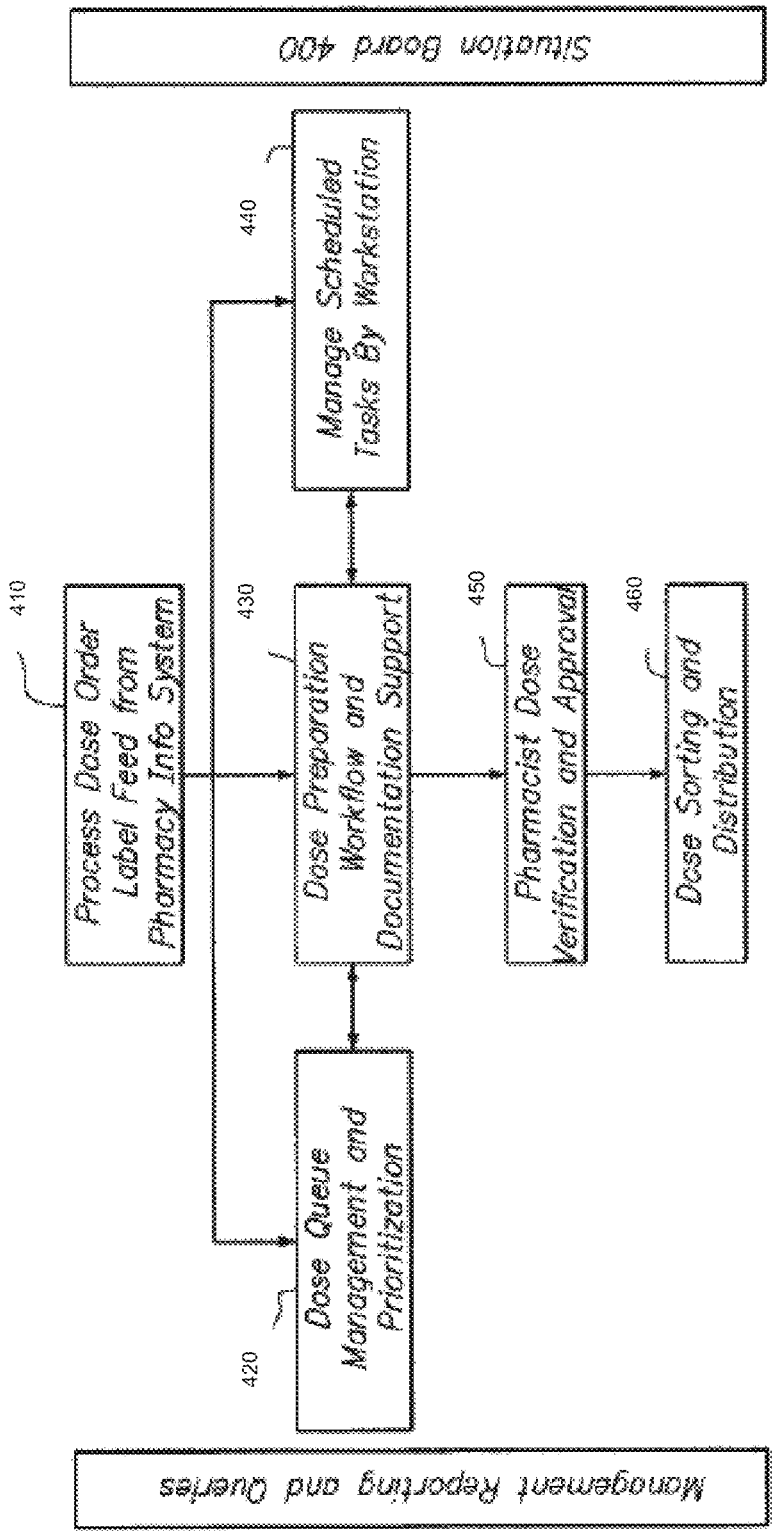
FIG. 4 is a schematic view depicting various functionalities of the pharmacy workflow management application executed by the local system shown in FIG. 2.

In turn, with reference to FIG. 4, once the dose orders have been processed 410 and provided dose order records stored in the local database 330, the pharmacy workflow management application 114 may provide for dose queue management and prioritization 420. Accordingly, an embodiment of dose queue management and prioritization 420 is described below.

Figure 5:
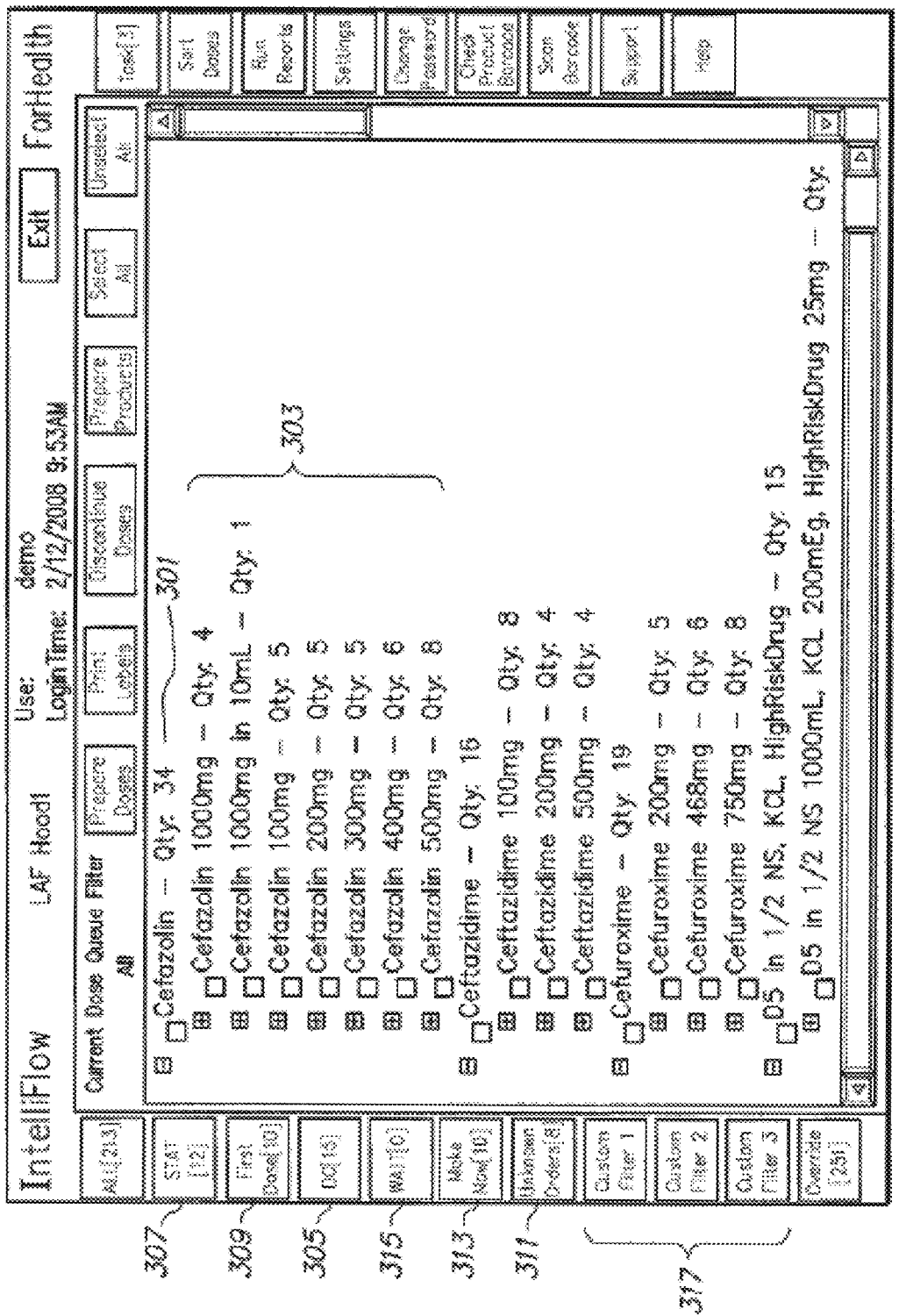
FIG. 5 is a view of an embodiment of a user interface of a pharmacy workflow management application with which dose order records stored by the pharmacy workflow management application may be managed.

For example, at each workstation or other terminal, the dose order queue may be sorted and displayed as a dose order record listing that includes the dose orders records in any number of different ways. For example, the dose orders can be sorted and displayed by drug type and can be further sorted by dosage amount as shown in FIG. 5. The total amount of dose orders for each drug can be displayed next to the drug name in a main banner 301 and then underneath the main banner, the various drug dosage amounts are listed along with the quantity of each that is currently needed (lines 303). For example, as shown in FIG. 5, the main banner shows that there are 34 orders for the drug Cefazolin and underneath, the various drug dosage amounts, such as Cefazolin 1000 mg; Cefazolin 100 mg; Cefazolin 200 mg, are listed along with the quantity that is needed for each. Other examples of interfaces for filtering, displaying, and/or otherwise managing a dose order record listing are presented below.

Figure 47:
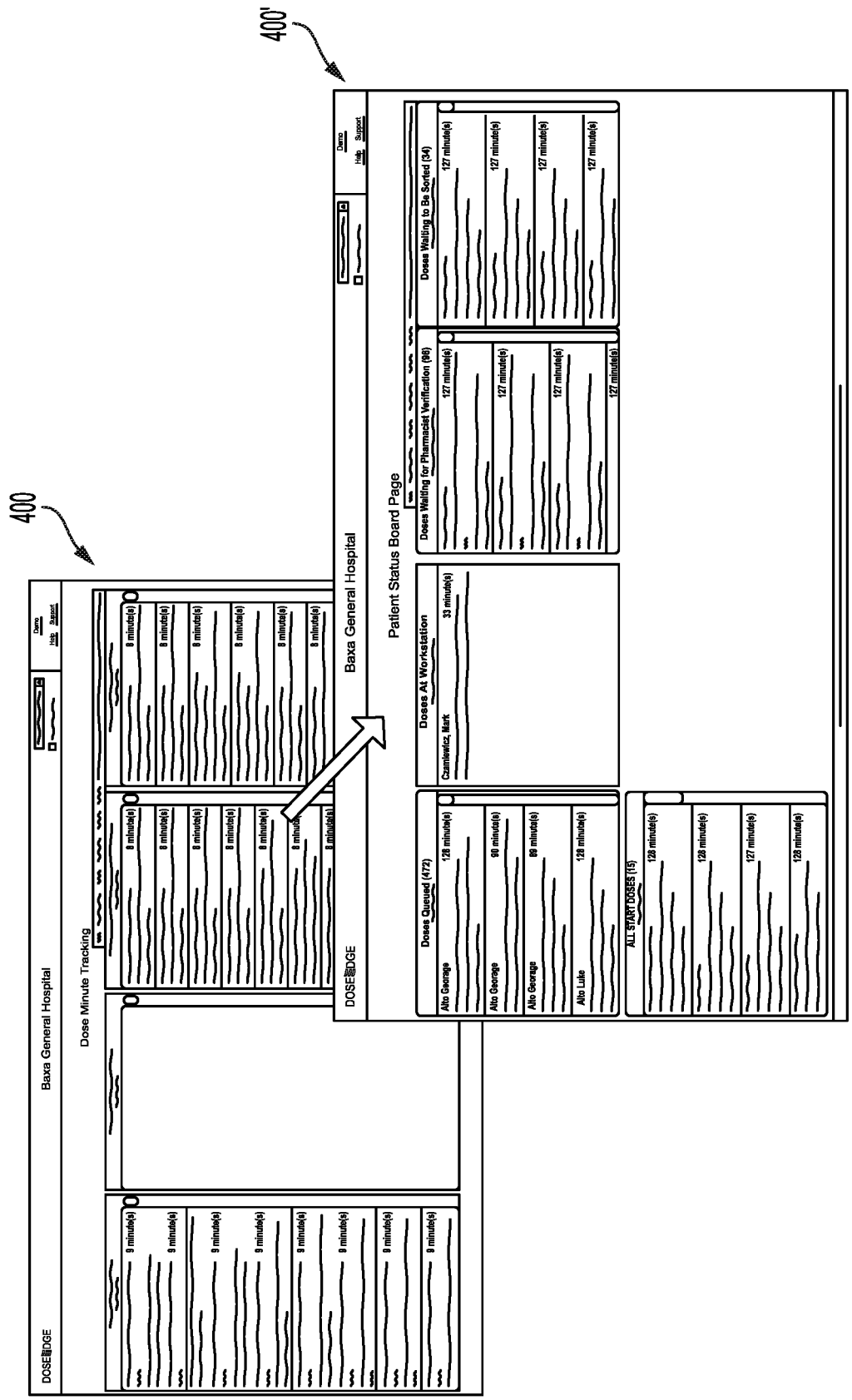
FIG. 47 depicts an embodiment of a situation board display that is customized according to a user profile.

Each dose order record listing can be displayed in a different manner to indicate information that is intended and helpful to the operators at the one or more workstations that process and fulfill the dose orders. For example, on the left column of the screen that is shown in FIG. 5, a box 305 labeled "DC" stands for discontinued dose orders which are orders that have been discontinued for some various reason and therefore, do not need to be processed and fulfilled. The box can have an associated color, such as purple, that allows individual dose orders to be indicated as being discontinued and therefore, should not be selected for processing and fulfillment. For example, the Cefazolin 500 mg (Qty: 8) dose order line can be displayed in purple, thereby indicating that this dose order is discontinued and should not be processed. Also along the left column are other status indicators, such as "STAT" 307, "First Dose" 309, "Unknown Drug" 311, "Make Now" 313 and "Wait" 315. These indicators can dictate a preferred order of selecting and fulfilling the dose orders. The status indicators may be stored as dose order metadata for a dose order record. The status indicators may be updated throughout the preparation process to provide the dose order record a different status based on the progress through the preparation process. Additionally, "First Dose" can indicate the highest priority dose orders which should be selected first before another dose order, including those dose orders that are labeled "STAT". Meanwhile, a situation board 400, illustratively depicted on FIG. 47, provides an overview of the queue for all drug orders that are being handled. The situation board 400 may provide an overview throughout the entire process of order preparation as shown in FIG. 4.

In addition and with returned reference to FIG. 5, other options available for selection by the operator at a station can be displayed, such as along the left column. For example, one or more filters 317 can be employed by the operator to filter the dose orders that are listed in the dose order queue. The filter 317 can be selected among standard ones, such as a filter that lists only those dose orders that can selected and fulfilled by the operator at a given workstation or the filter can be designed to only show only those dose orders that are classified as STAT orders and/or those that are classified as First Dose orders. Alternatively, the filter can be a custom filter that is created and defined by the workstation operator.

The dose order queue may also be displayed at a remote access terminal 314. Thus, the remote access terminal 314 may be operative to display the dose order queue according to the foregoing (e.g., where dose orders may be sorted and/or filtered for display). Furthermore, an administrator with proper administrative privileges may be operable to manage the dose orders contained in the dose order queue. As may be appreciated, this management may be facilitated within a terminal within the pharmacy 310 or by way of a remote access terminal 314.

With reference to FIGS. 6-12, additional embodiments of various user interface screens for an embodiment of a pharmacy workflow management application 1300 are depicted. As described above, the application 1300 may include a web-based management tool that may be presented to a user in a web browser or the like. For instance and as described above in relation to accessing the formulary management workspace 2210, a user may navigate to a particular web address and be presented with a login screen 1302.

With additional reference to FIG. 7, upon successfully authenticating the user, a navigation screen 1306 may be provided to the user. The navigation screen 1306 may include a plurality of links associated with various functions of the management in addition to the links 2200 described above in relation to the formulary management workspace. For example, the navigation screen 1306 may facilitate access to a dose order record listing for review or management of dose orders. Also, the navigation screen 1306 may facilitate access for a pharmacist to verification screens used to review and verify doses that have been prepared in the pharmacy by a pharmacy technician as are described in greater detail below. The navigation screen 1306 may include a link 1308 to a dose order management screen 1310. Selection of the link 1308 may result in the user being presented with the dose order management screen 1310 shown in FIG. 8.

The dose order management screen 1310 may include a dose order record listing 1312 that displays appropriate ones of the dose order records of the dose order queue stored in the local server 330. The dose order record listing 1312 may be arranged such that the individual dose order records are listed and divided by columns wherein each column corresponds with a different dose order record data field. As such, each dose order record data field column may be used to sort the dose order records in the dose order record listing 1312 (e.g., based on dose order metadata for each dose order record appearing in the dose order record listing). For example, the columns shown in FIG. 8 correspond to a dose identifier, does description, administration time, a relative time to administration, patient ID, patient name, patient location, a dose status, and a dose priority. In this regard, if desired the columns displayed in FIG. 8 may be used to sort the dose order record listing 1312 in ascending or descending order relative to the selected column.

The user may also utilize the dose order management screen 1310 to filter the display of the dose order record listing 1312. For example, the dose order management screen 1310 may include one or more tabs (e.g. 1314, 1316, etc.) that may be utilized to filter the dose order record listing 1312 according to status of the dose order records. For example, selection of tab 1314 by the user may filter the dose order records appearing in the dose order record listing 1312 such that dose order records with a status of "pending" may be displayed (i.e., including dose order records that have not yet been prepared). In this regard, selecting the tab 1314 may filter the dose order record listing 1312 such that dose order records but not yet been prepared may be shown. Selection of the tab 1316 may result in filtering of the dose order record listing 1312 such that dose order records are shown that have undergone preparation and are waiting verification by pharmacist. In this regard, the dose order records having a status indicating the dose orders are awaiting verification by a pharmacist may only be displayed in the dose order record listing 1312. It may be appreciated that additional tabs may be provided corresponding with different dose order statuses such as, for example, doses at initial review (i.e., doses not yet having been released for preparation), doses ready for preparation, doses awaiting in-line verification, verify doses awaiting sorting, doses awaiting rework, or any other appropriate status identifier that may be attributed to the dose order record.

The tabs 1314 or 1316 may also provide a user with a changeable graphical element that may allow for the user to be updated regarding various high-priority doses being added to the dose order record listing 1312. For example, if a STAT dose is populated into the dose order record listing 1312, a corresponding STAT dose indicator in the tab 1314 or 1316 may be updated to display the number of STAT doses currently in the dose order record listing 1312. Furthermore, the color indicator may be used to provide a quick reference to the user. For example, if a STAT dose is contained in the dose order record listing 1312, the STAT field in the tab 1314 or 1316 may be highlighted with a colored background (e.g., a red background that may be easily identifiable by the user even if not in close proximity with a display displaying the dose order management screen 1310).

The dose order management screen 1310 may also include a plurality of secondary filters 1318 that may be utilized to further filter the dose order record listing 1312. For example shown in FIG. 11, the secondary filters may include a selection of all doses, requeued doses, STAT doses, resume preparation doses (e.g., doses is preparation have been interrupted), rework doses, discontinue doses, doses placed on weight and/or hold, and suspected duplicate doses. It may further be appreciated that the secondary filters 1318 provided may be based upon the tab 1314 or 1316 selected. For example, when the tab 1314 is selected for display of dose order records that have not yet been prepared, the secondary filters 1318 displayed may include those listed above including an all dose filter, a requeued dose filter, a STAT dose filter, a resume preparation dose filter, a rework dose filter, a discontinued dose filter, a wait/hold dose filter, and a suspected duplicate dose filter. However, upon selection of tab 1316 to display dose order records that have been prepared and are awaiting verification, the secondary filters 1318 may be modified to include a wait/hold filter, and in-line filter (e.g., to only display doses awaiting in-line verification), a STAT filter, a final verification filter, and a being verified filter. A queue filter 1336 may also be provided to allow for configurable filters to be generated and applied to the dose order record listing 1312 based on a configurable comparison of the dose order queue to predetermined dose order record data field values as will be described in greater detail below.

Returning to FIG. 8, it may be appreciated that a dose order record 1320 may be selected from the dose order record listing 1312. The selected dose order record 1320 may be signified by a checkbox provided in the dose order record listing 1312 and/or highlighting of the selected dose order record 1320 from among the other dose order record in the dose order record listing 1312. As may be appreciated, multiple dose order records may be highlighted has selected dose order records 1320 such that batch processing may be facilitated on selected ones of the dose order records 1320. Selection of the selected dose order record 1320 may result in a plurality of dose order operation buttons being enabled. For example, dose order operations buttons may include a detail button 1322, a place on hold button 1324, a remove from hold button 1326, a discontinue button 1328, and modify button 1330. Selection of a dose order operation button by a user may result in performance of a corresponding operation to the selected dose order 1320. For example, selection of the detailed button 1322 may result in the dose order management tool 1300 displaying a dose detail screen 3500 as shown in FIG. 35 that provides additional details regarding the selected dose order 1320.

Figure 35:
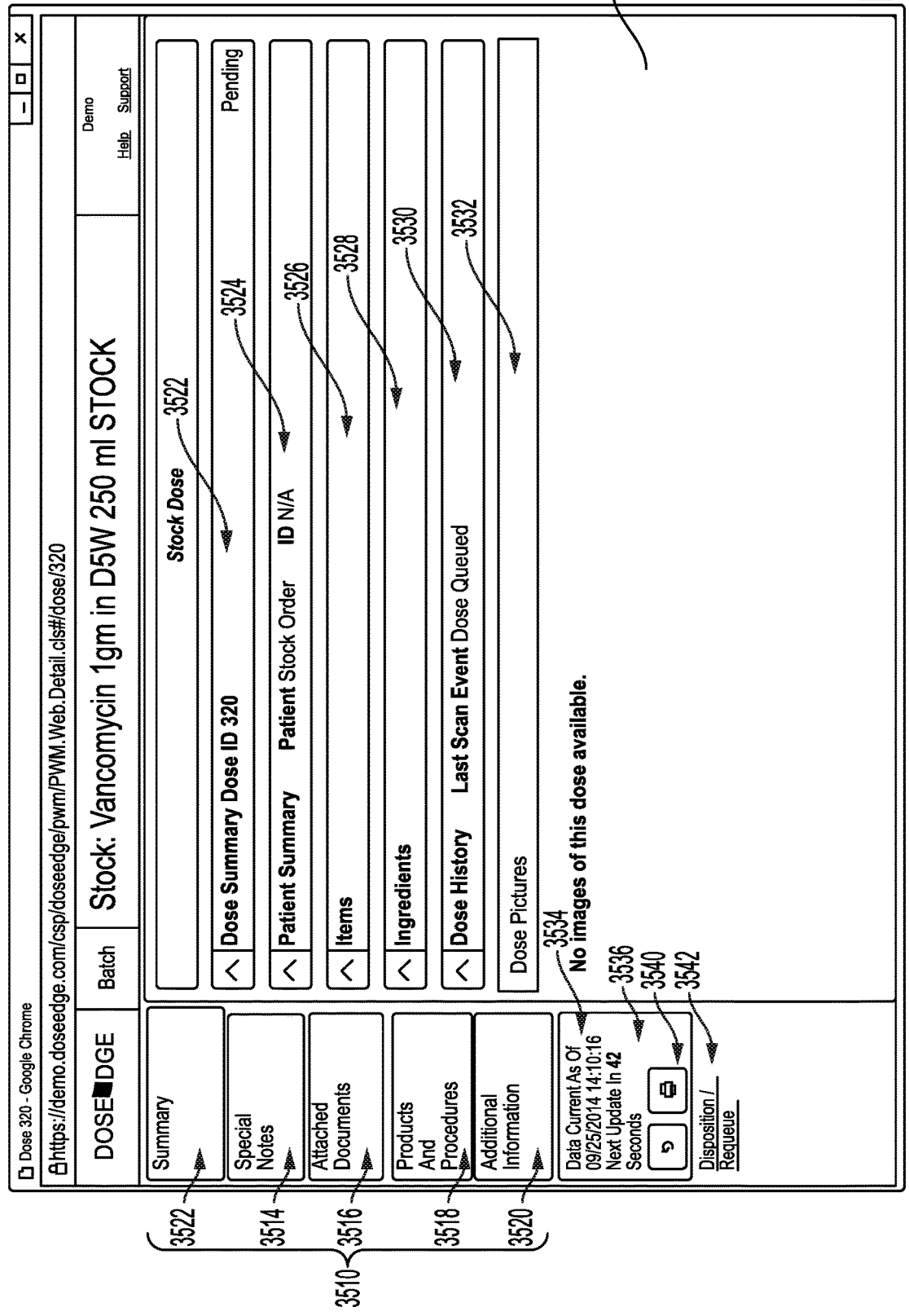
Figure 46:
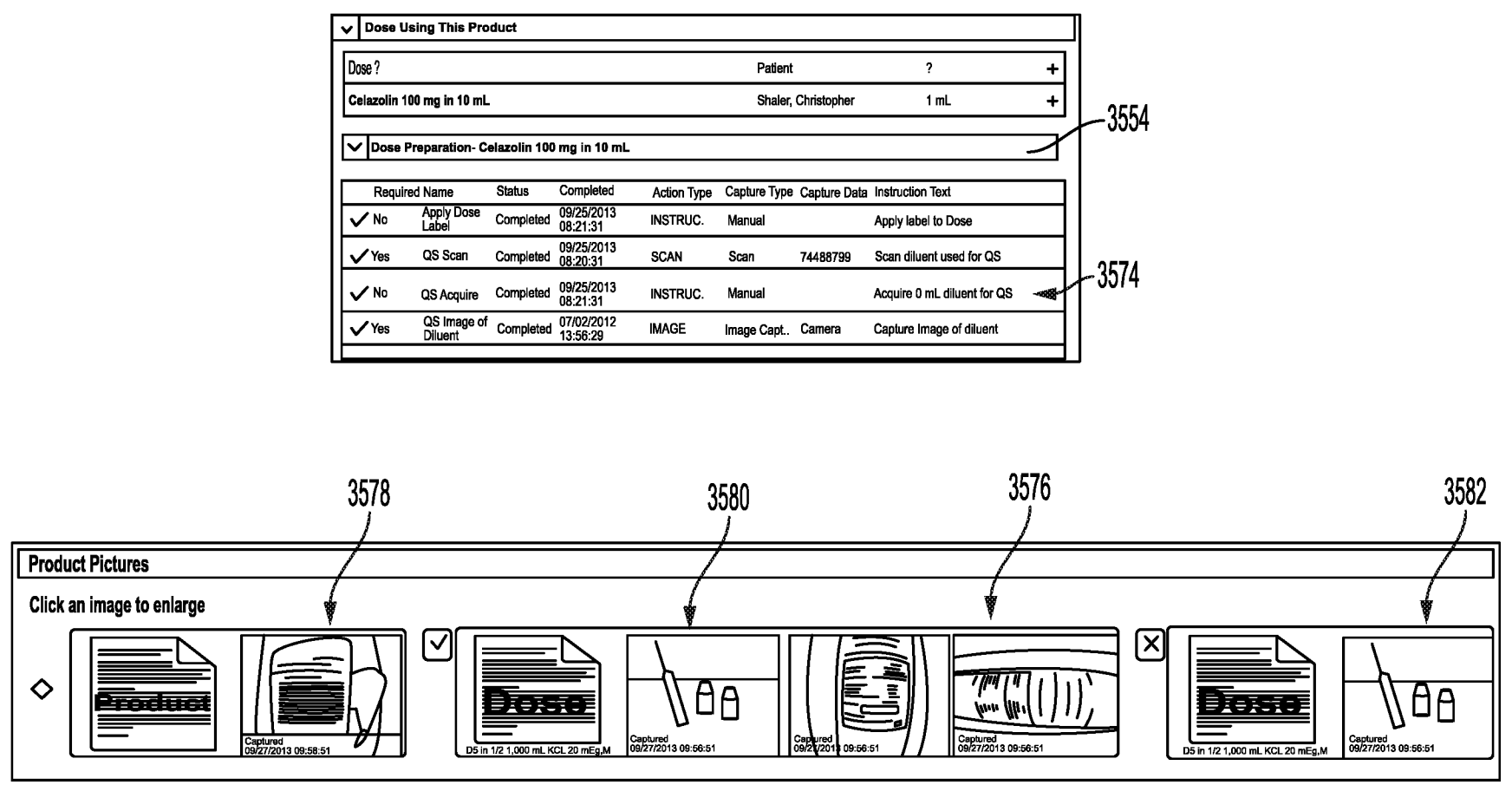

With further reference to FIG. 35, the dose detail screen 3500 may include a number of navigation tabs 3510 to allow for navigation to various portions of information regarding the selected dose order 1320. In FIG. 35, the summary tab 3512 is selected. In turn, the dose detail screen 3500 may include a number of collapsible and expandable data fields. For instance, the data fields may include a dose summary field 3522, a patient's summary field 3524, and items field 3526, and ingredients field 3528, a dose history field 3530. Furthermore, a dose pictures field 3532 may also be provided. For example, with further reference to FIG. 46, a dose pictures field 3532 is shown as populated with dose images 3576. The dose images 3576 may include product images 3578 regarding a product to be included in the dose associated with the selected dose order 1320. The dose images 3576 may also include current dose images 3580 regarding the current preparation of a dose corresponding to the selected dose order 1320. Additionally, the dose images 3576 may include prior dose images 3582 that may, for example, correspond to previous preparations of the dose associated with the dose order record that may have been rejected by a pharmacist during review or the like.

Figure 43:
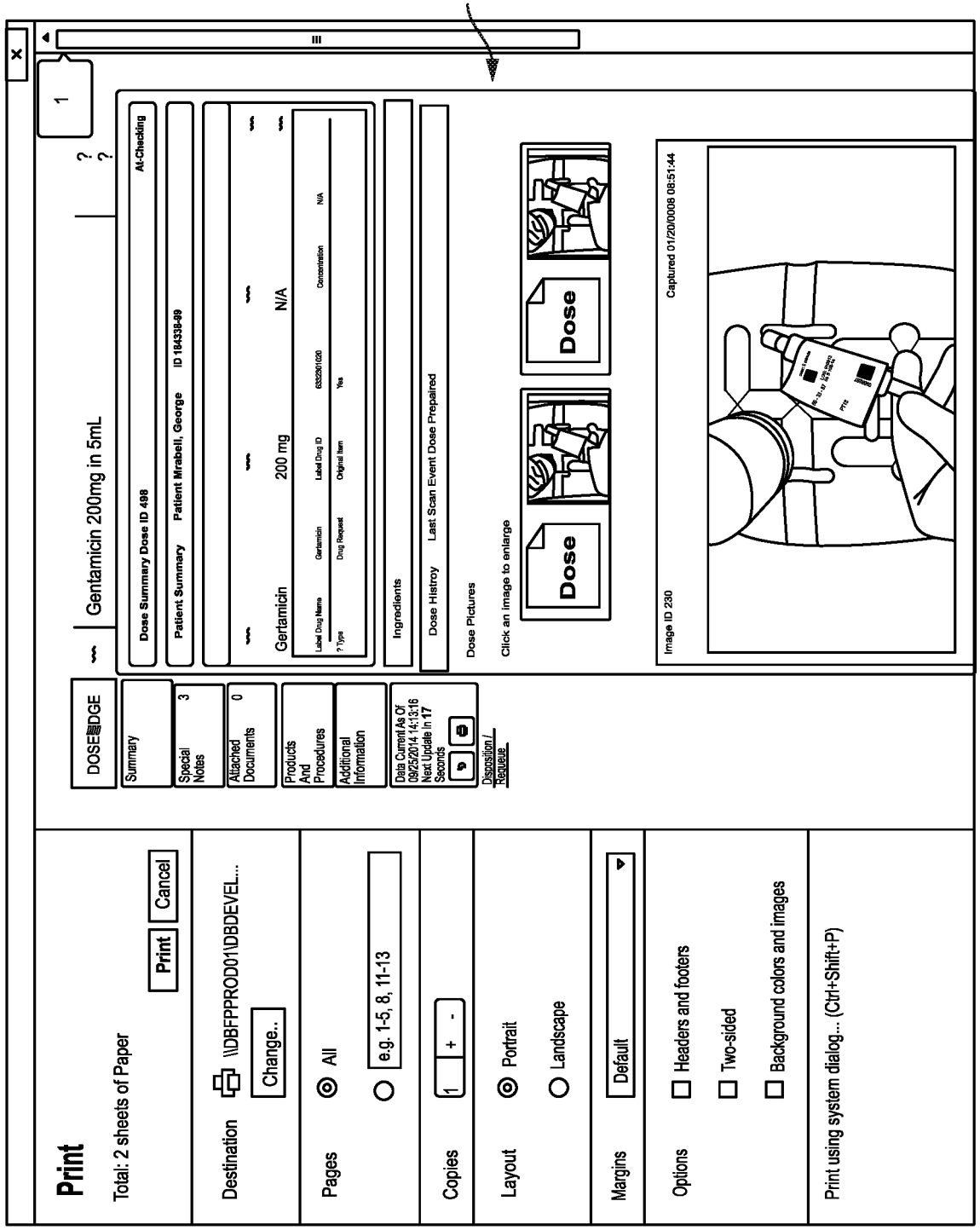

With further reference to FIG. 35, the dose detail screen 3500 may include a timestamp indication 3534 of the last update of the data displayed in the dose detail screen 3500. Furthermore, a clock value 3536 regarding the next update to the dose detail screen 3500 may be displayed. Further still, a refresh button 3538 may be presented that, upon selection, updates the data displayed in the dose detail screen 3500. Additionally, a print button 3540 is presented the user. As shown in FIG. 43, a print preview 3544 may be displayed upon selection of the print button 3540. The print preview 3544 may allow for selective printing of the data fields in the dose detail screen 3500 which are expanded at the time of selection of the print button 3540. Furthermore, any dose pictures associated with the selected dose order 1320 included in the dose pictures field 3532 may be displayed for printing in the print preview 3544. The dose detail screen 3500 may also include a disposition/requeue link 3542 that may allow a user to modify the status of the selected dose order 1320 from the dose detail screen 3500.

Figure 36:
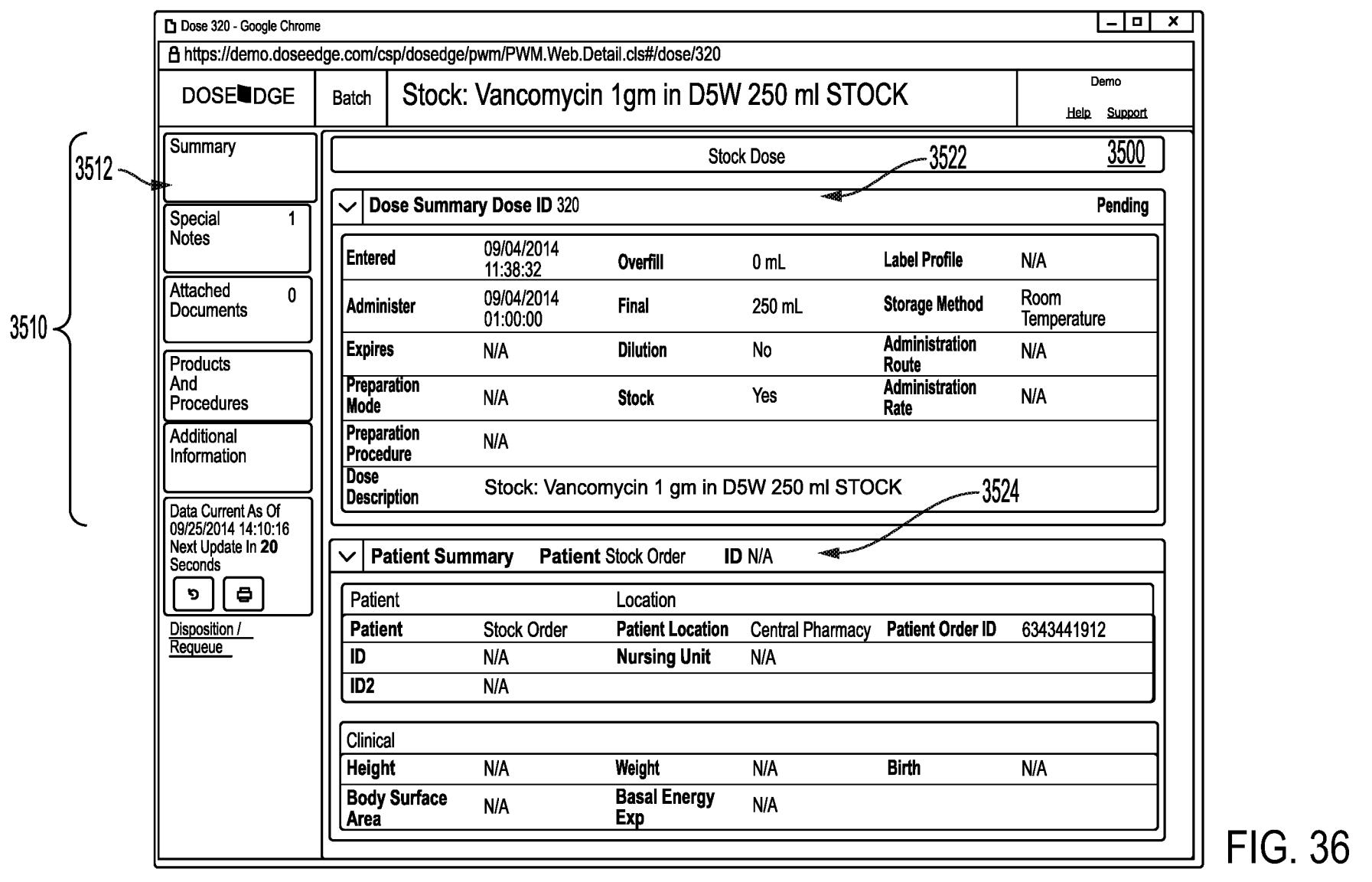

With reference to FIG. 36, the dose summary field 3522 is shown and expanded configuration. In this regard, details regarding the dose such as a time the dose was entered, a time the dose is to be administered or has been administered, a time in which the dose expires, a preparation mode of the dose, a preparation procedure for the dose, a dose description, a dose overfill amount, a final volume for the dose, whether the dose is a dilution, whether the dose is a stock dose, a label profile for the dose, a storage method for the dose, an administration route for the dose, and am administration rate for the dose may be displayed in the dose summary field 3522 when expanded. Additionally, the patient summary field 3524 is shown in an expanded configuration FIG. 36. The patient summary data field 3524 may include patient information such as a patient name, patient identifiers, a patient location, a nursing unit with which the patient is associated, a patient order ID number, or other information regarding the patient. Furthermore, clinical information regarding the patient may also be presented such as a height of the patient, a body surface area the patient, a weight of the patient, a basal energy expenditure of the patient, or a birth date of the patient.

With additional reference to FIG. 37, the items field 3526 is shown in an expanded configuration. In this regard, items associated with the selected dose order record 1320 may be depicted. Additionally, the ingredients field 3528 is shown as expanded in FIG. 37. In this regard, ingredients associated with the selected dose order record 1320 may be displayed including an amount, a concentration, and/or a volume of the ingredient. Further still, the dose history field 3530 is also expanded in FIG. 37. In this regard, various scan events related to the selected dose order record 1320 may be displayed in the dose history field 3530. For example, as shown in FIG. 37, a scanned event where the dose was queued may be shown including the entry date, entry time, user entered the dose, the workstation at which the dose was entered, and an event description may be provided. With further reference to FIG. 49, another example of a dose history field 3530 is displayed that includes a listing 3584 of previous scan events conducted relative to a selected dose order. With return reference to FIG. 35, the summary tab 3512 may also include dose pictures 3532. In this regard, images associated with the selected dose order record may be displayed in this field, such as, for example, current dose image 3580 depicted in FIG. 46.

Figure 38:
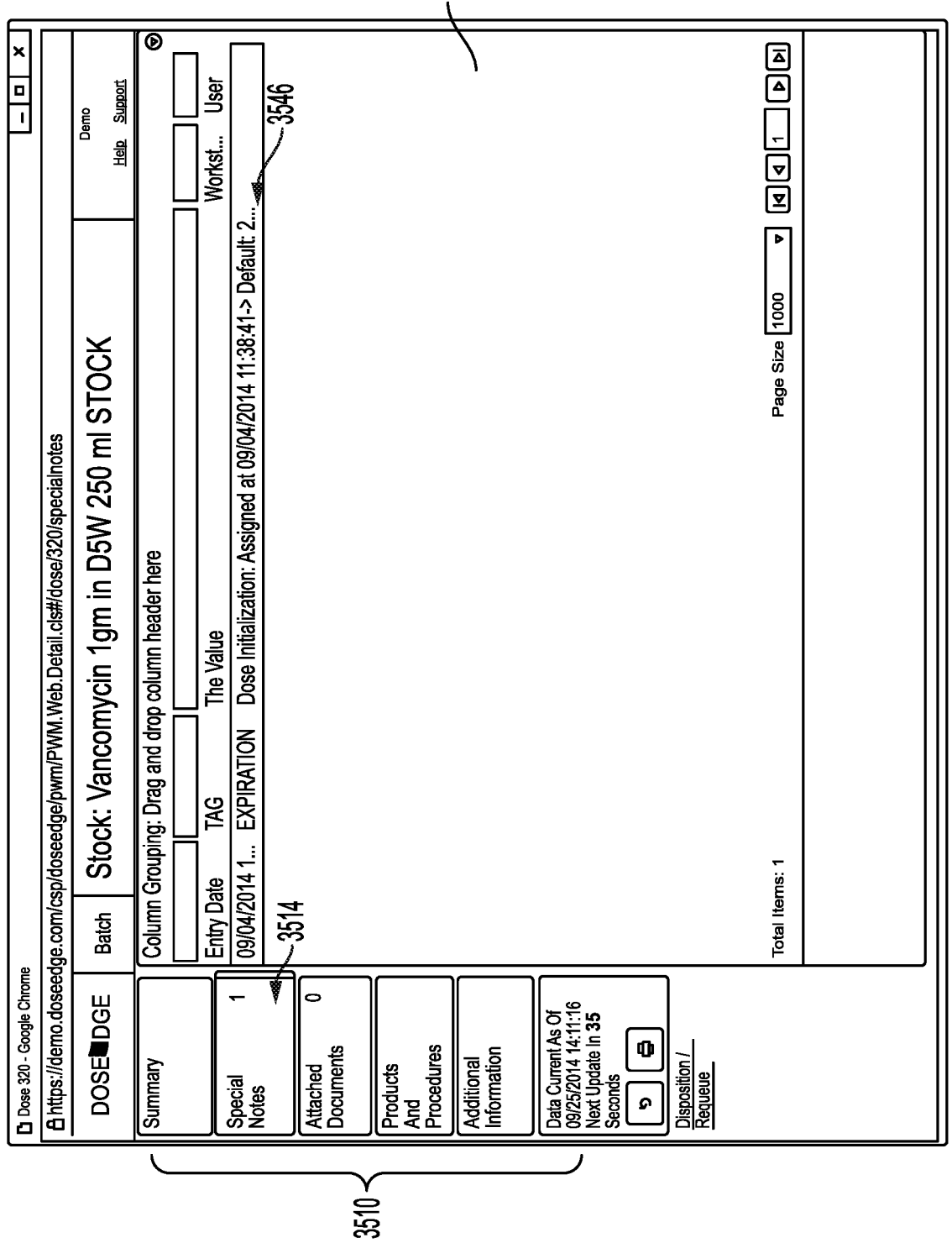
Figure 39:
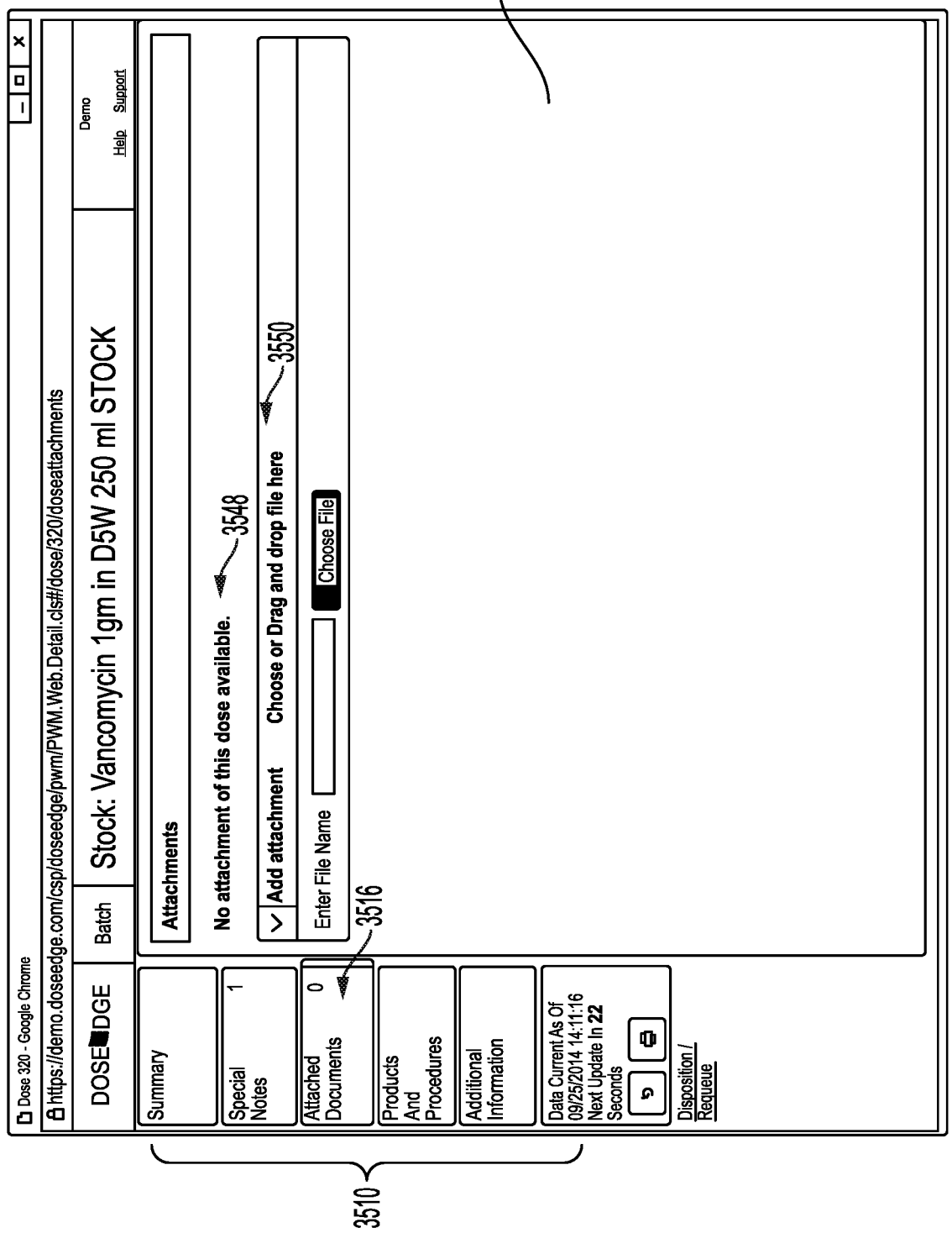

In FIG. 38, the special notes tab 3514 has been selected. In turn, the dose detail screen 3500 may include a listing 3546 of special notes in relation to the selected dose order 1320. FIG. 39 depicts the dose detail screen 3500 upon selection of the attached documents tab 3516. Upon selection of the attached documents tab 3516, the dose detail screen 3500 may display a listing 3548 of attached documents related to the selected dose order 1320.

Figure 44:
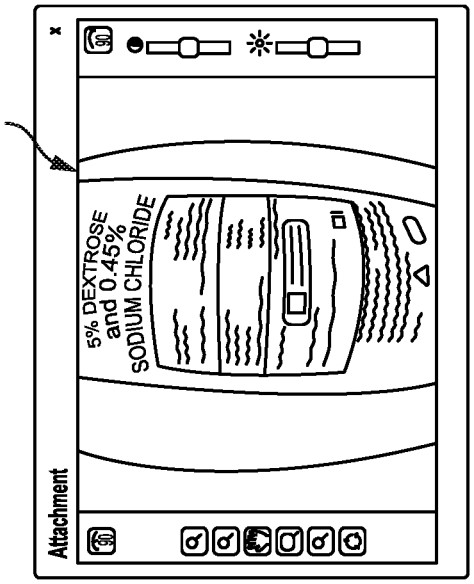

Furthermore, a document attachment field 3550 may be provided to allow user to select a file for association with the selected dose order 1320 by browsing profile to attach or may allow for a file to be dragged and dropped at the attachment field 3550 to associate an attachment with the selected dose order 1320. With further reference to FIG. 44, the attachment field 3550 is depicted with a listing 3566 of attached files associated with the selected dose order 1320. As may be appreciated, the attachments may include image files 3568, text files, portable document format (PDF) files 3570, or other relevant file formats as shown in FIG. 44.

Figure 40:
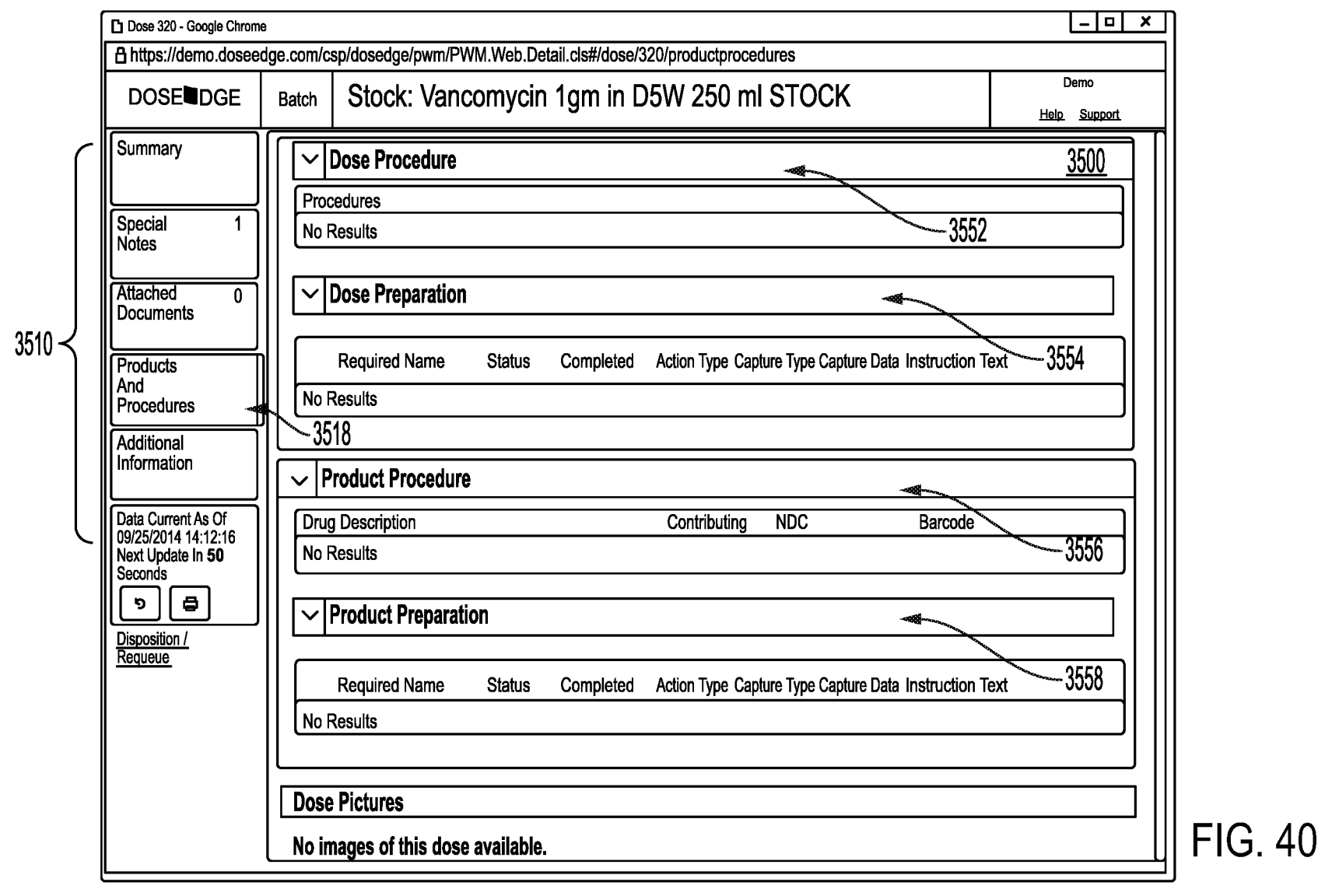

FIG. 40 shows the dose detail screen 3500 upon selection of the products and procedures tab 3518. Upon selection of the products and procedures tab 3518, a number of data fields including a dose procedure field 3552, a dose preparation field 3554, a product procedure field 3556, and a product preparation field 3558 may be displayed. The dose procedure field 3552 may provide a listing of procedures associated with preparation of the dose associated with the selected dose order 1320. The dose preparation field 3554 may show a listing of steps in relation to dose procedures that may be required to be accomplished in order to prepare the dose associated with the selected dose order 1320. For instance, with further reference to FIG. 46, a dose preparation field 3554 is shown as being populated with a listing 3574 of required steps for preparation of a selected order record 1320. In this regard, an identifier of the step, a status of the completion of the step, a time and date at which the step was completed, a capture type associated with the step, a capture date and time associated with the capture type for the step, and instruction text associated with the step may be displayed in the dose preparation field 3554.

With returned reference to FIG. 40, a product procedure field 3556 may provide procedures for preparation of products contained within the dose of the selected dose order 1320. In turn, the product preparation field 3558 may display steps associated with the preparation of a product for inclusion when preparing a dose associated with the selected dose 1320.

Figure 41:
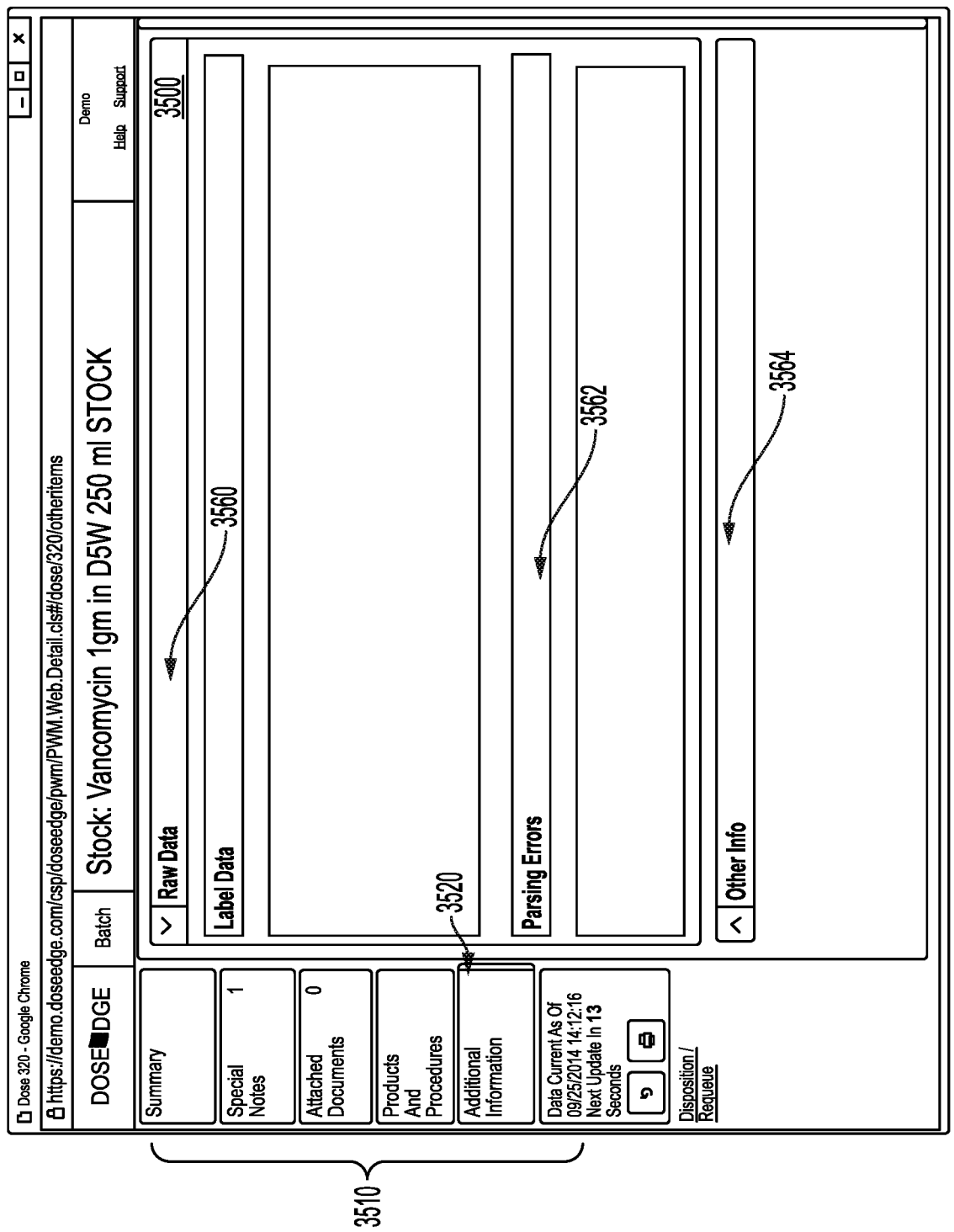

FIG. 41 depicts the dose detail screen 3500 upon selection of the additional information tab 3520. In this regard, a raw data field 3560 may be presented that provides a user information regarding the raw label data (e.g., has received from a print stream or the like). Additionally, parsing errors field 3562 may present to the user information regarding any parsing errors occurred upon parsing the incoming dose order for generation of the selected dose order record 1320. FIG. 42 depicts the other information field 3564 and expanded configuration. In this regard, additional information regarding the selected dose order record 1320 may be presented such as auxiliary data, barcode information, facility information, infusion rate information, this format information, dose administration frequency, as well as items contained within the selected dose order 1320.

FIG. 45 further depicts a clinical data field 3572 that may be displayed in a dose detail screen 3500. The clinical data field 3572 may include a listing of clinical ordered items 3574 in relation to a listing of items 3576 included in the dose. The clinical data field 3572 may be particularly useful in the field of a total parenteral nutrition (TPN) dose in which clinical ordered items 3574 may be used in relation to the items contained in the order 3576 to easily compare the requested dose ingredients 3574 with a compound a result listing 3572 to ensure that the correct items are included in the dose.

With return reference to FIG. 8, selection of the place on hold button 1324 may result in the selected dose order 1320 being placed on hold status. Selection of the remove from hold button 1326 may result in a selected dose order record 1320 that is currently a hold status being removed from hold status. It may be appreciated from FIG. 8, the selected dose order 1320 and the particular embodiment shown is not on hold, therefore the place on hold button 1324 may be enabled while the remove from hold button 1326 may be disabled. In contrast, if a selected dose order 1320 was a dose order with an on hold status, the place on hold button 1324 may be disabled and the removed from hold button 1326 may be enabled. Selection of the discontinue button 1328 may result in the selected dose order 1320 being discontinued (i.e., the status of the selected dose order 1320 may be changed to a discontinued status). Selection of the modify button 1330 may result in display of a dose modification screen 1348 that allows for one or more portions of dose order metadata to be modified as shown in FIG. 9.

Furthermore, the availability of a button for performing an operation relative to a dose order may be at least partially based on a level of authorization of a user. In turn, the enablement of one or more of the buttons that provide management functionality relative to the dose orders appearing in the dose order record listing 1312 may be based upon permission data as described above. As such, for example, a user may have the ability to place a dose order on hold or remove a dose order from hold using the place on hold button 1324 or remove from hold button 1326, but not have sufficient authorization to modify a dose order using the modify button 1330. Further still, a user may have authorization to view a dose order record listing 1312 alone without any authorization to modify a dose in any regard. Each of these permission identifications may be provided in permission data relative to the user.

Figure 9:
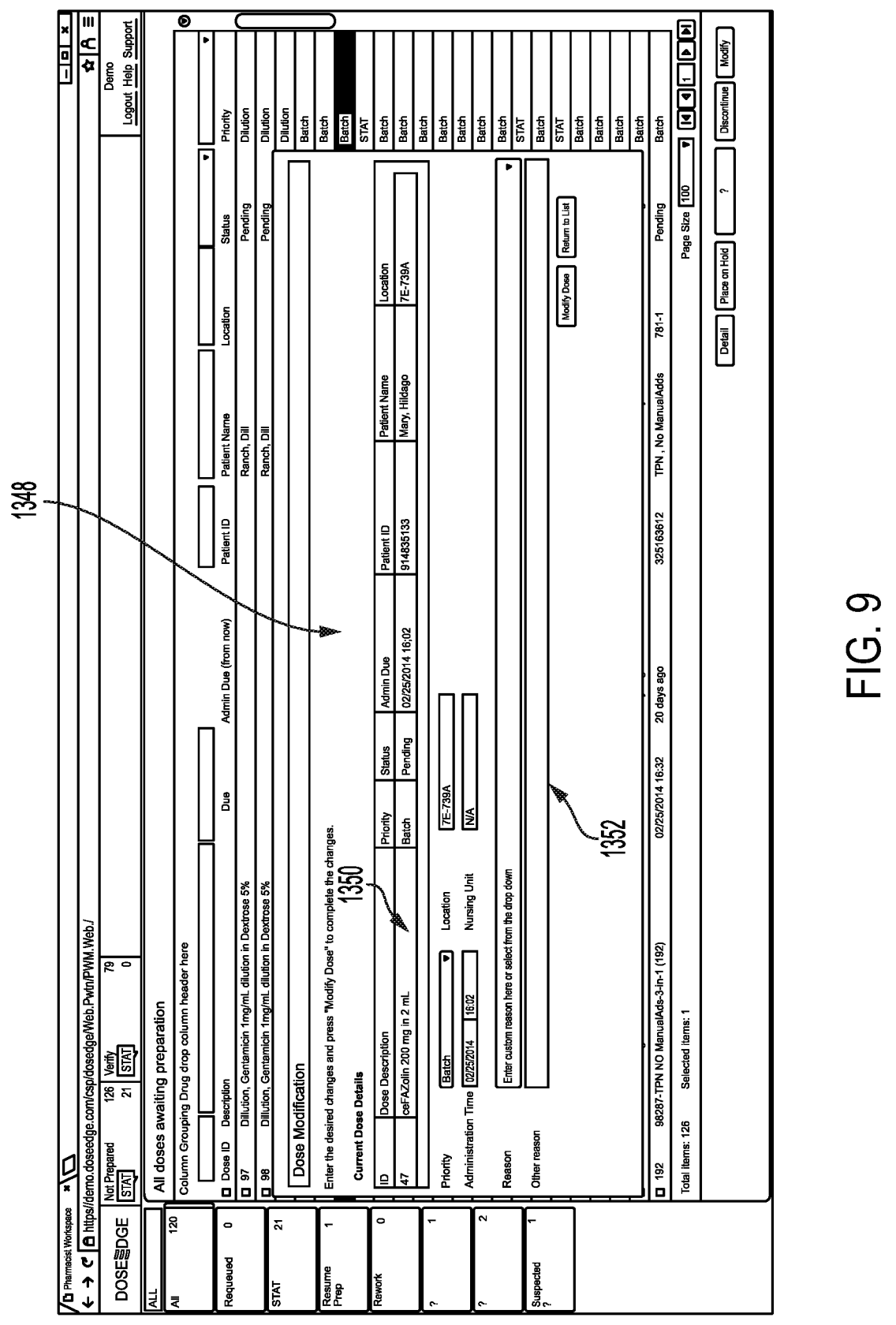

With continued reference to FIG. 9, the dose modification screen 1348 may be displayed upon selection of the modify button 1330 with respect to a selected dose order 1320. The dose modification screen 1348 may include the dose order record listing 1350 and a dose modification field 1352. The dose modification field 1352 may include one or more fields that allow for modification of one or more dose order record data fields associated with the selected dose order 1320. For example, the dose priority, dose location, administration time of the dose, nursing unit to which the patient for the dose belongs, or other parameters may be modified for the selected dose order record 1320. The dose modification field 1352 may also provide a field to accept a reason for the modification of the selected dose order record 1320. Providing a reason for modification of the dose may be required field that must be selected by user prior to allowing the dose order record to be modified. The reason may be selected from a drop-down field that may include a plurality of predefined reasons that may be selectable by a user. Additionally or alternatively, the user may enter a reason for the modification using free-form text entry in the other reason box. Furthermore, depending upon the authorization level of the user, the other reason provided by the user may be included for later selection and the reason drop-down list.

Figure 10:
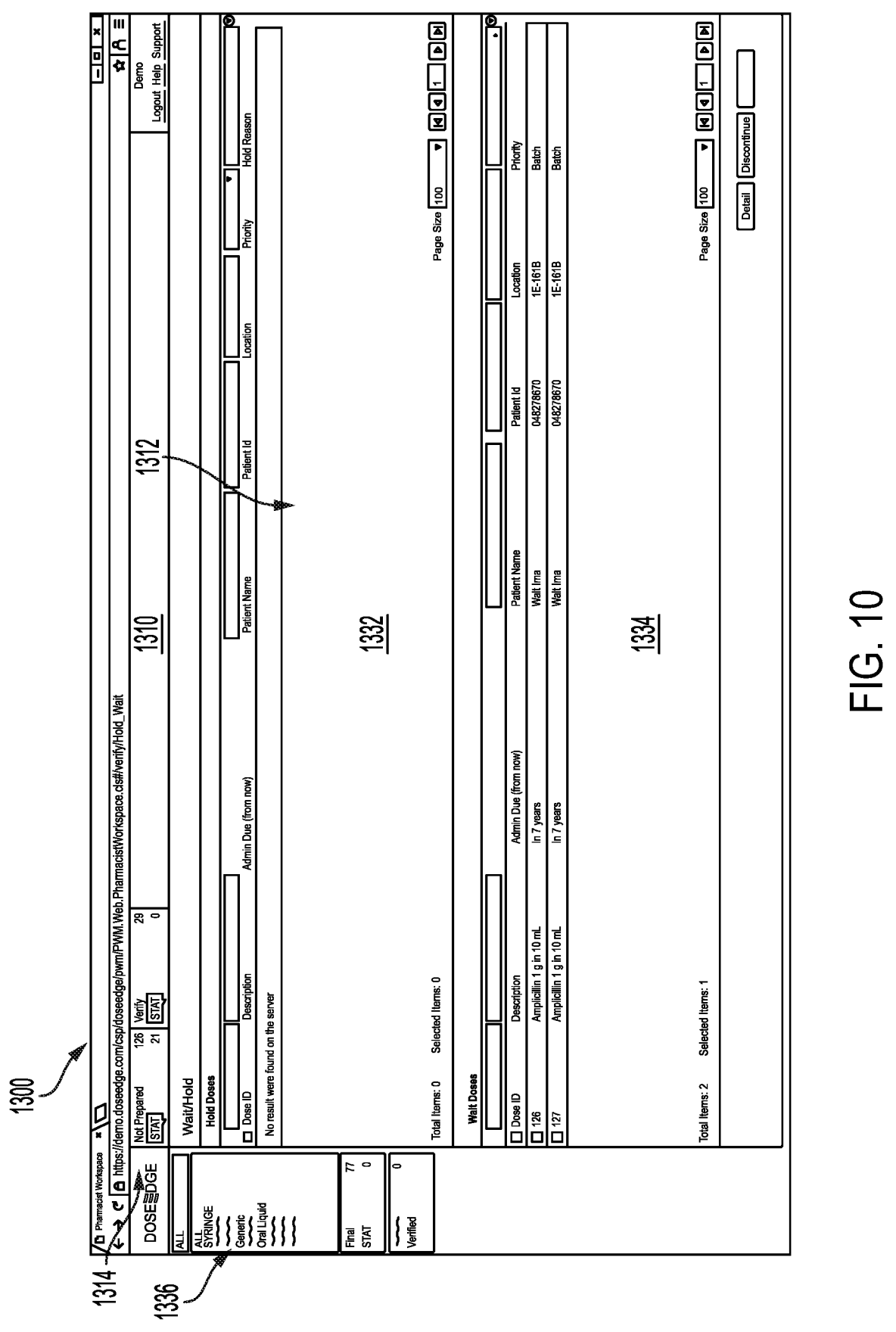

With further reference to FIG. 10, the dose order management screen 1310 is shown when the verify tab 1316 is selected. Upon selection of the verify 1316, doses that have been prepared and are waiting pharmacist verification may be displayed. Additional aspects related to pharmacist verification are described in greater detail below. Furthermore, FIG. 10 depicts the dose order management screen 1310 upon selection of a wait/hold secondary filter from the secondary filter list 1318. In this regard, the dose order record listing 1312 may be divided based upon a dose order record status of having a hold or wait status. Also shown in FIG. 10, a plurality of queue filters 1336 may also be provided. The queue filters 1336 may be configurable by a user and may allow for customization of filters to be provided. In this regard, the queue filters 1336 may include customizable parameter selection such that a filtered dose order record listing 1312 may be based upon any desired metadata for one or more dose order record data fields associated with the dose order records. That is, the queue filters 1336 may query any one or more of the dose order record data fields associated with each of the dose order records in return only those dose order records that match a query.

With further reference to FIG. 11, a further embodiment of the dose management screen 1310 is depicted. As shown in FIG. 11, the dose order record listing 1312 may be configurable to depict categorization of dose order records within the dose order record listing 1312. For example, user interface elements may allow for a column heading such as, for example, the patient name 1338 as shown in FIG. 11 to be dragged and dropped to a categorization bar 1340. Upon selection of the column heading 1338 for use in the categorization bar 1340, the corresponding column heading 1338 may appear in the categorization bar 1340. In turn, the dose order record listing 1312 may be configured to display dose order records according to category selected based upon the column heading 1338 selected. For example, shown in FIG. 11, the patient name column heading 1338 has been selected for use in the categorization bar 1340. In turn, the dose order record listing 1312 may be categorized according to patient name. Thus, the dose order record listing 1312 may include category headings 1342 within the dose order record listing 1312 such that associated dose order records 1344 corresponding to the category heading 1342 are presented. As may be appreciated, each category heading 1342 may be expanded or collapsed such that the associated dose order records 1344 for each category heading 1342 may be shown or hidden. It may be further appreciated the multiple category headings 1338 may be dragged and dropped to the categorization bar 1340. As such, the categorization within the dose order record listing 1312 may include a hierarchical listing such that a plurality of hierarchically displayed category headings 1342 may be provided in the dose order record listing 1312.

FIG. 11 also displays a column layout selection 1346 that allows for different column headings 1338 to be shown and/or hidden in the dose order record listing 1312. The column layout selection 1346 also allows for arrangement of the various column headings 1338. In this regard, the column layout selection 1346 may allow for user customization. In turn, the user may arrange the dose order record listing 1312 as desired including selection and/or arrangement of various column heads, categorization and/or filter results. In turn, once users authorized in the login screen 1302, the last used dose order record listing 1312 configuration or a default dose order record listing 1312 configuration any presented to the user.

Rules may also be used to otherwise assist in management of the dose order records in the dose order queue. For example, the local server 330 may also include or be in operative communication with a dose logic engine ("DLE"). The DLE may be operative to evaluate dose order records based on one or more portions of dose metadata stored in corresponding dose order record data fields. In this regard, anyone or more the portions of dose order metadata as described above may be utilized in a rule implemented by the DLE. Furthermore, conditions for execution of rules executed by the DLE may be established such that the rule may be performed at one or more times on dose order records. For example, one or more rules may be executed on a dose order record by the DLE when the dose order record is initially populated in the dose order queue and/or upon a subsequent condition being satisfied such as a change in status of the dose order record or the like. In any regard, a rule executed by the DLE may include scrutinizing one or more portions of dose metadata in view of a rule. For example, Boolean searching or the like may be utilized to identify whether a rule is to be applied to the dose order record based on the occurrence of a selected parameter in the dose order metadata. Upon determining that a rule applies to a dose order record, an operation may be associated with the rule that is in turn executed on dose order records determined to be applicable to the rule. The operation may be utilized to manage and/or modify the dose order record identified by the rule. For example, the operations may include changing a status of the dose order, modifying metadata of the dose order, or other appropriate operation with respect order record or metadata associated with the dose order record. Two such examples of operations that may perform by the DLE include identifying duplicate orders and/or discontinued orders.

In a duplicate order detection rule, the DLE may be operative to review a first dose order record in view of other dose order records within the dose order queue to determine if the first dose order record corresponds to a potential duplicate dose order. In this regard, the DLE may evaluate the metadata regarding the first dose order record to determine if other ones of the dose order records within the dose order queue match the identified metadata regarding the dose order to a predetermined correspondence. The predetermined correspondence may be selectable by a user of the management tool 1300. It may be appreciated that the matching of the metadata between the dose order records being reviewed and the other dose order records in the queue may not necessarily need to be identical. For example, the rule may be written such that if selected ones of the metadata fields are identical between the first dose order record being reviewed and the other dose order records in the dose order queue, the dose order record being reviewed may be flagged is a potential duplicate order. Such a rule may be applied to the first dose order record when the record is initially populated the dose order queue.

In this regard, with further reference to FIG. 12, may be appreciated that the dose order records that have been identified as a potential duplicate order may be sorted and presented to a user. In this regard, the dose order management screen 1310 may include a secondary filter for presenting suspect duplicates in the dose order record listing 1312. In this regard, the dose order record listing 1312 may be populated with suspected duplicates. In this regard, the dose order record listing 1312 may present a user in an original dose order record 1362 that is associated with one or more suspected duplicates 1364 based on exceeding a predetermined correspondence between the metadata of the suspected duplicates 1364 the original dose order record 1362.

Accordingly, upon selection of the suspected duplicate 1364, number of operation buttons may be enabled. For example, the user may select detail button 1366 to be presented with additional details regarding the suspected duplicate order 1364 and/or the original order 1362. In turn, the user may determine suspected duplicate 1364 may not in fact be a duplicate order, but rather be a valid order the should proceed preparation. In this regard, the user may select the ignore button 1368 to indicate that the suspected duplicate 1364 is not in fact a duplicate of the original order 1362. In contrast, should the user determine that the duplicate order 1364 is in fact duplicate of the original order 1362, the user may select the discontinue button 1370 to discontinue the duplicate order 1364 such that the duplicate order may be removed from the dose order queue. Upon selection of either the discontinue button 1370 or the ignore button 1368, the user may be present the dialog box that may require the user to identify the reason for the discontinuation or ignoring of the suspected duplicate status of the dose order.

Additionally, it may be recognized that the DLE may process incoming dose orders to determine if the order corresponds to a discontinuation of an order. That is, a common practice when processing dose orders is to indicate a discontinuation of a first order by subsequently sending a corresponding order to the first order at a later time with a discontinue status for the subsequently provided order. In prior approaches, the receipt of such a discontinued order may simply result in printing a label with the dose order details and a discontinuation status. This would in turn require a user to go through the printed dose order labels to locate the original dose order that was referenced in the discontinued dose order in order to replace the original dose order on a discontinued status. The DLE may be utilized to automate this process in the context of the dose order queue stored by the local server 330 by identifying receipt of a dose order in the dose order queue that contains a discontinued status and automatically matching the discontinued dose to one or more existing dose order records. Thus, receipt of a dose order with a discontinued status may trigger the DLE to perform a query of the dose order queue to identify corresponding ones of the dose orders in the dose order queue that exceed a predetermined correspondence to the discontinued dose order. For example, one or more overlapping or identical pieces of metadata between the discontinue dose order and the identified discontinued order in the dose order queue may be determined. The predetermined correspondence may be customizable by a user. In any regard, upon identification of a dose order record from the dose order queue that corresponds to a received discontinued dose order, the original dose order may automatically change the status of the one or more identified dose order records to a discontinued status.

The execution of a discontinued dose rule by the DLE may also at least partially be based upon the status of the one or more dose order records from the dose order queue that are identified as discontinued doses at the time the dose order records are identified. For example, in one example, the dose order for the dose order record identified as a discontinued dose may not yet have been prepared. In this regard, the DLE may simply change the status the dose order record to discontinued and remove the dose order record from the dose order queue such that the discontinued dose order record is not prepared. In contrast, the identified discontinued dose order record may have been prepared and verified and be in sort awaiting dispatch from the pharmacy. In this regard, the status of the dose order may be modified to discontinued and any resulting dose that was prepared for the dose order record may be changed from a dose to a product. That is, the dose order system may print a work in progress label or other identifier that allows the prepared dose to be moved to pharmacy stock for later use (e.g., to fulfill a later dose order received at the pharmacy). The modification of a dose to a produce may also occur in the case where a dose has been prepared and not yet verified. In this regard, the pharmacist that performs the verification may be presented with the status of the dose being discontinued.

In addition to the dose order record management functions related to the dose order records described above, the pharmacy workflow management application 114 may further be operative to provide dose order records to a workstation for the purpose of fulfilling or preparing the dose order record at the workstation. Any number of different workstations can be part of the system. For example, FIG. 2 shows a flowhood workstation A 500, a flowhood workstation B 510, and a chemo workstation 520. However, other workstations may be provided without limitation. For instance, those skilled in the art will recognize a number of different workstations that are often utilized in the pharmacy environment. Such workstations may include laminar flow hoods, biohazard cabinets, or other particularized workstations used in the preparation of specific doses. However, other workstations may also be included that do not actually prepare doses, but may be used for pharmacy management such as supervisory terminals (e.g. that perform web-based system management, query reporting, etc.), situation boards that display system status or the like, pharmacist review stations, or other appropriate workstations in operative communication with the local server 330 to communicate dose order record and associated metadata.

In any regard, the local server 330 may be operative to communicate with a workstation to provide information related to the dose order record thereto. For example, in order to prepare a medication dose at one of the workstations, data regarding a corresponding medication dose order record may be sent by the local server 330 to the appropriate workstation. As may be appreciated, the various workstations may be particularly suited for particular type of medication dose to be prepared. For instance, a dose of chemotherapy to be administered to a patient may be provided to the chemo workstation 520, whereas another type of dose may be prepared at another workstation within the local system 110.

With returned reference to FIG. 4, information related to dose order records may be forwarded to client applications executing on one or more workstations located within the pharmacy, hospital, or elsewhere. The workstation client application or technician can manage the various open tasks (e.g., orders to fill) by interacting with the workstation in order to follow a protocol or "recipe" mandated for a particular dose order or batch of orders, as indicated a block 440. The dose orders are prepared as doses at the workstation with the benefit of documentation support as indicated a block 430. The documentation support is provided to the technician to guide preparation and better ensure the doses are prepared in accordance with established protocols and policies. As described further below, the intermediate steps in the preparation of each dose order are subject to data capture to permit post preparation review of the steps taken to prepare each dose.

Figure 13:
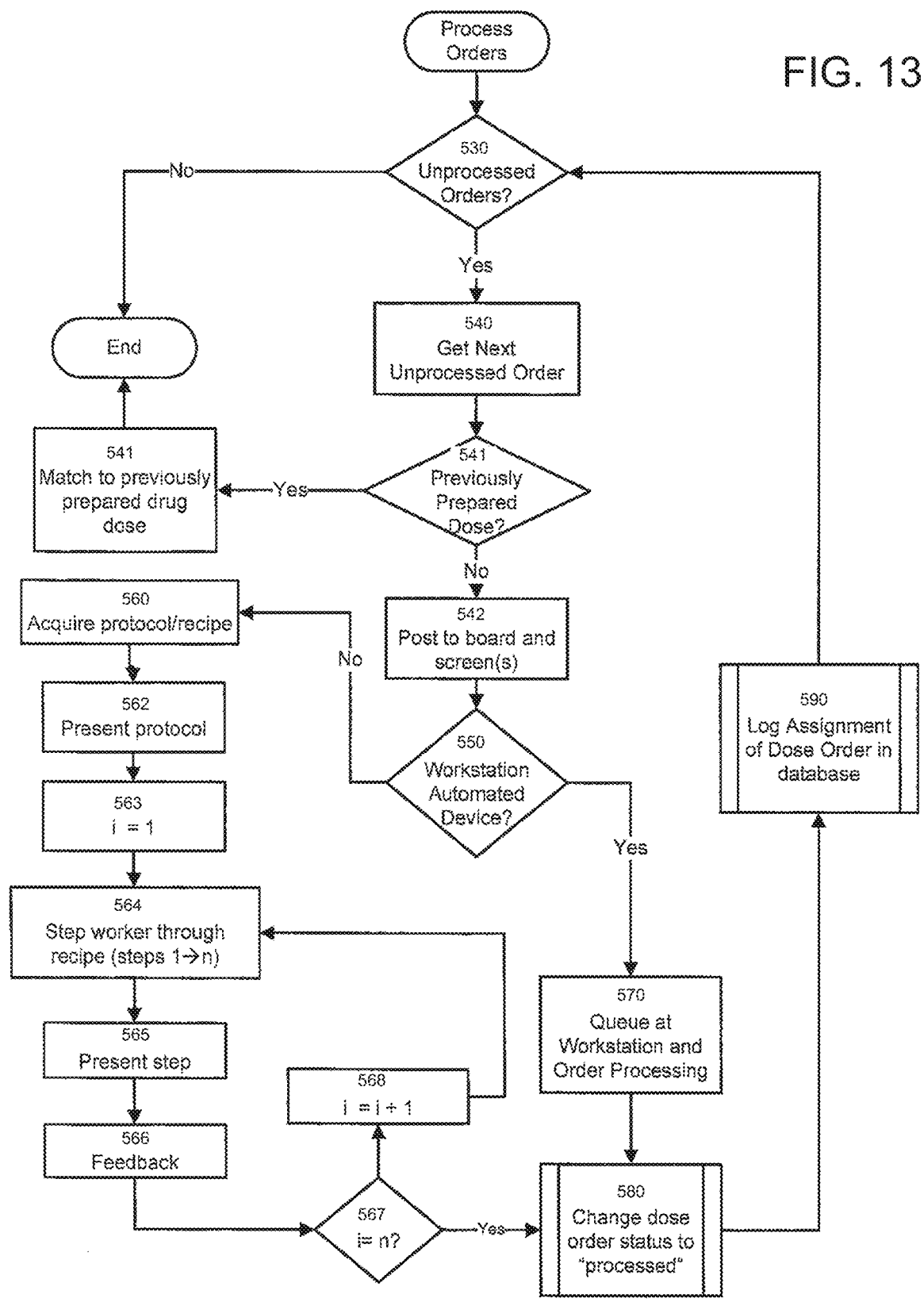
FIG. 13 depicts a flow chart of an embodiment of a method for processing dose order records to prepare a corresponding dose at a workstation.

Returning to the dose preparation workflow and documentation support 430 and management of scheduled tasks by the workstation 440 depicted in FIG. 4, an exemplary method performed in relation to these schematically depicted tasks as shown in FIG. 13. The order filling processing commences at step 530 at which it is determined whether there anyone to fill dose order records in the database.

If unfulfilled dose order records are in the database, unfulfilled dose order records are retrieved at step 540. At decision 541, it may be determined whether a dose previously prepared and stored which would satisfy the dose order. For disclosure of assist in the prepared dose orders in anticipation of need for such orders, see U.S. application Ser. No. 11/844,135, filed Aug. 23, 2007, entitled "Automated Centralized Preparation of Medications in Anticipation of Use," which is co-owned with the present application and hereby incorporated by reference in its entirety. If no such dose exists, the dose order may be posted to the dose order queue at each workstation and may also be posted to the situation board 400 at step 542. Additionally, the dose order record may be updated so that a status of the dose order records indicated as "pending" to signify the dose order is ready to be prepared. Optionally, the requirements for filling the dose order are retrieved and used to post the dose order to the dose order queues only those workstations that are suitable for handling such dose order. In this way, individual workstations may have a tailored queue of pending dose orders. In another arrangement, such tailored queues are provided to the individual workstations with the operator such workstation can expand the presentation to see other disorders in the queue even if not suitable for handling of the operators given workstation.

With returned reference to FIG. 13, at step 542, the drug order queue is generated and optionally one or more dose orders can be assigned to a particular workstation based on one or more rules that govern the distribution of dose orders to a particular workstation. The system may be configured so that the dose orders must be "pulled" from the dose order queue. In other words, an affirmative step may be required for the dose order to be assigned to particular workstation. For example, as discussed above, an operator at a given workstation may review the dose order queue and then select the dose orders that will be fulfilled at the given workstation (e.g., by using a touch screen display), at which time these orders are effectively assigned to workstation and are removed from the dose order queue.

In some instances the workstation is in the form of an automated device and therefore, the automated device has a selection module comprising code to automatically select those dose orders in the queue that can be fulfilled by the workstation. The selection can take into account number of different rules including the number of pending dose orders at this workstation, the availability of different drugs, etc. The automated device communicates with the local server 330 and selects and pulls dose order for filling.

However, even when the system is configured to operate in such a pull mode, the individual dose orders can be preassigned in the event that a dose order can only be fulfilled by a specific workstation, in which case the application 114 may recognize this fact and identifies that the particular dose order is intended for delivery to a particular workstation. For example, if the dose order that is received and processed step 541 is the type that can only be fulfilled by specific workstation (e.g., chemotherapy workstation), the dose order will be identified as such on the dose order queue in the workstation type is qualified for receiving and fulfilling the dose order can be notified (e.g., the chemo workstation 520 as shown in FIG. 2). Similarly, the type of dose order can be identified as a manual fill dose order on the situation board in one or more manual workstations can be alerted or to simply include the dose order on screen.

In another application, the system may be configured to "push" dose orders to the individual workstations. In this regard, the local server 330 may select which workstation is best capable of handling incoming dose order and assign the dose order to that workstation. Workstation may then be sent to the workstation fulfillment of the order. In this regard, the "pushing" dose orders to the individual workstations may be based on a multitude of factors including, for example, the type of workstation, the backlog of dose orders, the types of drugs located at a given workstation, the technician logged in at a given workstation, or other factors.

Furthermore, the application 114 can analyze the supplies necessary to fulfill the order. The list of required supplies may be compared to an inventory of supplies and their availability, optionally broken down by hospital, pharmacy location, or workstation. If there are insufficient supplies, additional supplies may be automatically order the relocation of supplies from one workstation to another may be ordered such that at least one workstation will have the necessary supplies to fulfill the dose order.

In an embodiment, a rule-based management of dose orders (e.g., by way of the DLE discussed above) may facilitate automatically assigning a dose order based on the preparation mode for the dose order. For example, the dose order may be evaluated with respect to at least one portion of dose order metadata stored in a dose order record data field associated with the dose order record. This evaluation may be performed upon population of the dose orders to the dose order queue. In turn, the evaluation may result in the preparation mode being assigned to an order. In turn, the user may be free of selecting the preparation mode associate of the dose order record, rather the preparation mode may be assigned automatically in response to the evaluation of the at least one portion of dose order metadata stored in the dose order record data field. The preparation mode assigned the dose order may be used, for example, to generate and/or select an appropriate preparation procedure for that dose order. Such preparation procedure may in turn be presented to a user when preparing the dose. As the preparation mode may be automatically attributed to the dose order based on application of a rule to the dose order, the user may not be required to select the preparation mode for the dose order. In turn, the dose order may be routed to an appropriate workstation where the user may be presented with the preparation procedure at least partially based on the automatically assigned preparation mode that is been associated with the dose order record by the system. Furthermore, dose orders that have the same preparation mode may also be grouped together into a micro batch in a queue view list.

In this regard, the pharmacy workflow management application 114 may allow for a dose order record to be communicated to a workstation for preparing a dose associated with the dose order record. As may be appreciated, the protocol or "recipe" corresponding to the dose order record may be provided to a technician at the workstation for use in preparing the dose. During the preparation of the dose, the technician may scan, enter, capture, or otherwise generate or record dose order metadata corresponding to the dose order being prepared. At least a portion of this information collected by the technician during preparation of the dose may be utilized to allow for a pharmacist review of the preparation of the dose as described in greater below.

With returned reference to FIG. 13, if the dose-order is one determined to be suited for manual preparation, then the process flow branches to block 560. At block 560, protocol information is retrieved. This is because, before the dose order record is dispatched to a manual workstation for action by the operator, additional information is provided to facilitate the manual fulfillment of the dose order at the selected workstation. This can be based on the determination that manual preparation is required and the assumption that providing additional information can improve safety, efficiency, and precision during fulfillment of the dose order. The management module can associate the additional information with the dose order record. For example, at step 560 the medication and form of dose (e.g., syringe, IV, oral dose etc.) specified by the dose order record can be examined so as to determine the protocol by which the dose of that medication should be prepared. The protocol can specify the steps (e.g., sanitization and documentation) that must be taken during preparation to comply with Food and Drug Administration regulations or any other governing procedures regarding the conduct of the pharmacy. Furthermore, the protocol associated with the dose order at steps 560 and 562, preferably is interactive in guiding the operator through the fulfillment process to achieve the same level of accuracy and dose safety which is typically associated with the automation. For example, the protocol can require the operator's input including logging of events at critical stages of the dose preparation process (e.g., requiring the operator to scan information related to the source drug containers).

The additional information (i.e., protocol) can be associated with the dose order record at step 562 for presentation to the operator. The association can be accomplished by attaching the protocol file to the dose order record, or otherwise communicating it electronically to the workstation selected for handling that dose order, or by printing a copy of the protocol to include with a printed order for the dose. In a paperless environment, the protocol is preferably displayed along with the display of the order or can appear as a hyperlink or call-up dialog box from within the order display at the workstation.

Figure 14:
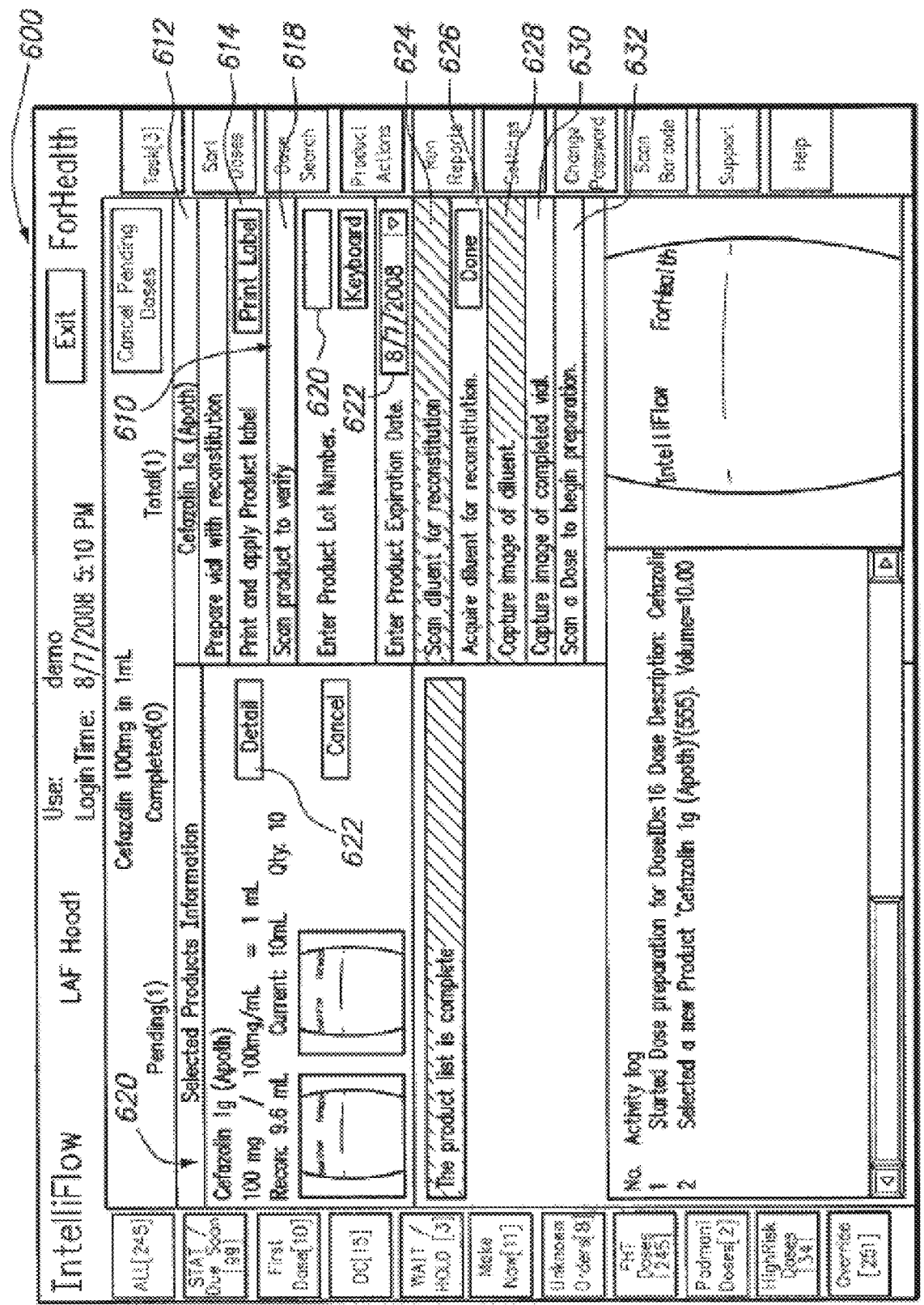
FIGS. 14-15 depict an embodiment of a user interface of a pharmacy workflow management application presented to a user when preparing a dose corresponding to a dose order record.

Referring briefly to FIG. 14, one exemplary screen 600 is illustrated that lists a number of steps generally indicated at 610 that are required to be performed to successfully prepare a medication product that is used to prepare a dose that is part of a dose order. On the left side of the screen, the drug to be prepared is clearly identified at 620, in this case Cefazolin 1 g (Apoth). This screen is an interactive screen in that the user can simply highlight different areas either to receive more information or to enter information. For example, there is a Detail button 622 near the drug identification and if additional information is needed concerning this particular drug order, the user can simply highlight this particular button (as by "clicking" the box).

On the right side of the screen are processing steps 610 that must be undertaken in order to prepare the requested dose. For example, a banner 612 indicates again the drug being produced is Cefazolin 1 g (Apoth) and below this banner there are a number of steps 610 that must be performed in order to produce the correct dose (drug product). The illustrated screen shows a first step 614 of printing and applying a product label. The label is printed by simply pressing the button 616 that is labeled "Print Label". As soon as the label is printed, the user is prompted to move on to the next step 618 which is a step of scanning the product to verify that the proper product is present at the workstation. Conventionally scanning equipment can be used to scan (e.g., a barcode) the product and then the user is prompted to enter the Product Lot Number in a box 620 that is provided and the user then enters the Product Expiration Date in another box 622. All this inputted information is used to confirm that the correct product (drug) is present and is being used in the preparation of the Cefazolin 1 g dose. In this regard, it may be appreciated pharmacy workflow management application 114 may require a previous step to be completed prior to moving to a subsequent step. Performance of some steps may include positive capture of information related to the dose being prepared. In turn, the sequence of the protocol presented for a dose may be documented and explicit steps in relation thereto may be required prior to progressing in the sequence.

In another aspect of the present invention, other identifying information can be used to assist in determining that the correct drug is present at the workstation and is suitable for use in fulfilling a pending drug order. More specifically, the Drug Listing Act of 1972 requires registered drug establishments to provide the Food and Drug Administration (FDA) with a current list of all drugs manufactured, prepared, propagated, compounded, or processed by it for commercial distribution. The National Drug Code (NDC) is a universal product identifier used in the United States for drugs intended for human use. The FDA inputs the full NDC number and the information submitted as part of the listing process into a database known as the Drug Registration and Listing System (DRLS). The information submitted as part of the listing process, the NDC number, DRLS, and the NDC Directory are used in the implementation and enforcement of the Act. In turn, the NDC for a drug may be recorded during the preparation of a dose. A formulary of the pharmacy workflow management application 114 may be cross-referenced to determine if the NDC received during preparation corresponds to a drug appropriate for the dose being prepared. If the NDC is appropriate as determined by reference to the formulary, the user may be allowed to sequence to the next step in the process. If the NDC does not match, the operator may not be allowed to progress and the fact that in incorrect NDC was provided may be noted. It will also be appreciated that some of this information can be inputted using a reader devices, such as a barcode reader, etc.

Dose order records stored in the local database can be ordered or arranged and displayed in the dose order queue and/or at the situation board in accordance with a rule base that operates on the database with one or more rules. The rules may be at least partially based on dose order metadata populating one or more dose order record data fields. For example, one rule can be to optimize fulfillment of the orders. Thus, like dose orders (e.g., dose orders with similar drug components as reflected in the dose order metadata) can be processed at the same workstation one after another and hence faster because there is less cross-contamination and medication changes (i.e., retrieval and storage). Thus, dose orders can be grouped by type or medication, such that dose records requiring the same medication or with no risk of cross-contamination can be processed in order by the same machine, or set of machines. In this regard, the rules are configured to sort the dose-orders by type or medication. Alternatively, dose order records can be prioritized by urgency (e.g., "First Doses" or "STAT"). For example, if a doctor urgently needs a specific medication, the data stream identifying the dose can include information indicating its urgency, and the dose order record can include such urgency information. Thus, the rule in this instance operates to re-sort an urgent order to near the front of the queue, or have that order identified (e.g., flagged) as urgent for immediate or expedited fulfillment. Through this or a similar mechanism, the next unfulfilled dose order retrieved at step 140 can be arranged in the queue to optimize throughput or to satisfy other rule-based priorities. Alternatively and as described above, urgent orders can simply be highlighted and/or labeled as such in the drug order queue presented at the workstation.

The workstation can include various tools and monitoring equipment to assist and perform quality control during the manual preparation of the dose order. Such tools and monitoring equipment can include barcode scanners, digital cameras, scales, hydrometers, spectrometers, and other tools that can be used to verify the properties of a substance. For example, a computer monitor at the workstation can prompt the operator to take certain measurements of the dose order being prepared and input the results of those measurements. Failure to input a measurement within an acceptable range can result in the system automatically rejecting the preparation. Furthermore, to prevent operator fraud, the system can prompt the operator to place the preparation on a scale, or within another instrument, that automates the measurement, thereby reducing the opportunity for the operator to intentionally or unintentionally deceive the system. In this regard, it should be appreciated that the protocol presented to the used at block 562 is preferably coded to capture the progress made toward dose fulfillment. Thus, steps taken in completing the protocol or recipe are preferably coupled with specific operator input such as photographing a drug vial, weighing a syringe, and the like, with the inputs being captured and included in a data record that can be forwarded to the pharmacist for review and approval. The data record can be a record storable in the Ensemble database that is used in a preferred embodiment of the invention.

In accordance with the present invention and as previously mentioned, the present system includes means, such as readers and the like, which allow a particular drug to be identified at step 618 and compared to a database to ensure that the identified drug is the drug which is being requested is the same drug which has been identified at a particular location (station) of the present system. Since the NDC includes product code information, such as the specific strength, dosage form and formulation, it can be used in drug identification step 618 of the present system. It will also be appreciated that the NDC number can provide a means for redundantly confirming the identification of the drug being used at the workstation to prepare the requested drug order. In other words, other identifying information that is printed or otherwise present on the drug product can be read and then the NDC number can be read and the two compared as part of an integrity check to ensure that the correct drug product is present at the workstation.

The next step 624 involves scanning the diluent that is used in the reconstitution process. Once again, conventional scanning or imaging techniques can be used to identify and confirm whether the correct diluent is being used in the reconstitution process. The step 626 involves acquiring the diluent for the reconstitution and then confirming its proper identity and the user can indicate that the step has been completed by pressing the button labeled "Done". The next step 628 can involve capturing the image of the diluent using conventionally techniques (e.g., a camera) and additional steps that can be performed are capturing the image of the completed vial 630 and scanning a dose to begin preparation of the individual dose 632. All of the information that is gathered in each of the steps is stored in the local database, preferably in the same record as or in association with the particular drug order being filled.

At any point, if a task performed in one of the steps is not verified as being correct, the operator is prevented from going onto the next step and the dose is not prepared.

Figure 15:
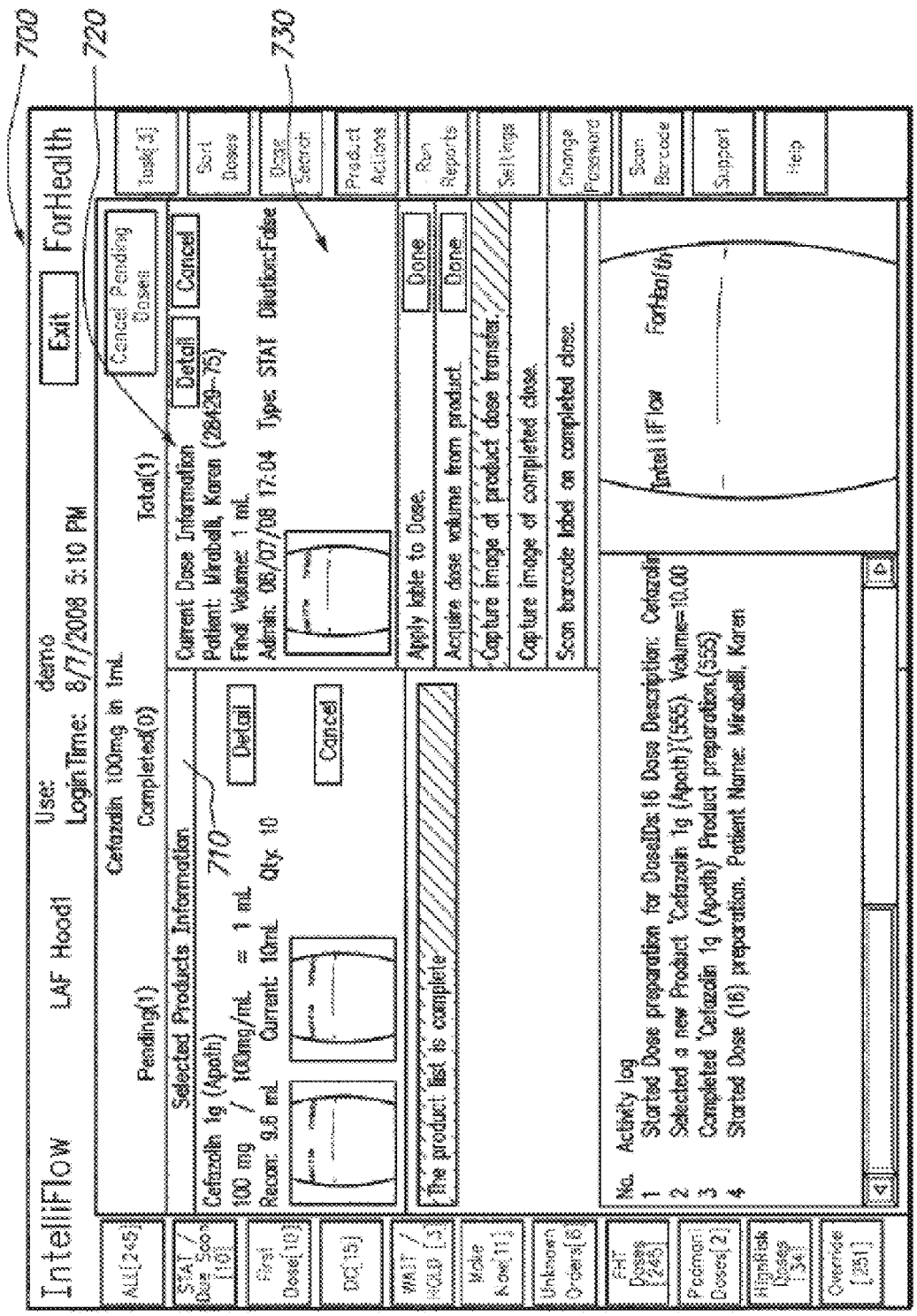

Also, with brief reference to FIG. 15, a sample screen 700 shows exemplary steps that are displayed to the operator to assist the operator in preparing a specific dose of medication. On the left side of the screen, a "Selected Products Information" section 710 is provided and lists the drug product that is being prepared. In this example, the drug product is Cefazolin 1 g (Apoth). On the right side of the screen is information 720 that relates to the current dose that is being prepared for a specific patient. For example, the patient's name (e.g., Karen Mirabelli) is clearly identified along with any identifying patient information (a patient number). The dose information also includes a final volume of the dose (e.g., 1 ml) and administration information is provided, such as a date and time (e.g., 8/7/08 17:04) when the dose is to be administered. The type of dose (e.g., STAT) can also be listed to alert the operator to any special processing information (e.g., the dose should be processed in an urgent manner).

The screen of FIG. 15 lists a number of steps 730 that are to be performed by the user to prepare the dose and fulfill the dose order. For example, one step may be the step of applying a label to the dose and once this task is performed, the user can indicate so by pressing a button that is labeled "Done". Another step can be to acquire the dose volume from the product and once this task is performed, the user can indicate so by pressing a button that is labeled "Done". Other steps that are to be performed and verified are capturing the image of the product dose transfer; capturing the image of the completed dose; and scanning the barcode label on the completed dose. Each of these steps must be verified as being properly completed before the user can continue with the other steps of the dose preparation process.

The NDC information also contains formulary information and this can be used at the workstation as the drug is being prepared in accordance with the steps shown and described with reference to FIG. 15. In particular, this information can be used as part of an integrity check (drug verification process) to ensure that the drug is being prepared properly.

As mentioned above, if it is determined at step 550 that the dose order record is suitable for automated handling, it will be queued at an appropriate automated workstation. Queuing the dose order record at a workstation presents a further opportunity to optimize the distribution of orders within the pharmacy. For example, it may not be feasible to determine at step 140 an optimal organization of dose order records to ensure that dose order records requiring similar medications are queued at the same workstation. Thus, at step 570, a particular dose order can be queued at an automated workstation that is known to be processing the same medication, or to any workstation at which a dose order involving the same medication was just queued (e.g., a workstation to which the dose order and protocol are provided at block 560. Re-ordering and queuing of dose orders can be very flexible if the urgency of the dose order is very low. For example, the dose orders can be queued in a less than optimal order with respect to time, but more efficient with respect to medication changes and cleanings to prevent cross-contamination. Optionally, the current workload and/or work distribution of dose orders to workstations can be tracked or monitored and presented to a user (e.g., presented on a centralized display) for management and performance monitoring.

Once the workstation fulfills the dose order, the status of the dose order record can be changed to indicate that it has been processed at step 580. The status change can be received by the pharmacy workflow management application 114 as an acknowledgement that the drug dosage form has been prepared, or as a "processed-order" status, and this can further result in an update to the dose order record, the inventory record, or both concerning any drug dosage forms that have been prepared but not yet delivered. Additionally, data concerning the assignment of the dose order to the selected workstation and the completion of the dose order can be logged in the database. Logging information concerning which workstation processed the dose order into the database (e.g., the local database 330), as indicated at step 590, enables complete tracking of both the dose-order processing steps and tracking of the prepared dose itself from its entry as data into the pharmacy system to its delivery to the patient. Accordingly, at step 590, the information can be logged into the local database 112.

The present system therefore provides a composite workflow application that can layer on top of a hospital's existing pharmacy information system 320, without requiring any changes to that system, in order to manage the production of IV doses (and other doses) in the pharmacy, track dose delivery from the pharmacy, prevent medication errors caused by incorrect dose preparation, capture detailed history of dose preparation (including images), and serve as a gateway to automation systems throughout the pharmacy, such as carousels, compounders, and IV robots.

Accordingly, the pharmacy workflow management application 114 may allow for a pharmacist review of a dose prior to the dose being distributed from the pharmacy is depicted in the pharmacy dose verification and approval step 450 of FIG. 4. In traditional approaches to pharmacist review, a pharmacist would often have to enter the pharmacy to verify work performed by a pharmacy technician. Oftentimes, such preparation environments comprise clean rooms such that the pharmacist might have to go through an extensive gowning process in order to access the area in which the dose is being prepared. In contrast, given the centralized storage of dose order metadata facilitated by the pharmacy workflow management application 114, a pharmacist may utilize a remote access terminal 314 or a client at the local system 110 that is external to the pharmacy, but still within the local system 110 to access, review, and approve or deny doses prepared by technicians.

Accordingly, the pharmacy workflow management application 114 may provide for remote inspection of prepared doses, thus facilitating the practice of telepharmacy, by which a pharmacist can inspect the dose preparation from any location inside the hospital or elsewhere so the dose is released more quickly and efficiently from the pharmacy. Accordingly, dose inspection/verification may be performed by a pharmacist from any location using the portal the present invention. Dose order record metadata stored at the local server 330 may be presented to the pharmacist for inspection and approval. The portal may be provided through a conventional web browser, optionally with the use of a plug-in or other active code that provides for review of the data presented such as, for example, magnification, rotation, contrast adjustments, and other adjustments to an image to facilitate interview.

In turn, a pharmacist may be presented with images associated with the preparation of the dose. The pharmacist can not only look at images of the final product, including the product label, and other related product information, such as a barcode information, but also, the pharmacist can review information and images that obtain the particular steps in the overall drug preparation process. For example, during a drug reconstitution process, the operator may step through the drug preparation as described above such that the operator must confirm each step is successfully completed prior to moving to the next step. One of the steps in the preparation of the dose may be the selection of a particular drug vial. The selection of the drug while may be captured using the camera to produce an image that may be later viewed by the pharmacist. Additionally or alternatively, a scanning event during which the operator identifies the drug vial being used by scanning a barcode on the drug vial may also produce data that is reviewable by the pharmacist. The pharmacist can view each or many of the steps are taken in order to confirm that steps properly completed in the protocol to prepare the preparation and thus, confirmed the dose is properly prepared. The remote verification facilitated by the pharmacy workflow management application 114 provides a superior and more complete way of inspecting and verifying a dose prior to releasing the dose to the patient because the pharmacist may be able to visually inspect multiple images and/or data obtained during the steps of preparing of the drug to confirm that the steps are carried out properly, and thus, ultimately conclude whether the dose order is properly prepared and should be released the patient. In contrast, traditional approaches may rely upon a pharmacist discussing with the technician the steps taken to prepared dose without any way to actually verify the steps performed. This improved verification may be important in many circumstances, including when the constituent components of the final dose include more than one clear fluid such that a visual inspection of the final dose alone cannot provide a basis for the pharmacist to confirm the accuracy of the dose. Thus, benefit results from the capture and review steps, regardless of whether the pharmacist is on-site or remotely situated.

Figure 16:
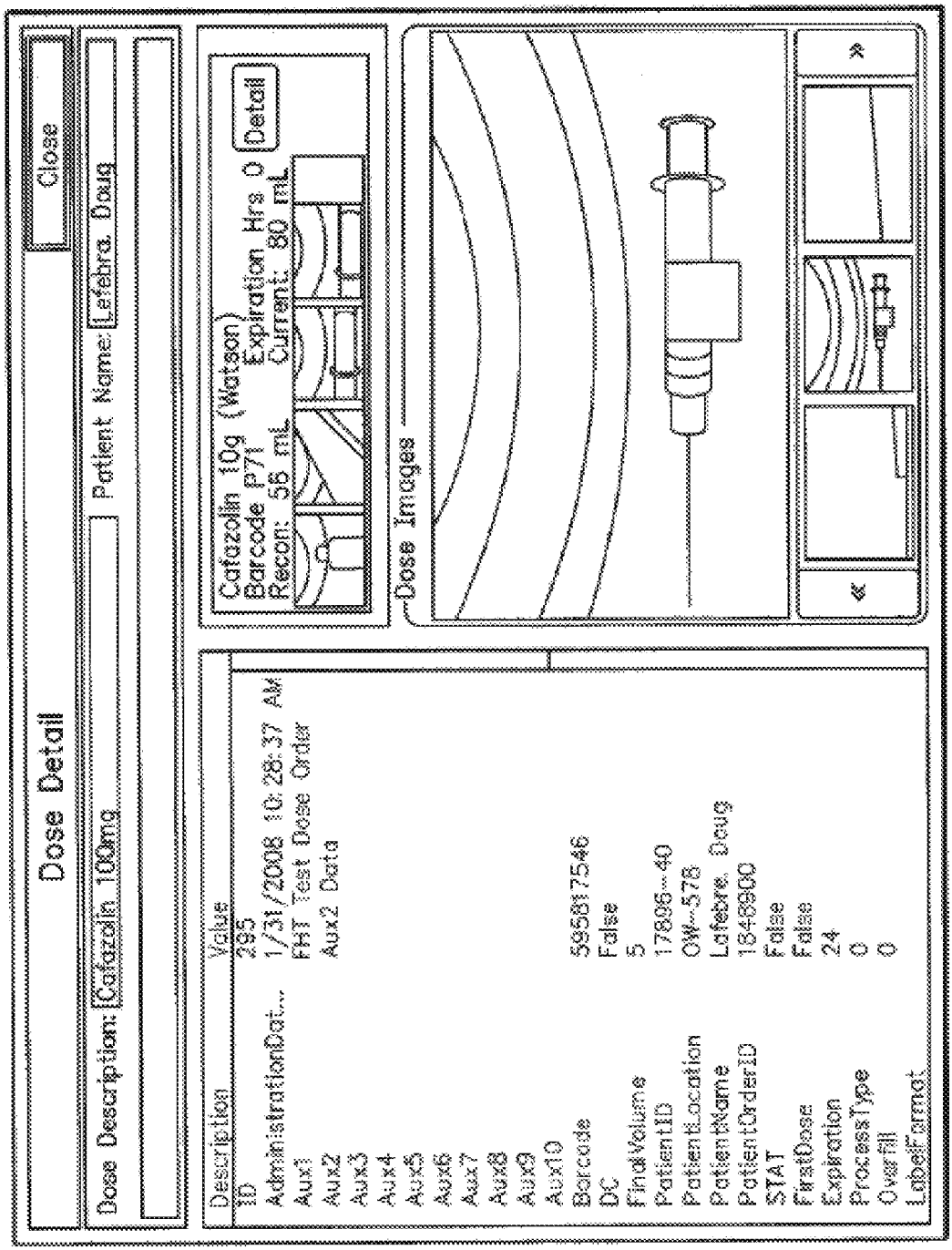
Figure 17:
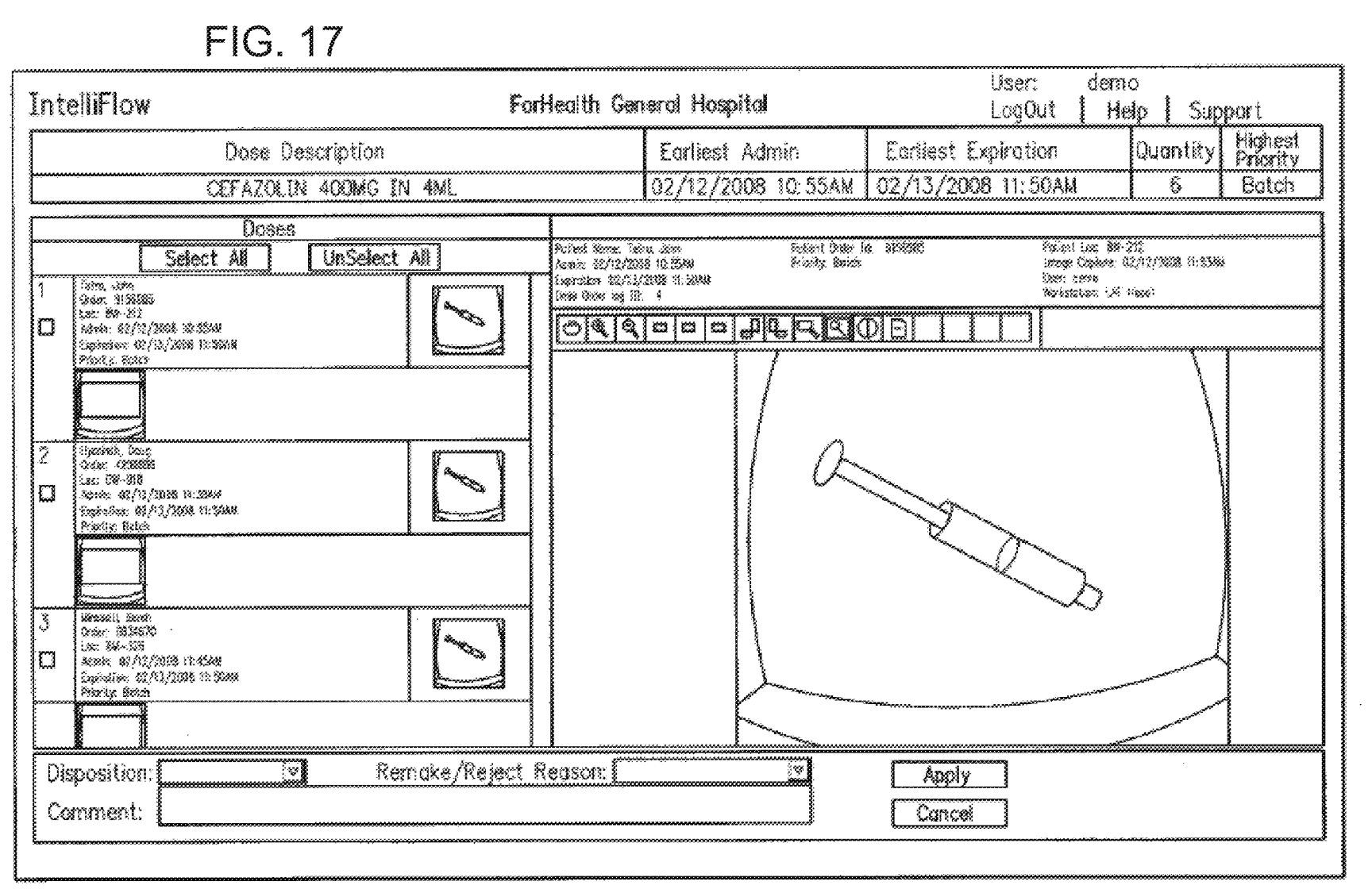

FIGS. 16 and 17 show an embodiment of a user interface for depicting various images that can be selected by a pharmacist in order to view a final dose order, in this case a syringe filled with medication. Different angles and different views are available to the pharmacist, as well as information that has been captured in other ways such as by scanning or weighing steps, if called for in the recipe at the workstation that prepared the final dose being inspected.

Preferably, the local server 330 includes web services or a communication module that enables the data records associated with the dose order and its production to be viewed through a conventional web-browser program. As such, the pharmacist no longer has to be physically within the pharmacy to inspect and verify dose orders and ultimately either approve and release the dose order or reject the dose order. The opportunities that this system presents are varied and great. For example, a number of pharmacies can subscribe to a service where pharmacists inspect and verify dose orders from a remote location, either all the time or after the close of normal business hours. In addition, when the drug orders are prepared by automated drug preparation devices as opposed to pharmacy clerks, the inspection and verification process can be outsourced to one or more pharmacists who review and verify the dose orders.

In addition, a panel of pharmacists can, at one or more remote locations, review the dose orders that have been prepared by a number of different workstations (both automated and manual), regardless of the location of such workstations. Each pharmacist can review all of the digital records and stored information as described above as part of the inspection process and then can approve the dose order for release if the pharmacist concludes that the dose order was properly prepared. The approval process can comprise messages communicated through the portal, e.g., a web-browser application such that the pharmacist simply logs into the system and approves particular orders by mouse-clicks, keystrokes, and other conventional inputs that are forwarded to the local server that was the source of that particular dose order. A conventional login process with password and optionally further user-authentication ensures that the pharmacist's identity is verified before providing access to the pharmacist to any dose order information. The system can be designed so that for each dose order, the pharmacist must enter a unique identifier, such as a password, in order to release the drug. The date and time of the inspection and release or rejection of the dose order is also logged. Optionally, this information can be associated with the dose order record so that the approval stage is saved together with the processing steps to fill the dose order. In this manner, a record of which pharmacist has approved a particular dose order can be saved.

It will be appreciated that an entity can be formed in which pharmacist-members span the world in different time zones so as to have a pharmacist available regardless of the time of day to inspect and release or reject a particular dose order. The pharmacists can thus be part of an organization or a corporation that offers this service to different pharmacies across the globe. To accommodate different languages, the software can be configured to offer the dose order information in different languages, which can be selected in a pull down menu on a screen, such as a login screen.

Figure 18:
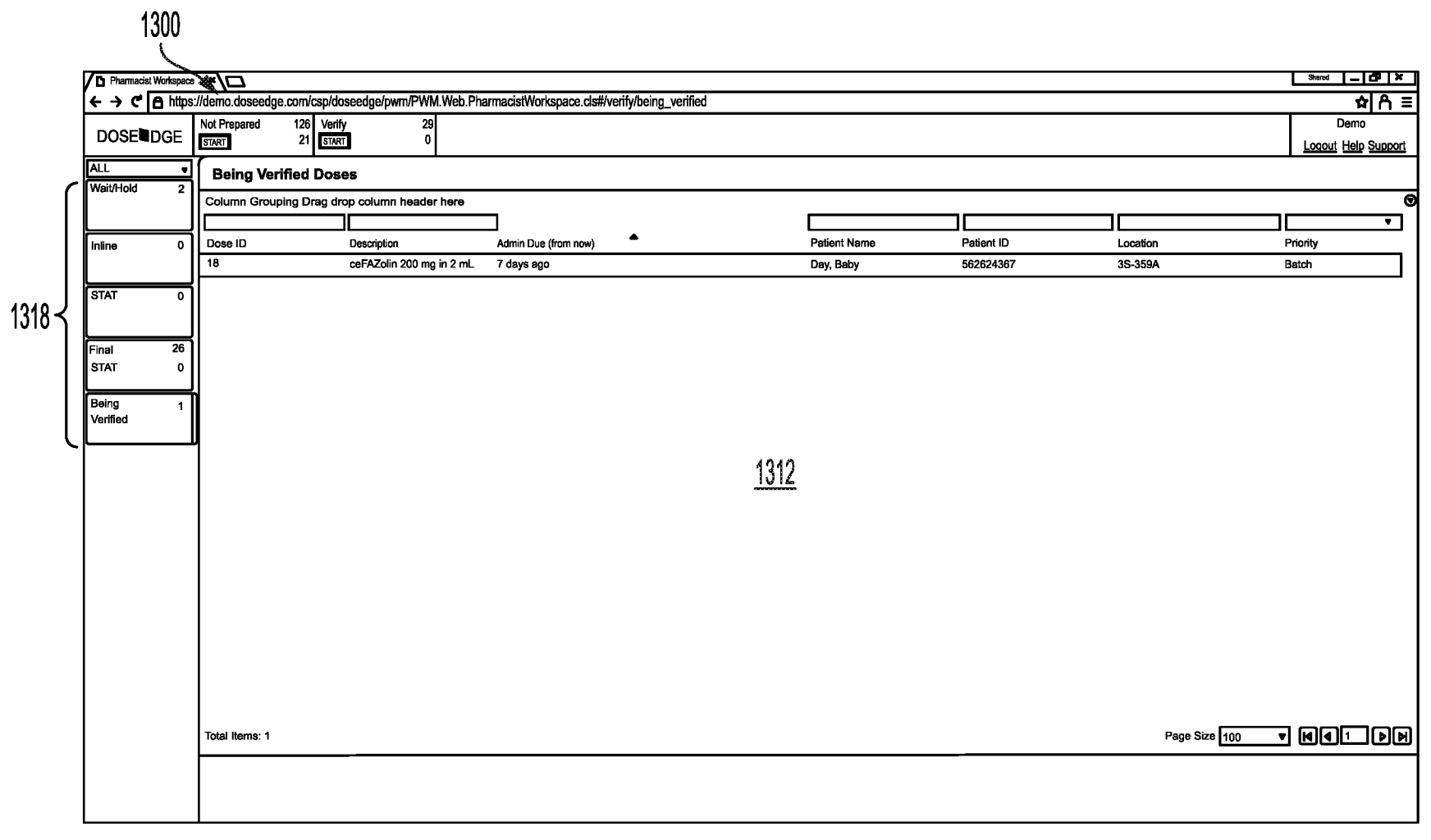

With further reference to FIG. 18, the dose order management tool 1300 may allow for a user to view and/or modify who has control over a dose order undergoing verification. For example, when a user selects a dose order record that has been prepared in order to verify the dose order, the dose order status may be changed to "at verification" or "claimed" to indicate that the dose is being verified by a user. However, under certain scenarios, the user may become distracted, be called away from the terminal at which verification is being performed, or otherwise be disposed such that the dose being verified remains in the claimed status without further action being taken with respect to the dose order. It may be beneficial to allow for another user to obtain control of the dose order record being verified such as for example, when a dose order associated with the verified dose order record is approaching administration time or if the dose order has a STAT priority or the like. Accordingly, with respect to FIG. 18, when tab 1316 is selected to display dose is awaiting verification, a secondary filter 1318 associated with doses being verified may be displayed to present a dose order record listing 1312 populated with dose order records with a claimed status. That is, upon selection of the being verified filter 1318, the dose order record listing 1312 may be populated with doses that are undergoing verification.

Figure 19A:
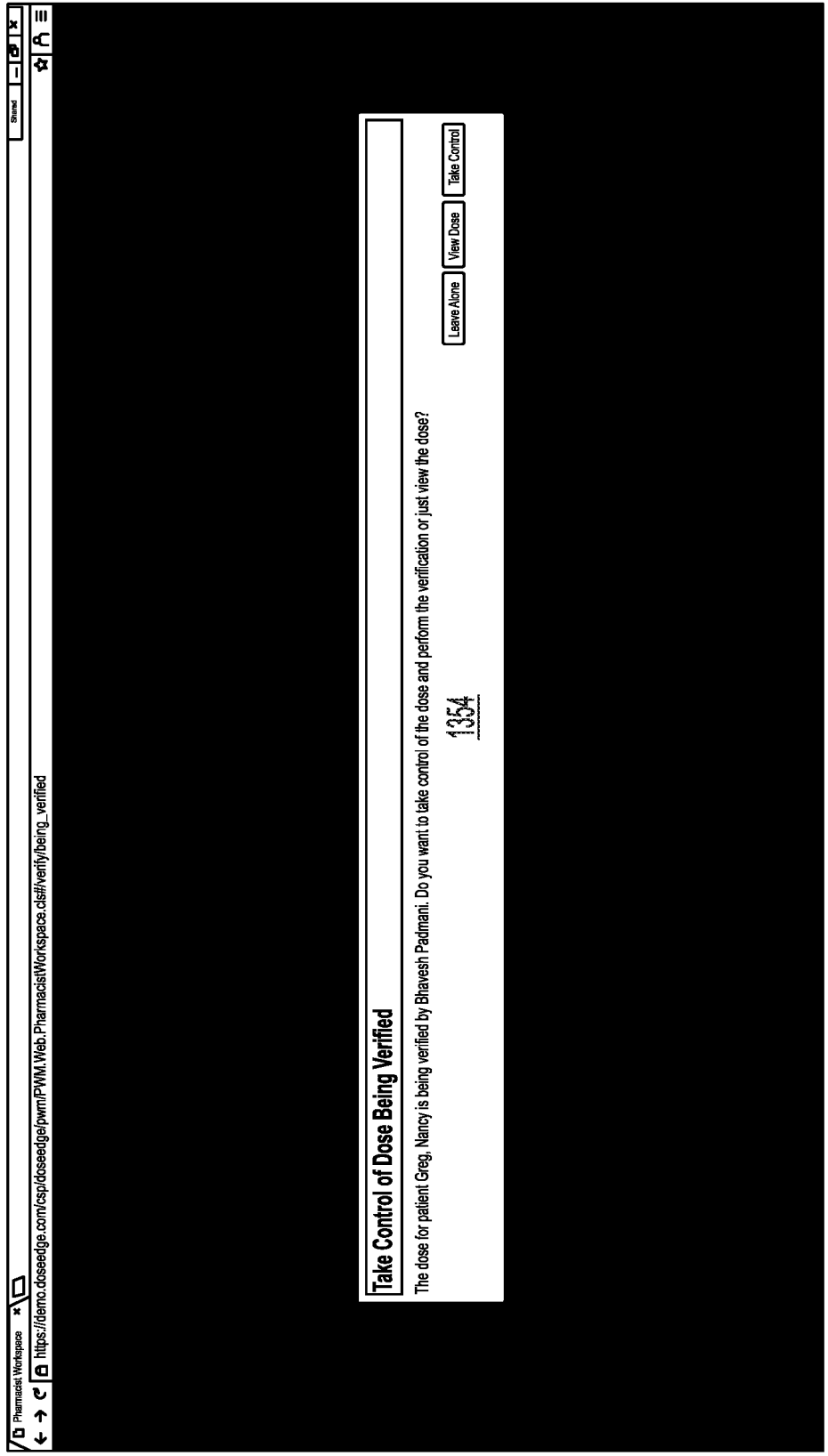

In turn, upon selection of a dose being verified by another user, a verification control dialog box 1354 may be displayed to the user as shown in FIG. 19A. The verification control dialog box 1354 may display to a user an indication of the other user who currently has control of (i.e., is verifying) the dose. The verification control dialog box 1354 may in turn include a number of controls (e.g., buttons) that provide for actions to be taken with respect to the dose being verified. For example, a user may select to leave the dose in the control of the other user by selection of the "leave alone" button. The user may also view details of the dose by selecting the "view dose" button. Finally the user may modify the control over the dose. In an embodiment, a control may be provided that allows a user to revoke the control over the dose from another user. Furthermore, as shown in FIG. 19A, a user may take control of the dose being verified by the other user by selecting the "take control" button.

Figure 19B:
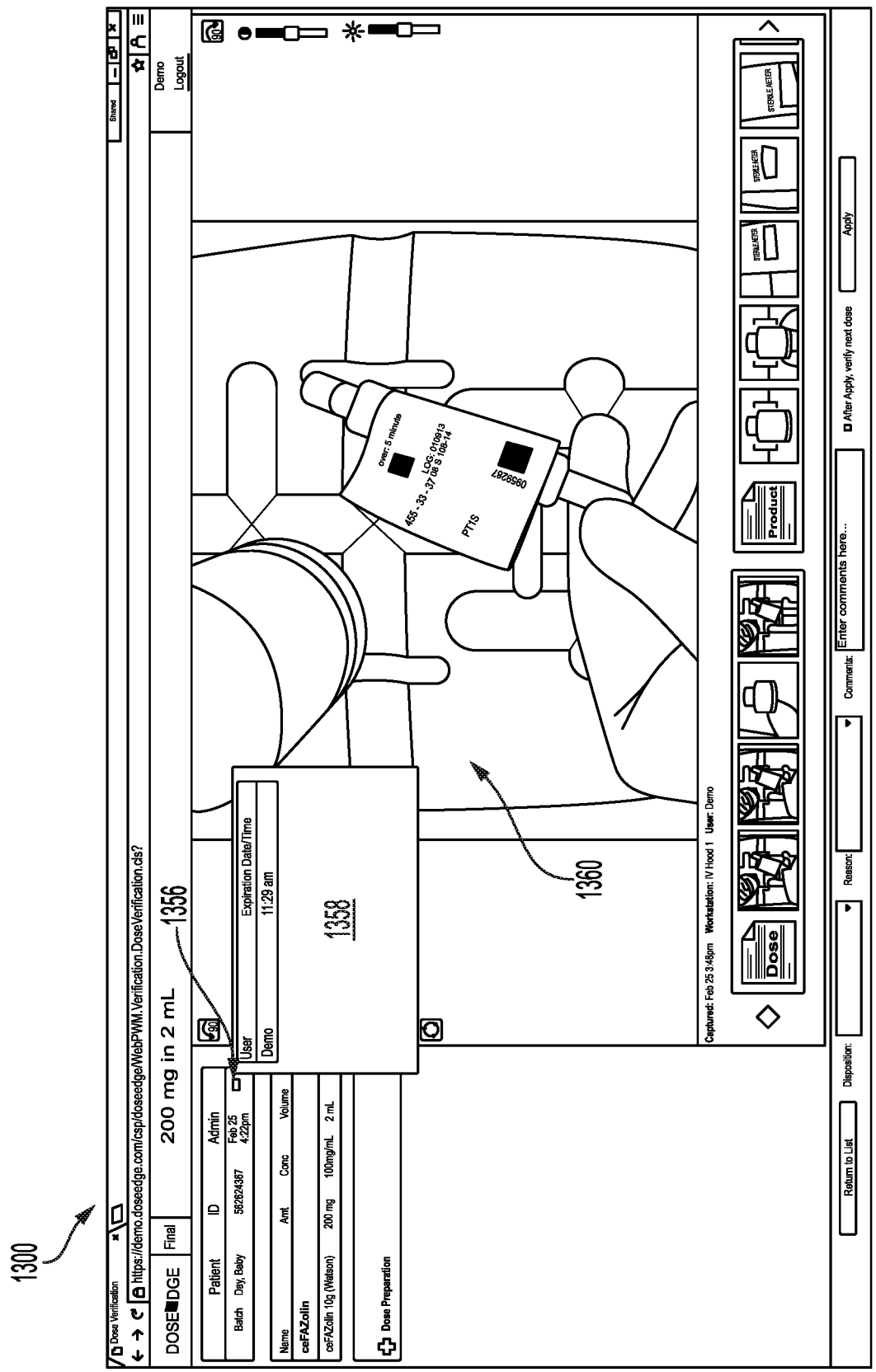
Figure 20:
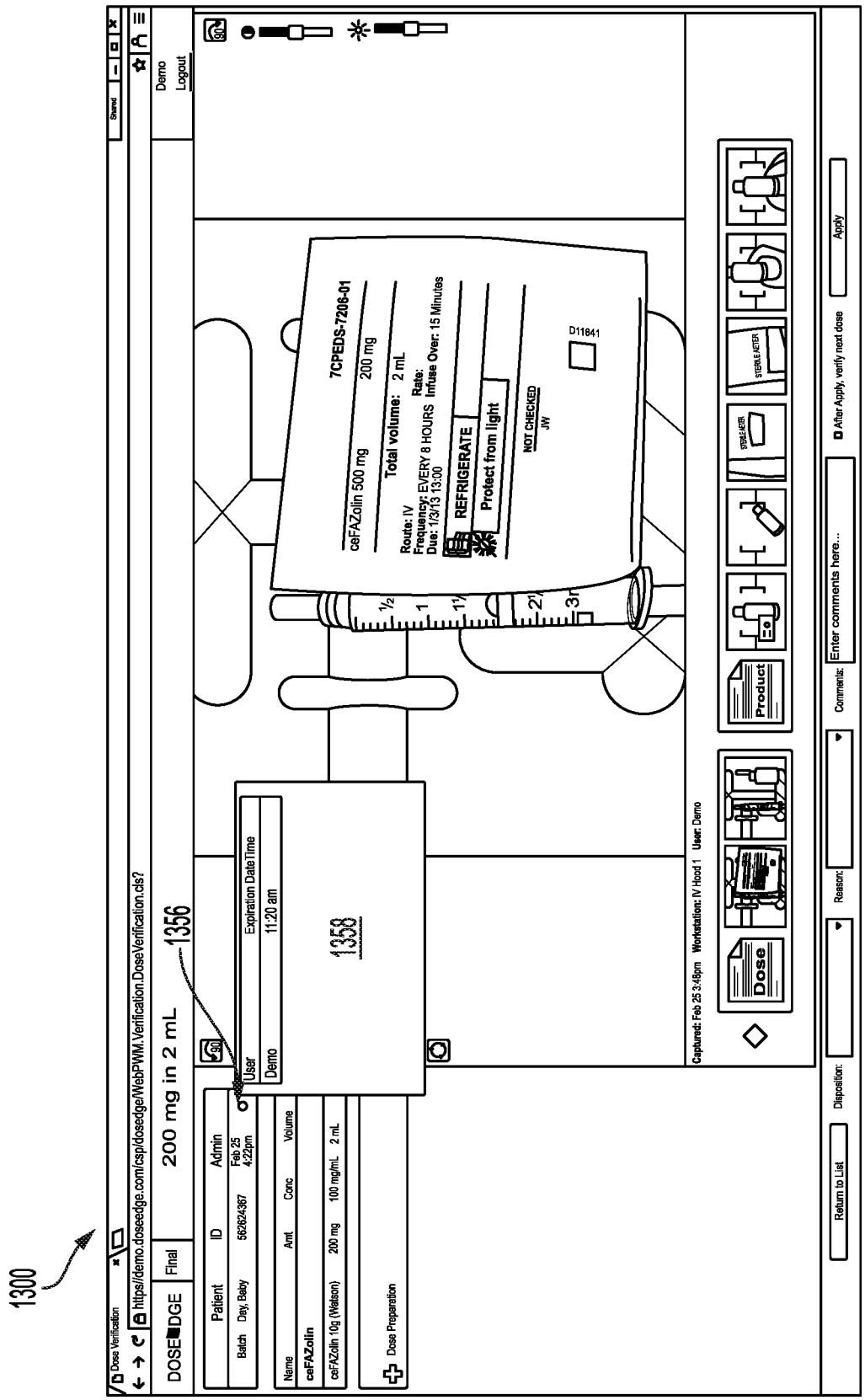

Upon selection of the "take control" button, a user may obtain control over the verification of the dose from the other user. In turn, a dose verification screen 1360 for the user to control the dose may be shown as depicted in FIG. 19B. Specifically, a dose control indicator 1356 may provide an indication that indicates the user has taken control over the verification of the dose. Selection of the dose control indicator 1356 may provide details regarding the user and an expiration time corresponding to the time at which the user's control over the dose may cease in a dose control information window 1358. Correspondingly, a dose verification screen 1360 of the other user may be updated such that the dose control indicator 1356 of the other users modified to indicate the user no longer controls the verification of the dose. Furthermore, the dose control information window 1358 may be updated to display to the other user name user who is currently controlling the dose.

After doses are prepared, the resulting physical dose may be tracked during the dose sorting and distribution 460 as shown in FIG. 4. That is, once the dose corresponding to the dose order is prepared, the resulting dose may be labeled, preferably at the dose preparation station so that the label is in close proximity to the prepared dose (as opposed to the conventional practice of centralized printing of all of the labels for dose-orders that enter the pharmacy. The association between the dose, the dose order, and the dose order record may be a result of linking the interrogation of a scannable element to the dose order record. A code supported by or secured to the dose itself and a code associated with a bin at the dosage form's current location can both be interrogated and then that information uploaded to a database to provide information regarding the whereabouts of the dose within the pharmacy. For example, the codes can be bar codes and can be sensed using a reader such as, for example, a bar code scanner. The particular scanner or reader used and the manner of scanning can be varied within the context of the invention to suit the requirements of a given implementation. Thus, for example, the code can be an optically scannable bar code or an interrogatable code such as an RFID tag that is supported in lieu of or in addition to bar codes, plain text, or other codes. The terms scanner, scanning, and scannable and/or reader, reading, or readable are intended to include wireless interrogation or passive data reception whether they are based on an optical read, a radio frequency interrogation or an interrogation in some other frequency band, or a form of passive wireless data reception. More generally, the codes in scannable or readable form are referred to as "tags." As the dose progresses through the process of preparing the dose, the dose and/or additional tags associated with various locations or processes can be scanned to track the dose through the preparation process. The process of scanning a tag associated with the dose to change the dose's status and/or location information may be referred to as a scan event. Some scan events may also be triggered scan events that function to change the status of the dose in the preparation process in response to a scan. For example, when the technician selects a dose to prepare, a dose label may be printed for the dose. The printed dose label may have a tag associated with the dose order. Scanning the dose order tag on the label may be a precursor in the protocol to initiate the preparation of the dose and my simultaneously trigger the status of the dose to change from, for example, "pending" to "in process."

The workflow process described herein may include a "kitting" function that organizes work into appropriate kits, prints picking documents to assist the technician in locating and securing the appropriate drugs and supplies. Bar codes or the like can be used to verify the selected drugs and the workflow process includes issuing a kit report that tracks the work into and through the IV room or other room.

Additionally, scanning of tags associated with a dose may allow a plurality of dose orders may be aggregated to define a transport collection. For example, a transport collection may be identified for a specific final destination within a facility for more efficient transport of doses to the final destination in the facility. As such, the final destination may, but is not required to, correspond to a physical location within a hospital or other care facility. In this regard, verified doses may be scanned to identify the dose order for the dose. Subsequently, a transport collection (e.g., a tag or other machine readable identifier) may be scanned to associate the dose order with the transport collection. In this regard, when the transport collection undergoes a scan event (e.g., corresponding to a change in location of transport collection), all dose order records that are associated with transport collection may be updated without requiring each dose order record and transport collection to be scanned.

The transport collections may be associated with the final destination. In this regard, prior to association of a dose order with transport collection, one or more portions of dose metadata may be scrutinized determine the appropriateness of the dose order being added to the transport collection. For example, a transport collection may be established that is to be distributed to a predetermined location within a hospital. As an example, a transport collection may be defined corresponding to a fourth floor nursing station. In this regard, if the dose order record has dose metadata associated with a corresponding dose order record data field that indicates the dose order is not to be transported to the fourth floor nursing station, a transport collection rule may prevent association of the dose order with the transport collection rule. In this regard, the rule may scrutinize dose order metadata associated with a dose order to determine the appropriateness of the dose order records in relation to the transport collection. As such, a dose order record that includes dose order metadata not associated with acceptable metadata for the dose order record may be disallowed from being associated with the transport collection. The metadata scrutinized by the transport collection rule may be any appropriate portion of metadata and not simply limited to a location provided in the dose order data. For example, it may be recognized that a location may be unacceptable for handle hazardous doses such as chemotherapy doses or the like. In this regard, any portion of dose order metadata regarding the dose order (e.g., drug identifiers like) may be utilized to define transport collection rules.

In connection with the tracking of the dose in the pharmacy, the pharmacy workflow management application 114 is further capable of responding to any status inquiries concerning a given dose order with order status (e.g., "unprocessed," "in-progress at {selected workstation}," "processed" and the like) and optionally a location (e.g., in bin A, on cart B, in pediatric ward, etc.). The pharmacy workflow management application 114 is also capable of monitoring and tracking the prepared dose through to its delivery with additional status information (e.g., dispensation to patient {X}), as discussed with reference to FIG. 21.

Other scan events may modify the status of a dose order record in response to a scan associated with a dose order record, where the scan is at least partially in connection with the dose preparation step associated with an independent pharmacy workflow operation to prepare a dose associated with the dose order record. That is, for example, when a technician or other user scanned the dose for a purpose associated with the preparation of the dose, other than a specific change in the status of the dose, the status the dose may also be modified in response to the independent preparation step. Accordingly, as shown in FIG. 50, scan event 5000 may be defined. The scan event may have a scan event abbreviation 5002 and a description 5004. In the event a specific barcode for scanning in association with the scan event 5000 is provided, the barcode may be provided as a description 5006. Additionally, a validation rule 5008 may be applied whereby scan events may only be applied certain types of doses. In the event the dose does not comply with the validation rule 5008, the validation rule error message 5010 may be provided. Furthermore, the status from which the trigger event changes the dose 5012 as well as the status to which the trigger event changes the dose 5014 may provided. In this regard, a scan event may be defined by its association with a scan of a dose order record or other information in relation to the preparation of the dose for purposes other than modifying the status of the dose. However, the dose status may also be updated at any time.

Figure 21:
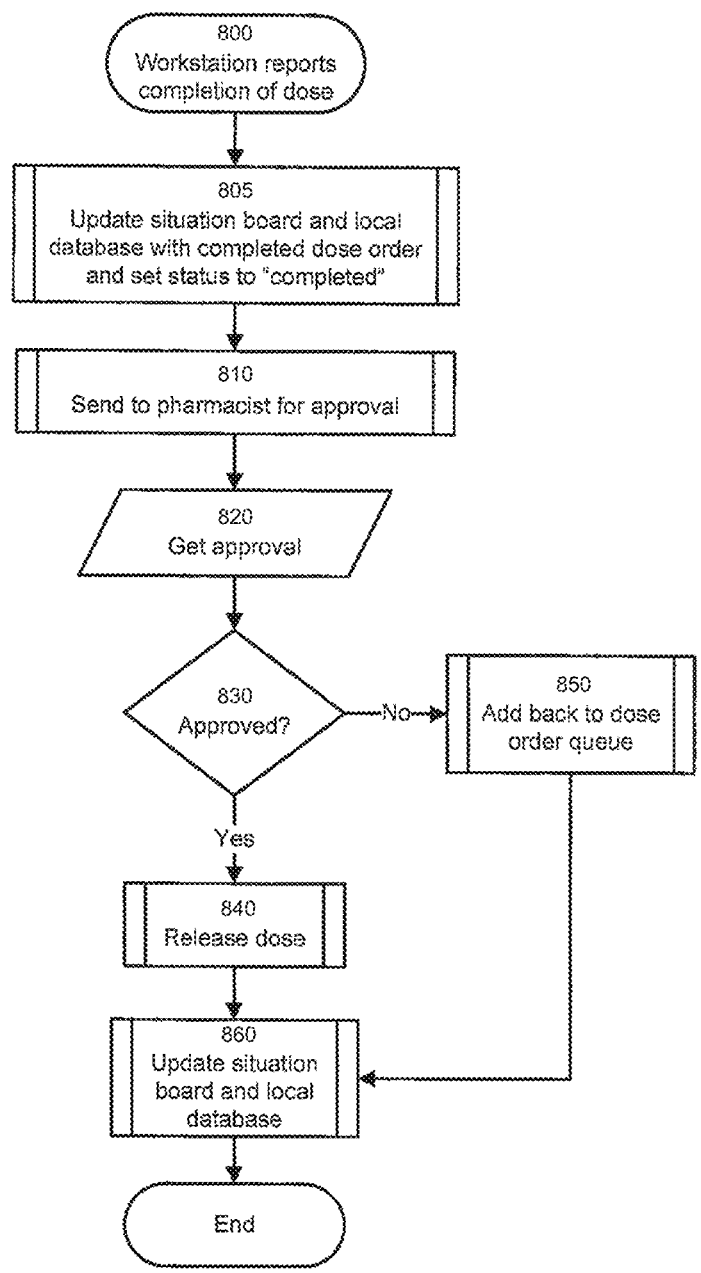
FIG. 21 depicts a flow chart of an embodiment of a method for review doses by a pharmacist.

In FIG. 21 a process flow is illustrated that commences when a workstation identifies a particular dose as having been completed, as indicated at terminator 800. The local database is updated with completion information at step 805, and this provides status information that can be referenced by persons outside of the pharmacy in response to a status inquiry and by the system in managing the distribution of subsequent dose orders. The identification preferably associates a unique identifier with the dose. The database record associated with the identified dose can be marked as completed. Alternatively, various other subsystems can be notified of the completion of the dose. For example, a storage subsystem that tracks medication that is "on-hand" can be updated with the prepared dose's record. Additionally, a delivery subsystem can be notified that the prepared dose is completed and ready for delivery to its destination. At a later time, for instance, according to a schedule, the information in the local database can be uploaded to a central server 390 that can be configured to communicate with the respective local databases of multiple pharmacy systems.

With continued reference to FIG. 21, in step 830, if the pharmacist approves the dose order, then the dose order is released in step 840 as described above. On the other hand, if at step 830 the pharmacist does not approve the dose order based on the information presented to the pharmacist, then the dose order is rejected and the original order is added back the dose order queue at step 850 for preparation anew. At step 860, the local database and the situation board are updated to reflect whether the dose order was released or not. At a later time, the local database can communicate the completed dose information including any dose-approvals and dose-rejections from the local server 330 to the central server 390.

As may be appreciated, dose tracking takes a number of forms. The situation board 400 provides one manner of dose tracking because it maintains a high level view of the work being performed in the pharmacy and because is configured to immediately instruct an observer regarding any incomplete work. Moreover, color coding or other formatting on the situation board can immediately identify the volume of work pending preparation, under preparation, or prepared but not yet checked out by a pharmacist (i.e., orders not yet approved for release). Such formatting may be based on a user profile associated with user authentication information used access the situation board 400. For example, with further reference to FIG. 47, a situation board 400 is depicted that, when accessed with a given user profile, may be displayed in the form of situation board 400', which may include color coding, alternative text presentations, or other formatted styles in relation to the data presented on the situation board 400. Furthermore, as depicted in FIG. 48, different sorting configurations such as a default sorting 4800 (e.g., where dose order records are sorted by priority for dose order page types, patient name for patient types, and expiration time/date for product page types), a sorting based on elapsed time in descending order 4802, or a sorting based on elapsed time and hastening order 4804 may be applied to the dose order records displayed in the situation board 400. In any regard, the appearance of the situation board 400 may be controlled by a style defined by a user profile. In turn, modifications to the style associated with the user profile may allow any of the foregoing or other changes to be easily made to the situation board 400 to customize the situation board 400 to a given installations need.

Dose tracking is also provided at each step in the dose preparation process, including without limitation, the selection and preparation of the ingredients, pharmacist checking, removal from the IV room for delivery to a patient, and the actual delivery of the dose to the floor. Each of these steps is part of the workflow process that is tracked in the system managed by the server 330. As well, there is a dose query function that permits any authorized user to probe the database to discover the current status of any particular dose or group of doses. Also, the situation board maintains alarms for doses that are due and also tracks doses whose preparation must be delayed because of limited stability in solution.

While the invention has been illustrated and described in detail in the drawings and foregoing description, such illustration and description is to be considered as exemplary and not restrictive in character. For example, certain embodiments described hereinabove may be combinable with other described embodiments and/or arranged in other ways (e.g., process elements may be performed in other sequences). Accordingly, it should be understood that only the preferred embodiment and variants thereof have been shown and described and that all changes and modifications that come within the spirit of the invention are desired to be protected.

What is claimed is:

1. A system for pharmacy workspace queue management in a pharmacy workflow management application, comprising:
- a server operating the pharmacy workflow management application;
- an access terminal remote from and in operative communication with the pharmacy workflow management application, wherein said pharmacy workflow management application is operable to access a plurality of dose order records corresponding to dose orders received at said server in response to a request for said plurality of dose order records received from the access terminal; and
- a user interface provided at said access terminal for displaying said plurality of dose order records received from the pharmacy workflow management application,
- wherein said server is operable to receive, from said access terminal, user authentication information corresponding to a given user of said access terminal,
- wherein said pharmacy workflow management application is operable to associate, at said server, said user authentication information with a profile for said given user, the profile being associated with a pre-defined default layout having user interface elements that are defined at least partially based on said profile of said given user, and
- wherein said pharmacy workflow management application causes said user interface to display said plurality of dose order records in the pre-defined default layout that is defined at least partially based on said profile of said given user.

2. The system of claim 1, wherein said plurality of dose order records includes at least a first dose order record corresponding to a first dose order that has not been prepared and at least a second dose order record corresponding to a second dose order that has been prepared and has not yet been verified by a pharmacist.

3. The system of claim 2, wherein said user interface is operable to display a plurality of pages, wherein a first page of said plurality of pages is associated with managing dose orders having a wait/hold status, a second page of said plurality of pages is associated with managing dose orders having an inline dose status, and a third page of said plurality of pages is associated with a pharmacist workspace queue management function.

4. The system of claim 3, wherein said pharmacist workspace queue management function is selected from the group consisting of: managing dose order on STAT dose, managing dose order on final/STAT dose, and managing dose order being verified.

5. The system of claim 1, wherein said user interface is operable to display a plurality of collapsible areas.

6. The system of claim 5, wherein said plurality of collapsible areas includes a plurality of data attributes of at least one of said plurality of dose order records, and wherein said plurality of collapsible areas is associated with at least one of a plurality of informational groups, and wherein said data attributes are arranged with at least one of said plurality of collapsible areas at least partially based on an association between said data attributes and at least one of said plurality of informational groups, and wherein said plurality of informational groups is selected from the group consisting of: dose information, patient information, clinical information, formulary information, and documentation information.

7. The system of claim 5, wherein said plurality of collapsible areas is configured to hide information when collapsed, and wherein said configuration of said plurality of collapsible areas is associated with said profile of said given user.

8. The system of claim 7, wherein said user interface is configured to display said plurality of collapsible areas in accordance with said profile such that the profile indicates which of the collapsible areas are operable to hide information upon said given user's initial login.

9. The system of claim 2, wherein said user interface is configured to display numerical values of said plurality of dose order records according to an Institute for Safe Medical Practice ("ISMP") standard format, and wherein said user interface is configured to receive a user input in a first format and is further configured to modify the first format to conform to the ISMP standard format when the first format mismatches the ISMP standard format.

10. The system of claim 2, wherein said user interface is configured to display a print view of at least one of said plurality of dose order records.

11. The system of claim 10, wherein said print view includes detailed dose information and product information, and wherein one collapsible area of a plurality of collapsible areas corresponds to a collapsible material properties field that is adapted for user input to define a material name.

12. The system of claim 2, wherein said pharmacy workflow management application is operable to enable modification of at least one of said plurality of dose order records, displayable at said user interface, wherein said modification comprises dragging an external document, at said user interface, to a document input page of said user interface such that said external document is provided as an attachment to at least one of said plurality of dose order records and the attachment is associatively displayed along with the at least one of said plurality of dose order records.

13. The system of claim 2, wherein said plurality of dose order records comprises a plurality of external document attachments, and wherein said user interface is configurable to display said external document attachments for at least one of said plurality of dose order records, and wherein each of the plurality of external document attachments is included in a listing that indicates each of the plurality of external document attachments is associated with a respective dose order record.

14. The system of claim 2, wherein said plurality of dose order records is associable with a data table of said user interface, and wherein said plurality of dose order records comprises a plurality of characteristics, and wherein said pharmacy workflow management application is operable to modify at least one of said dose order records.

15. The system of claim 14, wherein said user interface is configurable to display, for each of said plurality of dose order records, dose history, product history, and scan event data.

16. The system of claim 15, wherein each of said plurality of dose order records is stored in corresponding relation to one or more dose order record data fields populated with dose order metadata regarding each dose order record, and wherein at least one dose order record data field corresponds to a dose order status indication of said at least one dose order record in relation to a dose preparation step of said at least one dose order record, and wherein said scan event data is at least partially based on said dose order status metadata.

17. A system for use in communicating information pertaining to a pharmacy workspace queue in a pharmacy workflow management application, comprising:
- an access terminal remote from and in operative communication with the pharmacy workflow management application operated by a server, wherein said pharmacy workflow management application is operable to access a plurality of dose order records corresponding to dose orders received at said server in response to a request for said plurality of dose order records by a given user via the access terminal; and a user interface provided at the remote access terminal for displaying said plurality of dose order records to said given user at said user interface such that a first dose order record and a second dose order record each appear in at least one distinct module of a common dashboard, wherein said dashboard is comprised of a plurality of modules configurable to communicate a status of at least one of said plurality of dose orders in said pharmacy workspace queue to said given user, and wherein said configuration is at least partially based on a profile for said given user, and wherein said server is operable to receive, from said access terminal, user authentication information corresponding to said given user of said access terminal, wherein said pharmacy workflow management application is operable to associate, at said server, said user authentication information with the profile for said given user, the profile being associated with the configuration of the plurality of said modules for communicating the status of at least one of said plurality of dose orders in said pharmacy workspace queue, and wherein said pharmacy workflow management application causes said user interface to display the plurality of said modules to communicate the status of at least one of said plurality of dose orders in said pharmacy workspace queue.

18. The system of claim 17, wherein said plurality of dose order records includes at least a first dose order record corresponding to a first dose order that has not been prepared and at least a second dose order record corresponding to second dose order that has been prepared and has not yet been verified by a pharmacist.

19. The system of claim 18, wherein said configuration of said modules are is associated with a module profile, and wherein said pharmacy workflow management application is operable to associate said profile with said module profile, and wherein the user interface is operable to display said plurality of modules in accordance with said module profile.

20. The system of claim 19, wherein said module profile includes alphanumerical customization preferences, wherein said alphanumerical customization preferences include a color preference, a font preference, a size preference, and a text effects preference.

21. The system of claim 18, wherein said pharmacy workflow management application is operable to sort said plurality of dose orders of said at least one module at least partially based on a plurality of sorting criterion, wherein a first sorting criterion of the plurality of sorting criterion includes a dose priority, a second sorting criterion of the plurality of sorting criterion includes a patient name, and a third sorting criterion of the plurality of sorting criterion includes at least one of an expiration date and an expiration time.

22. The system of claim 21, wherein said sorting comprises sorting said plurality of dose orders of said at least one module at least partially based on sorting criteria in ascending or descending order.

23. The system of claim 19, wherein said each of said plurality of dose order records is associated with a durational indicator that indicates a length of time elapsed since a milestone event, wherein said milestone event represents a change of status of at least one of said plurality of dose order records.

24. The system of claim 23, wherein said change of status corresponds to identifying modified dose order metadata regarding at least one of said plurality of dose order records, wherein said modified dose order metadata is modified with respect to corresponding portions of dose order metadata at least partially obtained in response to an input received from said user.

25. The system of claim 18, wherein said configuration is at least partially based on a cascading style sheet declaration contained within a single file and defined by the profile.

* * * * *